US011957960B2

(12) United States Patent
Bissonnette et al.

(10) Patent No.: US 11,957,960 B2
(45) Date of Patent: Apr. 16, 2024

(54) METHOD AND SYSTEM FOR USING ARTIFICIAL INTELLIGENCE TO ADJUST PEDAL RESISTANCE

(71) Applicant: Rehab2Fit Technologies Inc., Longmont, CO (US)

(72) Inventors: Michael Bissonnette, Denver, CO (US); Luis Berga, Austin, TX (US); Steven Mason, Las Vegas, NV (US); Philip Powers, Denver, CO (US); James D. Steidl, Denver, CO (US)

(73) Assignee: Rehab2Fit Technologies Inc., Longmont, CO (US)

( * ) Notice: Subject to any disclaimer, the term of this patent is extended or adjusted under 35 U.S.C. 154(b) by 0 days.

(21) Appl. No.: 17/395,656

(22) Filed: Aug. 6, 2021

(65) Prior Publication Data

US 2022/0016486 A1 Jan. 20, 2022

Related U.S. Application Data

(63) Continuation-in-part of application No. 16/869,954, filed on May 8, 2020.
(Continued)

(51) Int. Cl.
*A63B 24/00* (2006.01)
*A63B 21/00* (2006.01)
(Continued)

(52) U.S. Cl.
CPC .... *A63B 24/0087* (2013.01); *A63B 21/00076* (2013.01); *A63B 21/4033* (2015.10);
(Continued)

(58) Field of Classification Search
CPC ...... A63B 2024/009; A63B 2024/0093; A63B 2024/0096; A63B 2024/0065;
(Continued)

(56) References Cited

U.S. PATENT DOCUMENTS

| 59,915 A | 11/1866 | Lallement |
| 363,522 A | 5/1887 | Knous |

(Continued)

FOREIGN PATENT DOCUMENTS

| CA | 3193419 A1 | 3/2022 |
| CN | 2885238 Y | 4/2007 |

(Continued)

OTHER PUBLICATIONS

Claris Healthcare Inc., Claris Reflex Patient Rehabilitation System Brochure, retrieved on Oct. 2, 2019, 5 pages, https://clarisreflex.com/.

(Continued)

*Primary Examiner* — Sundhara M Ganesan
(74) *Attorney, Agent, or Firm* — Dickinson Wright PLLC; Stephen A. Mason; Jonathan H. Harder

(57) ABSTRACT

A method is disclosed for using an artificial intelligence engine to modify resistance of one or more pedals of an exercise device. The method includes generating, by the artificial intelligence engine, a machine learning model trained to receive one or more measurements as input, and outputting, based on the one or more measurements, a control instruction that causes the exercise device to modify the resistance of the one or more pedals. The method includes receiving the one or more measurements from a sensor associated with the one or more pedals of the exercise device, determining whether the one or more measurements satisfy a trigger condition, and responsive to determining that the one or more measurements satisfy the trigger condition, transmitting the control instruction to the exercise device.

17 Claims, 62 Drawing Sheets

Related U.S. Application Data

(60) Provisional application No. 63/168,175, filed on Mar. 30, 2021, provisional application No. 62/858,244, filed on Jun. 6, 2019, provisional application No. 62/846,434, filed on May 10, 2019.

(51) Int. Cl.

| | | |
|---|---|---|
| *A63B 21/002* | (2006.01) | |
| *A63B 21/005* | (2006.01) | |
| *A63B 21/22* | (2006.01) | |
| *A63B 22/00* | (2006.01) | |
| *A63B 22/06* | (2006.01) | |
| *A63B 22/18* | (2006.01) | |
| *A63B 23/035* | (2006.01) | |
| *A63B 23/04* | (2006.01) | |
| *A63B 23/08* | (2006.01) | |
| *A63B 23/12* | (2006.01) | |
| *A63B 71/06* | (2006.01) | |
| *G06N 20/00* | (2019.01) | |
| *G16H 20/30* | (2018.01) | |
| *G16H 50/20* | (2018.01) | |

(52) U.S. Cl.
CPC .... *A63B 22/0605* (2013.01); *A63B 23/03533* (2013.01); *A63B 23/0355* (2013.01); *A63B 23/0417* (2013.01); *A63B 23/1209* (2013.01); *A63B 24/0006* (2013.01); *A63B 24/0062* (2013.01); *A63B 71/0622* (2013.01); *G06N 20/00* (2019.01); *G16H 20/30* (2018.01); *G16H 50/20* (2018.01); *A63B 21/0023* (2013.01); *A63B 21/0058* (2013.01); *A63B 21/225* (2013.01); *A63B 2022/0038* (2013.01); *A63B 2022/0041* (2013.01); *A63B 2022/0094* (2013.01); *A63B 2022/0617* (2013.01); *A63B 22/18* (2013.01); *A63B 23/085* (2013.01); *A63B 2024/0009* (2013.01); *A63B 2024/0059* (2013.01); *A63B 2024/0065* (2013.01); *A63B 2024/0093* (2013.01); *A63B 2024/0096* (2013.01); *A63B 2071/063* (2013.01); *A63B 2071/0652* (2013.01); *A63B 2071/0655* (2013.01); *A63B 2071/0675* (2013.01); *A63B 2071/068* (2013.01); *A63B 2071/0683* (2013.01); *A63B 2220/24* (2013.01); *A63B 2220/30* (2013.01); *A63B 2220/40* (2013.01); *A63B 2220/51* (2013.01); *A63B 2220/52* (2013.01); *A63B 2220/805* (2013.01); *A63B 2225/15* (2013.01); *A63B 2225/20* (2013.01); *A63B 2225/50* (2013.01); *A63B 2230/06* (2013.01); *A63B 2230/207* (2013.01); *A63B 2230/30* (2013.01)

(58) Field of Classification Search
CPC .... A63B 2024/0068; A63B 2024/0071; A63B 2024/0078; A63B 2024/0081; A63B 24/0062; A63B 24/0075; A63B 24/0084; A63B 24/0087; A63B 71/00616; A63B 71/0619; A63B 71/0622; A63B 2071/0625; A63B 2071/0627; A63B 2071/063; A63B 2071/0633; A63B 2071/0636; A63B 2071/0638; A63B 2071/0641; A63B 2071/0644; A63B 2071/0647; A63B 2071/065; A63B 2071/0652; A63B 2071/0655; A63B 2071/0658; A63B 2071/068; A63B 2071/0675; A63B 2071/0677; A63B 2071/0683; A63B 2071/0686; A63B 2071/0694; A63B 22/06; A63B 22/0605; A63B 22/0664; A63B 22/0694; A63B 2022/0611; A63B 2022/0617; A63B 2022/0623; A63B 2022/0629; A63B 2022/0635; A63B 2022/0641; A63B 2022/0647; A63B 2022/0652; A63B 2022/0658; A63B 2022/067; A63B 2022/0676; A63B 2022/0682; A63B 2022/0688; A63B 21/0058; A63B 21/0059; A63B 21/00076; A63B 21/4033; A63B 23/03533; A63B 23/0355; A63B 23/0417; A63B 23/1209; A63B 24/0006; A63B 21/0023; A63B 21/225; A63B 22/18; A63B 23/085; A63B 24/0059; A63B 2022/0038; A63B 2022/0041; A63B 2022/0094; A63B 2024/0009; A63B 2220/24; A63B 2220/30; A63B 2220/40; A63B 2220/51; A63B 2220/52; A63B 2220/805; A63B 2225/15; A63B 2225/20; A63B 2225/50; A63B 2230/06; A63B 2230/207; A63B 2230/30; A63B 2230/42; A63B 2230/50; G06N 20/00; G06N 20/30; G16H 20/30; G16H 50/20
USPC .................................................. 482/4, 9, 51
See application file for complete search history.

(56) References Cited

U.S. PATENT DOCUMENTS

| | | |
|---|---|---|
| 446,671 A | 2/1891 | Elliott |
| 610,157 A | 8/1898 | Campbell |
| 631,276 A | 8/1899 | Bulova |
| 823,712 A | 6/1906 | Uhlmann |
| 1,149,029 A | 8/1915 | Clark |
| 1,227,743 A | 5/1917 | Burgedorff |
| 1,784,230 A | 12/1930 | Freeman |
| 1,820,372 A | 8/1931 | Blomquist |
| 3,017,180 A | 1/1962 | Aronsohn |
| 3,081,645 A | 3/1963 | Bergfors |
| 3,100,640 A | 8/1963 | Weitzel |
| 3,137,014 A | 6/1964 | Meucci |
| 3,143,316 A | 8/1964 | Shapiro |
| 3,213,852 A | 10/1965 | Zent |
| 3,572,699 A | 3/1971 | Nies |
| 3,713,438 A | 1/1973 | Knutsen |
| 3,744,480 A | 7/1973 | Gause et al. |
| 3,888,136 A | 6/1975 | Lapeyre |
| 4,079,957 A | 3/1978 | Blease |
| 4,222,376 A | 9/1980 | Martin |
| 4,408,613 A | 10/1983 | Relyea |
| 4,436,097 A | 3/1984 | Cunningham |
| 4,446,753 A | 5/1984 | Nagano |
| 4,477,072 A | 10/1984 | DeCloux |
| 4,499,900 A | 2/1985 | Petrofsky et al. |
| 4,509,742 A | 4/1985 | Cones |
| 4,519,604 A | 5/1985 | Arzounian |
| 4,538,804 A | 9/1985 | Zibell |
| 4,572,501 A | 2/1986 | Durham et al. |
| 4,606,241 A | 8/1986 | Fredriksson |
| 4,611,807 A | 9/1986 | Castillo |
| 4,616,823 A | 10/1986 | Yang |
| 4,618,141 A | 10/1986 | Ashworth |
| 4,648,287 A | 3/1987 | Preskitt |
| 4,673,178 A | 6/1987 | Dwight |
| 4,822,032 A | 4/1989 | Whitmore et al. |
| 4,824,104 A | 4/1989 | Bloch |
| 4,824,132 A | 4/1989 | Moore |
| 4,850,245 A | 7/1989 | Feamster et al. |
| 4,858,942 A | 8/1989 | Rodriguez |
| 4,860,763 A | 8/1989 | Schminke |
| 4,869,497 A | 9/1989 | Stewart et al. |
| 4,915,374 A | 4/1990 | Watkins |
| 4,930,768 A | 6/1990 | Lapcevic |
| 4,932,650 A | 6/1990 | Bingham et al. |

(56) References Cited

U.S. PATENT DOCUMENTS

| | | |
|---|---|---|
| 4,961,570 A | 10/1990 | Chang |
| 5,137,501 A | 8/1992 | Mertesdorf |
| 5,139,255 A | 8/1992 | Sollami |
| 5,161,430 A | 11/1992 | Febey |
| 5,184,991 A | 2/1993 | Brangi |
| 5,202,794 A | 4/1993 | Schnee et al. |
| 5,230,672 A | 7/1993 | Brown et al. |
| 5,240,417 A | 8/1993 | Smithson et al. |
| 5,247,853 A | 9/1993 | Dalebout |
| 5,256,115 A | 10/1993 | Scholder et al. |
| 5,256,117 A | 10/1993 | Potts et al. |
| D342,299 S | 12/1993 | Birrell et al. |
| 5,282,748 A | 2/1994 | Little |
| 5,284,131 A | 2/1994 | Gray |
| 5,316,532 A | 5/1994 | Butler |
| 5,318,487 A | 6/1994 | Golen |
| 5,324,241 A | 6/1994 | Artigues et al. |
| 5,336,147 A | 8/1994 | Sweeney, III |
| 5,338,272 A | 8/1994 | Sweeney, III |
| 5,361,649 A | 11/1994 | Slocum, Jr. |
| D353,421 S | 12/1994 | Gallivan |
| 5,429,140 A | 7/1995 | Burdea et al. |
| 5,458,022 A | 10/1995 | Mattfeld et al. |
| 5,474,083 A | 12/1995 | Church |
| 5,487,713 A | 1/1996 | Butler |
| 5,566,589 A | 10/1996 | Buck |
| 5,580,338 A | 12/1996 | Scelta et al. |
| 5,676,349 A | 10/1997 | Wilson |
| 5,685,804 A | 11/1997 | Whan-Tong et al. |
| 5,738,636 A | 4/1998 | Saringer et al. |
| 5,857,943 A | 1/1999 | Murray |
| 5,860,941 A | 1/1999 | Saringer et al. |
| 5,950,813 A | 9/1999 | Hoskins et al. |
| 5,980,431 A | 11/1999 | Miller |
| 6,001,046 A | 12/1999 | Chang |
| 6,007,459 A | 12/1999 | Burgess |
| 6,013,007 A | 1/2000 | Root |
| 6,036,623 A | 3/2000 | Mitchell |
| 6,053,847 A | 4/2000 | Stearns et al. |
| 6,077,201 A | 6/2000 | Cheng |
| 6,102,834 A | 8/2000 | Chen |
| 6,110,130 A | 8/2000 | Kramer |
| 6,155,958 A | 12/2000 | Goldberg |
| 6,162,189 A | 12/2000 | Girone et al. |
| 6,182,029 B1 | 1/2001 | Friedman |
| D438,580 S | 3/2001 | Shaw |
| 6,253,638 B1 | 7/2001 | Bermudez |
| 6,267,735 B1 | 7/2001 | Blanchard et al. |
| 6,273,863 B1 | 8/2001 | Avni et al. |
| D450,100 S | 11/2001 | Hsu |
| D450,101 S | 11/2001 | Hsu |
| D451,972 S | 12/2001 | Easley |
| D452,285 S | 12/2001 | Easley |
| 6,336,891 B1 | 1/2002 | Fedrigon |
| 6,347,290 B1 | 2/2002 | Bartlett |
| D454,605 S | 3/2002 | Lee |
| 6,371,891 B1 | 4/2002 | Speas |
| D459,776 S | 7/2002 | Lee |
| 6,413,190 B1 | 7/2002 | Wood et al. |
| 6,430,436 B1 | 8/2002 | Richter |
| 6,436,058 B1 | 8/2002 | Krahner et al. |
| 6,450,923 B1 | 9/2002 | Vatti |
| 6,474,193 B1 | 11/2002 | Farney |
| 6,491,649 B1 | 12/2002 | Ombrellaro |
| 6,514,085 B2 | 2/2003 | Slattery et al. |
| 6,535,861 B1 | 3/2003 | OConnor et al. |
| 6,543,309 B2 | 4/2003 | Heim |
| D475,424 S | 6/2003 | Lee |
| 6,589,139 B1 | 7/2003 | Butterworth |
| 6,601,016 B1 | 7/2003 | Brown et al. |
| 6,602,191 B2 | 8/2003 | Quy |
| 6,613,000 B1 | 9/2003 | Reinkensmeyer et al. |
| 6,626,800 B1 | 9/2003 | Casler |
| 6,626,805 B1 | 9/2003 | Lightbody |
| 6,640,122 B2 | 10/2003 | Manoli |
| D482,416 S | 11/2003 | Yang |
| 6,640,662 B1 | 11/2003 | Baxter |
| 6,652,425 B1 | 11/2003 | Martin et al. |
| D484,931 S | 1/2004 | Tsai |
| 6,820,517 B1 | 11/2004 | Farney |
| 6,865,969 B2 | 3/2005 | Stevens |
| 6,890,312 B1 | 5/2005 | Priester et al. |
| 6,895,834 B1 | 5/2005 | Baatz |
| 6,902,513 B1 | 6/2005 | McClure |
| 6,902,515 B2 | 6/2005 | Howell et al. |
| 6,960,155 B2 | 11/2005 | Chien |
| 7,022,048 B1 | 4/2006 | Fernandez |
| 7,058,453 B2 | 6/2006 | Nelson et al. |
| 7,063,643 B2 | 6/2006 | Arai |
| 7,156,665 B1 | 1/2007 | OConnor et al. |
| 7,156,780 B1 | 1/2007 | Fuchs et al. |
| 7,169,085 B1 | 1/2007 | Killin et al. |
| 7,204,788 B2 | 4/2007 | Andrews |
| 7,209,886 B2 | 4/2007 | Kimmel |
| 7,226,394 B2 | 6/2007 | Johnson |
| RE39,904 E | 10/2007 | Lee |
| 7,406,003 B2 | 7/2008 | Burkhardt et al. |
| D575,836 S | 8/2008 | Hsiao |
| 7,491,154 B2 | 2/2009 | Yonehana |
| 7,507,188 B2 | 3/2009 | Nurre |
| 7,510,512 B1 | 3/2009 | Taggett |
| 7,594,879 B2 | 9/2009 | Johnson |
| 7,628,730 B1 | 12/2009 | Watterson |
| 7,713,176 B1 | 5/2010 | Farney |
| 7,778,851 B2 | 8/2010 | Schoenberg et al. |
| 7,789,800 B1 | 9/2010 | Watterson |
| 7,809,601 B2 | 10/2010 | Shaya et al. |
| 7,833,135 B2 | 11/2010 | Radow et al. |
| 7,837,472 B1 | 11/2010 | Elsmore |
| 7,955,219 B2 | 6/2011 | Birrell et al. |
| 7,969,315 B1 | 6/2011 | Ross et al. |
| 7,988,599 B2 | 8/2011 | Ainsworth et al. |
| 8,012,107 B2 | 9/2011 | Einav et al. |
| 8,021,270 B2 | 9/2011 | D'Eredita |
| 8,029,415 B2 | 10/2011 | Ashby |
| 8,038,578 B2 | 10/2011 | Olrik et al. |
| 8,079,937 B2 | 12/2011 | Bedell et al. |
| 8,113,991 B2 | 2/2012 | Kutliroff |
| 8,177,732 B2 | 5/2012 | Einav et al. |
| 8,287,434 B2 | 10/2012 | Zavadsky et al. |
| 8,298,123 B2 | 10/2012 | Hickman |
| 8,371,990 B2 | 2/2013 | Shea |
| 8,409,060 B2 | 4/2013 | Hsu |
| 8,419,593 B2 | 4/2013 | Ainsworth et al. |
| 8,444,534 B2 | 5/2013 | Mckee |
| 8,465,398 B2 | 6/2013 | Lee et al. |
| 8,506,458 B2 * | 8/2013 | Dugan .................. A63F 13/65 |
| | | 482/901 |
| 8,540,515 B2 | 9/2013 | Williams et al. |
| 8,540,516 B2 | 9/2013 | Williams et al. |
| 8,556,778 B1 | 10/2013 | Dugan |
| 8,607,465 B1 | 12/2013 | Edwards |
| 8,613,689 B2 | 12/2013 | Dyer et al. |
| 8,672,812 B2 | 3/2014 | Dugan |
| 8,751,264 B2 | 6/2014 | Beraja et al. |
| 8,784,273 B2 | 7/2014 | Dugan |
| 8,818,496 B2 | 8/2014 | Dziubinski et al. |
| 8,823,448 B1 | 9/2014 | Shen |
| 8,845,493 B2 | 9/2014 | Watterson et al. |
| 8,849,681 B2 | 9/2014 | Hargrove et al. |
| 8,864,628 B2 | 10/2014 | Boyette et al. |
| 8,893,287 B2 | 11/2014 | Gjonej et al. |
| 8,979,711 B2 | 3/2015 | Dugan |
| 9,028,368 B2 | 5/2015 | Ashby |
| 9,044,630 B1 | 6/2015 | Lampert et al. |
| 9,144,709 B2 * | 9/2015 | Reich ............... A63B 21/00178 |
| 9,167,281 B2 | 10/2015 | Petrov et al. |
| D744,050 S | 11/2015 | Colburn |
| 9,248,071 B1 | 2/2016 | Benda et al. |
| 9,272,185 B2 | 3/2016 | Dugan |
| 9,272,186 B2 * | 3/2016 | Reich ................ A63B 23/1209 |
| 9,283,434 B1 | 3/2016 | Wu |
| 9,308,417 B2 | 4/2016 | Grundy |
| 9,311,789 B1 | 4/2016 | Gwin |

(56) References Cited

U.S. PATENT DOCUMENTS

| | | |
|---|---|---|
| 9,312,907 B2 | 4/2016 | Auchinleck et al. |
| 9,367,668 B2 | 6/2016 | Flynt et al. |
| 9,409,054 B2 | 8/2016 | Dugan |
| 9,443,205 B2 | 9/2016 | Wall |
| 9,474,935 B2 | 10/2016 | Abbondanza et al. |
| 9,480,873 B2 | 11/2016 | Chuang |
| 9,481,428 B2 | 11/2016 | Gros et al. |
| 9,486,382 B1 | 11/2016 | Boss |
| 9,514,277 B2 | 12/2016 | Hassing et al. |
| 9,530,325 B2 | 12/2016 | Hall |
| 9,566,472 B2 | 2/2017 | Dugan |
| 9,579,056 B2 | 2/2017 | Rosenbek et al. |
| 9,629,558 B2 * | 4/2017 | Yuen .................. A61B 5/6838 |
| 9,640,057 B1 | 5/2017 | Ross |
| 9,707,147 B2 | 7/2017 | Levital et al. |
| 9,713,744 B2 | 7/2017 | Suzuki |
| D793,494 S | 8/2017 | Mansfield et al. |
| D794,142 S | 8/2017 | Zhou |
| 9,717,947 B2 | 8/2017 | Lin |
| 9,737,761 B1 | 8/2017 | Sivaraj |
| 9,782,621 B2 | 10/2017 | Chiang et al. |
| 9,802,076 B2 | 10/2017 | Murray et al. |
| 9,802,081 B2 | 10/2017 | Ridgel et al. |
| 9,813,239 B2 | 11/2017 | Chee et al. |
| 9,827,445 B2 | 11/2017 | Marcos et al. |
| 9,849,337 B2 | 12/2017 | Roman et al. |
| 9,868,028 B2 | 1/2018 | Shin |
| 9,872,087 B2 | 1/2018 | DelloStritto et al. |
| 9,872,637 B2 | 1/2018 | Kording et al. |
| 9,914,053 B2 | 3/2018 | Dugan |
| 9,919,198 B2 | 3/2018 | Romeo et al. |
| 9,937,382 B2 | 4/2018 | Dugan |
| 9,939,784 B1 | 4/2018 | Berardinelli |
| 9,977,587 B2 | 5/2018 | Mountain |
| 9,987,188 B1 | 6/2018 | Diao |
| 9,993,181 B2 | 6/2018 | Ross |
| 10,004,946 B2 | 6/2018 | Ross |
| D826,349 S | 8/2018 | Oblamski |
| 10,052,518 B2 | 8/2018 | Lagree |
| 10,055,550 B2 | 8/2018 | Goetz |
| 10,058,473 B2 | 8/2018 | Oshima et al. |
| 10,074,148 B2 | 9/2018 | Cashman et al. |
| 10,089,443 B2 | 10/2018 | Miller et al. |
| 10,111,643 B2 | 10/2018 | Shulhauser et al. |
| 10,130,311 B1 | 11/2018 | De Sapio et al. |
| 10,137,328 B2 | 11/2018 | Baudhuin |
| 10,143,395 B2 | 12/2018 | Chakravarthy et al. |
| 10,155,134 B2 | 12/2018 | Dugan |
| 10,159,872 B2 | 12/2018 | Sasaki et al. |
| 10,173,094 B2 | 1/2019 | Gomberg |
| 10,173,097 B2 * | 1/2019 | Gomberg ........... A63B 22/0605 |
| 10,198,928 B1 | 2/2019 | Ross et al. |
| 10,226,663 B2 | 3/2019 | Gomberg et al. |
| 10,231,664 B2 | 3/2019 | Ganesh |
| 10,244,990 B2 | 4/2019 | Hu et al. |
| 10,258,823 B2 | 4/2019 | Cole et al. |
| 10,278,883 B2 | 5/2019 | Walsh |
| 10,325,070 B2 | 6/2019 | Beale et al. |
| 10,327,697 B1 | 6/2019 | Stein et al. |
| 10,369,021 B2 | 8/2019 | Zoss et al. |
| 10,380,866 B1 | 8/2019 | Ross et al. |
| 10,424,033 B2 | 9/2019 | Romeo |
| 10,430,552 B2 | 10/2019 | Mihai |
| D866,957 S | 11/2019 | Ross et al. |
| 10,468,131 B2 | 11/2019 | Macoviak et al. |
| 10,475,323 B1 | 11/2019 | Ross |
| 10,475,537 B2 | 11/2019 | Purdie et al. |
| 10,492,977 B2 | 12/2019 | Kapure et al. |
| 10,507,358 B2 | 12/2019 | Kinnunen et al. |
| 10,532,000 B1 | 1/2020 | De Sapio |
| 10,532,785 B2 | 1/2020 | Stillman |
| 10,542,914 B2 | 1/2020 | Forth et al. |
| 10,546,467 B1 * | 1/2020 | Luciano, Jr. ........ G07F 17/3295 |
| 10,572,626 B2 | 2/2020 | Balram |
| 10,576,331 B2 | 3/2020 | Kuo |
| 10,625,114 B2 | 4/2020 | Ercanbrack |
| 10,660,534 B2 | 5/2020 | Lee et al. |
| 10,678,890 B2 | 6/2020 | Bitran et al. |
| 10,685,092 B2 | 6/2020 | Paparella et al. |
| 10,716,969 B2 | 7/2020 | Hoang |
| 10,777,200 B2 | 9/2020 | Will et al. |
| D899,605 S | 10/2020 | Ross et al. |
| 10,792,495 B2 | 10/2020 | Izvorski et al. |
| 10,867,695 B2 | 12/2020 | Neagle |
| 10,874,905 B2 | 12/2020 | Belson et al. |
| D907,143 S | 1/2021 | Ach et al. |
| 10,881,911 B2 | 1/2021 | Kwon et al. |
| 10,918,332 B2 | 2/2021 | Belson et al. |
| 10,931,643 B1 | 2/2021 | Neumann |
| 10,946,239 B2 | 3/2021 | Berry |
| 10,987,176 B2 | 4/2021 | Poltaretskyi et al. |
| 10,991,463 B2 | 4/2021 | Kutzko et al. |
| 11,000,735 B2 | 5/2021 | Orady et al. |
| 11,040,238 B2 | 6/2021 | Colburn |
| 11,045,709 B2 | 6/2021 | Putnam |
| 11,065,170 B2 | 7/2021 | Yang et al. |
| 11,065,527 B2 | 7/2021 | Putnam |
| 11,069,436 B2 | 7/2021 | Mason et al. |
| 11,071,597 B2 | 7/2021 | Posnack et al. |
| 11,075,000 B2 | 7/2021 | Mason et al. |
| 11,087,865 B2 | 8/2021 | Mason et al. |
| 11,093,904 B2 | 8/2021 | Humble |
| 11,101,028 B2 | 8/2021 | Mason et al. |
| 11,107,591 B1 | 8/2021 | Mason |
| 11,139,060 B2 | 10/2021 | Mason et al. |
| 11,161,011 B2 * | 11/2021 | Neumann .......... A63B 24/0062 |
| 11,179,596 B2 | 11/2021 | Karys |
| D939,096 S | 12/2021 | Lee |
| D939,644 S | 12/2021 | Ach et al. |
| D940,891 S | 1/2022 | Lee |
| 11,229,727 B2 | 1/2022 | Tatonetti |
| 11,270,795 B2 | 3/2022 | Mason et al. |
| 11,272,879 B2 | 3/2022 | Wiedenhoefer et al. |
| 11,278,766 B2 | 3/2022 | Lee |
| 11,282,599 B2 | 3/2022 | Mason et al. |
| 11,282,604 B2 | 3/2022 | Mason et al. |
| 11,282,608 B2 | 3/2022 | Mason et al. |
| 11,284,797 B2 | 3/2022 | Mason et al. |
| D948,639 S | 4/2022 | Ach et al. |
| 11,295,848 B2 | 4/2022 | Mason et al. |
| 11,309,085 B2 | 4/2022 | Mason et al. |
| 11,311,772 B1 | 4/2022 | Bowers et al. |
| 11,317,975 B2 | 5/2022 | Mason et al. |
| 11,325,005 B2 | 5/2022 | Mason et al. |
| 11,328,807 B2 | 5/2022 | Mason et al. |
| 11,337,648 B2 | 5/2022 | Mason |
| 11,348,683 B2 | 5/2022 | Guaneri et al. |
| 11,386,176 B2 | 7/2022 | Galitsky |
| 11,404,150 B2 | 8/2022 | Guaneri et al. |
| 11,410,768 B2 | 8/2022 | Mason et al. |
| 11,422,841 B2 | 8/2022 | Jeong |
| 11,433,276 B2 | 9/2022 | Bissonnette |
| 11,458,354 B2 | 10/2022 | Bissonnette et al. |
| 11,458,363 B2 | 10/2022 | Powers et al. |
| 11,495,355 B2 | 11/2022 | McNutt et al. |
| 11,508,258 B2 | 11/2022 | Nakashima et al. |
| 11,524,210 B2 | 12/2022 | Kim et al. |
| 11,527,326 B2 | 12/2022 | McNair et al. |
| 11,532,402 B2 | 12/2022 | Farley et al. |
| 11,534,654 B2 | 12/2022 | Silcock et al. |
| D976,339 S | 1/2023 | Li |
| 11,636,944 B2 | 4/2023 | Hanrahan et al. |
| 11,663,673 B2 | 5/2023 | Pyles |
| 11,701,548 B2 | 7/2023 | Posnack et al. |
| 2001/0011025 A1 | 8/2001 | Ohki |
| 2002/0072452 A1 | 6/2002 | Torkelson |
| 2002/0143279 A1 | 10/2002 | Porter et al. |
| 2002/0160883 A1 | 10/2002 | Dugan |
| 2002/0183599 A1 | 12/2002 | Castellanos |
| 2003/0013072 A1 | 1/2003 | Thomas |
| 2003/0036683 A1 | 2/2003 | Kehr et al. |
| 2003/0045402 A1 | 3/2003 | Pyle |
| 2003/0064860 A1 | 4/2003 | Yamashita |
| 2003/0064863 A1 | 4/2003 | Chen |

(56) References Cited

U.S. PATENT DOCUMENTS

| | | |
|---|---|---|
| 2003/0083596 A1 | 5/2003 | Kramer et al. |
| 2003/0092536 A1 | 5/2003 | Romanelli et al. |
| 2003/0093012 A1 | 5/2003 | Wiley et al. |
| 2003/0109814 A1 | 6/2003 | Rummerfield |
| 2003/0181832 A1 | 9/2003 | Carnahan et al. |
| 2004/0102931 A1 | 5/2004 | Ellis et al. |
| 2004/0106502 A1 | 6/2004 | Sher |
| 2004/0110602 A1 | 6/2004 | Feldman |
| 2004/0147969 A1 | 7/2004 | Mann et al. |
| 2004/0172093 A1 | 9/2004 | Rummerfield |
| 2004/0194572 A1 | 10/2004 | Kim |
| 2004/0204959 A1 | 10/2004 | Moreano et al. |
| 2004/0259693 A1 | 12/2004 | Chien |
| 2004/0263473 A1 | 12/2004 | Cho |
| 2005/0015118 A1 | 1/2005 | Davis et al. |
| 2005/0020411 A1 | 1/2005 | Andrews |
| 2005/0043153 A1 | 2/2005 | Krietzman |
| 2005/0049122 A1 | 3/2005 | Vallone et al. |
| 2005/0085346 A1 | 4/2005 | Johnson |
| 2005/0085353 A1* | 4/2005 | Johnson ............ A63B 22/0007 482/110 |
| 2005/0101463 A1 | 5/2005 | Chen |
| 2005/0274220 A1 | 12/2005 | Reboullet |
| 2006/0003871 A1 | 1/2006 | Houghton et al. |
| 2006/0046905 A1 | 3/2006 | Doody, Jr. et al. |
| 2006/0064329 A1 | 3/2006 | Abolfathi et al. |
| 2006/0079817 A1 | 4/2006 | Dewald |
| 2006/0122039 A1 | 6/2006 | Lee et al. |
| 2006/0135325 A1 | 6/2006 | Holness |
| 2006/0199700 A1 | 9/2006 | LaStayo et al. |
| 2006/0229164 A1 | 10/2006 | Einav |
| 2006/0247095 A1 | 11/2006 | Rummerfield |
| 2006/0252607 A1 | 11/2006 | Holloway |
| 2006/0258520 A1 | 11/2006 | Bowser |
| 2007/0021277 A1 | 1/2007 | Kuo |
| 2007/0042868 A1 | 2/2007 | Fisher et al. |
| 2007/0093360 A1 | 4/2007 | Neff |
| 2007/0099766 A1 | 5/2007 | Pyles |
| 2007/0118389 A1 | 5/2007 | Shipon |
| 2007/0137307 A1 | 6/2007 | Gruben et al. |
| 2007/0149364 A1* | 6/2007 | Blau .................. A63B 24/00 482/8 |
| 2007/0173392 A1 | 7/2007 | Stanford |
| 2007/0194939 A1 | 8/2007 | Alvarez et al. |
| 2007/0243980 A1 | 10/2007 | Bowser |
| 2007/0271065 A1 | 11/2007 | Gupta et al. |
| 2007/0287597 A1 | 12/2007 | Cameron |
| 2008/0021834 A1 | 1/2008 | Holla et al. |
| 2008/0082356 A1 | 4/2008 | Friedlander et al. |
| 2008/0119333 A1 | 5/2008 | Bowser |
| 2008/0139975 A1 | 6/2008 | Einav |
| 2008/0153592 A1 | 6/2008 | James-Herbert |
| 2008/0161166 A1 | 7/2008 | Lo |
| 2008/0161733 A1 | 7/2008 | Einav et al. |
| 2008/0281633 A1 | 11/2008 | Burdea et al. |
| 2008/0300914 A1 | 12/2008 | Karkanias et al. |
| 2008/0318738 A1 | 12/2008 | Chen |
| 2009/0011907 A1 | 1/2009 | Radow et al. |
| 2009/0023556 A1 | 1/2009 | Daly et al. |
| 2009/0058635 A1 | 3/2009 | LaLonde et al. |
| 2009/0070138 A1 | 3/2009 | Langheier et al. |
| 2009/0211395 A1 | 8/2009 | Mule |
| 2009/0221407 A1 | 9/2009 | Hauk |
| 2009/0239714 A1 | 9/2009 | Sellers |
| 2009/0270227 A1 | 10/2009 | Ashby |
| 2009/0287503 A1 | 11/2009 | Angell et al. |
| 2009/0299766 A1 | 12/2009 | Friedlander et al. |
| 2010/0022354 A1* | 1/2010 | Fisher ................ A63B 71/0622 482/8 |
| 2010/0029445 A1 | 2/2010 | Lee |
| 2010/0035726 A1* | 2/2010 | Fisher ................ A63B 24/0084 482/8 |
| 2010/0035729 A1 | 2/2010 | Pandozy |
| 2010/0048358 A1 | 2/2010 | Tchao et al. |
| 2010/0076786 A1 | 3/2010 | Dalton et al. |
| 2010/0121160 A1 | 5/2010 | Stark et al. |
| 2010/0152629 A1 | 6/2010 | Haas |
| 2010/0173747 A1 | 7/2010 | Chen et al. |
| 2010/0216168 A1 | 8/2010 | Heinzman et al. |
| 2010/0234184 A1 | 9/2010 | Le Page et al. |
| 2010/0248899 A1 | 9/2010 | Bedell et al. |
| 2010/0248905 A1 | 9/2010 | Lu |
| 2010/0261585 A1 | 10/2010 | Hauk |
| 2010/0268304 A1 | 10/2010 | Matos |
| 2010/0298102 A1 | 11/2010 | Bosecker et al. |
| 2010/0331144 A1 | 12/2010 | Rindfleisch |
| 2011/0010188 A1 | 1/2011 | Yoshikawa et al. |
| 2011/0047108 A1 | 2/2011 | Chakrabarty et al. |
| 2011/0071003 A1 | 3/2011 | Watterson |
| 2011/0118084 A1 | 5/2011 | Tsai et al. |
| 2011/0118086 A1* | 5/2011 | Radow ............ A63B 21/00196 482/5 |
| 2011/0119212 A1 | 5/2011 | De Bruin et al. |
| 2011/0143898 A1 | 6/2011 | Trees |
| 2011/0165995 A1 | 7/2011 | Paulus |
| 2011/0172058 A1 | 7/2011 | Deaconu |
| 2011/0172059 A1 | 7/2011 | Watterson et al. |
| 2011/0195819 A1 | 8/2011 | Shaw et al. |
| 2011/0218814 A1 | 9/2011 | Coats |
| 2011/0256983 A1 | 10/2011 | Malack |
| 2011/0275483 A1 | 11/2011 | Dugan |
| 2011/0275486 A1 | 11/2011 | Hsu |
| 2011/0306846 A1 | 12/2011 | Osorio |
| 2012/0004932 A1 | 1/2012 | Sorkey et al. |
| 2012/0040799 A1 | 2/2012 | Jaquish |
| 2012/0041771 A1 | 2/2012 | Cosentino et al. |
| 2012/0065987 A1 | 3/2012 | Farooq et al. |
| 2012/0116258 A1 | 5/2012 | Lee |
| 2012/0167709 A1 | 7/2012 | Chen et al. |
| 2012/0183939 A1 | 7/2012 | Aragones et al. |
| 2012/0190502 A1 | 7/2012 | Paulus et al. |
| 2012/0220427 A1 | 8/2012 | Ashby |
| 2012/0232438 A1 | 9/2012 | Cataldi et al. |
| 2012/0259648 A1 | 10/2012 | Mallon et al. |
| 2012/0295240 A1 | 11/2012 | Walker et al. |
| 2012/0296455 A1 | 11/2012 | Ohnemus et al. |
| 2012/0310667 A1 | 12/2012 | Altman et al. |
| 2012/0323346 A1 | 12/2012 | Ashby |
| 2013/0029808 A1 | 1/2013 | Kuo |
| 2013/0029809 A1 | 1/2013 | Spevak |
| 2013/0102440 A1 | 4/2013 | Hutchins et al. |
| 2013/0116094 A1 | 5/2013 | Chen |
| 2013/0123071 A1 | 5/2013 | Rhea |
| 2013/0123667 A1 | 5/2013 | Komatireddy et al. |
| 2013/0137550 A1* | 5/2013 | Skinner ............ A63B 23/03541 482/8 |
| 2013/0178334 A1 | 7/2013 | Brammer |
| 2013/0211281 A1 | 8/2013 | Ross et al. |
| 2013/0253943 A1 | 9/2013 | Lee et al. |
| 2013/0274069 A1 | 10/2013 | Watterson et al. |
| 2013/0282157 A1 | 10/2013 | Shin et al. |
| 2013/0296987 A1 | 11/2013 | Rogers et al. |
| 2013/0318027 A1 | 11/2013 | Almogy et al. |
| 2013/0332616 A1 | 12/2013 | Landwehr |
| 2013/0345025 A1 | 12/2013 | van der Merwe |
| 2013/0345604 A1 | 12/2013 | Nakamura |
| 2014/0006042 A1 | 1/2014 | Keefe et al. |
| 2014/0011640 A1 | 1/2014 | Dugan |
| 2014/0031173 A1 | 1/2014 | Huang |
| 2014/0089836 A1 | 3/2014 | Damani et al. |
| 2014/0113768 A1 | 4/2014 | Lin et al. |
| 2014/0113776 A1 | 4/2014 | Jaguan |
| 2014/0155129 A1 | 6/2014 | Dugan |
| 2014/0172442 A1 | 6/2014 | Broderick |
| 2014/0172460 A1 | 6/2014 | Kohli |
| 2014/0087341 A1 | 7/2014 | Hall |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0195103 A1 | 7/2014 | Nassef |
| 2014/0207264 A1 | 7/2014 | Quy |
| 2014/0207486 A1 | 7/2014 | Carty et al. |
| 2014/0228649 A1 | 8/2014 | Rayner et al. |
| 2014/0243160 A1 | 8/2014 | Lim |

(56) References Cited

U.S. PATENT DOCUMENTS

| | | | |
|---|---|---|---|
| 2014/0246499 A1* | 9/2014 | Proud | H04Q 9/00 |
| | | | 235/492 |
| 2014/0256511 A1 | 9/2014 | Smith | |
| 2014/0257535 A1 | 9/2014 | Morris et al. | |
| 2014/0257837 A1 | 9/2014 | Walker et al. | |
| 2014/0274564 A1* | 9/2014 | Greenbaum | A63B 21/225 |
| | | | 482/5 |
| 2014/0274565 A1* | 9/2014 | Boyette | A63B 22/0694 |
| | | | 482/6 |
| 2014/0274622 A1 | 9/2014 | Leonhard | |
| 2014/0309083 A1 | 10/2014 | Dugan | |
| 2014/0322686 A1 | 10/2014 | Kang | |
| 2014/0330186 A1 | 11/2014 | Hyde | |
| 2015/0025816 A1 | 1/2015 | Ross | |
| 2015/0045700 A1 | 2/2015 | Cavanagh et al. | |
| 2015/0065303 A1 | 3/2015 | Born | |
| 2015/0065305 A1 | 3/2015 | Dalton | |
| 2015/0088544 A1 | 3/2015 | Goldberg | |
| 2015/0094192 A1 | 4/2015 | Skwortsow et al. | |
| 2015/0099458 A1 | 4/2015 | Weisner et al. | |
| 2015/0099952 A1 | 4/2015 | Lain et al. | |
| 2015/0112230 A1 | 4/2015 | Iglesias | |
| 2015/0130830 A1 | 5/2015 | Nagasaki | |
| 2015/0141200 A1 | 5/2015 | Murray et al. | |
| 2015/0149217 A1 | 5/2015 | Kaburagi | |
| 2015/0151162 A1 | 6/2015 | Dugan | |
| 2015/0158549 A1 | 6/2015 | Gros et al. | |
| 2015/0161331 A1 | 6/2015 | Teynik | |
| 2015/0165263 A1 | 6/2015 | Golen | |
| 2015/0238817 A1 | 8/2015 | Watterson | |
| 2015/0257679 A1 | 9/2015 | Ross | |
| 2015/0258365 A1 | 9/2015 | Neill et al. | |
| 2015/0265209 A1 | 9/2015 | Zhang | |
| 2015/0290061 A1* | 10/2015 | Stafford | A63B 22/0089 |
| | | | 5/600 |
| 2015/0328496 A1 | 11/2015 | Eder | |
| 2015/0339442 A1 | 11/2015 | Oleynik | |
| 2015/0341812 A1 | 11/2015 | Dion et al. | |
| 2015/0351664 A1 | 12/2015 | Ross | |
| 2015/0351665 A1 | 12/2015 | Ross | |
| 2015/0360069 A1 | 12/2015 | Marti et al. | |
| 2015/0379232 A1 | 12/2015 | Mainwaring et al. | |
| 2015/0379430 A1 | 12/2015 | Dirac et al. | |
| 2016/0007885 A1 | 1/2016 | Basta et al. | |
| 2016/0009169 A1* | 1/2016 | Biderman | A61B 5/0002 |
| | | | 701/22 |
| 2016/0023081 A1 | 1/2016 | Popa-Simil et al. | |
| 2016/0045170 A1 | 2/2016 | Migita | |
| 2016/0082772 A1* | 3/2016 | Biderman | B60K 7/00 |
| | | | 301/6.5 |
| 2016/0096073 A1 | 4/2016 | Rahman et al. | |
| 2016/0117471 A1 | 4/2016 | Belt et al. | |
| 2016/0136483 A1 | 5/2016 | Reich | |
| 2016/0143593 A1 | 5/2016 | Fu et al. | |
| 2016/0151670 A1 | 6/2016 | Dugan | |
| 2016/0166833 A1 | 6/2016 | Bum | |
| 2016/0166881 A1 | 6/2016 | Ridgel et al. | |
| 2016/0184634 A1 | 6/2016 | Yanev | |
| 2016/0193306 A1 | 7/2016 | Rabovsky et al. | |
| 2016/0220866 A1 | 8/2016 | Feichtinger et al. | |
| 2016/0220867 A1 | 8/2016 | Flaherty | |
| 2016/0271438 A1 | 9/2016 | Weisz | |
| 2016/0271452 A1 | 9/2016 | Lagree | |
| 2016/0275259 A1 | 9/2016 | Nolan et al. | |
| 2016/0287166 A1 | 10/2016 | Tran | |
| 2016/0302721 A1 | 10/2016 | Wiedenhoefer et al. | |
| 2016/0317860 A1 | 11/2016 | Baudhuin et al. | |
| 2016/0317869 A1 | 11/2016 | Dugan | |
| 2016/0322078 A1* | 11/2016 | Bose | G01P 13/00 |
| 2016/0325140 A1 | 11/2016 | Wu | |
| 2016/0332028 A1 | 11/2016 | Melnik | |
| 2017/0003311 A1 | 1/2017 | Lay | |
| 2017/0004260 A1 | 1/2017 | Moturu et al. | |
| 2017/0014671 A1 | 1/2017 | Burns, Sr. | |
| 2017/0021827 A1 | 1/2017 | Seagraves | |
| 2017/0033375 A1 | 2/2017 | Ohmori et al. | |
| 2017/0036055 A1 | 2/2017 | Fleming | |
| 2017/0042467 A1 | 2/2017 | Herr et al. | |
| 2017/0046488 A1 | 2/2017 | Pereira | |
| 2017/0065849 A1 | 3/2017 | Konishi | |
| 2017/0065851 A1 | 3/2017 | Deluca et al. | |
| 2017/0065873 A1 | 3/2017 | Hall | |
| 2017/0080320 A1 | 3/2017 | Smith | |
| 2017/0095670 A1* | 4/2017 | Ghaffari | A61N 1/36139 |
| 2017/0095692 A1* | 4/2017 | Chang | A61B 5/6804 |
| 2017/0095693 A1* | 4/2017 | Chang | G16H 40/40 |
| 2017/0100628 A1 | 4/2017 | Wilt | |
| 2017/0100637 A1 | 4/2017 | Princen et al. | |
| 2017/0106242 A1 | 4/2017 | Dugan | |
| 2017/0113092 A1* | 4/2017 | Johnson | A63B 22/0015 |
| 2017/0128769 A1 | 5/2017 | Long et al. | |
| 2017/0132947 A1 | 5/2017 | Maeda et al. | |
| 2017/0136296 A1 | 5/2017 | Barrera et al. | |
| 2017/0143261 A1 | 5/2017 | Wiedenhoefer et al. | |
| 2017/0147752 A1 | 5/2017 | Toru | |
| 2017/0147789 A1 | 5/2017 | Wiedenhoefer et al. | |
| 2017/0148297 A1 | 5/2017 | Ross | |
| 2017/0168555 A1 | 6/2017 | Munoz et al. | |
| 2017/0172466 A1 | 6/2017 | Eriksson | |
| 2017/0181698 A1 | 6/2017 | Wiedenhoefer et al. | |
| 2017/0190052 A1 | 7/2017 | Jaekel et al. | |
| 2017/0209766 A1 | 7/2017 | Riley et al. | |
| 2017/0216670 A1 | 8/2017 | Kuroda et al. | |
| 2017/0235882 A1 | 8/2017 | Orlov et al. | |
| 2017/0235906 A1 | 8/2017 | Dorris et al. | |
| 2017/0243028 A1 | 8/2017 | LaFever et al. | |
| 2017/0262604 A1 | 9/2017 | Francois | |
| 2017/0265800 A1 | 9/2017 | Auchinleck et al. | |
| 2017/0266501 A1 | 9/2017 | Sanders et al. | |
| 2017/0278209 A1 | 9/2017 | Olsen et al. | |
| 2017/0282015 A1* | 10/2017 | Wicks | A63B 24/0075 |
| 2017/0283508 A1 | 10/2017 | Demopulos et al. | |
| 2017/0300654 A1 | 10/2017 | Stein et al. | |
| 2017/0304680 A1 | 10/2017 | Schmidt | |
| 2017/0312614 A1* | 11/2017 | Tran | G06F 3/00 |
| 2017/0323481 A1 | 11/2017 | Tran et al. | |
| 2017/0329917 A1 | 11/2017 | McRaith et al. | |
| 2017/0329933 A1 | 11/2017 | Brust | |
| 2017/0333755 A1 | 11/2017 | Rider | |
| 2017/0337033 A1 | 11/2017 | Duyan et al. | |
| 2017/0337334 A1 | 11/2017 | Stanczak | |
| 2017/0344726 A1 | 11/2017 | Duffy et al. | |
| 2017/0347923 A1 | 12/2017 | Roh | |
| 2017/0360586 A1 | 12/2017 | Dempers et al. | |
| 2017/0361165 A1 | 12/2017 | Miller | |
| 2017/0368413 A1* | 12/2017 | Shavit | A63B 24/0075 |
| 2018/0001181 A1 | 1/2018 | Prellwitz et al. | |
| 2018/0017806 A1 | 1/2018 | Wang et al. | |
| 2018/0034920 A1* | 2/2018 | Gopalan | G06N 3/006 |
| 2018/0034922 A1* | 2/2018 | Gopalan | G06N 20/00 |
| 2018/0036593 A1 | 2/2018 | Ridgel et al. | |
| 2018/0052962 A1 | 2/2018 | Van Der Koijk et al. | |
| 2018/0056104 A1* | 3/2018 | Cromie | A63B 21/4007 |
| 2018/0060494 A1 | 3/2018 | Dias et al. | |
| 2018/0064991 A1 | 3/2018 | Yanev | |
| 2018/0071565 A1 | 3/2018 | Gomberg et al. | |
| 2018/0071566 A1 | 3/2018 | Gomberg et al. | |
| 2018/0071569 A1 | 3/2018 | Gomberg et al. | |
| 2018/0071570 A1 | 3/2018 | Gomberg et al. | |
| 2018/0071571 A1 | 3/2018 | Gomberg et al. | |
| 2018/0071572 A1 | 3/2018 | Gomberg et al. | |
| 2018/0075205 A1 | 3/2018 | Moturu et al. | |
| 2018/0078843 A1 | 3/2018 | Tran et al. | |
| 2018/0085615 A1 | 3/2018 | Astolfi et al. | |
| 2018/0096111 A1 | 4/2018 | Wells et al. | |
| 2018/0102190 A1 | 4/2018 | Hogue et al. | |
| 2018/0111034 A1 | 4/2018 | Watterson | |
| 2018/0116741 A1 | 5/2018 | Garcia Kilroy et al. | |
| 2018/0140927 A1 | 5/2018 | Kito | |
| 2018/0154240 A1 | 6/2018 | Hall | |
| 2018/0177612 A1 | 6/2018 | Trabish et al. | |
| 2018/0177664 A1 | 6/2018 | Choi et al. | |
| 2018/0178059 A1* | 6/2018 | Kim | A63B 24/0075 |

(56) References Cited

U.S. PATENT DOCUMENTS

| | | |
|---|---|---|
| 2018/0178061 A1 | 6/2018 | O'larte et al. |
| 2018/0199855 A1 | 7/2018 | Odame et al. |
| 2018/0200577 A1 | 7/2018 | Dugan |
| 2018/0220935 A1 | 8/2018 | Tadano et al. |
| 2018/0228682 A1 | 8/2018 | Bayerlein et al. |
| 2018/0236307 A1 | 8/2018 | Hyde et al. |
| 2018/0240552 A1 | 8/2018 | Tuyl et al. |
| 2018/0253991 A1* | 9/2018 | Tang .................... G16H 50/30 |
| 2018/0256079 A1 | 9/2018 | Yang et al. |
| 2018/0263530 A1 | 9/2018 | Jung |
| 2018/0263535 A1 | 9/2018 | Cramer |
| 2018/0263552 A1 | 9/2018 | Graman et al. |
| 2018/0264312 A1 | 9/2018 | Pompile et al. |
| 2018/0271432 A1 | 9/2018 | Auchinleck et al. |
| 2018/0272184 A1 | 9/2018 | Vassilaros et al. |
| 2018/0280784 A1 | 10/2018 | Romeo et al. |
| 2018/0296143 A1 | 10/2018 | Anderson et al. |
| 2018/0296157 A1 | 10/2018 | Bleich et al. |
| 2018/0326243 A1 | 11/2018 | Badi et al. |
| 2018/0330058 A1 | 11/2018 | Bates |
| 2018/0330810 A1 | 11/2018 | Gamarnik |
| 2018/0330824 A1 | 11/2018 | Athey et al. |
| 2018/0290017 A1 | 12/2018 | Fung |
| 2018/0353812 A1 | 12/2018 | Lannon et al. |
| 2018/0360340 A1 | 12/2018 | Rehse et al. |
| 2018/0373844 A1 | 12/2018 | Ferrandez-Escamez et al. |
| 2019/0009135 A1 | 1/2019 | Wu |
| 2019/0019163 A1 | 1/2019 | Batey et al. |
| 2019/0019573 A1 | 1/2019 | Lake et al. |
| 2019/0019578 A1 | 1/2019 | Vaccaro |
| 2019/0030415 A1* | 1/2019 | Volpe, Jr. .............. A63B 22/02 |
| 2019/0031284 A1 | 1/2019 | Fuchs |
| 2019/0046794 A1 | 2/2019 | Goodall et al. |
| 2019/0060699 A1 | 2/2019 | Frederick et al. |
| 2019/0060708 A1* | 2/2019 | Fung ...................... G06F 3/012 |
| 2019/0065970 A1 | 2/2019 | Bonutti et al. |
| 2019/0066832 A1 | 2/2019 | Kang et al. |
| 2019/0076701 A1 | 3/2019 | Dugan |
| 2019/0080802 A1 | 3/2019 | Ziobro et al. |
| 2019/0088356 A1 | 3/2019 | Oliver et al. |
| 2019/0090744 A1 | 3/2019 | Mahfouz |
| 2019/0091506 A1 | 3/2019 | Gatelli et al. |
| 2019/0111299 A1 | 4/2019 | Radcliffe et al. |
| 2019/0115097 A1 | 4/2019 | Macoviak et al. |
| 2019/0118038 A1 | 4/2019 | Tana et al. |
| 2019/0126099 A1* | 5/2019 | Hoang .................. A63F 13/335 |
| 2019/0132948 A1* | 5/2019 | Longinotti-Buitoni ...................... A61B 5/743 |
| 2019/0134454 A1* | 5/2019 | Mahoney ............... A63F 13/24 |
| 2019/0137988 A1* | 5/2019 | Cella ................ G06V 10/7784 |
| 2019/0167988 A1 | 6/2019 | Shahriari et al. |
| 2019/0172587 A1 | 6/2019 | Park et al. |
| 2019/0175988 A1 | 6/2019 | Volterrani et al. |
| 2019/0183715 A1 | 6/2019 | Kapure et al. |
| 2019/0192912 A1 | 6/2019 | Radow |
| 2019/0200920 A1* | 7/2019 | Tien ..................... A61B 5/0205 |
| 2019/0209891 A1* | 7/2019 | Fung .................... G06F 3/0338 |
| 2019/0223797 A1 | 7/2019 | Tran |
| 2019/0228856 A1 | 7/2019 | Leifer |
| 2019/0232108 A1* | 8/2019 | Kovach .................. G16H 40/63 |
| 2019/0240103 A1 | 8/2019 | Hepler et al. |
| 2019/0240541 A1 | 8/2019 | Denton et al. |
| 2019/0244540 A1* | 8/2019 | Errante ................. G09B 5/065 |
| 2019/0247718 A1 | 8/2019 | Blevins |
| 2019/0262655 A1 | 8/2019 | Lentine |
| 2019/0269343 A1 | 9/2019 | Ramos Murguialday et al. |
| 2019/0274523 A1 | 9/2019 | Bates et al. |
| 2019/0275368 A1 | 9/2019 | Maroldi |
| 2019/0282857 A1 | 9/2019 | Hapola |
| 2019/0290965 A1* | 9/2019 | Oren ...................... G16H 20/30 |
| 2019/0304584 A1* | 10/2019 | Savolainen .......... A63B 24/0087 |
| 2019/0307983 A1 | 10/2019 | Goldman |
| 2019/0314681 A1 | 10/2019 | Yang |
| 2019/0336815 A1 | 11/2019 | Hsu |
| 2019/0344123 A1 | 11/2019 | Rubin et al. |
| 2019/0354632 A1 | 11/2019 | Mital et al. |
| 2019/0362242 A1 | 11/2019 | Pillai et al. |
| 2019/0366146 A1 | 12/2019 | Tong et al. |
| 2019/0388728 A1* | 12/2019 | Wang .................. A63B 24/0006 |
| 2020/0005928 A1 | 1/2020 | Daniel |
| 2020/0006639 A1 | 1/2020 | Wu et al. |
| 2020/0038703 A1 | 2/2020 | Cleary et al. |
| 2020/0051446 A1 | 2/2020 | Rubinstein et al. |
| 2020/0066390 A1 | 2/2020 | Svendrys et al. |
| 2020/0085300 A1 | 3/2020 | Kwatra et al. |
| 2020/0086163 A1 | 3/2020 | Karys |
| 2020/0093418 A1 | 3/2020 | Kluger et al. |
| 2020/0114207 A1 | 4/2020 | Weldemariam |
| 2020/0143922 A1 | 5/2020 | Chekroud et al. |
| 2020/0151595 A1 | 5/2020 | Jayalath et al. |
| 2020/0151646 A1* | 5/2020 | De La Fuente Sanchez ............... G06Q 10/06398 |
| 2020/0152339 A1 | 5/2020 | Pulitzer et al. |
| 2020/0160198 A1 | 5/2020 | Reeves et al. |
| 2020/0170876 A1 | 6/2020 | Kapure et al. |
| 2020/0176098 A1 | 6/2020 | Lucas et al. |
| 2020/0197744 A1 | 6/2020 | Schweighofer |
| 2020/0221975 A1 | 7/2020 | Basta et al. |
| 2020/0237291 A1 | 7/2020 | Raja |
| 2020/0267487 A1* | 8/2020 | Siva .................... H04R 1/1091 |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289878 A1 | 9/2020 | Arn et al. |
| 2020/0289879 A1 | 9/2020 | Hacking et al. |
| 2020/0289880 A1 | 9/2020 | Hacking et al. |
| 2020/0289881 A1* | 9/2020 | Hacking .......... A63B 21/00072 |
| 2020/0289889 A1 | 9/2020 | Hacking et al. |
| 2020/0293712 A1 | 9/2020 | Potts et al. |
| 2020/0303063 A1 | 9/2020 | Sharma et al. |
| 2020/0334972 A1* | 10/2020 | Gopalakrishnan ..... G16H 80/00 |
| 2020/0357299 A1 | 11/2020 | Patel et al. |
| 2020/0365256 A1 | 11/2020 | Hayashitani et al. |
| 2020/0395112 A1 | 12/2020 | Ronner |
| 2020/0401224 A1 | 12/2020 | Cotton |
| 2020/0410893 A1 | 12/2020 | Ridington |
| 2020/0411162 A1 | 12/2020 | Lien et al. |
| 2021/0005224 A1 | 1/2021 | Rothschild et al. |
| 2021/0005319 A1 | 1/2021 | Otsuki et al. |
| 2021/0035674 A1 | 2/2021 | Volosin et al. |
| 2021/0046373 A1 | 2/2021 | Smith |
| 2021/0074178 A1 | 3/2021 | Ilan et al. |
| 2021/0076981 A1 | 3/2021 | Hacking et al. |
| 2021/0077860 A1 | 3/2021 | Posnack et al. |
| 2021/0098129 A1 | 4/2021 | Neumann |
| 2021/0100628 A1 | 4/2021 | Posnack et al. |
| 2021/0101051 A1 | 4/2021 | Posnack et al. |
| 2021/0113877 A1 | 4/2021 | Chin |
| 2021/0113890 A1 | 4/2021 | Posnack et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134412 A1 | 5/2021 | Guaneri et al. |
| 2021/0134416 A1 | 5/2021 | Mason et al. |
| 2021/0134419 A1 | 5/2021 | Mason et al. |
| 2021/0134425 A1 | 5/2021 | Mason et al. |
| 2021/0134426 A1 | 5/2021 | Mason et al. |
| 2021/0134427 A1 | 5/2021 | Mason et al. |
| 2021/0134428 A1 | 5/2021 | Mason et al. |
| 2021/0134429 A1 | 5/2021 | Mason et al. |
| 2021/0134430 A1 | 5/2021 | Mason et al. |
| 2021/0134432 A1 | 5/2021 | Mason et al. |
| 2021/0134456 A1 | 5/2021 | Posnack et al. |
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |
| 2021/0142893 A1 | 5/2021 | Guaneri et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0186419 A1 | 6/2021 | Van Ee et al. |

(56) References Cited

U.S. PATENT DOCUMENTS

| | | |
|---|---|---|
| 2021/0202090 A1 | 7/2021 | ODonovan et al. |
| 2021/0202103 A1 | 7/2021 | Bostic et al. |
| 2021/0244998 A1 | 8/2021 | Hacking et al. |
| 2021/0245003 A1 | 8/2021 | Turner |
| 2021/0251562 A1 | 8/2021 | Jain |
| 2021/0268335 A1 | 9/2021 | Mizukura |
| 2021/0272677 A1 | 9/2021 | Barbee |
| 2021/0343384 A1 | 11/2021 | Purushothaman et al. |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |
| 2021/0350914 A1 | 11/2021 | Guaneri et al. |
| 2021/0350926 A1 | 11/2021 | Mason et al. |
| 2021/0361514 A1 | 11/2021 | Choi et al. |
| 2021/0366587 A1 | 11/2021 | Mason et al. |
| 2021/0383909 A1 | 12/2021 | Mason et al. |
| 2021/0391091 A1 | 12/2021 | Mason |
| 2021/0398668 A1 | 12/2021 | Chock et al. |
| 2021/0407670 A1 | 12/2021 | Mason et al. |
| 2021/0407681 A1 | 12/2021 | Mason et al. |
| 2022/0000556 A1 | 1/2022 | Casey et al. |
| 2022/0001232 A1 | 1/2022 | DeForest |
| 2022/0016480 A1 | 1/2022 | Bissonnette et al. |
| 2022/0016485 A1 | 1/2022 | Bissonnette et al. |
| 2022/0020469 A1 | 1/2022 | Tanner |
| 2022/0044806 A1 | 2/2022 | Sanders et al. |
| 2022/0047921 A1 | 2/2022 | Bissonnette et al. |
| 2022/0072362 A1 | 3/2022 | Hopson |
| 2022/0079690 A1 | 3/2022 | Mason et al. |
| 2022/0080256 A1 | 3/2022 | Arn et al. |
| 2022/0105384 A1 | 4/2022 | Hacking et al. |
| 2022/0105385 A1 | 4/2022 | Hacking et al. |
| 2022/0105390 A1 | 4/2022 | Yuasa |
| 2022/0115133 A1 | 4/2022 | Mason et al. |
| 2022/0118218 A1 | 4/2022 | Bense et al. |
| 2022/0126169 A1 | 4/2022 | Mason |
| 2022/0133576 A1 | 5/2022 | Choi et al. |
| 2022/0148725 A1 | 5/2022 | Mason et al. |
| 2022/0158916 A1 | 5/2022 | Mason et al. |
| 2022/0176039 A1 | 6/2022 | Lintereur et al. |
| 2022/0181004 A1 | 6/2022 | Zilca et al. |
| 2022/0183557 A1 | 6/2022 | Mason et al. |
| 2022/0193491 A1 | 6/2022 | Mason et al. |
| 2022/0230729 A1 | 7/2022 | Mason et al. |
| 2022/0238222 A1 | 7/2022 | Neuberg |
| 2022/0238223 A1 | 7/2022 | Mason et al. |
| 2022/0262483 A1 | 8/2022 | Rosenberg et al. |
| 2022/0262504 A1 | 8/2022 | Bratty et al. |
| 2022/0266094 A1 | 8/2022 | Mason et al. |
| 2022/0270738 A1 | 8/2022 | Mason et al. |
| 2022/0273985 A1 | 9/2022 | Jeong et al. |
| 2022/0273986 A1 | 9/2022 | Mason |
| 2022/0288460 A1 | 9/2022 | Mason |
| 2022/0288461 A1 | 9/2022 | Ashley et al. |
| 2022/0288462 A1 | 9/2022 | Ashley et al. |
| 2022/0293257 A1 | 9/2022 | Guaneri et al. |
| 2022/0300787 A1 | 9/2022 | Wall et al. |
| 2022/0304881 A1 | 9/2022 | Choi et al. |
| 2022/0304882 A1 | 9/2022 | Choi |
| 2022/0305328 A1 | 9/2022 | Choi et al. |
| 2022/0314072 A1 | 10/2022 | Bissonnette et al. |
| 2022/0314073 A1 | 10/2022 | Bissonnette et al. |
| 2022/0314074 A1 | 10/2022 | Bissonnette et al. |
| 2022/0314075 A1 | 10/2022 | Mason et al. |
| 2022/0314077 A1 | 10/2022 | Bissonnette et al. |
| 2022/0323826 A1 | 10/2022 | Khurana |
| 2022/0327714 A1 | 10/2022 | Cook et al. |
| 2022/0327807 A1 | 10/2022 | Cook et al. |
| 2022/0328181 A1 | 10/2022 | Mason et al. |
| 2022/0330823 A1 | 10/2022 | Janssen |
| 2022/0331663 A1 | 10/2022 | Mason |
| 2022/0338761 A1 | 10/2022 | Maddahi et al. |
| 2022/0339052 A1 | 10/2022 | Kim |
| 2022/0339501 A1 | 10/2022 | Mason et al. |
| 2022/0395232 A1 | 12/2022 | Locke |
| 2022/0401783 A1 | 12/2022 | Choi |
| 2022/0415469 A1 | 12/2022 | Mason |
| 2022/0415471 A1 | 12/2022 | Mason |
| 2023/0001268 A1 | 1/2023 | Bissonnette et al. |
| 2023/0013530 A1 | 1/2023 | Mason |
| 2023/0014598 A1 | 1/2023 | Mason et al. |
| 2023/0029639 A1 | 2/2023 | Roy |
| 2023/0048040 A1 | 2/2023 | Hacking et al. |
| 2023/0051751 A1 | 2/2023 | Hacking et al. |
| 2023/0058605 A1 | 2/2023 | Mason |
| 2023/0060039 A1 | 2/2023 | Mason |
| 2023/0072368 A1 | 3/2023 | Mason |
| 2023/0078793 A1 | 3/2023 | Mason |
| 2023/0119461 A1 | 4/2023 | Mason |
| 2023/0190100 A1 | 6/2023 | Stump |
| 2023/0201656 A1 | 6/2023 | Hacking et al. |
| 2023/0207097 A1 | 6/2023 | Mason |
| 2023/0207124 A1 | 6/2023 | Walsh et al. |
| 2023/0215539 A1 | 7/2023 | Rosenberg et al. |
| 2023/0215552 A1 | 7/2023 | Khotilovich et al. |
| 2023/0245747 A1 | 8/2023 | Rosenberg et al. |
| 2023/0245748 A1 | 8/2023 | Rosenberg et al. |
| 2023/0245750 A1 | 8/2023 | Rosenberg et al. |
| 2023/0245751 A1 | 8/2023 | Rosenberg et al. |
| 2023/0253089 A1 | 8/2023 | Rosenberg et al. |
| 2023/0255555 A1 | 8/2023 | Sundaram et al. |
| 2023/0263428 A1 | 8/2023 | Hull et al. |
| 2023/0274813 A1 | 8/2023 | Rosenberg et al. |
| 2023/0282329 A1 | 9/2023 | Mason et al. |
| 2023/0364472 A1 | 11/2023 | Posnack |
| 2023/0368886 A1 | 11/2023 | Rosenberg |
| 2023/0377711 A1 | 11/2023 | Rosenberg |
| 2023/0377712 A1 | 11/2023 | Rosenberg |
| 2023/0386639 A1 | 11/2023 | Rosenberg |
| 2023/0395231 A1 | 12/2023 | Rosenberg |
| 2023/0395232 A1 | 12/2023 | Rosenberg |

FOREIGN PATENT DOCUMENTS

| | | |
|---|---|---|
| CN | 101964151 A | 2/2011 |
| CN | 201889024 U | 7/2011 |
| CN | 202220794 U | 5/2012 |
| CN | 102670381 A | 9/2012 |
| CN | 103263336 A | 8/2013 |
| CN | 103390357 A | 11/2013 |
| CN | 103473631 A | 12/2013 |
| CN | 103488880 A | 1/2014 |
| CN | 103501328 A | 1/2014 |
| CN | 103721343 A | 4/2014 |
| CN | 203677851 U | 7/2014 |
| CN | 104335211 A | 2/2015 |
| CN | 105620643 A | 6/2016 |
| CN | 105683977 A | 6/2016 |
| CN | 103136447 B | 8/2016 |
| CN | 105894088 A | 8/2016 |
| CN | 105930668 A | 9/2016 |
| CN | 205626871 U | 10/2016 |
| CN | 106127646 A | 11/2016 |
| CN | 106236502 A | 12/2016 |
| CN | 106510985 A | 3/2017 |
| CN | 106621195 A | 5/2017 |
| CN | 107066819 | 8/2017 |
| CN | 107430641 A | 12/2017 |
| CN | 107551475 A | 1/2018 |
| CN | 107736982 A | 2/2018 |
| CN | 107930021 A | 4/2018 |
| CN | 108078737 A | 5/2018 |
| CN | 208224811 A | 12/2018 |
| CN | 109191954 A | 1/2019 |
| CN | 109363887 A | 2/2019 |
| CN | 208573971 U | 3/2019 |
| CN | 110148472 | 8/2019 |
| CN | 110201358 A | 9/2019 |
| CN | 110215188 A | 9/2019 |
| CN | 110322957 A | 10/2019 |

(56) References Cited

FOREIGN PATENT DOCUMENTS

| | | |
|---|---|---|
| CN | 110808092 A | 2/2020 |
| CN | 110931103 A | 3/2020 |
| CN | 110993057 A | 4/2020 |
| CN | 111105859 A | 5/2020 |
| CN | 111111110 A | 5/2020 |
| CN | 111370088 A | 7/2020 |
| CN | 111460305 A | 7/2020 |
| CN | 111790111 A | 10/2020 |
| CN | 212141371 U | 12/2020 |
| CN | 112289425 A | 1/2021 |
| CN | 212624809 U | 2/2021 |
| CN | 112603295 A | 4/2021 |
| CN | 213190965 U | 5/2021 |
| CN | 113384850 A | 9/2021 |
| CN | 113499572 A | 10/2021 |
| CN | 215136488 U | 12/2021 |
| CN | 113885361 A | 1/2022 |
| CN | 114049961 A | 2/2022 |
| CN | 114203274 A | 3/2022 |
| CN | 216258145 U | 4/2022 |
| CN | 114632302 A | 6/2022 |
| CN | 114694824 A | 7/2022 |
| CN | 114898832 A | 8/2022 |
| CN | 114983760 A | 9/2022 |
| CN | 217472652 U | 9/2022 |
| CN | 110270062 B | 10/2022 |
| CN | 218420859 U | 2/2023 |
| CN | 115954081 A | 4/2023 |
| DE | 95019 C | 1/1897 |
| DE | 7628633 U1 | 12/1977 |
| DE | 8519150 U1 | 10/1985 |
| DE | 3732905 A1 | 7/1988 |
| DE | 19619820 A1 | 12/1996 |
| DE | 29620008 U1 | 2/1997 |
| DE | 19947926 A1 | 4/2001 |
| DE | 102018202497 A1 | 8/2018 |
| DE | 102018211212 A1 | 1/2019 |
| DE | 102019108425 B3 | 8/2020 |
| EP | 199600 A2 | 10/1986 |
| EP | 0383137 A2 | 8/1990 |
| EP | 634319 A2 | 1/1995 |
| EP | 1034817 A1 | 9/2000 |
| EP | 1159989 A1 | 12/2001 |
| EP | 1391179 A1 | 2/2004 |
| EP | 1968028 | 9/2008 |
| EP | 2564904 A1 | 3/2013 |
| EP | 1909730 B1 | 4/2014 |
| EP | 2815242 A4 | 12/2014 |
| EP | 2869805 A | 5/2015 |
| EP | 2997951 A1 | 3/2016 |
| EP | 2688472 B1 | 4/2016 |
| EP | 3264303 A1 | 1/2018 |
| EP | 3323473 A1 | 5/2018 |
| EP | 3627514 A1 | 3/2020 |
| EP | 3671700 A1 | 6/2020 |
| EP | 3688537 A1 | 8/2020 |
| EP | 3731733 A1 | 11/2020 |
| EP | 3984508 A1 | 4/2022 |
| EP | 3984509 A1 | 4/2022 |
| EP | 3984510 A1 | 4/2022 |
| EP | 3984511 A1 | 4/2022 |
| EP | 3984512 A1 | 4/2022 |
| EP | 3984513 A1 | 4/2022 |
| EP | 4054699 A1 | 9/2022 |
| EP | 4112033 A1 | 1/2023 |
| FR | 2527541 A2 | 12/1983 |
| FR | 3127393 A1 | 3/2023 |
| GB | 141664 A | 11/1920 |
| GB | 2336140 A | 10/1999 |
| GB | 2372459 A | 8/2002 |
| GB | 2512431 A | 10/2014 |
| GB | 2591542 B | 3/2022 |
| IN | 201811043670 A | 7/2018 |
| JP | 2000005339 A | 1/2000 |
| JP | 2003225875 A | 8/2003 |
| JP | 2005227928 A | 8/2005 |
| JP | 2005227928 A1 | 8/2005 |
| JP | 2009112336 A | 5/2009 |
| JP | 2013515995 A | 5/2013 |
| JP | 3193662 U | 10/2014 |
| JP | 3198173 U | 6/2015 |
| JP | 5804063 B2 | 11/2015 |
| JP | 2019028647 A | 2/2019 |
| JP | 2019134909 A | 8/2019 |
| JP | 6573739 B1 | 9/2019 |
| JP | 6659831 B2 | 3/2020 |
| JP | 6710357 B1 | 6/2020 |
| JP | 6775757 B1 | 10/2020 |
| JP | 2021027917 A | 2/2021 |
| JP | 6871379 B2 | 5/2021 |
| JP | 2022521378 A | 4/2022 |
| JP | 3238491 U | 7/2022 |
| JP | 7198364 B2 | 12/2022 |
| JP | 7202474 B2 | 1/2023 |
| JP | 7231750 B2 | 3/2023 |
| JP | 7231751 B2 | 3/2023 |
| JP | 7231752 B2 | 3/2023 |
| KR | 20020009724 A | 2/2002 |
| KR | 200276919 Y1 | 5/2002 |
| KR | 20020065253 A | 8/2002 |
| KR | 100582596 B1 | 5/2006 |
| KR | 101042258 B1 | 6/2011 |
| KR | 101258250 B1 | 4/2013 |
| KR | 101325581 B1 | 11/2013 |
| KR | 20140128630 A | 11/2014 |
| KR | 20150017693 A | 2/2015 |
| KR | 20150078191 A | 7/2015 |
| KR | 101580071 B1 | 12/2015 |
| KR | 101647620 B1 | 8/2016 |
| KR | 20160093990 A | 8/2016 |
| KR | 20170038837 A | 4/2017 |
| KR | 20180004928 A | 1/2018 |
| KR | 20190029175 A | 3/2019 |
| KR | 20190056116 A | 5/2019 |
| KR | 101988167 B1 | 6/2019 |
| KR | 101969392 B1 | 8/2019 |
| KR | 102055279 B1 | 12/2019 |
| KR | 102088333 B1 | 3/2020 |
| KR | 20200025290 A | 3/2020 |
| KR | 20200029180 A | 3/2020 |
| KR | 102116664 B1 | 5/2020 |
| KR | 102116968 B1 | 5/2020 |
| KR | 20200056233 A | 5/2020 |
| KR | 102120828 B1 | 6/2020 |
| KR | 102121586 B1 | 6/2020 |
| KR | 102142713 B1 | 8/2020 |
| KR | 102162522 B1 | 10/2020 |
| KR | 20200119665 A | 10/2020 |
| KR | 102173553 B1 | 11/2020 |
| KR | 102180079 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102224618 B1 | 3/2021 |
| KR | 102246049 B1 | 4/2021 |
| KR | 102246050 B1 | 4/2021 |
| KR | 102246051 B1 | 4/2021 |
| KR | 102246052 B1 | 4/2021 |
| KR | 20210052028 A | 5/2021 |
| KR | 102264498 B1 | 6/2021 |
| KR | 102352602 B1 | 1/2022 |
| KR | 102352603 B1 | 1/2022 |
| KR | 102352604 B1 | 1/2022 |
| KR | 20220004639 A | 1/2022 |
| KR | 102387577 B1 | 4/2022 |
| KR | 102421437 B1 | 7/2022 |
| KR | 20220102207 A | 7/2022 |
| KR | 102427545 B1 | 8/2022 |
| KR | 102467495 B1 | 11/2022 |
| KR | 102467496 B1 | 11/2022 |
| KR | 102469723 B1 | 11/2022 |
| KR | 102471990 B1 | 11/2022 |
| KR | 20220145989 A | 11/2022 |

(56) References Cited

FOREIGN PATENT DOCUMENTS

| | | |
|---|---|---|
| KR | 20220156134 A | 11/2022 |
| KR | 102502744 B1 | 2/2023 |
| KR | 20230019349 A | 2/2023 |
| KR | 20230019350 A | 2/2023 |
| KR | 20230026556 A | 2/2023 |
| KR | 20230026668 A | 2/2023 |
| KR | 20230040526 | 3/2023 |
| KR | 20230050506 A | 4/2023 |
| KR | 20230056118 A | 4/2023 |
| KR | 102528503 B1 | 5/2023 |
| KR | 102531930 B1 | 5/2023 |
| KR | 102532766 B1 | 5/2023 |
| KR | 102539190 B1 | 6/2023 |
| RU | 2014131288 A | 2/2016 |
| TW | 200910231 A | 3/2009 |
| TW | M474545 U | 3/2014 |
| TW | I442956 B | 7/2014 |
| TW | 201531278 A | 8/2015 |
| TW | M638437 U | 3/2023 |
| WO | 1998009687 A1 | 3/1998 |
| WO | 0149235 A2 | 7/2001 |
| WO | 0151083 A2 | 7/2001 |
| WO | 2001050387 A1 | 7/2001 |
| WO | 2001056465 A1 | 8/2001 |
| WO | 02062211 A2 | 8/2002 |
| WO | 02093312 A2 | 11/2002 |
| WO | 2003043494 A1 | 5/2003 |
| WO | 2005018453 A1 | 3/2005 |
| WO | 2006004430 A2 | 1/2006 |
| WO | 2006012694 A1 | 2/2006 |
| WO | 2007102709 A1 | 9/2007 |
| WO | 2008114291 A1 | 9/2008 |
| WO | 2009008968 A1 | 1/2009 |
| WO | 2011025322 A2 | 3/2011 |
| WO | 2012128801 A1 | 9/2012 |
| WO | 2013002568 A2 | 1/2013 |
| WO | 2023164292 A1 | 3/2013 |
| WO | 2013122839 A1 | 8/2013 |
| WO | 2014011447 A1 | 1/2014 |
| WO | 2014163976 A1 | 10/2014 |
| WO | 2015026744 A1 | 2/2015 |
| WO | 2015065298 A1 | 5/2015 |
| WO | 2015082555 A1 | 6/2015 |
| WO | 2015112945 A1 | 7/2015 |
| WO | 2016154318 A1 | 9/2016 |
| WO | 2017030781 A1 | 2/2017 |
| WO | 2017166074 A1 | 5/2017 |
| WO | 2017091691 A1 | 6/2017 |
| WO | 2017165238 A1 | 9/2017 |
| WO | 2018081795 A1 | 5/2018 |
| WO | 2018171853 A1 | 9/2018 |
| WO | 2019022706 A1 | 1/2019 |
| WO | 2019075185 A1 | 4/2019 |
| WO | 2019143940 A1 | 7/2019 |
| WO | 2020075190 A1 | 4/2020 |
| WO | 2020130979 A1 | 6/2020 |
| WO | 2020149815 A2 | 7/2020 |
| WO | 2020229705 A1 | 11/2020 |
| WO | 2020245727 A1 | 12/2020 |
| WO | 2020249855 A1 | 12/2020 |
| WO | 2020252599 A1 | 12/2020 |
| WO | 2020256577 A1 | 12/2020 |
| WO | 2021021447 A1 | 2/2021 |
| WO | 2021022003 A1 | 2/2021 |
| WO | 2021038980 A1 | 3/2021 |
| WO | 2021055427 A1 | 3/2021 |
| WO | 2021061061 A1 | 4/2021 |
| WO | 2021090267 A1 | 5/2021 |
| WO | 2021138620 A1 | 7/2021 |
| WO | 2022047006 A1 | 3/2022 |
| WO | 2022092493 A1 | 5/2022 |
| WO | 2022092494 A1 | 5/2022 |
| WO | 2022212532 A1 | 10/2022 |
| WO | 2022212883 A1 | 10/2022 |
| WO | 2022212921 A1 | 10/2022 |
| WO | 2022216498 A1 | 10/2022 |
| WO | 2023008680 A1 | 2/2023 |
| WO | 2023008681 A1 | 2/2023 |
| WO | 2023022319 A1 | 2/2023 |
| WO | 2023022320 A1 | 2/2023 |
| WO | 2023052695 A1 | 4/2023 |
| WO | 2023091496 A1 | 5/2023 |
| WO | 2023215155 A1 | 11/2023 |
| WO | 2023230075 A1 | 11/2023 |

OTHER PUBLICATIONS

Fysiomed, 16983—Vario adjustable pedal arms, retrieved on Aug. 4, 2020, 1 page, https://www.fysiomed.com/en/products/16983-vario-adjustable-pedal-arms.

HCL Fitness, HCI Fitness PhysioTrainer Upper Body Ergonometer, announced 2009 [online], retrieved on Aug. 19, 2021, 8 pages, www.amazon.com/HCI-Fitness-PhysioTrainer-Upper-Ergonometer/dp/B001 P5GUGM.

HCL Fitness, HCI Fitness PhysioTrainer Pro, 2017, retrieved on Aug. 23, 2021, 6 pages, https://www.amazon.com/HCI-Fitness-Physio Trainer-Electronically-Controlled/dp/B0759YMW78/.

Matrix, R3xm Recumbent Cycle, retrieved on Aug. 19, 2021, 7 pages, https://www.matrixfitness.com/en/cardio/cycles/r3xm-recumbent.

ROM3 Rehab, ROM3 Rehab System, Apr. 20, 2015, retrieved on Aug. 31, 2018, 12 pages, https://vimeo.com/125438463.

Davenport et al., "The Potential for Artificial Intelligence in Healthcare", 2019, Future Healthcare Journal 2019, vol. 6, No. 2: Year: 2019, pp. 1-5.

Ahmed et al., "Artificial Intelligence With Multi-Functional Machine Learning Platform Development for Better Healthcare and Precision Medicine", 2020, Database (Oxford), 2020:baaa010. doi: 10.1093/database/baaa010 (Year: 2020), pp. 1-35.

Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pp. 671-680, XP055914810.

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.

Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.

Yin Chieh et al., "A Virtual Reality-Cycling Training System for Lower Limb Balance Improvement", BioMed Research International, vol. 2016, pp. 1-10.

Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.

Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.

Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.

Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.

Website for "Pedal Exerciser", p. 1, retrieved on Sep. 9, 2022 from https://www.vivehealth.com/collections/physical-therapy-equipment/products/pedalexerciser.

Website for "Functional Knee Brace with ROM", p. 1, retrieved on Sep. 9, 2022 from http://medicalbrace.gr/en/product/functional-knee-brace-with-goniometer-mbtelescopicknee/.

(56) References Cited

OTHER PUBLICATIONS

Website for "ComfySplints Goniometer Knee", pp. 1-5, retrieved on Sep. 9, 2022 from https://www.comfysplints.com/product/knee-splints/.
Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.
Website for "Neoprene Knee Brace with goniometer—Patella ROM MB.4070", pp. 1-4, retrieved on Sep. 9, 2022 from https://www.fortuna.com.gr/en/product/neoprene-knee-brace-with-goniometer-patella-rom-mb-4070/.
Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.
Ahmed et al., "Artificial intelligence with multi-functional machine learning platform development for better healthcare and precision medicine," Database, 2020, pp. 1-35.
Davenport et al., "The potential for artificial intelligence in healthcare," Digital Technology, Future Healthcare Journal, 2019, pp. 1-5, vol. 6, No. 2.
Website for "OxeFit XS1", pp. 1-3, retrieved on Sep. 9, 2022 from https://www.oxefit.com/xs1.
Website for "Preva Mobile", pp. 1-6, retrieved on Sep. 9, 2022 from https://www.precor.com/en-us/resources/introducing-preva-mobile.
Website for "J-Bike", pp. 1-3, retrieved on Sep. 9, 2022 from https://www.magneticdays.com/en/cycling-for-physical-rehabilitation.
Website for "Excy", pp. 1-12, retrieved on Sep. 9, 2022 from https://excy.com/portable-exercise-rehabilitation-excy-xcs-pro/.
Website for "OxeFit XP1", p. 1, retrieved on Sep. 9, 2022 from https://www.oxefit.com/xp1.
Barrett et al., "Artificial intelligence supported patient self-care in chronic heart failure: a paradigm shift from reactive to predictive, preventive and personalised care," EPMA Journal (2019), pp. 445-464.
Oerkild et al., "Home-based cardiac rehabilitation is an attractive alternative to No. cardiac rehabilitation for elderly patients with coronary heart disease: results from a randomised clinical trial," BMJ Open Accessible Medical Research, Nov. 22, 2012, pp. 1-9.
Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders (2017) 17:66, pp. 1-11.
Thomas et al., "Home-Based Cardiac Rehabilitation," Circulation, 2019, pp. e69-e89.
Thomas et al., "Home-Based Cardiac Rehabilitation," Journal of the American College of Cardiology, vol. 74, Nov. 1, 2019, pp. 133-153.
Thomas et al., "Home-Based Cardiac Rehabilitation," HHS Public Access, Oct. 2020, pp. 1-39.
Dittus et al., "Exercise-Based Oncology Rehabilitation: Leveraging the Cardiac Rehabilitation Model," Journal of Cardiopulmonary Rehabilitation and Prevention 2015, pp. 130-139.
Chen et al., "Home-based cardiac rehabilitation improves quality of life, aerobic capacity, and readmission rates in patients with chronic heart failure," Medicine (2018) 97:4, pp. 1-5.
Lima de Melo Ghisi et al., "A systematic review of patient education in cardiac patients: Do they increase knowledge and promote health behavior change?," Patient Education and Counseling, 2014, pp. 1-15.
Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.
Beene et al., "AI and Care Delivery: Emerging Opportunities for Artificial Intelligence to Transform How Care Is Delivered," Nov. 2019, American Hospital Association, pp. 1-12.
Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.
Jeong et al., "Computer-assisted upper extremity training using interactive biking exercise (iBikE) platform," Sep. 2012, pp. 1-5, 34th Annual International Conference of the IEEE EMBS.
International Search Report and Written Opinion for PCT/US2023/014137, dated Jun. 9, 2023, 13 pages.
Website for "Esino 2022 Physical Therapy Equipments Arm Fitness Indoor Trainer Leg Spin Cycle Machine Exercise Bike for Elderly," https://www.made-in-china.com/showroom/esinogroup/product-detailYdZtwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.
Abedtash, "An Interoperable Electronic Medical Record-Based Platform for Personalized Predictive Analytics", ProQuest LLC, Jul. 2017, 185 pages.
Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.
Androutsou et al., "A Smartphone Application Designed to Engage the Elderly in Home-Based Rehabilitation," Frontiers in Digital Health, Sep. 2020, vol. 2, Article 15, 13 pages.
Silva et al., "SapoFitness: A mobile health application for dietary evaluation," 2011 IEEE 13th International Conference on U e-Health Networking, Applications and Services, Columbia, MO, USA, 2011, 6 pages.
Wang et al., "Interactive wearable systems for upper body rehabilitation: a systematic review," Journal of NeuroEngineering and Rehabilitation, 2017, 21 pages.
Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.
Nijjar et al., "Randomized Trial of Mindfulness-Based Stress Reduction in Cardiac Patients Eligible for Cardiac Rehabilitation," Scientific Reports, 2019, 12 pages.
Lara et al., "Human-Robot Sensor Interface for Cardiac Rehabilitation," IEEE International Conference on Rehabilitation Robotics, Jul. 2017, 8 pages.
Ishraque et al., "Artificial Intelligence-Based Rehabilitation Therapy Exercise Recommendation System," 2018 IEEE Mit Undergraduate Research Technology Conference (URTC), Cambridge, MA, USA, 2018, 5 pages.
Zakari et al., "Are There Limitations to Exercise Benefits in Peripheral Arterial Disease?," Frontiers in Cardiovascular Medicine, Nov. 2018, vol. 5, Article 173, 12 pages.
You et al., "Including Blood Vasculature into a Game—Theoretic Model of Cancer Dynamics," Games 2019, 10, 13, 22 pages.
Jeong et al., "Computer-assisted upper extremity training using interactive biking exercise (iBikE) platform," Sep. 2012, 34th Annual International Conference of the IEEE EMBS, 5 pages.
Gerbild et al., "Physical Activity to Improve Erectile Dysfunction: A Systematic Review of Intervention Studies," Sexual Medicine, 2018, 15 pages.

\* cited by examiner

Today's Session

1. Warm Up Cycle
2. Seated March
3. Sit-to-Stand
4. Calf Raise
5. Hamstring Curl Equipment Needed: None Total Time: 18 Minutes

| Excercise | Sitting Knee Extension | Chair Rise / Squat |
|---|---|---|
| Description | Start with feet on ground while sitting in chair. Then lift one foot and straighten the knee and hold. | Start with feet on ground while sitting in chair. Stand pp and keep tension trough your gluteus maximus. |
| Image | 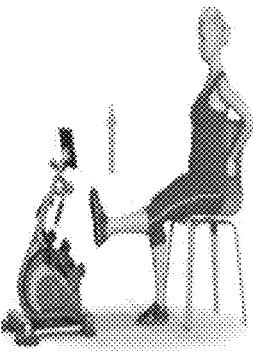 | 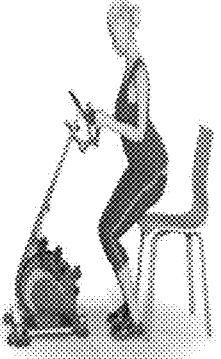 |
| Levels | Level 1<br>Level 2<br>Level 3 | Level 2<br>Level 3<br>Level 4<br>Level 5 |
| Section | Warm up | Warm up<br>Cardio<br>Strength |
| Component (Exercise Goal) | Flexibility | Strength<br>Endurance |
| Swap it out with | Cycling Quad Set | Standing hip extension<br>Wider base squat<br>Hip thrust |
| Too Easy | Increase reps / Decrease rest | Change cadence to increase time of descent, Add reps up to 15, Add sets up to 4, Decrease rest |
| Too Hard | Decrease reps / Increase rest | Increase seat height, Add reps up Standing hip, extension, Increase stance width, Hip Thrust |
| Reps (starting level) | 5-15<br>Level 1-5 | 5-15<br>Level 1-5 |
| # of sets (starting level) | Level 2-2<br>Level 3-3<br>Level 4-4 | Level 2-2<br>Level 3-3<br>Level 4-4 |
| Time Per Rep | 5 Sec/rep | 2 Sec/rep |
| Rest Time Per Set | 30 Sec<br>Up to 90 if they need | 30 Sec<br>Up to 90 if they need |
| Body Part Excercised | Whole leg, Lateral hip, Medial hip, Posterior hip, Hamstrings, Quadriceps, Hip flexion | Whole leg, Posterior hip and hamstrings, Medial hip and quadriceps |
| Intensity | Low Intensity | High Intensity |

*FIG. 27B*

| A | B | C | D | E | F | G | H | I |
|---|---|---|---|---|---|---|---|---|
| ID | Name | MET Score | Description | Difficulty (E,M,H) | Exercise Levels | Sections | Goals | Difficulty Decrease ID |
| 1 | Sitting Knee Extension | 3.5 | Start with fee on ground while sitting in chair. Then lift one foot and straighten the knee and hold. | M | 1,2,4 | 3,4 | | 2 |
| 2 | Sitting Knee Extension | 3 | Swap out quad set | E | 1,2,4 | 3,4 | | 0 |
| 3 | Sitting Knee Extension | 4 | Progress to sit to stand (can start with higher surface is needed) as that is more beneficial than starting at this level. | H | 1,2,4 | 3,4 | | 1 |
| 4 | Sit to Stand | 3.5 | Start with feet on ground while sitting in chair. Stand up and keep tension through your gluteus maximus. | M | 2,3,4,5 | 2,3 | | 5 |

*FIG. 41A*

| A | B |
|---|---|
| ID | Name |
| 1 | Rom |
| 2 | Strength |
| 3 | Endurance |
| 4 | Balance |
| 5 | Mobility |

*FIG. 41B*

| A | B |
|---|---|
| ID | Name |
| 1 | Hip Flexor |
| 2 | Posterior Hip |
| 3 | Hamstring |
| 4 | Lateral Hip |
| 5 | Stretch |
| 6 | Whole Leg |
| 7 | Medical Hip |
| 8 | Quads |
| 9 | Biceps |
| 10 | Shoulders |
| 11 | Upper Back |
| 12 | Glutes |
| 13 | Chest |
| 14 | Side Glutes |
| 15 | Truck Rotator |

*FIG. 41C*

| A | B | C | D | E | F | G | H |
|---|---|---|---|---|---|---|---|
| ID | Name | Body Part That Need Improvement | Component 1st Priority | Component 2nd Priority | Component 3rd Priority | Component 4th Priority | Component 5th Priority |
| 1 | Getting rid of knee pain | | 1 | 2 | 4 | 5 | 3 |
| 2 | Getting up/down stairs | 12,8,1,2,15,4,7,17,18,1,2 | 1 | 2 | 4 | 3 | 5 |
| 3 | Gardening/ Yardwork | 12,8,24,14,25,13,10,11 | 1 | 2 | 4 | 5 | 4 |
| 4 | Playing with grandkinds | 1,2,3,4,5,6,7,8,9,10,11,12,13, 14,15,16,17,18,19,20,21,22,2 3,24,25,26,27,28,29,30,31 | 1 | 2 | 3 | 4 | 5 |
| 5 | Walking Long (if inactive/Running Longer (if active) | 1,2,4,7,30,22,20,13 | 1 | 3 | 3 | 4 | 5 |

FIG. 41D

| A | B | C | D | E | F | G |
|---|---|---|---|---|---|---|
| Week ID | Component 1st Priority Percentage of Exercises | Component 2nd Priority Percentage of Exercises | Component 3rd Priority Percentage of Exercises | Component 4th Priority Percentage of Exercises | Component 5th Priority Percentage of Exercises | Total % |
| 1 | 0.4 | 0.4 | 0.2 | 0 | 0 | 1 |
| 2 | 0.4 | 0.3 | 0.2 | 0.05 | 0.05 | 1 |
| 3 | 0.35 | 0.3 | 0.25 | 0.05 | 0.05 | 1 |
| 4 | 0.2 | 0.25 | 0.25 | 0.15 | 0.15 | 1 |
| 5 | 0.2 | 0.2 | 0.2 | 0.2 | 0.2 | 1 |
| 6 | 0.2 | 0.2 | 0.2 | 0.2 | 0.2 | 1 |

FIG. 41E

METHOD AND SYSTEM FOR USING ARTIFICIAL INTELLIGENCE TO ADJUST PEDAL RESISTANCE

CROSS-REFERENCES TO RELATED APPLICATIONS

This application is a continuation-in-part of and claims priority to U.S. application Ser. No. 16/869,954, filed May 8, 2020, titled "System, Method and Apparatus for Rehabilitation and Exercise", which claims priority to both U.S. Prov. Application No. 62/858,244, filed Jun. 6, 2019, titled "System for Individualized Rehabilitation Using Load Cells in Handles and Foot Plates and Providing Haptic Feedback to a User" and U.S. Prov. Application No. 62/846,434, filed May 10, 2019, titled "Exercise Machine". The current application further claims priority to U.S. Prov. Application No. 63/168,175, filed Mar. 30, 2021, titled "System and Method for an Artificial Intelligence Engine That Uses a Multi-Disciplinary Data Source to Determine Comorbidity Information Pertaining to Users and to Generate Exercise Plans for Desired User Goals". All applications are hereby incorporated by reference in their entirety for all purposes.

TECHNICAL FIELD

This disclosure relates to exercise machines. More specifically, this disclosure relates to a method and system for using artificial intelligence to adjust pedal resistance.

BACKGROUND

Exercise and rehabilitation devices, such as an cycling machine and balance equipment, are used to facilitate exercise, strength training, osteogenesis, and/or rehabilitation of a user. A user may perform an exercise (e.g., cycling, balancing, bench press, pull down, arm curl, etc.) using the osteogenic isometric exercise, rehabilitation, and/or strength training equipment to improve osteogenesis, bone growth, bone density, muscular hypertrophy, flexibility, balance, coordination, reduce pain, decrease rehabilitation time, increase strength, or some combination thereof. The isometric exercise, rehabilitation, and/or strength training equipment may include moveable portions onto which the user adds a load or balances. For example, to perform a cycling exercise, the user may sit in a seat, place each of the user's feet on a respective pedal of an cycling machine, and push on the pedals with the user's feet while each of the pedals rotate in a circular motion. To perform a balancing exercise, the user may stand on a balance board and balance on top of the balance board as it shifts in one or more directions. The isometric exercise, rehabilitation, and/or strength training equipment may include non-movable portions onto which the user adds load. For example, to perform a leg-press-style exercise, the user may sit in a seat, place each of the user's feet on a respective foot plate, and push on the feet plates with the user's feet while the foot plates remain in the same position.

SUMMARY

Representative embodiments set forth herein disclose various techniques for an adjustment of exercise based on artificial intelligence, exercise plan, and user feedback. As used herein, the terms "exercise apparatus," "exercise device," "electromechanical device," "exercise machine," "rehabilitation device," "cycling machine" "balance board," and "isometric exercise and rehabilitation assembly" may be used interchangeably. The terms "exercise apparatus," "exercise device," "electromechanical device," "exercise machine," "rehabilitation device," "cycling machine" "balance board," and "isometric exercise and rehabilitation assembly" may also refer to an osteogenic, strength training, isometric exercise, and/or rehabilitation assembly.

In one embodiment, a method is disclosed for using an artificial intelligence engine to modify a resistance of one or more pedals of an exercise device. The method includes generating, by the artificial intelligence engine, a machine learning model trained to receive one or more measurements as input, and outputting, based on the one or more measurements, a control instruction that causes the exercise device to modify the resistance of the one or more pedals. The method includes receiving the one or more measurements from a sensor associated with the one or more pedals of the exercise device, determining whether the one or more measurements satisfy a trigger condition, and responsive to determining that the one or more measurements satisfy the trigger condition, transmitting the control instruction to the exercise device.

In one embodiment, a method is disclosed for using an artificial intelligence engine to perform a control action. The control action is based on one or more measurements from a wearable device. The method includes generating, by the artificial intelligence engine, a machine learning model trained to receive the one or more measurements as input, and outputting, based on the one or more measurements, a control instruction that causes the control action to be performed. The method includes receiving the one or more measurements from the wearable device being worn by a user, determining whether the one or more measurements indicate, during an interval training session, that one or more characteristics of the user are within a desired target zone, and responsive to determining that the one or more measurements indicate the one or more characteristics of the user are not within the desired target zone during the interval training session, performing the control action.

In one embodiment, a method is disclosed for using an artificial intelligence engine to modify resistance of one or more pedals of an exercise device. The method includes generating, by the artificial intelligence engine, a machine learning model trained to receive one or more measurements as input, and outputting, based on the one or more measurements, a control instruction that causes the exercise device to modify, independently from each other, the resistance of the one or more pedals. The method includes, while a user performs an exercise using the exercise device, receiving the one or more measurements from the one or more sensors associated with the one or more pedals of the exercise device, and determining, based on the one or more measurements, a quantifiable or qualitative modification to the resistance provided by a pedal of the one or more pedals. In one embodiment, the resistance provided by another pedal of the one or more pedals is not modified. The method includes transmitting the control instruction to the exercise device to cause the resistance provided by the pedal to be modified.

In one embodiment, a method is disclosed for using an artificial intelligence engine to present a user interface capable of presenting the progress of a user in one or more domains. The method includes generating, by the artificial intelligence engine, a machine learning model trained to receive one or more measurements as input, and outputting, based on the one or more measurements, a user interface that causes one or more graphical elements to dynamically change position on the user interface. The method includes, while a user performs an exercise using the exercise device, receiving the one or more measurements from the one or more sensors associated with the exercise device, and presenting, on a computing device associated with the exercise device, one or more sections of the user interface. The one or more sections of the user interface may each be related to a separate domain comprising the one or more domains and wherein, based on the one or more measurements, each section may include the one or more graphical elements placed.

In one embodiment, a method is disclosed for using an artificial intelligence engine to interact with a user of an exercise device during an exercise session. The method includes generating, by the artificial intelligence engine, a machine learning model trained to receive data as input, and based on the data, to provide an output. The method includes, while a user performs an exercise using the exercise device, receiving the data from an input peripheral of a computing device associated with the user, and based on the data being received from the input peripheral, determining, via the machine learning model, the output such that control of an aspect of the exercise device is enabled.

In one embodiment, a method is disclosed for using an artificial intelligence engine to onboard a user for an exercise plan. The method includes generating, by the artificial intelligence engine, a machine learning model trained to receive as input both onboarding data associated with a user and an onboarding protocol and, based on the onboarding data and the onboarding protocol, output an exercise plan. The method includes, while a user performs an exercise using the exercise device, receiving the onboarding data associated with the user. The method includes determining, by the machine learning model using the onboarding data and the onboarding protocol, a fitness level of the user, wherein the onboarding protocol comprises exercises with tiered difficulty levels, wherein the onboarding protocol increases a difficulty level for a subsequent exercise comprising the exercises when the user completes an exercise comprising the exercises, and, further wherein, based on a completion state of a last exercise performed by the user, the fitness level of the user is determined. The method includes, by associating the difficulty level for each exercise with the fitness level of the user, selecting a difficulty level for each exercise comprising the exercise plan.

In one embodiment, a tangible, non-transitory computer-readable medium storing instructions that, when executed, cause a processing device to perform any of the operations of any of the methods disclosed herein.

In one embodiment, a system includes a memory device storing instructions and a processing device communicatively coupled to the memory device. The processing device may execute the instructions to perform any of the operations of any of the methods disclosed herein.

Other technical features may be readily apparent to one skilled in the art from the following figures, descriptions, and claims.

BRIEF DESCRIPTION OF THE DRAWINGS

For a detailed description of example embodiments, reference will now be made to the accompanying drawings in which:

FIG. 27B illustrates an example data structure including a set of exercises tagged by exercise level of a user;

FIG. 41A-41E illustrates an example data source including information pertaining to exercises and physical activity goals;

NOTATION AND NOMENCLATURE

Figure 1:
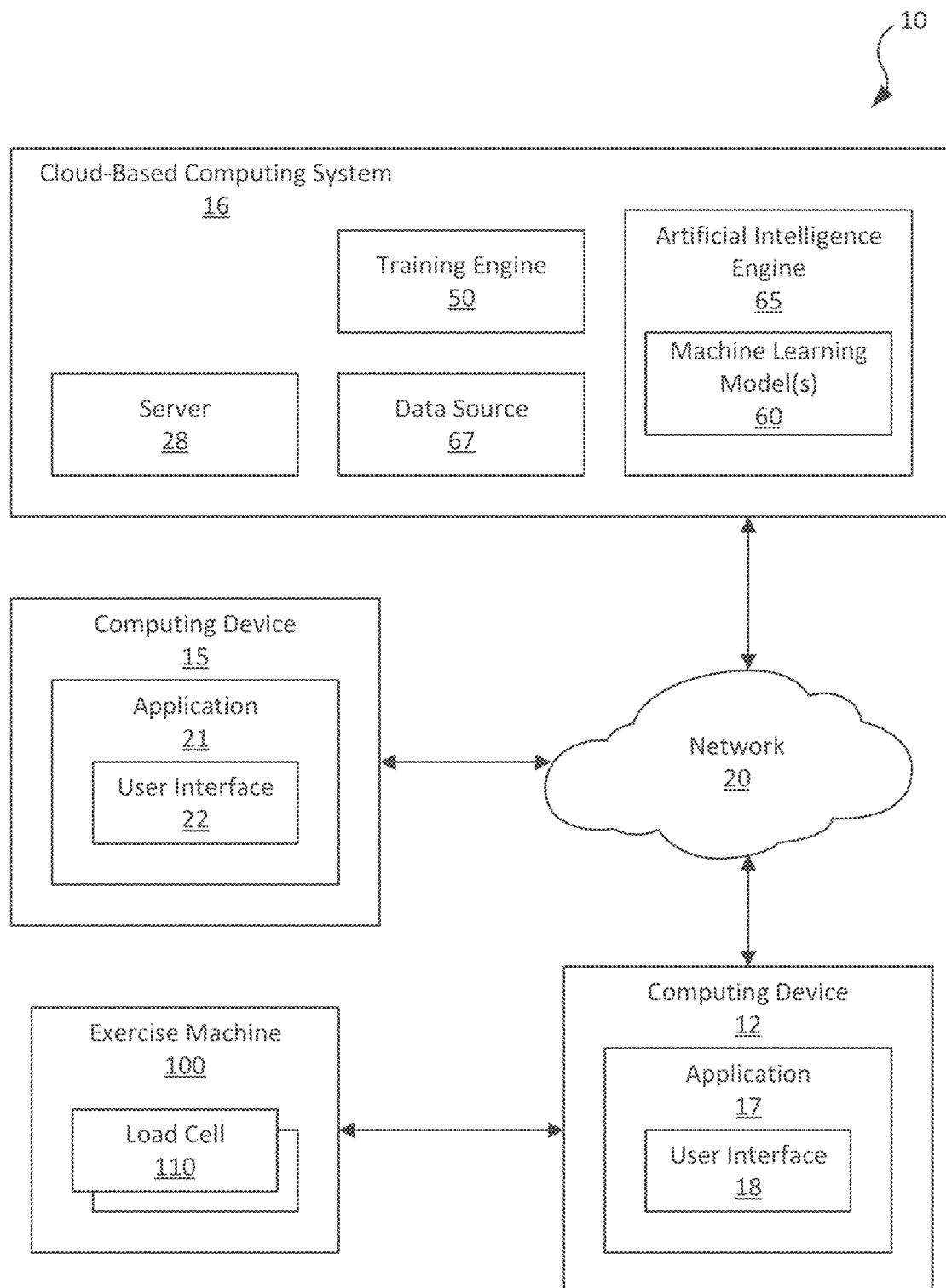
FIG. 1 illustrates a high-level component diagram of an illustrative system architecture according to certain embodiments of this disclosure.
Figure 2:
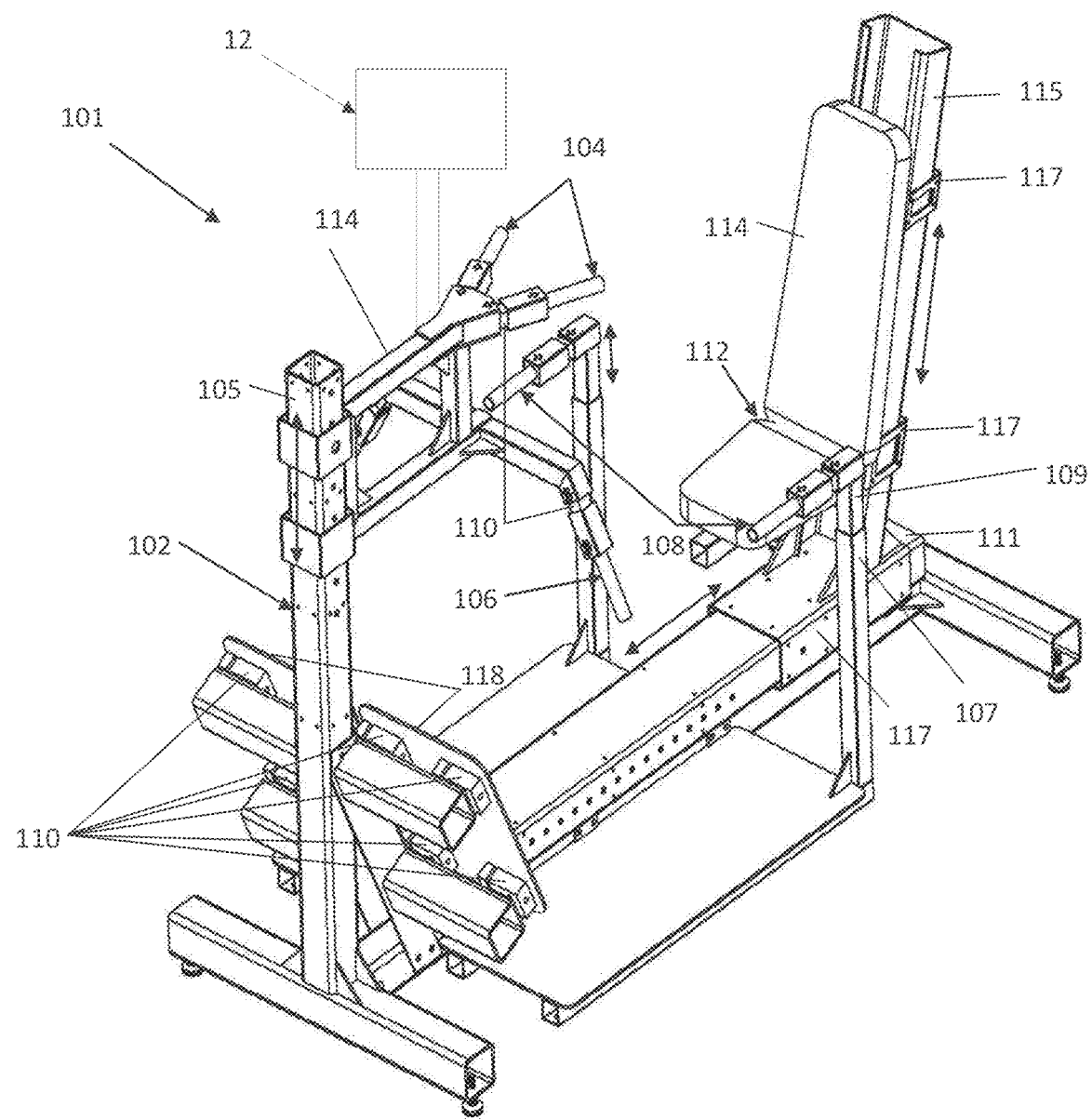
FIG. 2 illustrates an elevated perspective view of one embodiment of an isometric exercise and rehabilitation assembly.
Figure 3:
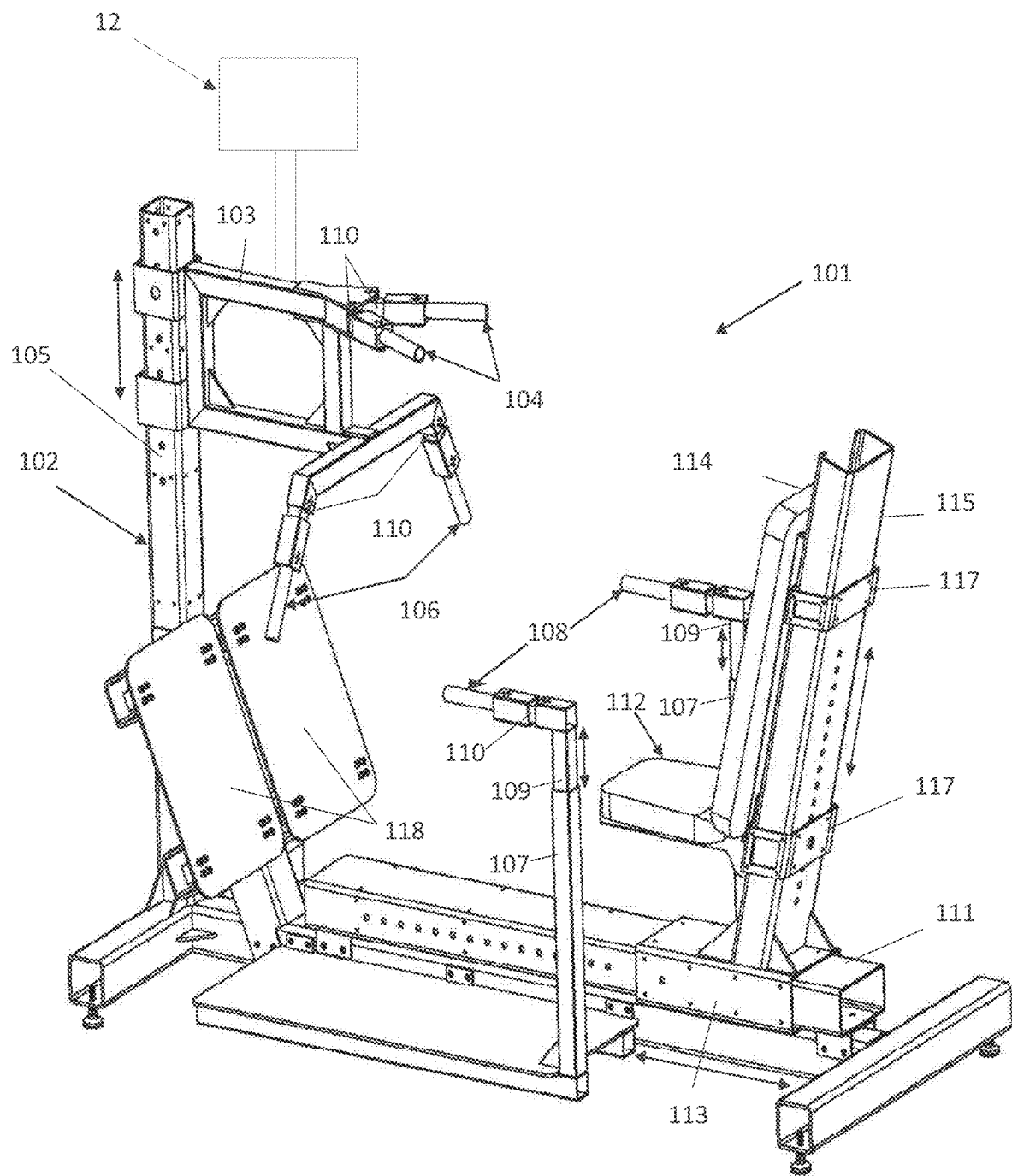
FIG. 3 illustrates a perspective view of the isometric exercise and rehabilitation assembly.
Figure 4:
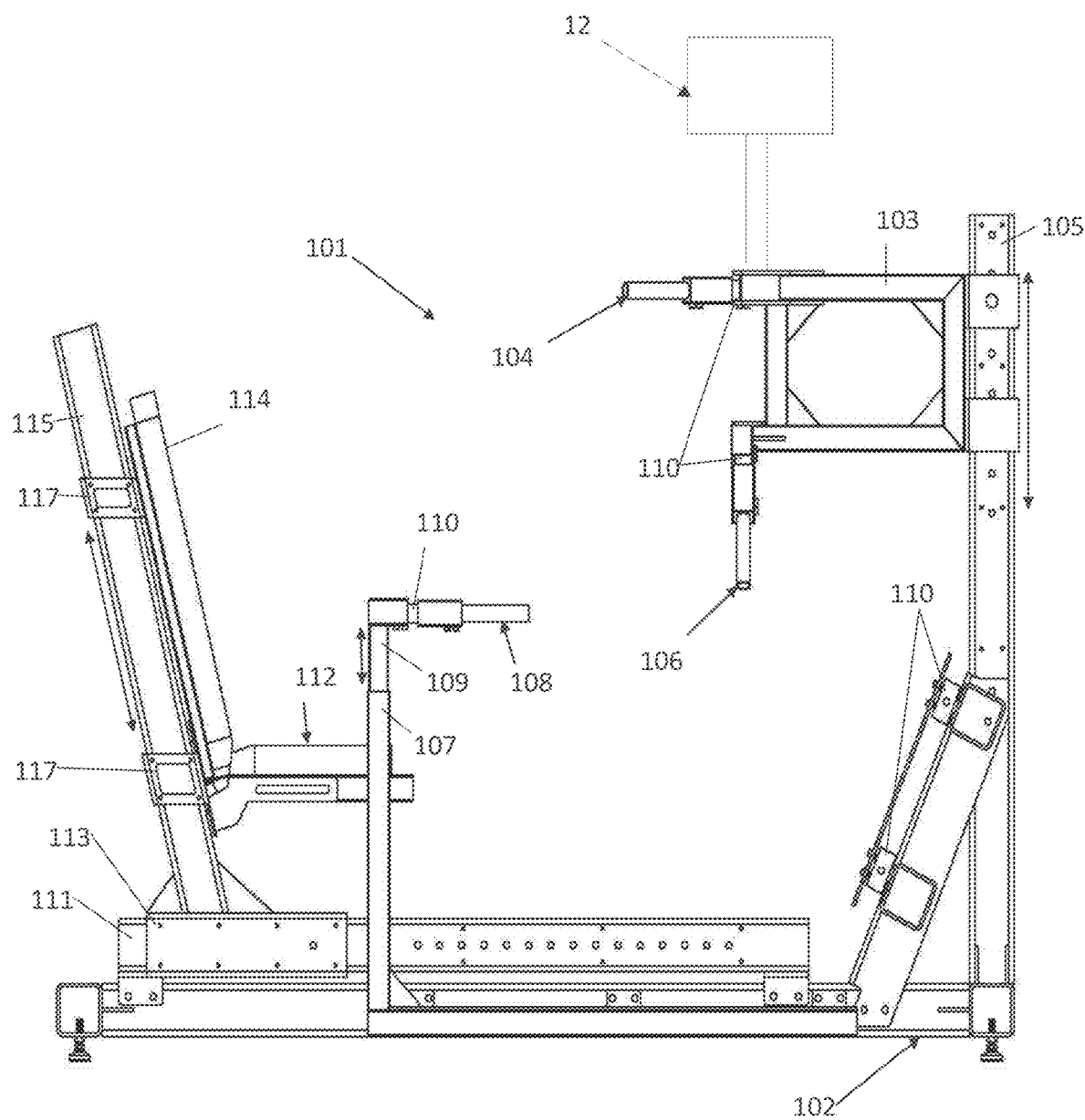
FIG. 4 illustrates a side view of the isometric exercise and rehabilitation assembly.
Figure 5:
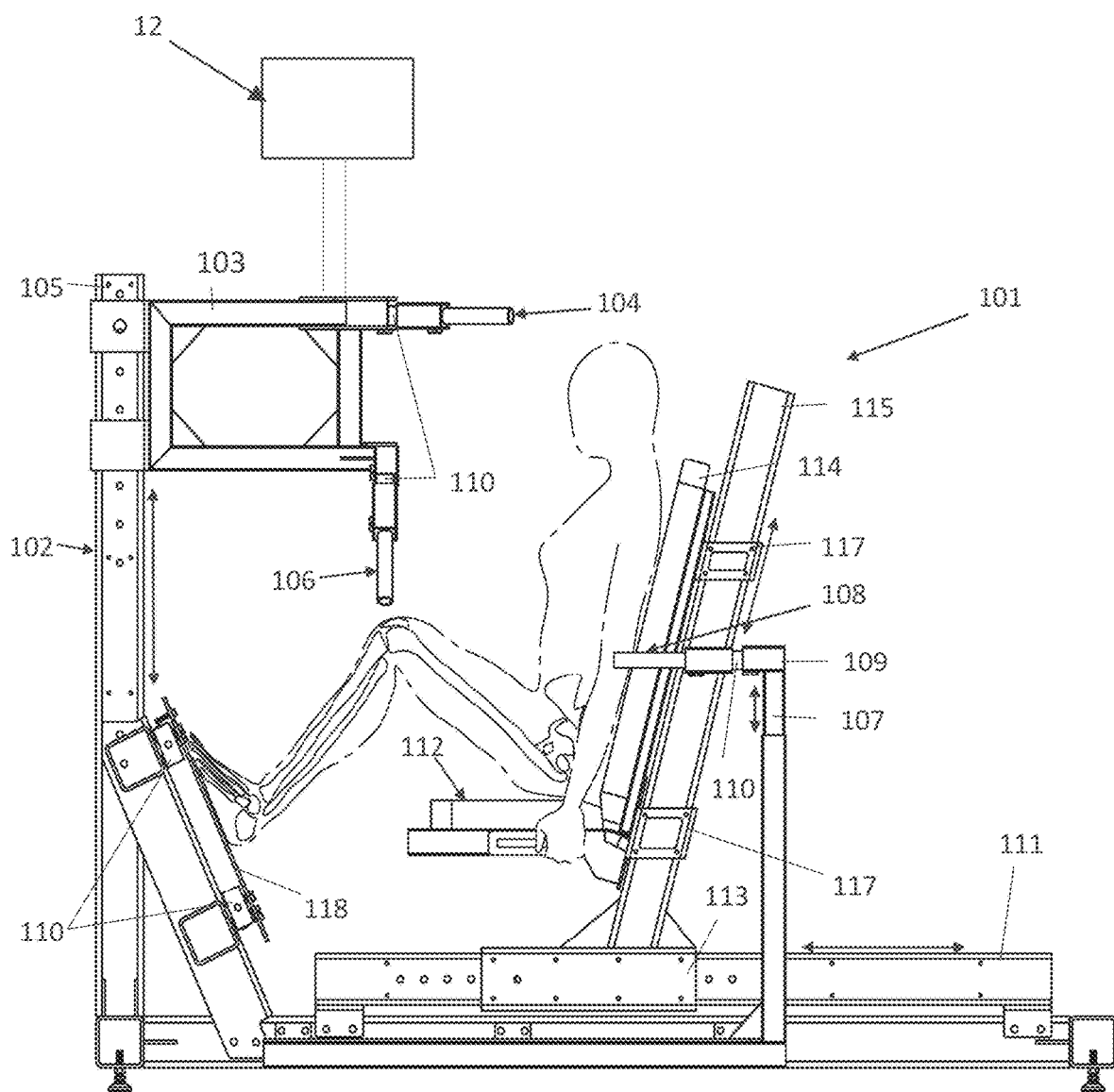
FIG. 5 illustrates a side view of the isometric exercise and rehabilitation assembly with a user performing a leg-press-style exercise.
Figure 6:
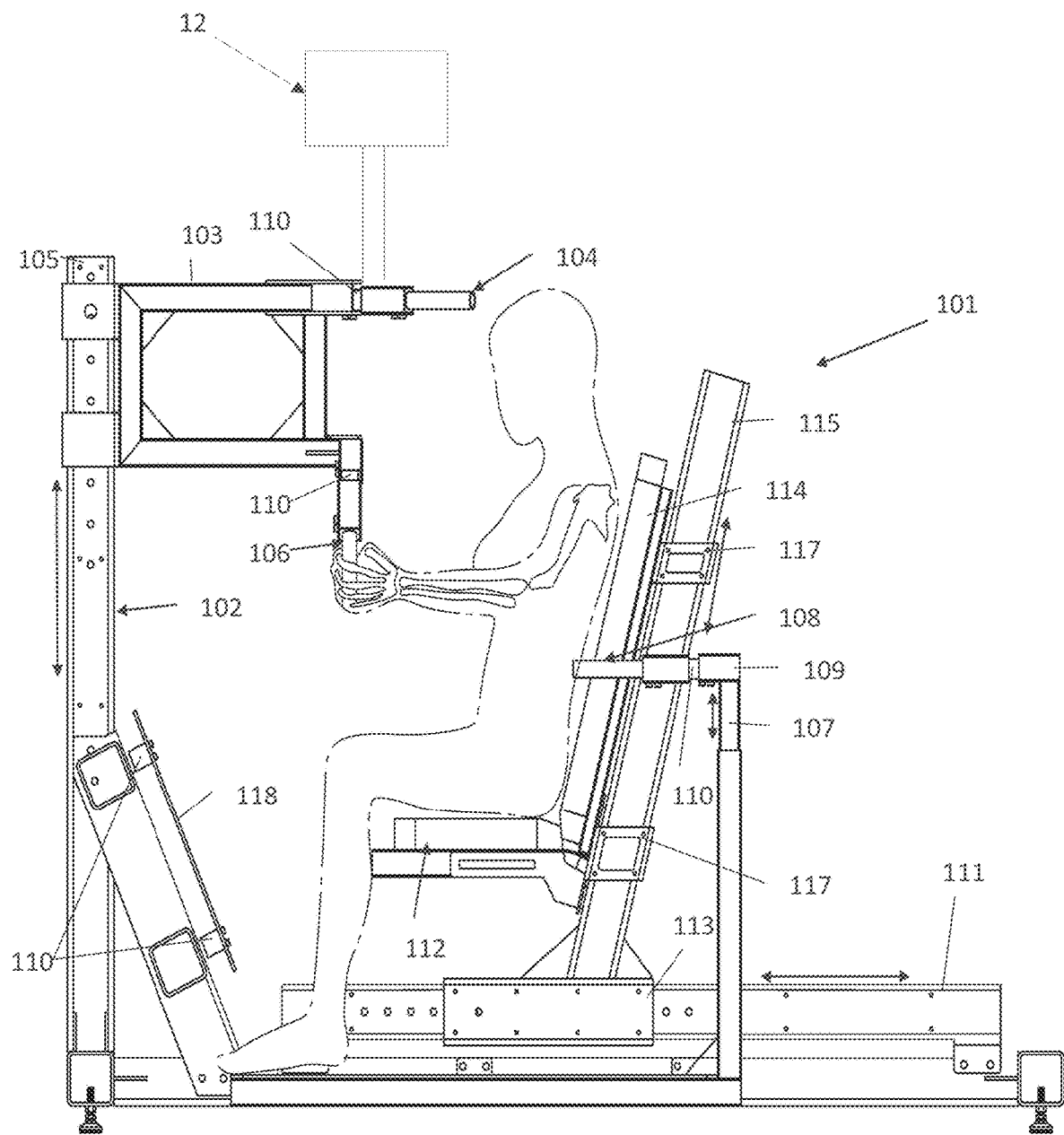
FIG. 6 illustrates a side view of the isometric exercise and rehabilitation assembly with a user performing a chest-press-style exercise.
Figure 7:
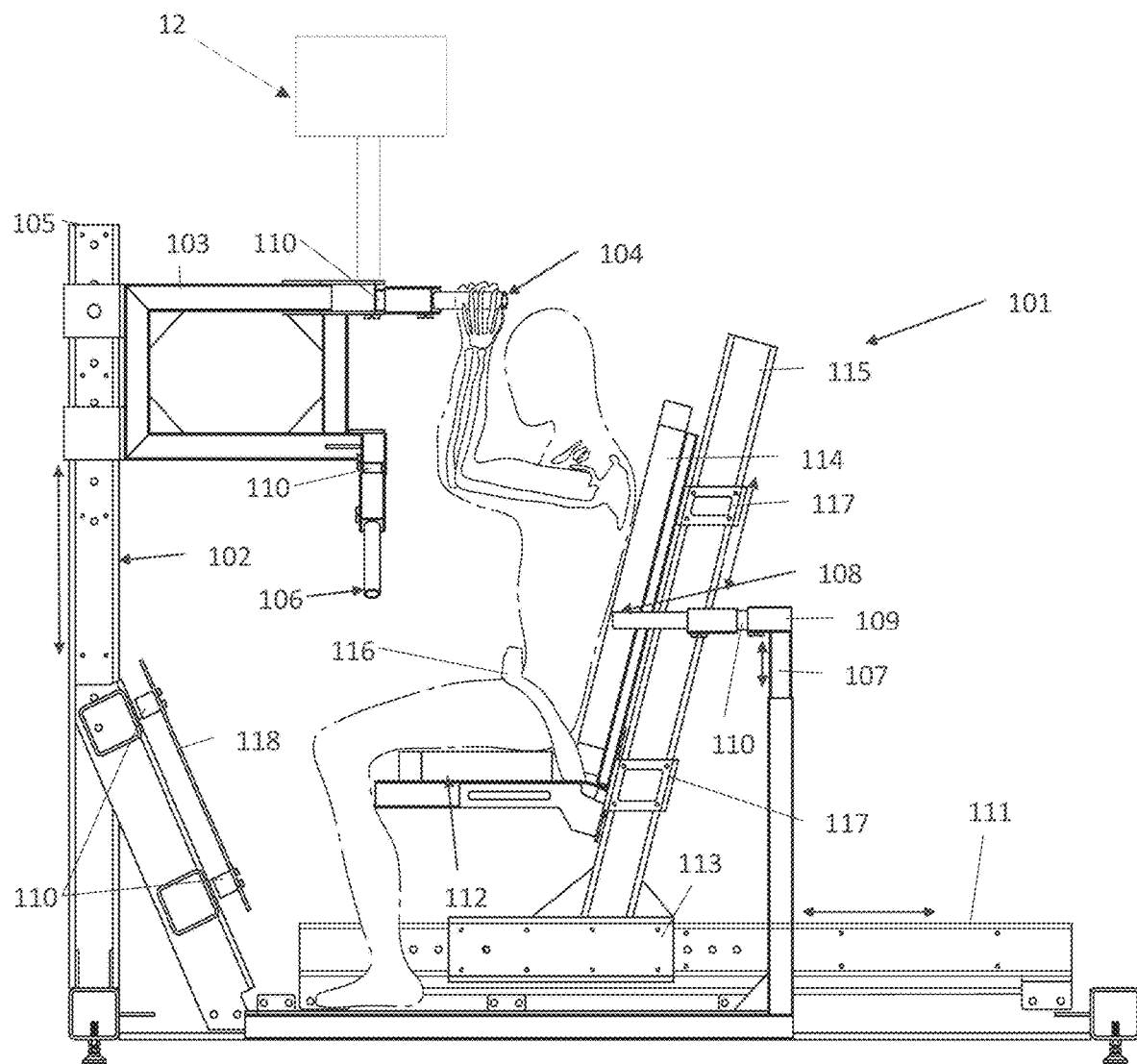
FIG. 7 illustrates a side view of the isometric exercise and rehabilitation assembly with a user performing a core-pull-style exercise.
Figure 8:
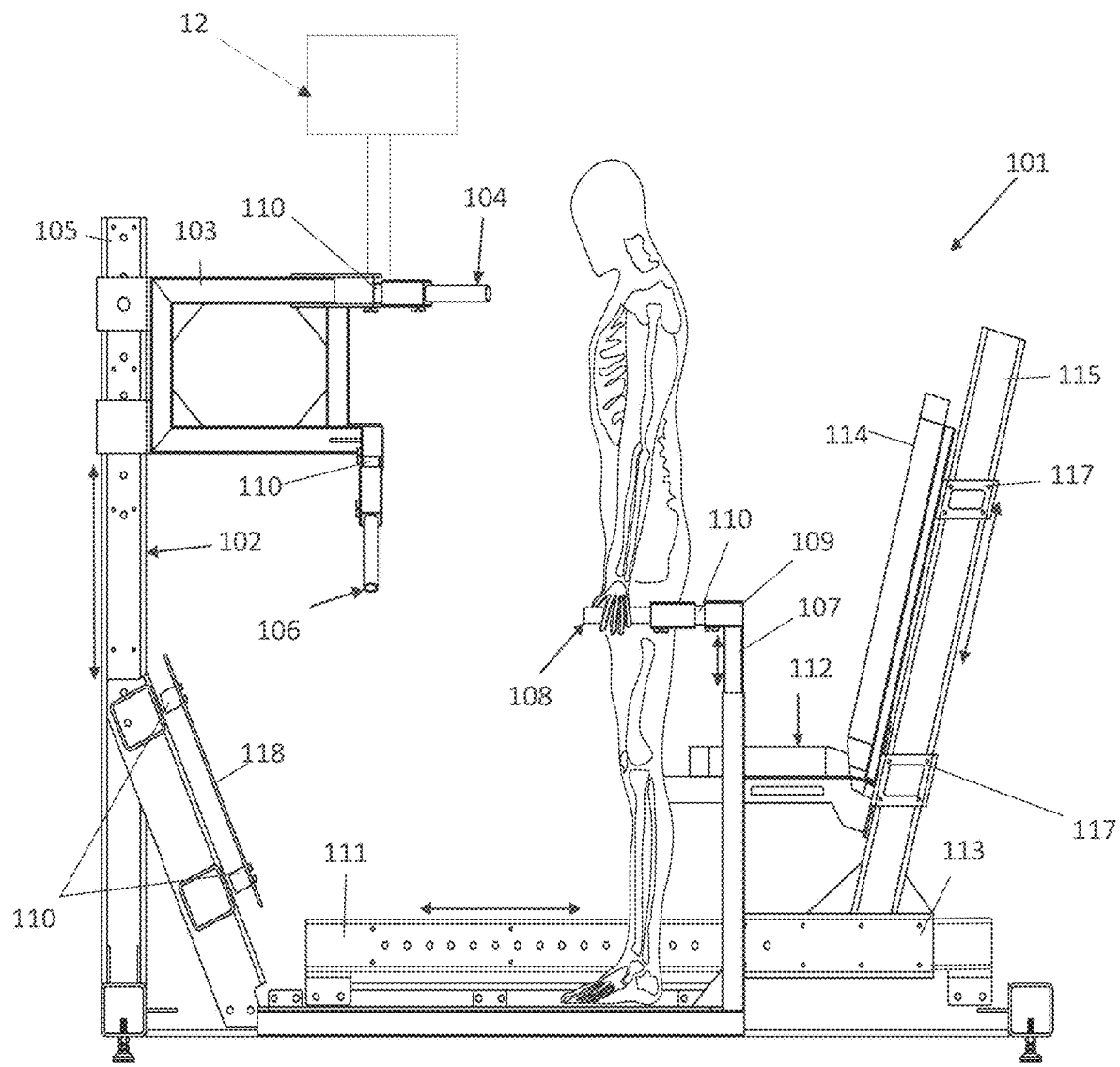
FIG. 8 illustrates a side view of the isometric exercise and rehabilitation assembly with a user performing a suitcase-lift-style exercise.

Various terms are used to refer to particular system components. Different entities may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

Various terms are used to refer to particular system components. Different entities may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer or section from another region, layer or section. Terms such as "first," "second," and other numerical terms, when used herein, do not imply a sequence or order unless clearly indicated by the context. Thus, a first element, component, region, layer or section discussed below could be termed a second element, component, region, layer or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), solid state drives (SSDs), flash memory, or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

The term "bone geometry" may refer to bone diameter, bone density, bone shape, bone cross-section, bone length, bone weight, or any suitable bone dimension(s) and/or measurement(s).

The term "empirical data" may refer to data obtained and/or derived based on observation, experience, measurement, and/or research.

The term "strain," when used in context with a bone of a user, may refer to an amount, proportion, or degree of deformation of the bone material.

The terms "exercise machine" and "isometric exercise and rehabilitation assembly" may be used interchangeably herein.

The terms "body part" and "body portion" may be used interchangeably herein.

An exercise plan may include one or more exercise sessions. Each exercise session may include one or more exercises of any type (e.g., cycling, running, pull-ups, sit-ups, stretching, yoga, etc.). The one or more exercises may include or be based on various specifications (e.g., parameters, properties, values, attributes, etc.), such as a number of repetitions, a number of sets, a periodicity, a frequency, a difficulty level, an amount of weight, a range of motion, a degree of flexion, a degree of extension, a skill level, or the like.

Definitions for other certain words and phrases are provided throughout this patent document. Those of ordinary skill in the art should understand that in many if not most instances, such definitions apply to prior as well as future uses of such defined words and phrases.

DETAILED DESCRIPTION

As typically healthy people grow from infants to children to adults, they experience bone growth. Such, growth, however, typically stops at approximately age 30. After that point, without interventions as described herein, bone loss (called osteoporosis), can start to occur. This does not mean that the body stops creating new bone. Rather, it means that the rate at which it creates new bone tends to slow, while the rate at which bone loss occurs tends to increase.

In addition, as people age and/or become less active than they once were, they may experience muscle loss. For example, muscles that are not used often may reduce in muscle mass. As a result, the muscles become weaker. In some instances, people may be affected by a disease, such as muscular dystrophy, that causes the muscles to become progressively weaker and to have reduced muscle mass. To increase the muscle mass and/or reduce the rate of muscle loss, people may exercise a muscle to cause muscular hypertrophy, thereby strengthening the muscle as the muscle grows. Muscular hypertrophy may refer to an increase in a size of skeletal muscle through a growth in size of its component cells. There are two factors that contribute to muscular hypertrophy, (i) sarcoplasmic hypertrophy (increase in muscle glycogen storage), and (ii) myofibrillar hypertrophy (increase in myofibril size). The growth in the cells may be caused by an adaptive response that serves to increase an ability to generate force or resist fatigue.

The rate at which such bone or muscle loss occurs generally accelerates as people age. A net growth in bone can ultimately become a net loss in bone, longitudinally across time. By the time, in general, women are over 50 and men are over 70, net bone loss can reach a point where brittleness of the bones is so great that the risk of life-altering fractures can occur. Examples of such fractures include fractures of the hip and femur. Of course, fractures can also occur due to participation in athletics or due to accidents. In such cases, it is just as relevant to have a need for bone growth which heals or speeds the healing of the fracture.

To understand why such fractures occur, it is useful to recognize that bone is itself porous, with a somewhat-honeycomb like structure. This structure may be dense and therefore stronger or it may be variegated, spread out and/or sparse, such latter structure being incapable of continuously or continually supporting the weight (load) stresses experienced in everyday living. When such loads exceed the support capability of the structure at a stressor point or points, a fracture occurs. This is true whether the individual had a fragile bone structure or a strong one: it is a matter of physics, of the literal "breaking point."

It is therefore preferable to have a means of mitigating or ameliorating bone loss and of healing fractures. Further, it is preferable to encourage new bone growth, thus increasing the density of the structure described hereinabove. The increased bone density may increase the load-bearing capacities of the bone, thus making first or subsequent fractures less likely to occur. Reduced fractures may improve a quality of life of the individual. The process of bone growth itself is referred to as osteogenesis, literally the creation of bone.

It is also preferable to have a means for mitigating or ameliorating muscle mass loss and weakening of the muscles. Further, it is preferable to encourage muscle growth by increasing the muscle mass through exercise. The increased muscle mass may enable a person to exert more force with the muscle and/or to resist fatigue in the muscle for a longer period of time.

In order to create new bone, at least three factors are necessary. First, the individual must have a sufficient intake of calcium, but second, in order to absorb that calcium, the individual must have a sufficient intake and absorption of Vitamin D, a matter problematic for those who have cystic fibrosis, who have undergone gastric bypass surgery or have other absorption disorders or conditions which limit absorption. Separately, supplemental estrogen for women and supplemental testosterone for men can further ameliorate bone loss. On the other hand, abuse of alcohol and smoking can harm one's bone structure. Medical conditions such as, without limitation, rheumatoid arthritis, renal disease, overactive parathyroid glands, diabetes or organ transplants can also exacerbate osteoporosis. Ethical pharmaceuticals such as, without limitation, hormone blockers, seizure medications and glucocorticoids are also capable of inducing such exacerbations. But even in the absence of medical conditions as described hereinabove, Vitamin D and calcium taken together do not create osteogenesis to a desirable degree or ameliorate bone loss to a desirable degree.

To achieve osteogenesis, therefore, one must add in the third factor: exercise. Specifically, one must subject one's bones to a force at least equal to certain multiple of body weight, such multiples varying depending on the individual and the specific bone in question. As used herein, "MOB" means Multiples of Body Weight. It has been determined through research that subjecting a given bone to a certain threshold MOB (this may also be known as a "weight-bearing exercise"), even for an extremely short period of time, one simply sufficient to exceed the threshold MOB, encourages and fosters osteogenesis in that bone.

Further, a person can achieve muscular hypertrophy by exercising the muscles for which increased muscle mass is desired. Strength training and/or resistance exercise may cause muscle tissue to increase. For example, pushing against or pulling on a stationary object with a certain amount of force may trigger the cells in the associated muscle to change and cause the muscle mass to increase.

In some embodiments disclosed herein, a control system for an exercise machine is disclosed, not only capable of enabling an individual, preferably an older, less mobile individual or preferably an individual recovering from a fracture, to engage easily in osteogenic exercises and/or muscle strengthening exercises, but capable of using predetermined thresholds or dynamically calculating them, such that the person using the machine can be immediately informed through real-time visual and/or other sensorial feedback, that the osteogenic threshold has been exceeded, thus triggering osteogenesis for the subject bone (or bones), and/or that the muscular strength threshold has been exceeded, thereby triggering muscular hypertrophy for the subject muscle (or muscles). The control system may be used to improve compliance with an exercise plan including one or more exercises.

The control system may receive one or more load measurements associated with forces exerted by both the left and right sides on left and right portions (e.g., handles, foot plate or platform) of the exercise machine to enhance osteogenesis, bone growth, bone density improvement, and/or muscle mass. The one or more load measurements may be a left load measurement of a load added to a left load cell on a left portion of the exercise machine and a right load measurement of a load added to a right load cell on a right portion of the exercise machine. A user interface may be provided by the control system that presents visual representations of the separately measured left load and right load where the respective left load and right load are added to the respective left load cell and right load cell at the subject portions of the exercise machine.

In some embodiments, initially, the control system may receive load measurements via a data channel associated with each exercise of the machine. For example, there may be a data channel for a leg-press-style exercise, a pull-down-style exercise, a suitcase-lift-style exercise, an arm-curl-style exercise, and so forth. Each data channel may include one or more load cells (e.g., a left load cell and a right load cell) that measure added load or applied force and transmit the load measurement to the control system via its respective data channel. The control system may receive the load measurements from each of the data channels at a first rate (e.g., 1 Hertz). If the control system detects a load from a data channel (e.g., hands resting on the handles including the respective load cells, or feet resting on the feet plate including the respective load cells), the control system may set that data channel as active and start reading load measurements from that data channel at a second rate (e.g., 10 Hertz) that is higher than the first rate. Further, the control system may set the other exercises associated with the other data channels as inactive and stop reading load measurements from the other data channels until the active exercise is complete. The active exercise may be complete when the one or more load measurements received via the data channel exceed one or more target thresholds. In some embodiments, the control system may determine an average load measurement by accumulating raw load measurements over a certain period of time (e.g., 5 seconds) and averaging the raw load measurements to smooth the data (e.g., eliminates jumps or spikes in data) in an average load measurement.

The control system may compare the one or more load measurements (e.g., raw load measurements, or averaged load measurements) to one or more target thresholds. In some embodiments, a single load measurement may be compared to a single specific target threshold (e.g., a one-to-one relationship). In some embodiments, a single load measurement may be compared to more than one specific target threshold (e.g., a one-to-many relationship). In some embodiments, more than one load measurement may be compared to a single specific target threshold (e.g., a many-to-one relationship). In some embodiments, more than one load measurement may be compared to more than one specific target threshold (e.g., a many-to-many relationship).

The target thresholds may be an osteogenesis target threshold, a muscular strength target threshold, and/or a rehabilitation threshold. The osteogenesis target threshold may be determined based on a disease protocol pertaining to the user, an age of the user, a gender of the user, a sex of the user, a height of the user, a weight of the user, a bone density of the user, etc. A disease protocol may refer to any illness, disease, fracture, or ailment experienced by the user and any treatment instructions provided by a caretaker for recovery and/or healing. The disease protocol may also include a condition of health where the goal is avoid a problem. The muscular strength target threshold may be determined based on a historical performance of the user using the exercise machine (e.g., amount of pounds lifted for a particular exercise, amount of force applied associated with each body part, etc.) and/or other exercise machines, a fitness level (e.g., how active the user is) of the user, a diet of the user, a protocol for determining a muscular strength target, etc. The rehabilitation target threshold may be determined based on historical performance of the user using the exercise machine (e.g., amount of force applied associated with each body part, speed of cycling, level of stability, etc.) and/or other exercise machines, a fitness level (e.g., how active the user is, the flexibility of the user, etc.) of the user, a diet of the user, an exercise plan for determining a rehabilitation target, the condition of the user (e.g., type of surgery the user underwent, the type of injury the user sustained), physical characteristics of the user (e.g., an age of the user, a gender of the user, a sex of the user, a height of the user, a weight of the user, a bone density of the user), condition of the user's body part(s) (e.g., the pain level of a user), an exertion level of a user (e.g., how easy/hard the exercise session is for the user), any other suitable characteristic, or combination thereof.

The control system may determine whether the one or more load measurements exceed the one or more target thresholds. Responsive to determining that the one or more load measurements exceed the one or more target thresholds, the control system may cause a user interface to present an indication that the one or more target thresholds have been exceeded and an exercise is complete. Additionally, when the one or more target thresholds are exceeded, the control system may cause the user interface to present an indication that instructs the user to apply additional force (less than a safety limit) to attempt to set a personal maximum record of weight lifted, pressed, pulled, or otherwise exert force thereupon for that exercise.

Further, the user interface may present an indication when a load measurement is approaching a target threshold for the user. In another example, when the load measurement exceeds the target threshold, the user interface may present an indication that the target threshold has been exceeded, that the exercise is complete, and if there are any remaining incomplete exercises in the exercise plan, that there is another exercise to be completed by the user. If there are no remaining exercises in the exercise plan to complete, then the user interface may present an indication that all exercises in the exercise plan are complete and the user can rest. In addition, when the exercise plan is complete, the control system may generate a performance report that presents various information (e.g., charts and graphs of the right and left load measurements received during each of the exercises, left and right maximum loads for the user received during each of the exercises, historical right and left load measurements received in the past, comparison of the current right and left load measurements with the historical right and left load measurement, an amount of pounds lifted or pressed that is determined based on the load measurements for each of the exercises, percent gained in load measurements over time, etc.).

Further, the one or more load measurements may each be compared to a safety limit. For example, a left load measurement and a right load measurement may each be compared to the safety limit for the user. The safety limit may be determined for the user based on the user's disease protocol. There may be different safety limits for different portions of the user's body on the left and the right side, one extremity versus another extremity, a top portion of the user's body and a body portion of the user's body, etc., and for different exercises. For example, if someone underwent left knee surgery, the safety limit for a user for a left load measurement for a leg-press-style exercise may be different from the safety limit for a right load measurement for that exercise and user. If the safety limit is exceeded, an indication may be presented on the user interface to instruct to reduce the amount of force the user is applying and/or to instruct the user to stop applying force because the safety limit is exceeded.

For those with any or all of the osteoporosis-exacerbating medical conditions described herein, such a control system and exercise machine can slow the rate of net bone loss by enabling osteogenesis to occur without exertions which would not be possible for someone whose health is fragile, not robust. Another benefit of the present disclosure, therefore, is its ability to speed the healing of fractures in athletically robust individuals. Further, another benefit is the increase in muscle mass by using the exercise machine to trigger muscular hypertrophy. The control system may provide an automated interface that improves compliance with an exercise plan by using a real-time feedback loop to measure loads added during each of the exercises, compare the load measurements to target thresholds and/or safety limits that are uniquely determined for the user using the exercise machine, and provide various indications based on the comparison. For example, the indications pertain to when the user should add more load, when the target thresholds are exceeded, when the safety limit is exceeded, when the exercise is complete, when the user should begin another exercise, and so forth.

Bone Exercises and their Benefits

The following exercises achieve bone strengthening results by exposing relevant parts of a user to isometric forces which are selected multiples of body weight (MOB) of the user, a threshold level above which bone mineral density increases. A MOB may be any fraction or rational number excluding zero. The specific MOB-multiple threshold necessary to effect such increases will naturally vary from individual to individual and may be more or less for any given individual. "Bone-strengthening," as used herein, specifically includes, without limitation, a process of osteogenesis, whether due to the creation of new bone as a result of an increase in the bone mineral density; or proximately to the introduction or causation of microfractures in the underlying bone. The exercises referred to are as follows.

Leg Press

A leg-press-style exercise to improve isometric muscular strength in the following key muscle groups: gluteals, hamstrings, quadriceps, spinal extensors and grip muscles as well as to increase resistance to skeletal fractures in leg bones such as the femur. In one example, the leg-press-style exercise can be performed approximately 4.2 MOB or more of the user.

Chest Press

A chest-press-style exercise to improve isometric muscular strength in the following key muscle groups: pectorals, deltoids, and tricep and grip muscles as well as in increasing resistance to skeletal fractures in the humerus, clavicle, radial, ulnar and rib pectoral regions. In one example, the chest-press-style exercise can be performed at approximately 2.5 MOB or more of the user.

Suitcase Lift

A suitcase-lift-style exercise to improve isometric muscular strength in the following key muscle groups: gluteals, hamstrings, quadriceps, spinal extensors, abdominals, and upper back and grip muscles as well as to increase resistance to skeletal fractures in the femur and spine. In one example, the suitcase-lift-style exercise can be performed at approximately 2.5 MOB or more of the user.

Arm Curl

An arm-curl-style exercise to improve isometric muscular strength in the following key muscle groups: biceps, brachialis, brachioradialis, grip muscles and trunk as well as in increasing resistance to skeletal fractures in the humerus, ribs and spine. In one example, the arm-curl-style exercise can be performed at approximately 1.5 MOB or more of the user.

Core Pull

A core-pull-style exercise to improve isometric muscular strength in the following key muscle groups: elbow flexors, grip muscles, latissimus dorsi, hip flexors and trunk as well as in increasing resistance to skeletal fractures in the ribs and spine. In one example, the core-pull-style exercise can be performed at approximately 1.5 MOB or more of the user.

Grip Strength

A grip-strengthening-style exercise which may preferably be situated around a station in an exercise machine, in order to improve strength in the muscles of the hand and forearm. Grip strength is medically salient because it has been positively correlated with better states of health.

In some embodiments, a balance board may be communicatively coupled to the control system. For example, the balance board may include a network interface that communicates with the control system via any suitable interface protocol (e.g., Bluetooth, WiFi, cellular). The balance board may include pressure sensors and may obtain measurements of locations and amount of pressure applied to the balance board. The measurements may be transmitted to the control system. The control system may present a game or interactive exercise on a user interface. The game or interactive exercise may modify screens or adjust graphics that are displayed based on the measurements received from the balance board. The balance board may be used by a user to perform any suitable type of plank (e.g., knee plank, regular feet and elbow plank, table plank with elbows, or the like). Accordingly, the balance board may be configured to be used with arms on the balance board, knees on the balance board, and/or feet standing on the balance board. The games or interactive exercises may encourage the user during the game or interactive exercises to increase compliance and neuro-motor control after a surgery, for example.

The exercise machine, balance board, wristband, goniometer, and/or any suitable accessory may be used for various reasons in various markets. For example, users may use the exercise machine, balance board, wristband, goniometer, and/or any suitable accessory in the orthopedic market if the users suffer from chronic musculosketal pain (e.g., knees, hips, shoulders, and back). The exercise machine, balance board, wristband, goniometer, and/or any suitable accessory may be used to help with prehabilitation (prehab), as well as optimize post-surgical outcomes. Users may use the exercise machine, balance board, wristband, goniometer, and/or any suitable accessory in the back and neck pain market if the users suffer with chronic back and neck pain and they want to avoid surgery and experience long-term relief, as well as users that are in recovery following surgery. Users may use the exercise machine, balance board, wristband, goniometer, and/or any suitable accessory in the cardiovascular market if they desire to prevent or recover from life-threatening cardiovascular disease, especially heart attacks and stroke. Users may use the exercise machine, balance board, wristband, goniometer, and/or any suitable accessory in the neurological market if they desire to recover from stroke, or have conditions like Parkinson's Disease and/or Multiple Sclerosis, and the users desire to achieve better balance, strength, and muscle symmetry in order to slow progression of the medical condition.

In some embodiments, bone growth, muscle growth, rehabilitation, prehabilitation, and the like may be needed to perform certain physical activities. For example, a person may require a certain amount of muscle mass to move an object having a particular weight. While the physical activity may be desirable, some people may lack the appropriate bone mass, muscle mass, or physical ability in general to perform the physical activity. In one example, a grandparent may desire to play with their grandchildren, and may want to select that physical activity as a goal. However, the grandparent may not be aware of what levels of attainment are associated with the physical activity goal of playing with their grandchildren. As used herein, levels of attainment may refer to any physical, emotional, intellectual or other quality associated with such attainment, e.g., strength, endurance, balance, intelligence, neurological responsiveness, emotional well-being, range of motion, and mobility. A user may lack the proper knowledge, training, and/or education to determine which exercises to perform to target appropriate body portions used, for example, to achieve the appropriate levels of attainment to be able to play with their grandchildren. Further, another problem that users may experience is the ability to determine when the user may be at risk for having or developing various comorbitities in a real-time or near real-time manner. Such knowledge may be useful for a user to prevent the comorbidity from arising and/or to encourage or suggest to a user to consult with a health professional to take preventative care measures.

Accordingly, some embodiments of the present disclosure provide a technical solution for enabling a user to select one or more physical activity goals they desire to achieve and for generating an improved exercise plan that enables the user to achieve the one or more physical activity goals. The system may use an artificial intelligence engine to generate machine learning models that use one or more curated, multi-disciplinary data sources to generate the improved exercise plan. A given data source may include associations between the selected physical activity goal and one or more levels of attainment pertaining to achieving the physical life goal, associations between the one or more levels of attainment and one or more body portions, and associations between the one or more body portions and one or more exercises that target the one or more body portions. Using the data source, the artificial intelligence engine may generate a machine learning model to use the associations to generate improved exercise plans. Further, a machine learning model may be trained to predict a length of time it will take a user, if they follow the improved exercise plan, to achieve their physical activity life goal.

The levels of attainment may be objectively monitored and/or measured using various performance measurements from one or more sensors, characteristics of users of the exercise machine, user-reported difficulty levels of exercises, user-reported pain levels, and the like. An onboarding protocol may be used to establish a baseline describing a fitness level of the user, and the fitness level of the user, in the improved exercise plan, may be used to select difficulty levels of exercises. A machine learning model may be trained to perform the onboarding protocol and to determine the fitness level of the user. The improved exercise plan may be dynamically updated based on characteristics of the user, selected physical activity levels, performance measurements, user-reported difficulties of the exercises, user-reported pain levels, and the like. In some embodiments, to comply with the exercise plan, the exercise machine may be controlled using a signal that indicates changing an attribute of an operating parameter of the exercise machine. The control system may change the attribute of the operating parameter in response to receiving the signal.

In some embodiments, numerous enhanced user interfaces may be used to enable the user to create a profile, select physical activity goals, view generated improved exercise plans, perform exercises, view/listen to multimedia regarding the exercises, provider user-reported feedback, view comorbidity information, view evidential trails for the comorbidity information and the exercise plans, control the exercise machine, and the like. The user interfaces may present information in a beneficial manner, especially on a small screen used by mobile devices (e.g., smartphones, tablets), such that the user is presented with pertinent information without having to drill down into numerous other user interfaces or to open up different applications or websites. Accordingly, the enhanced user interface may improve the user's experience using a computing device, thus providing a technical improvement to computing technology.

The following discussion is directed to various embodiments of the present disclosure. Although these embodiments are given as examples, the embodiments disclosed should not be interpreted, or otherwise used, as limiting the scope of the disclosure, including the claims. In addition, one of ordinary skill in the art will understand that the following description has broad application, and the discussion of any embodiment is meant only to be exemplary of that embodiment, and not intended to intimate that the scope of the disclosure, including the claims, is limited to that embodiment.

FIG. 1 illustrates a high-level component diagram of an illustrative system architecture 10 according to certain embodiments of this disclosure. In some embodiments, the system architecture 10 may include a computing device 12 communicatively coupled to an exercise machine 100. The computing device 12 may also be communicatively coupled with a computing device 15 and a cloud-based computing system 16. As used herein, a cloud-based computing system refers, without limitation, to any remote or distal computing system accessed over a network link. Each of the computing device 12, computing device 15, and/or the exercise machine 100 may include one or more processing devices, memory devices, and network interface devices. In some embodiments, the computing device 12 may be included as part of the structure of the exercise machine 100. In some embodiments, the computing device 12 may be separate from the exercise machine 100. For example, the computing device 12 may be a smartphone, tablet, laptop, or the like.

The network interface devices may enable communication via a wireless protocol for transmitting data over short distances, such as Bluetooth, ZigBee, near field communication (NFC), etc. In some embodiments, the computing device 12 is communicatively coupled to the exercise machine 100 via Bluetooth. Additionally, the network interface devices may enable communicating data over long distances, and in one example, the computing device 12 may communicate with a network 20. Network 20 may be a public network (e.g., connected to the Internet via wired (Ethernet) or wireless (WiFi)), a private network (e.g., a local area network (LAN), wide area network (WAN), virtual private network (VPN)), or a combination thereof.

The computing device 12 may be any suitable computing device, such as a laptop, tablet, smartphone, or computer. The computing device 12 may include a display that is capable of presenting a user interface 18 of an application 17. The application 17 may be implemented in computer instructions stored on the one or more memory devices of the computing device 12 and executable by the one or more processing devices of the computing device 12. The application 17 may be a stand-alone application that is installed on the computing device 12 or may be an application (e.g., website) that executes via a web browser. The user interface 18 may present various screens to a user that enable the user to login, enter personal information (e.g., health information; a disease protocol prescribed by a physician, trainer, or caretaker; age; gender; activity level; bone density; weight; height; patient measurements; etc.), view an exercise plan, initiate an exercise in the exercise plan, view visual representations of left load measurements and right load measurements that are received from left load cells and right load cells during the exercise, view a weight in pounds that are pushed, lifted, or pulled during the exercise, view an indication when the user has almost reached a target threshold, view an indication when the user has exceeded the target thresholds, view an indication when the user has set a new personal maximum for a load measurement and/or pounds pushed, lifted, or pulled, view an indication when a load measurement exceeds a safety limit, view an indication to instruct the user to begin another exercise, view an indication that congratulates the user for completing all exercises in the exercise plan, and so forth, as described in more detail below. The computing device 12 may also include instructions stored on the one or more memory devices that, when executed by the one or more processing devices of the computing device 12, perform operations to control the exercise machine 100.

The computing device 15 may execute an application 21. The application 21 may be implemented in computer instructions stored on the one or more memory devices of the computing device 15 and executable by the one or more processing devices of the computing device 15. The application 21 may present a user interface 22 including various screens to a physician, trainer, or caregiver that enable the person to create an exercise plan for a user based on a treatment (e.g., surgery, medical procedure, etc.) the user underwent and/or injury (e.g., sprain, tear, fracture, etc.) the user suffered, view progress of the user throughout the exercise plan, and/or view measured properties (e.g., force exerted on portions of the exercise machine 100) of the user during exercises of the exercise plan. The exercise plan specific to a patient may be transmitted via the network 20 to the cloud-based computing system 16 for storage and/or to the computing device 12 so the patient may begin the exercise plan. The exercise plan may specifying one or more exercises that are available at the exercise machine 100.

The exercise machine 100 may be an osteogenic, muscular strengthening, isometric exercise and/or rehabilitation assembly. Solid state, static, or isometric exercise and rehabilitation equipment (e.g., exercise machine 100) can be used to facilitate osteogenic exercises that are isometric in nature and/or to facilitate muscular strengthening exercises. Such exercise and rehabilitation equipment can include equipment in which there are no moving parts while the user is exercising. While there may be some flexing under load, incidental movement resulting from the tolerances of interlocking parts, and parts that can move while performing adjustments on the exercise and rehabilitation equipment, these flexions and movements can comprise, without limitation, exercise and rehabilitation equipment from the field of isometric exercise and rehabilitation equipment.

The exercise machine 100 may include various load cells 110 disposed at various portions of the exercise machine 100. For example, one or more left load cells 110 may be located at one or more left feet plates or platforms, and one or more right load cells may be located at one or more right feet plates or platforms. Also, one or more left load cells may be located at one or more left handles, and one or more right load cells may be located at one or more right handles. Each exercise in the exercise system may be associated with both a left and a right portion (e.g., handle or foot plate) of the exercise machine 100. For example, a leg-press-style exercise is associated with a left foot plate and a right foot plate. The left load cell at the left foot plate and the right load cell at the right foot plate may independently measure a load added onto the left foot plate and the right foot plate, respectively, and transmit the left load measurement and the right load measurement to the computing device 12. The load added onto the load cells 110 may represent an amount of weight added onto the load cells. In some embodiments, the load added onto the load cells 110 may represent an amount of force exerted by the user on the load cells. Accordingly, the left load measurement and the right load measurement may be used to present a left force (e.g., in Newtons) and a right force (e.g., in Newtons). The left force and right force may be totaled and converted into a total weight in pounds for the exercise. Each of the left force, the right force, and/or the total weight in pounds may be presented on the user interface 18.

In some embodiments, the cloud-based computing system 16 may include one or more servers 28 that form a distributed, grid, and/or peer-to-peer (P2P) computing architecture. Each of the servers 28 may include one or more processing devices, memory devices, data storage, and/or network interface devices. The servers 28 may be in communication with one another via any suitable communication protocol. The servers 28 may store profiles for each of the users that use the exercise machine 100. The profiles may include information about the users such as one or more disease protocols, one or more exercise plans, a historical performance (e.g., loads applied to the left load cell and right load cell, total weight in pounds, etc.) for each type of exercise that can be performed using the exercise machine 100, health, age, race, credentials for logging into the application 17, and so forth.

In some embodiments, the cloud-based computing system 16 may include a training engine 50 and/or an artificial intelligence engine 65. The cloud-based computing system 16 may include one or more servers 28 that execute the artificial intelligence engine 65 that uses one or more machine learning models 60 to perform at least one of the embodiments disclosed herein. In some embodiments, the training engine 50 may be included as part of the artificial intelligence engine 65 and the artificial intelligence engine 65 may execute the training engine 50. In some embodiments, the artificial intelligence engine 65 may use the training engine 50 to generate the one or more machine learning models 60.

The artificial intelligence engine 65, the training engine 50, and/or the one or more machine learning models 60 may be communicatively coupled to the servers 28 or may be included in one of the servers 28. In some embodiments, the artificial intelligence engine 65, the training engine 50, and/or the machine learning models 60 may be included in the computing device 12.

The one or more of machine learning models 60 may refer to model artifacts created, using training data that includes training inputs and corresponding target outputs (correct answers for respective training inputs), by the artificial intelligence engine 65 and/or the training engine 50. The training engine 50 may find patterns in the training data that map the training input to the target output (the answer to be predicted), and provide the machine learning models 60 that capture these patterns. As described in more detail below, the set of machine learning models 60 may be composed of, e.g., a single level of linear or non-linear operations (e.g., a support vector machine (SVM)) or may be a deep network, i.e., a machine learning model composed of multiple levels of non-linear operations. Examples of deep networks are neural networks, including convolutional neural networks, recurrent neural networks with one or more hidden layers, and fully connected neural networks.

In some embodiments, the training data may include various inputs (e.g., a physical activity goal, range of motion of users, user-reported pain level of users, user-reported difficulty levels of exercises, exercise information, levels of attainment, characteristics of users (e.g., age, weight, height, gender, procedures performed, condition of user, goals for outcomes of exercising, etc.), performance measurements, and the like) and mapped outputs. The mapped outputs may include an exercise plan composed on various exercise sessions each including various exercises, schedule of the exercise sessions, etc. In some embodiments, the training data may include other inputs (e.g., state of the exercise session, exercise, exercise machine 100; progress of the user; events; characteristics of the user; measurements received from sensors, etc.) and other mapped outputs. The other mapped outputs may include comorbidity information pertaining to the user. The other mapped outputs may further include multimedia (e.g., video/audio) clips or segments for a virtual coach to speak, graphic images, video, and the like to be presented on the user interface 18 of the computing device 12 before, during, or after the user performs the exercises. The virtual coach may be implemented in computer instructions as part of application 17 executing on the computing device 12. The virtual coach may be driven and controlled by artificial intelligence (e.g., via one or more machine learning models 60). For example, the machine learning model 60 may be trained to implement the virtual coach. Further, the training data may include inputs pertaining to user feedback and/or progress of the user and outputs pertaining to a persona for the virtual coach to implement.

The training data may include inputs of the progress of the user (e.g., completion of an exercise) and output various incentives, rewards, and/or certificates. The training data may include inputs of the progress of the user and/or the exercise plan and may output notifications pertaining to the progress and/or the exercise plan. The training data may include inputs of user-reported pain levels, user-reported difficulty of exercises, difficulty levels of the exercises, etc. and may include mapped outputs of modifying the exercise plan (e.g., removing an exercise, switching an exercise or to another exercise, adding an exercise, modifying an exercise session, adding an exercise session, removing an exercise session, etc.). The training data may include one or more of measurements from sensors and/or of characteristics of users and may further include mapped outputs of control instructions that modify operating parameters of the exercise device 100, as described further herein. Further, the training data may include one or more user inputs and mapped outputs of a virtual character to present on a user interface, as described further herein. Further, the training data may include one or more data outputs (e.g., user feedback) and mapped outputs related to controlling an aspect of the exercise device 100. Further, the training data may include one or more measurements and mapped outputs related to modifying, on a user interface, various icons in a manner that positions or repositions the various icons relative to graphical elements that represent domains associated with an exercise plan, as described further herein. Further, the training data may include onboarding data and/or an onboarding protocol, as well as mapped outputs of an exercise plan, as described further herein. The machine learning model 60 may be trained using any and/or all of the training data.

In some embodiments, the training engine 50 may train the machine learning models 60 to output an exercise plan, wherein such plan may include a schedule of exercise sessions and selected exercises for each of the exercise sessions. Based on the inputs described herein, the trained machine learning model 60 may select the exercises by filtering a set of exercises included in a tagged data structure (e.g., data source). The machine learning model 60 may be trained to control the virtual coach executing on the computing device 12. The machine learning model 60 may also be trained to provide incentives, rewards, and/or certificates to the user. The machine learning model 60 may also be trained to modify the exercise plan and/or directly or indirectly control the exercise machine 100 based on the progress of the user and/or feedback of the user (e.g., indications of a difficulty level of an exercise). For example, if the user indicates an exercise is too easy, the machine learning model 60 may choose a new intensity for the exercise and the cloud-based computing system 16 may distally control the exercise machine 100 by increasing the intensity. Any suitable number of machine learning models 60 may be used. For example, separate machine learning models 60 may be used for each respective function described above, and the machine learning models 60 may be linked such that the output from one machine learning model 60 may be input into another machine learning model 60.

The cloud-based computing system may include a data source 67 that stores the training data for the training engine 50 and/or the artificial intelligence engine 65 to use to train the one or more machine learning models 60. The data source may include exercises, physical activity goals, levels of attainment, body portions targeted by exercises, weights and/or parameters used to configure a prioritization of certain levels of attainment throughout an exercise schedule, comorbidity information, health-related information, audio segments, video segments, motivational quotations, and so forth. The data source 67 may include various tags and/or keys (e.g., primary, foreign, etc.) to associate items of the data with each other in the data source 67. The data source 67 may be a relational database, a pivot table, or any suitable type of data structure configured to store data used for any of the operations described herein.

FIGS. 2-8 illustrates one or more embodiments of an osteogenic, isometric exercise and rehabilitation assembly 101. An aspect of the disclosure includes an isometric exercise and rehabilitation assembly 101. The assembly 101 can include a frame 102. The assembly 101 can further include one or more pairs of load handles 104, 106, 108 (e.g., three shown) supported by the frame 102. Each load handle in one of the pairs of load handles 104, 106, 108 can be symmetrically spaced from each other relative to a vertical plane of the assembly 101. For example, the vertical plane can bisect the assembly 101 in a longitudinal direction.

During exercise, a user can grip and apply force to one of the pairs of load handles 104, 106, 108. The term "apply force" can include a single force, more than one force, a range of forces, etc. and may be used interchangeably with "addition of load". Each load handle in the pairs of load handles 104, 106, 108 can include at least one load cell 110 for separately and independently measuring a force applied to, or a load added onto, respective load handles. Further, each foot plate 118 (e.g., a left foot plate and a right foot plate) can include at least one load cell 110 for separately and independently measuring a force applied to, or a load added onto, respective foot plates.

The placement of a load cell 110 in each pair of load handles 104, 106, 108 and/or feet plates 118 can provide the ability to read variations in force applied between the left and right sides of the user. This allows a user or trainer to understand relative strength. This is also useful in understanding strength when recovering from an injury.

In some embodiments, the assembly 101 further can include the computing device 12. One or more of the load cells 110 can be individually in electrical communication with the computing device 12 either via a wired or wireless connection. In some embodiments, the user interface 18 presented via a display of the computing device 12 may indicate how to perform an exercise, how much force is being applied, a target force to be applied, historical information for the user about how much force they applied at prior sessions, comparisons to averages, etc., as well as additional information, recommendations, notifications, and/or indications described herein.

In some embodiments, the assembly 101 further includes a seat 112 supported by the frame 102 in which a user sits while applying force to the load handles and/or feet plates. In some embodiments, the seat 112 can include a support such as a backboard 114. In some embodiments, the position of the seat 112 is adjustable in a horizontal and/or vertical dimension. In some embodiments, the angle of the seat 112 is adjustable. In some embodiments, the angle of the backboard 114 is adjustable. Examples of how adjustments to the seat 112 and backboard 114 can be implemented include, but are not limited to, using telescoping tubes and pins, hydraulic pistons, electric motors, etc. In some embodiments, the seat 112 can further include a fastening system 116 (FIG. 7), such as a seat belt, for securing the user to the seat 112.

In one example, the seat 112 can include a base 113 that is slidably mounted to a horizontal rail 111 of the frame 102. The seat 112 can be selectively repositionable and secured as indicated by the double-headed arrow. In another example, the seat 112 can include one or more supports 117 (e.g., two shown) that are slidably mounted to a substantially vertical rail 115 of the frame 102. The seat 112 can be selectively repositionable and secured as indicated by the double-headed arrow.

In some embodiments, a pair of feet plate 118 can be located angled toward and in front of the seat 112. The user can apply force to the feet plate 118 (FIG. 5) while sitting in the seat 112 during a leg-press-style exercise. The leg-press-style exercise can provide or enable osteogenesis, bone growth or bone density improvement for a portion of the skeletal system of the user. Further, the leg-press-style exercise can provide or enable muscular hypertrophy for one or more muscles of the user. In a leg-press-style exercise, the user can sit in the seat 112, place their feet on respective feet plates 118, and push on the pair of feet plate 118 using their legs.

In some embodiments, adjustments can be made to the position of the pair of feet plate 118. For example, these adjustments can include the height of the pair of feet plate 118, the distance between the pair of feet plate 118 and the seat 112, the distance between each handle of the pair of feet plate 118, the angle of the pair of feet plate 118 relative to the user, etc. In some embodiments, to account for natural differences in limb length or injuries, each foot plate of the pair of feet plate 118 can be adjusted separately.

In some embodiments, a first pair of load handles 104 can be located above and in front of the seat 112. The user can apply force to the load handles 104 (FIG. 7) while being constrained in the seat 112 by the fastening system 116 in a core-pull-style exercise. The core-pull-style exercise can provide or enable osteogenesis, bone growth or bone density improvement for a portion of the skeletal system of the user. Further, the core-pull-style exercise can provide or enable muscular hypertrophy for one or more muscles of the user. In a core-pull-style exercise, while the lower body of the user is restrained from upward movement by the fastening system 116, the user can sit in the seat 112, apply the fastening system 116, hold the first pair of load handles 104, and pull on the first pair of load handles 104 using their arms.

In some embodiments, adjustments can be made to the position of the first pair of load handles 104. For example, these adjustments can include the height of the first pair of load handles 104, the distance between the first pair of load handles 104 and the seat 112, the distance between each handle of the first pair of load handles 104, the angle of the first load handles 104 relative to the user, etc. In some embodiments, to account for natural differences in limb length or injuries, each handle of the first pair of load handles 104 can be adjusted separately.

In one example, the first pair of load handles 104 can include a sub-frame 103 that is slidably mounted to a vertical rail 105 of the frame 102. The first pair of load handles 104 can be selectively repositionable and secured as indicated by the double-headed arrow.

In some embodiments, a second pair of load handles 106 can be spaced apart from and in the front of the seat 112. While seated (FIG. 6), the user can apply force to the second pair of load handles 106 in a chest-press-style exercise. The chest-press-style exercise can provide or enable osteogenesis, bone growth or bone density improvement for another portion of the skeletal system of the user. Further, the chest-press-style exercise can provide or enable muscular hypertrophy for one or more muscles of the user. In a chest-press-style exercise, the user can sit in the seat 112, hold the second pair of load handles 106, and push against the second pair of load handles 106 with their arms.

In some embodiments, adjustments can be made to the position of the second pair of load handles 106. These adjustments can include the height of the second pair of load handles 106, the distance between the second pair of load handles 106 and the seat 112, the distance between each handle of the second pair of load handles 106, the angle of the second load handles 106 relative to the user, etc. In some embodiments, to account for natural differences in limb length or injuries, each handle of the second pair of load handles 106 can be adjusted separately.

In one example, the second pair of load handles 106 can include the sub-frame 103 that is slidably mounted to the vertical rail 105 of the frame 102. The sub-frame 103 can be the same sub-frame 103 provided for the first pair of load handles 104, or a different, independent sub-frame. The second pair of load handles 106 can be selectively repositionable and secured as indicated by the double-headed arrow.

In some embodiments (FIG. 8), a third pair of load handles 108 can be located immediately adjacent the seat 112, such that the user can stand and apply force in a suitcase-lift-style exercise. The suitcase-lift-style exercise can provide or enable osteogenesis, bone growth or bone density improvement for still another portion of the skeletal system of the user. Further, the suitcase-lift-style exercise can provide or enable muscular hypertrophy for one or more muscles of the user. Examples of the third pair of load handles 108 can extend horizontally along a pair of respective axes that are parallel to the vertical plane. The third pair of load handles 108 can be horizontally co-planar, such that a user can apply force to them in a suitcase-lift-style exercise. In the suitcase-lift-style exercise, the user can stand on the floor or a horizontal portion of the frame 102, bend their knees, grip the third pair of load handles 108, and extend their legs to apply an upward force to the third pair of load handles 108.

In some embodiments, adjustments can be made to the position of the third pair of load handles 108. These adjustments can include the height of the third pair of load handles 108, the distance between the third pair of load handles 108 and the seat 112, the distance between each handle of the third pair of load handles 108, the angle of the third load handles 108 relative to the user, etc. In some embodiments, to account for natural differences in limb length or injuries, each handle of the third pair of load handles 108 can be adjusted separately.

In one example, each load handle 108 of the third pair of load handles 108 can include a sub-frame 109 that is slidably mounted in or to a vertical tube 107 of the frame 102. Each load handle 108 of the third pair of load handles 108 can be selectively repositionable and secured as indicated by the double-headed arrows.

In other embodiments (not shown), the third pair of load handles 108 can be reconfigured to be coaxial and located horizontally in front of the user along an axis that is perpendicular to the vertical plane. The user can apply force to the third pair of load handles 108 in a deadlift-style exercise. Like the suitcase-lift-style exercise, the deadlift-style exercise can provide or enable osteogenesis, bone growth or bone density improvement for a portion of the skeletal system of the user. Further, the deadlift-style exercise can provide or enable muscular hypertrophy for one or more muscles of the user. In the deadlift-style exercise, the user can stand on the floor or a horizontal portion of the frame 102, bend their knees, hold the third pair of load handles 108 in front of them, and extend their legs to apply an upward force to the third pair of load handles 108. In some embodiments, the third pair of load handles 108 can be adjusted (e.g., rotated) from the described coaxial position used for the deadlift-style exercise, to the parallel position (FIGS. 7, 8) used for the suitcase lift-style exercise. The third pair of load handles 108, or others, can be used in a grip strengthening-style exercise to improve strength in the muscles of the hand and forearm.

Figure 9:
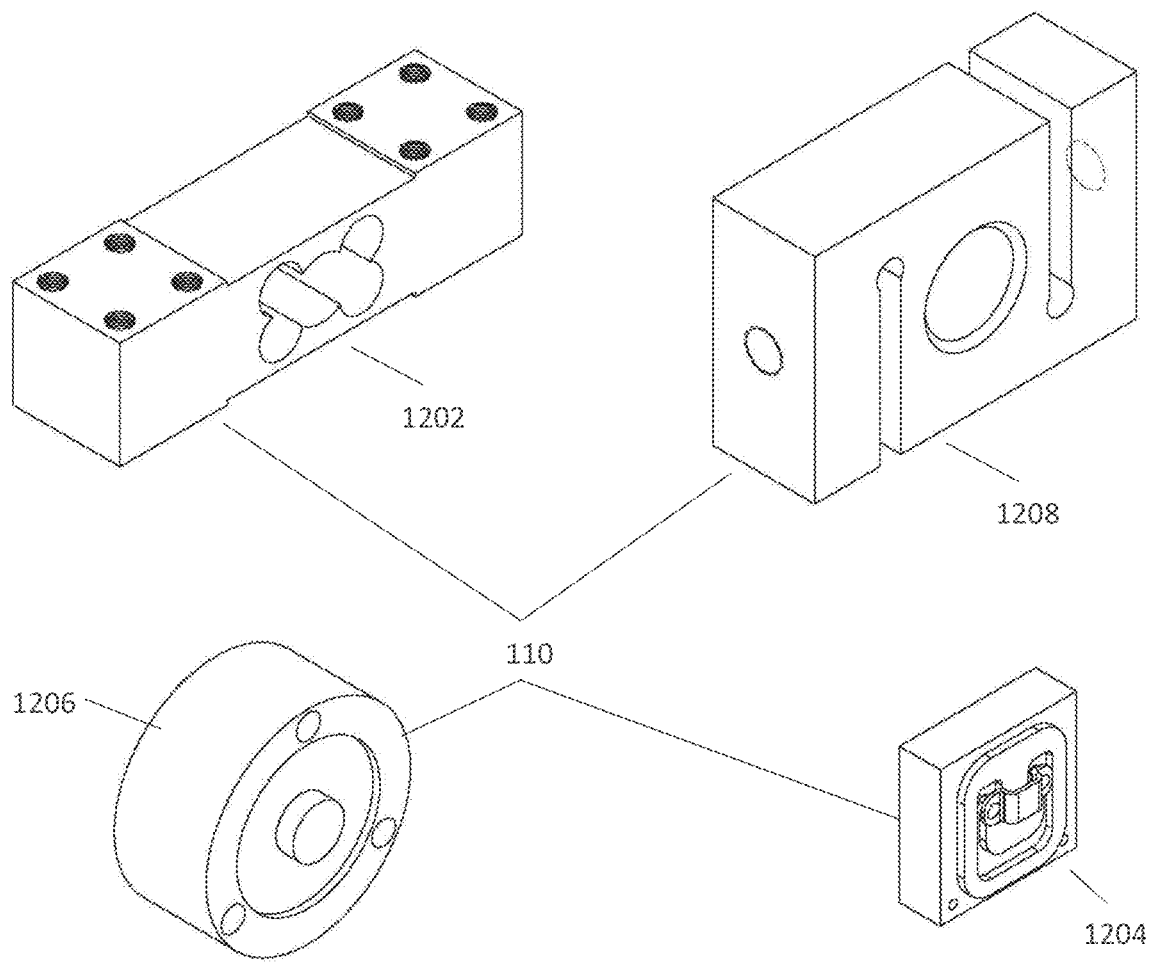
FIG. 9 illustrates four examples of load cells that can be used in the isometric exercise assembly.

FIG. 9 depicts several options for the load cells 110. In some embodiments, the load cells 110 can be piezoelectric load cells, such as PACEline CLP Piezoelectric Subminiature Load Washers. In other embodiments, the load cells 110 can be hydraulic load cells, such as NOSHOK hydraulic load cells. In some versions, the load cells 110 can include strain gauges. Embodiments of the strain gauges can be bending-type strain gauges, such as Omega SGN-4/20-PN 4 mm grid, 20 ohm nickel foil resistors. Other examples of the strain gauges can be double-bending-type strain gauges 1202, such as Rudera Sensor RSL 642 strain gauges. Still other embodiments of the strain gauges can be half-bridge-type strain gauges 1204, such as Onyehn 4pcs 50 kg Human Scale Load Cell Resistance Half-bridge/Amplifier Strain Weight Sensors with 1pcs HX711 AD Weight Modules for Arduino DIY Electronic Scale strain gauges. In some embodiments, the strain gauges can be S-type strain gauges 1206, such as SENSORTRONICS S-TYPE LOAD CELL 60001 strain gauges. Additionally, the strain gauges can be button-type strain gauges 1208, such as Omega LCGB-250 250 lb Capacity Load Cells. Naturally, the load cells 110 can comprise combinations of these various examples. The embodiments described herein are not limited to these examples.

Figure 10:
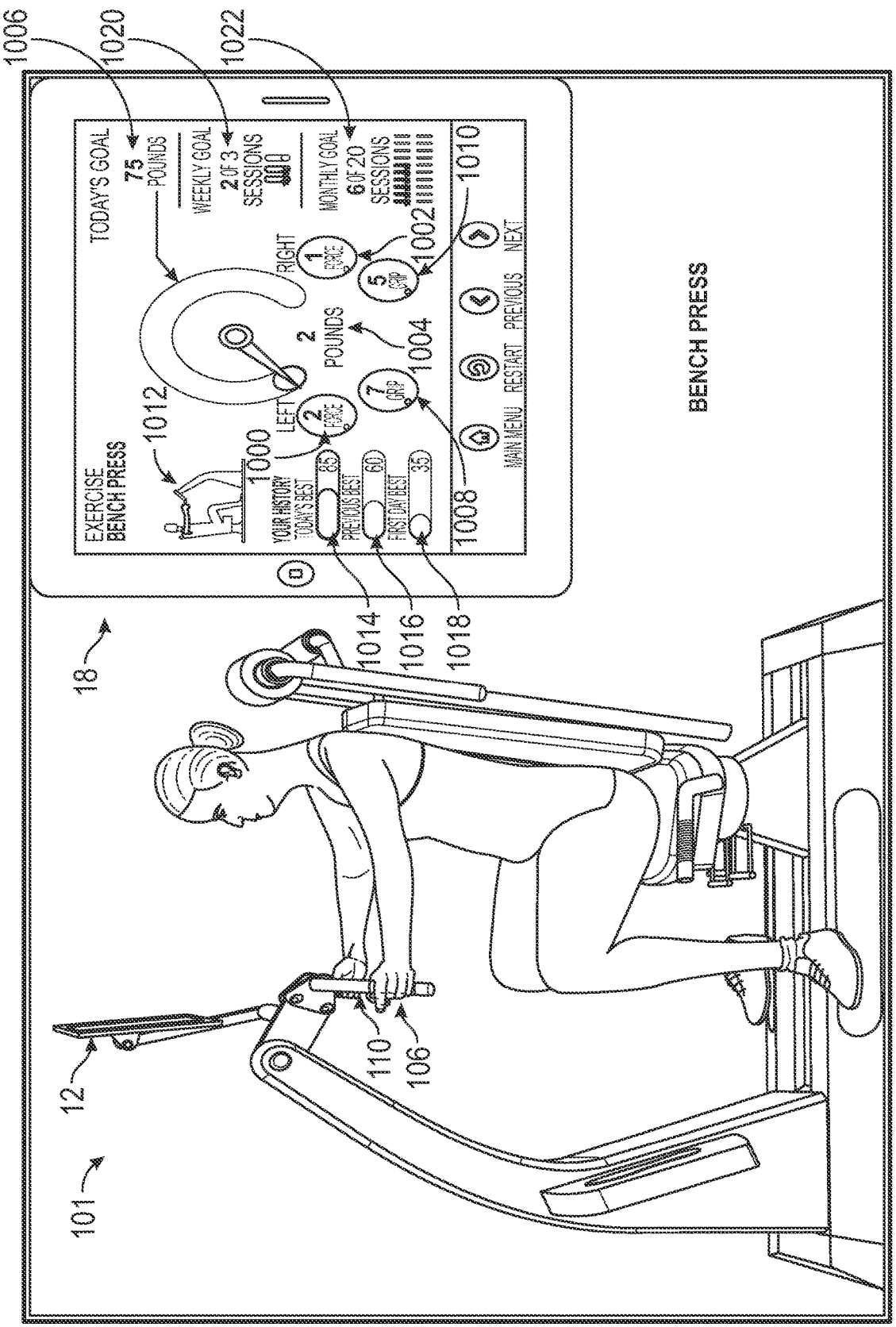
FIG. 10 illustrates a side view of a second embodiment of the isometric exercise and rehabilitation assembly with the user performing a chest-press-style exercise and a user interface presenting information to the user.

FIGS. 10-13 illustrate views of a second embodiment of the isometric exercise and rehabilitation assembly 101. FIG. 10 illustrates a side view of the second embodiment of the isometric exercise and rehabilitation assembly 101 with the user performing a chest-press-style exercise and a user interface 18 presenting information to the user. As depicted, the user is the gripping second pair of load handles 106. A left load cell 110 and a right load cell 110 may be located at a left load handle 106 and a right load handle 106, respectively, in the second pair of load handles 106. The user may push on the second pair of load handles 106 to add load to the left load cell 110 and the right load cell 110. The left load cell 110 may transmit a left load measurement to the computing device 12, and the right load cell 110 may transmit a right load measurement to the computing device 12. The computing device 12 may use the load measurements to provide various real-time feedback on the user interface 18 as the user performs the chest-press-style exercise.

In general, the user interface 18 may present real-time visual feedback of the current load measurements or the current forces corresponding to the load measurements, a weight in pounds associated with the load measurements, incentive messages that encourage the user to exceed target thresholds (e.g., to trigger osteogenesis and/or muscular hypertrophy) and/or set personal records for maximum loads, historical performance of the user performing the exercise, and/or scripted prompts that display images of one or more body portions indicating proper technique for performing the exercise. The control system may provide various multimedia (visual, audio) and/or haptic feedback to encourage the user to exceed their target thresholds.

Initially, when the user has not added load onto any portion of the exercise machine 100 including one or more load cells 110, the computing device 12 may be operating in an idle mode. During the idle mode, the computing device 12 may be receiving load measurements at a first frequency from each data channel associated with an exercise. For example, there may be four data channels, one for each of a chest-press-style exercise, a leg-press-style exercise, a suitcase-lift-style exercise, and a pulldown-style exercise. Although four data channels are described for explanatory purposes, it should be understood that there may be any suitable number of data channels, where "any" refers to one or more. Each data channel may provide load measurements to the computing device 12 from a respective left load cell and a respective right load cell that are located at the portion of the exercise machine 100 where the user pushes or pulls for the respective exercises. The user interface 18 may present the load measurement from each left and right load cells (e.g., 8 load measurements for the 4 data channels associated with the 4 exercises). Further, any target thresholds and/or safety limits for the user performing the exercises may be presented on the user interface 18 during the idle mode. For example, a left target threshold, a right target load threshold, a safety limit, and/or a total weight target threshold for each of the exercises may be presented on the user interface 18 during the idle mode.

If the computing device 12 detects a minimum threshold amount of load (e.g., at least 10 pound-force (lbf)) added onto any of the load cells, the computing device switches from an idle mode to an exercise mode. The data channel including the load cell that sent the detected load measurement may be set to active by the computing device 12. Further, the computing device 12 may set the other data channels to inactive and may stop receiving load measurements from the load cells corresponding to the inactive data channels. The computing device 12 may begin reading data from the load cells at the active data channel at a second frequency higher (e.g., high frequency data collection) than the first frequency when the computing device 12 was operating in the idle mode. Further, the user interface 18 may switch to presenting information pertaining to the exercise associated with the active data channel and stop presenting information pertaining to the exercises associated with the inactive data channels.

For example, the user may grip the second pair of handles 106 and apply force. The computing device 12 may detect the load from the load cells 110 located at the second pair of handles 106 and may set the data channel associated with the chest-press-style exercise to active to begin high frequency data collection from the load cells 110 via the active data channel.

As depicted, the user interface 18 presents a left load measurement 1000 as a left force and a right load measurement 1002 as a right force in real-time or near real-time as the user is pressing on the second pair of handles 106. The values of the forces for the left load measurement 1000 and the right load measurement 1002 are presented. There are separate visual representations for the left load measurement 1000 and the right load measurement 1002. In some embodiments, these load measurements 1000 and 1002 may be represented in a bar char, line chart, graph, or any suitable visual representation. In some embodiments, a left target threshold and a right target threshold for the user may be presented on the user interface 18. In some embodiments, there may be more than one left target threshold and more than one right target threshold. For example, the left target thresholds may relate to an osteogenesis target threshold determined using a user's disease protocol and/or a muscular strength target threshold determined using a historical performance of the user for a particular exercise. The right target thresholds may relate to an osteogenesis target threshold determined using a user's disease protocol and/or a muscular strength target threshold determined using a historical performance of the user for a particular exercise. For example, if the user fractured their left arm and is rehabilitating the left arm, but the user's right arm is healthy, the left osteogenesis target threshold may be different from the right osteogenesis target threshold.

If the left load measurement 1000 exceeds any of the left target thresholds, an indication (e.g., starburst) may be presented on the user interface 18 indicating that the particular left target threshold has been exceeded and/or osteogenesis and/or muscular hypertrophy has been triggered in one or more portions of the body. If the right load measurement 1002 exceeds any of the right target thresholds, an indication (e.g., starburst) may be presented on the user interface 18 indicating that the particular right target threshold has been exceeded and/or osteogenesis and/or muscular hypertrophy has been triggered in another portion of the body. Further, if either or both of the left and right target thresholds are exceeded, the indication may indicate that the exercise is complete and a congratulatory message may be presented on the user interface 18. In some embodiments, another message may be presented on the user interface 18 that encourages the user to continue adding load to set a new personal maximum left load measurement and/or right load measurement for the exercise.

In some embodiments, there may be a single target threshold to which both the left load measurement and the right load measurement are compared. If either of the left or right load measurement exceed the single target threshold, the above-described indication may be presented on the user interface 18.

In some embodiments, there may be a single safety limit to which the left and right load measurements are compared. The single safety limit may be determined based on the user's disease protocol (e.g., what type of disease the user has, a severity of the disease, an age of the user, the height of the user, the weight of the user, what type of injury the user sustained, what type of surgery the user underwent, the portion of the body affected by the disease, the exercise plan to rehabilitate the user's body, instructions from a caregiver, etc.). If either or both of the left and right load measurements exceed the single safety limit, an indication may be presented on the user interface 18. The indication may warn the user that the safety limit has been exceeded and recommend to reduce the amount of load added to the load cells 110 associated with the exercise being performed by the user.

In some embodiments, more than one safety limit may be used. For example, if the user is rehabilitating a left leg, but a right leg is healthy, there may be a left safety limit that is determined for the left leg based on the user's disease protocol and there may be a right safety limit for the left leg determined based on the user's disease protocol. The left load measurement may be compared to the left safety limit, and the right load measurement may be compared to the right safety limit. If either or both the left load measurement and/or the right load measurement exceed the left safety limit and/or the right safety limit, respectively, an indication may be presented on the user interface 18. The indication may warn the user that the respective safety limit has been exceeded and recommend to reduce the amount of load added to the load cells 110 associated with the exercise being performed by the user.

Further, a total weight 1004 in pounds that is determined based on the left and right load measurements is presented on the user interface 18. The total weight 1004 may dynamically change as the user adds load onto the load cells 110. A target weight 1006 for the exercise for the current day is also presented. This target weight 1006 may be determined based on the user's historical performance for the exercise. If the total weight 1004 exceeds the target weight 1006, an indication (e.g., starburst) may be presented on the user interface 18 indicating that osteogenesis and/or muscular hypertrophy has been triggered. Further, the indication may indicate that the exercise is complete and a congratulatory message may be presented on the user interface 18. In some embodiments, another message may be presented on the user interface 18 that encourages the user to continue adding load to set a new personal maximum record for the exercise.

Additionally, the user interface 18 may present a left grip strength 1008 and a right grip strength 1010. In some embodiments, the left grip strength and the right grip strength may be determined based on the left load measurement and the right load measurement, respectively. Numerical values representing the left grip strength 1008 and the right grip strength 1010 are displayed. Any suitable visual representation may be used to present the grip strengths (e.g., bar chart, line chart, etc.). The grip strengths may only be presented when the user is performing an exercise using handles.

The user interface 18 may also present a prompt 1012 that indicates the body position the user should be in to perform the exercise, as well as indicate which body portions will be targeted by performing the exercise. The user interface 18 may present other current and historical information related to the user performing the particular exercise. For example, the user interface 18 may present a visual representation 1014 of the user's maximum weight lifted, pressed, pulled, or otherwise exerted force for the day or a current exercise session. The user interface 18 may present a visual representation 1016 of the user's previous maximum weight lifted, pressed, pulled, or otherwise exerted force. The user interface 18 may present a visual representation 1018 of the user's maximum weight lifted, pressed, pulled, or otherwise exerted force the first time the user performed the exercise. The user interface 18 may present one or more visual representations 1020 for a weekly goal including how many sessions should be performed in the week and progress of the sessions as they are being performed. The user interface 18 may present a monthly goal including how many sessions should be performed in the month and progress of the sessions as they are being performed. Additional information and/or indications (e.g., incentivizing messages, recommendations, warnings, congratulatory messages, etc.) may be presented on the user interface 18, as discussed further below.

Figure 11:
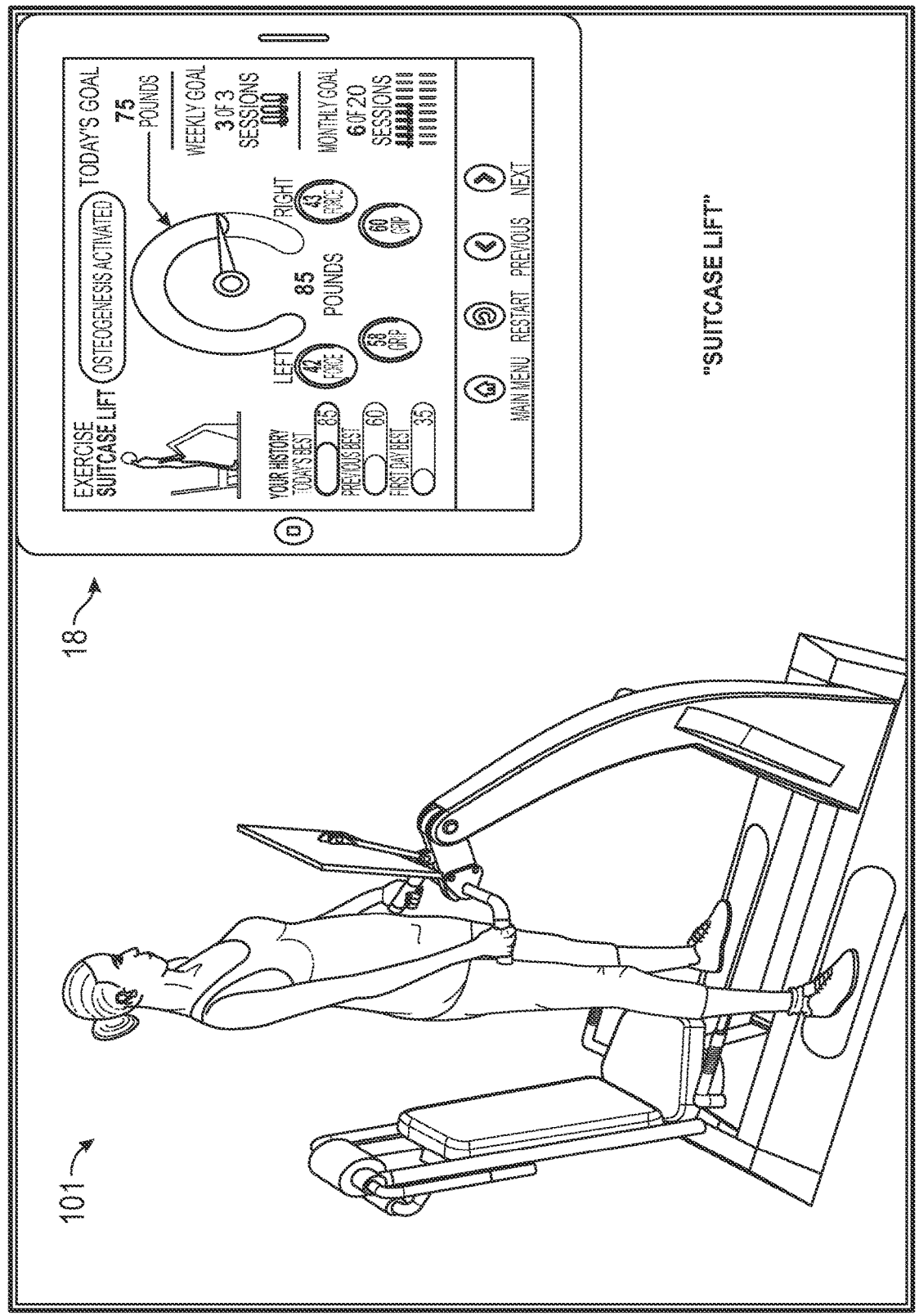
FIG. 11 illustrates a side view of the second embodiment of the isometric exercise and rehabilitation assembly with a user performing a suitcase-lift-style exercise and a user interface presenting information to the user.

FIG. 11 illustrates a side view of the second embodiment of the isometric exercise and rehabilitation assembly 101 with a user performing a suitcase-lift-style exercise and the user interface 18 presenting information to the user. The user interface 18 may present similar types of information as discussed above with regards to FIG. 10, but the information in the user interface 18 in FIG. 11 may be tailored for the suit-case-lift-style exercise. That is, the data channel for the suitcase-lift-style exercise may be set to active when the computing device 12 detects load measurements from load cells corresponding to the suitcase-lift-style exercise, and the computing device 12 may present the various visual representations described with regards to FIG. 10 on the user interface 18 in FIG. 11 based on at least the load measurements for the suitcase-lift-style exercise.

Figure 12:
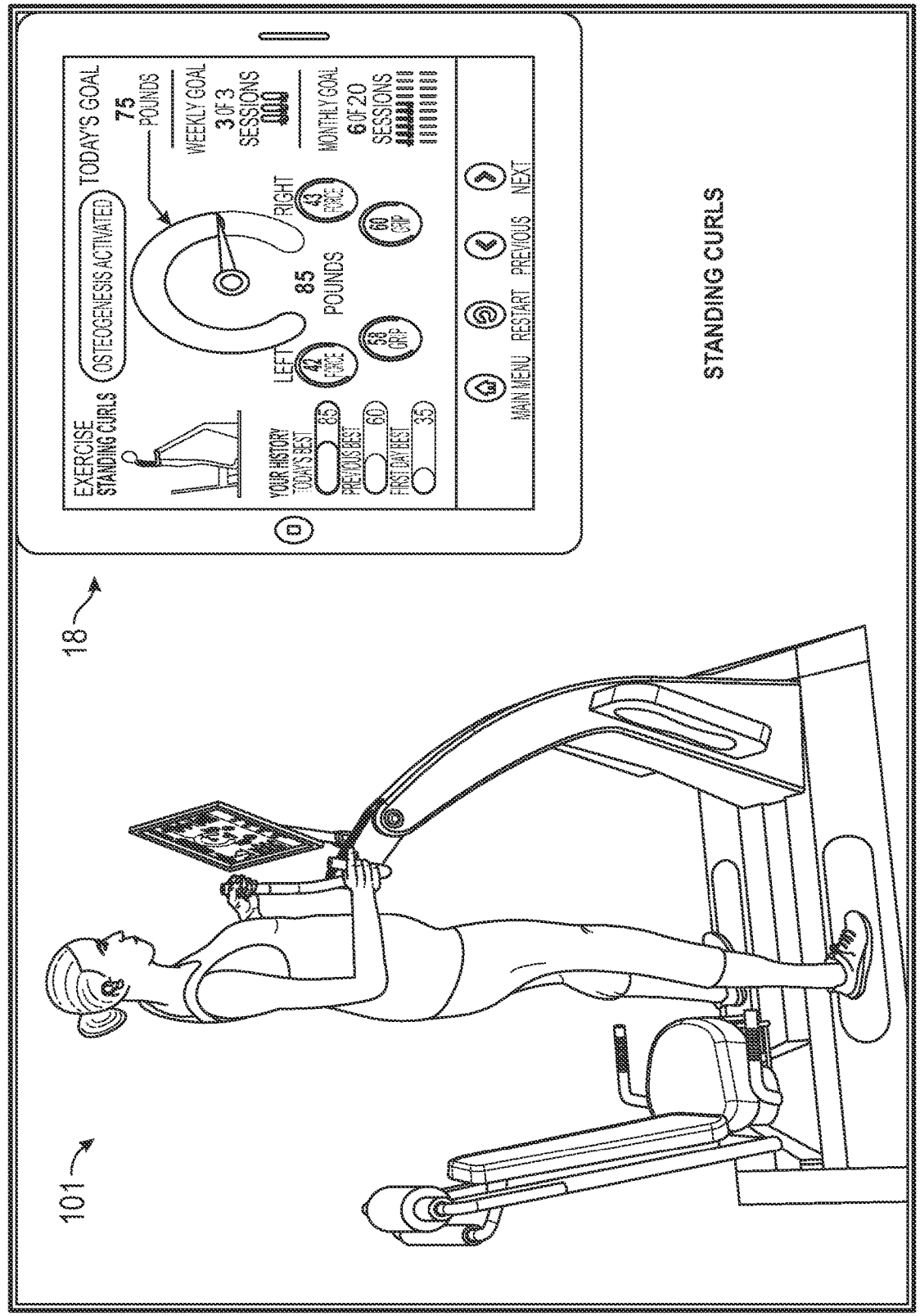
FIG. 12 illustrates a side view of the second embodiment of the isometric exercise and rehabilitation assembly with a user performing an arm-curl-style exercise and a user interface presenting information to the user.

FIG. 12 illustrates a side view of the second embodiment of the isometric exercise and rehabilitation assembly 101 with a user performing an arm-curl-style exercise and a user interface presenting information to the user. The user interface 18 may present similar types information as discussed above with regards to FIG. 10, but the information in the user interface 18 in FIG. 12 may be tailored for the arm-curl-style exercise. That is, the data channel for the arm-curl-style exercise may be set to active when the computing device 12 detects load measurements from load cells corresponding to the arm-curl-style exercise, and the computing device 12 may present the various visual representations described with regards to FIG. 10 on the user interface 18 in FIG. 12 based on at least the load measurements for the arm-curl-style exercise.

Figure 13:
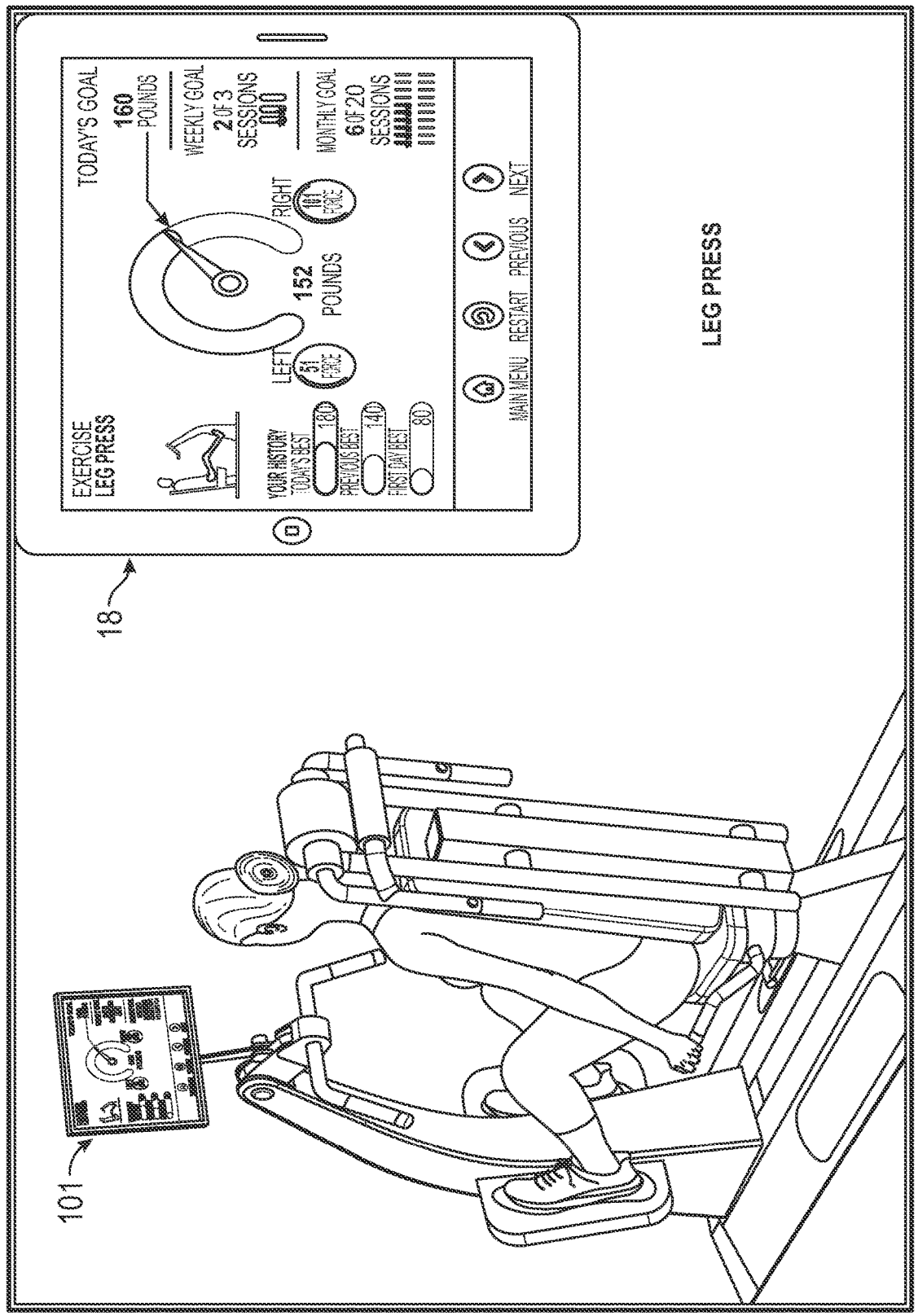
FIG. 13 illustrates a side view of the second embodiment of the isometric exercise and rehabilitation assembly with a user performing a leg-press-style exercise and a user interface presenting information to the user.

FIG. 13 illustrates a side view of the second embodiment of the isometric exercise and rehabilitation assembly 101 with a user performing a leg-press-style exercise and a user interface presenting information to the user. The user interface 18 may present similar types information as discussed above with regards to FIG. 10, but the information in the user interface 18 in FIG. 13 may be tailored for the leg-press-style exercise. That is, the data channel for the leg-press-style exercise may be set to active when the computing device 12 detects load measurements from load cells corresponding to the leg-press-style exercise, and the computing device 12 may present the various visual representations described with regards to FIG. 10 on the user interface 18 in FIG. 13 based on at least the load measurements for the leg-press-style exercise.

Figure 14:
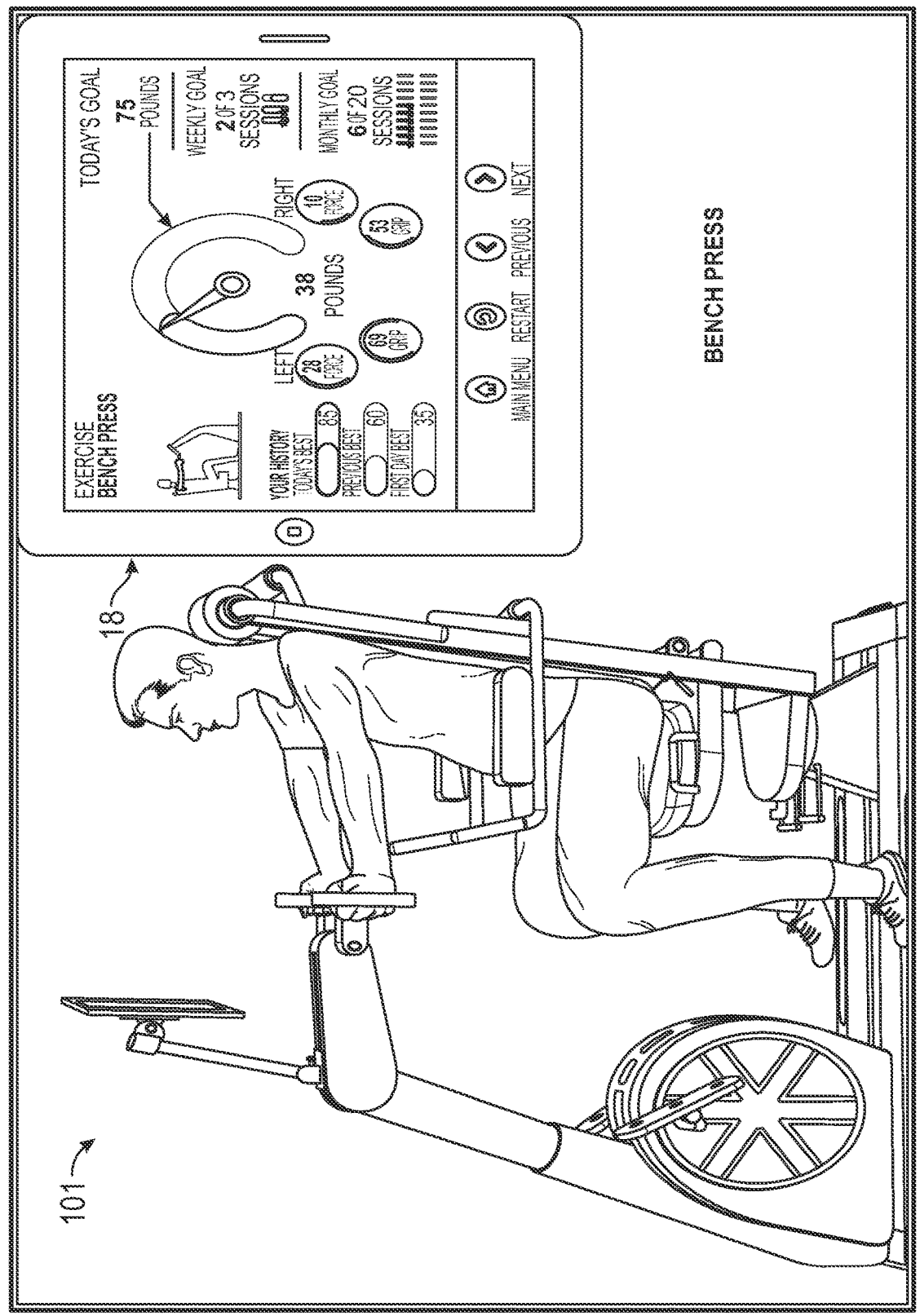
FIG. 14 illustrates a side view of a third embodiment of the isometric exercise and rehabilitation assembly with the user performing a chest-press-style exercise and a user interface presenting information to the user.

FIGS. 14-18 illustrate views of a third embodiment of the isometric exercise and rehabilitation assembly 101. FIG. 14 illustrates a side view of the third embodiment of the isometric exercise and rehabilitation assembly 100 with the user performing a chest-press-style exercise and a user interface 18 presenting information to the user. The user interface 18 in FIG. 14 may present similar types of information as discussed above with regards to FIG. 10.

Figure 15:
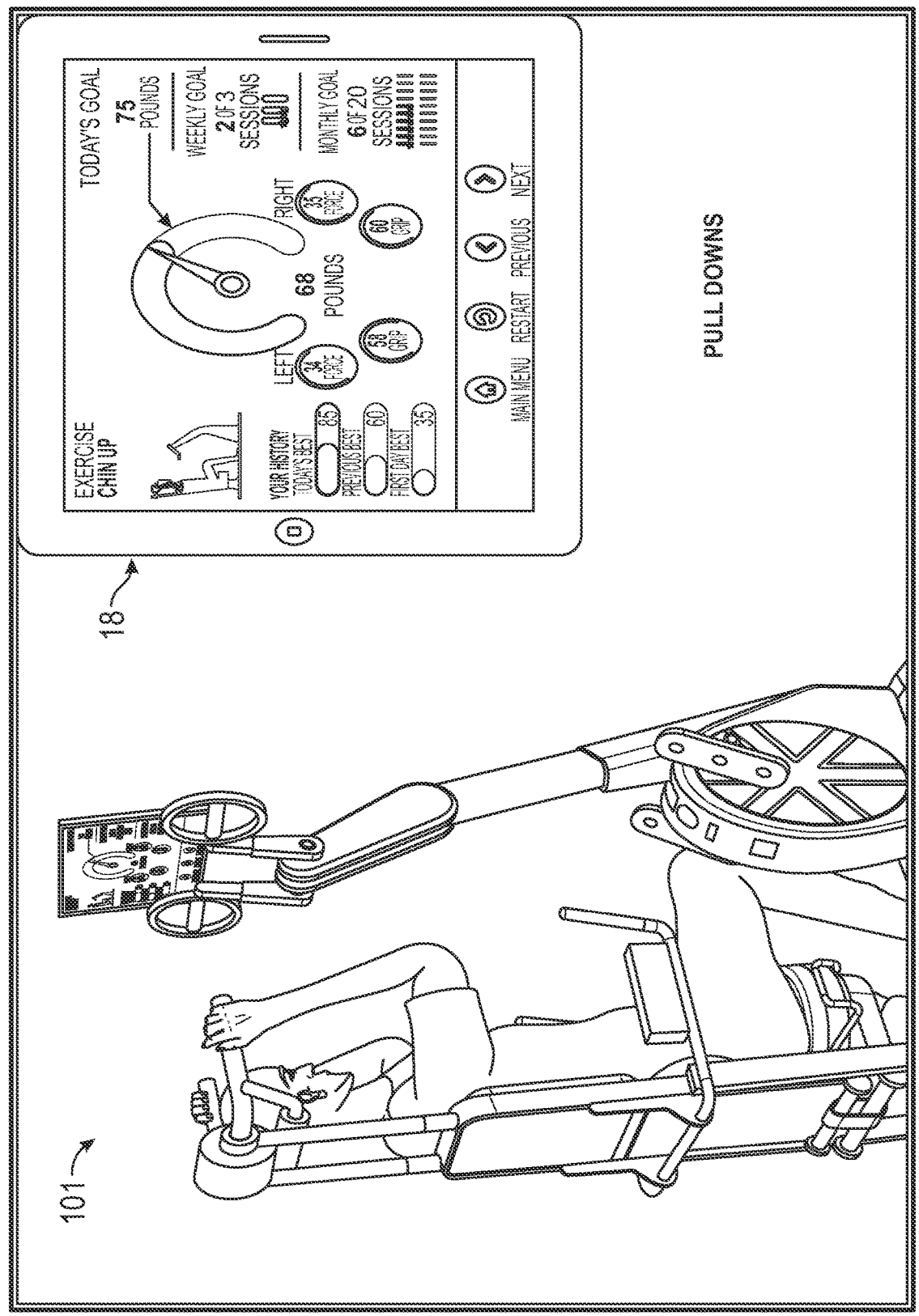
FIG. 15 illustrates a side view of the third embodiment of the isometric exercise and rehabilitation assembly with the user performing a pull-down-style exercise and a user interface presenting information to the user.

FIG. 15 illustrates a side view of the third embodiment of the isometric exercise and rehabilitation assembly 101 with the user performing a pull-down-style exercise and a user interface 18 presenting information to the user. The user interface 18 may present similar types of information as discussed above with regards to FIG. 10, but the information in the user interface 18 in FIG. 15 may be tailored for the pull-down-style exercise. That is, the data channel for the pull-down-style exercise may be set to active when the computing device 12 detects load measurements from load cells corresponding to the pull-down-style exercise, and the computing device 12 may present the various visual representations described with regards to FIG. 10 on the user interface 18 in FIG. 15 based on at least the load measurements for the pull-down-style exercise.

Figure 16:
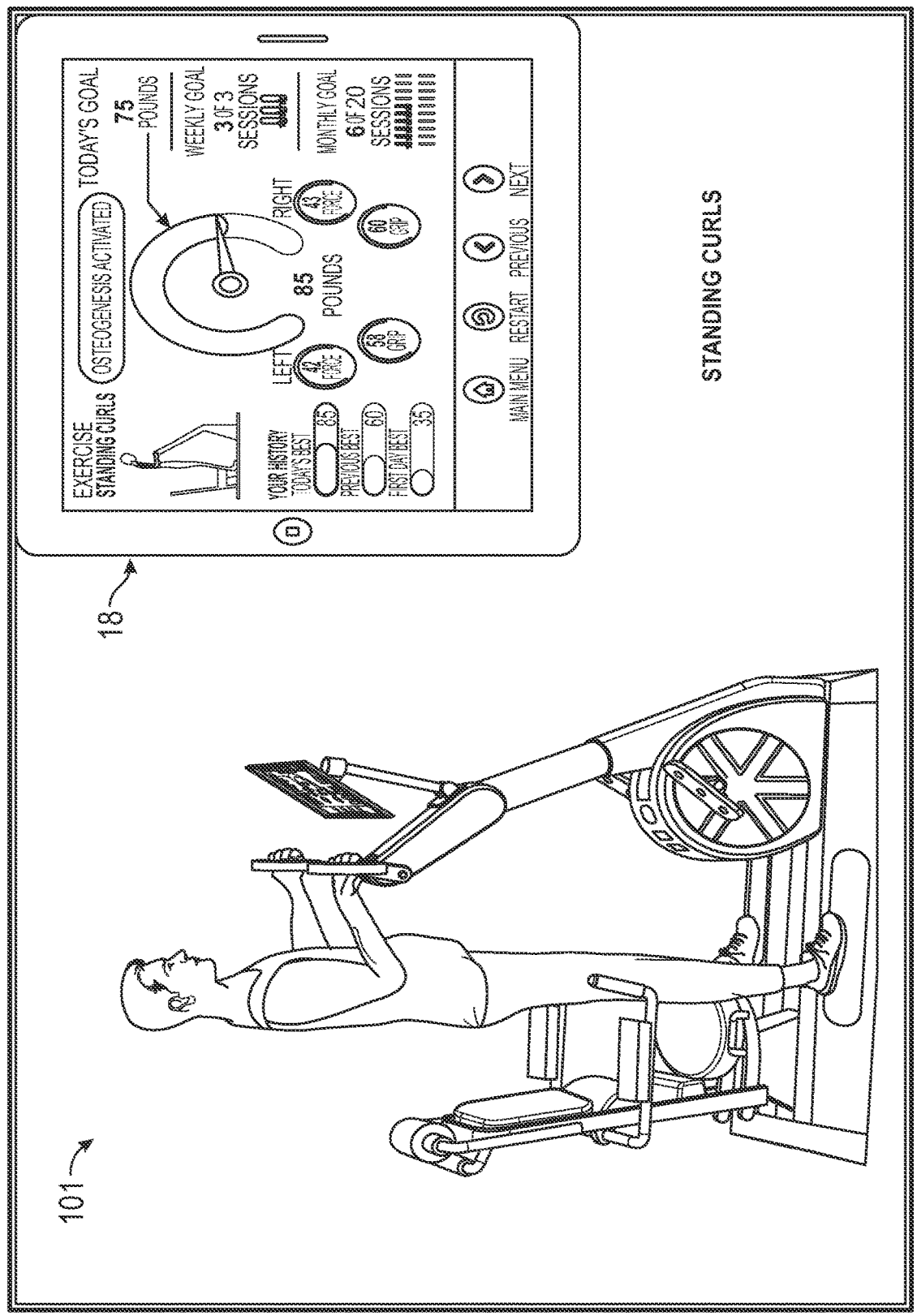
FIG. 16 illustrates a side view of the third embodiment of the isometric exercise and rehabilitation assembly with a user performing an arm-curl-style exercise and a user interface presenting information to the user.

FIG. 16 illustrates a side view of the third embodiment of the isometric exercise and rehabilitation assembly 101 with a user performing an arm-curl-style exercise and a user interface 18 presenting information to the user. The user interface 18 may present similar types of information as discussed above with regards to FIG. 12.

Figure 17:
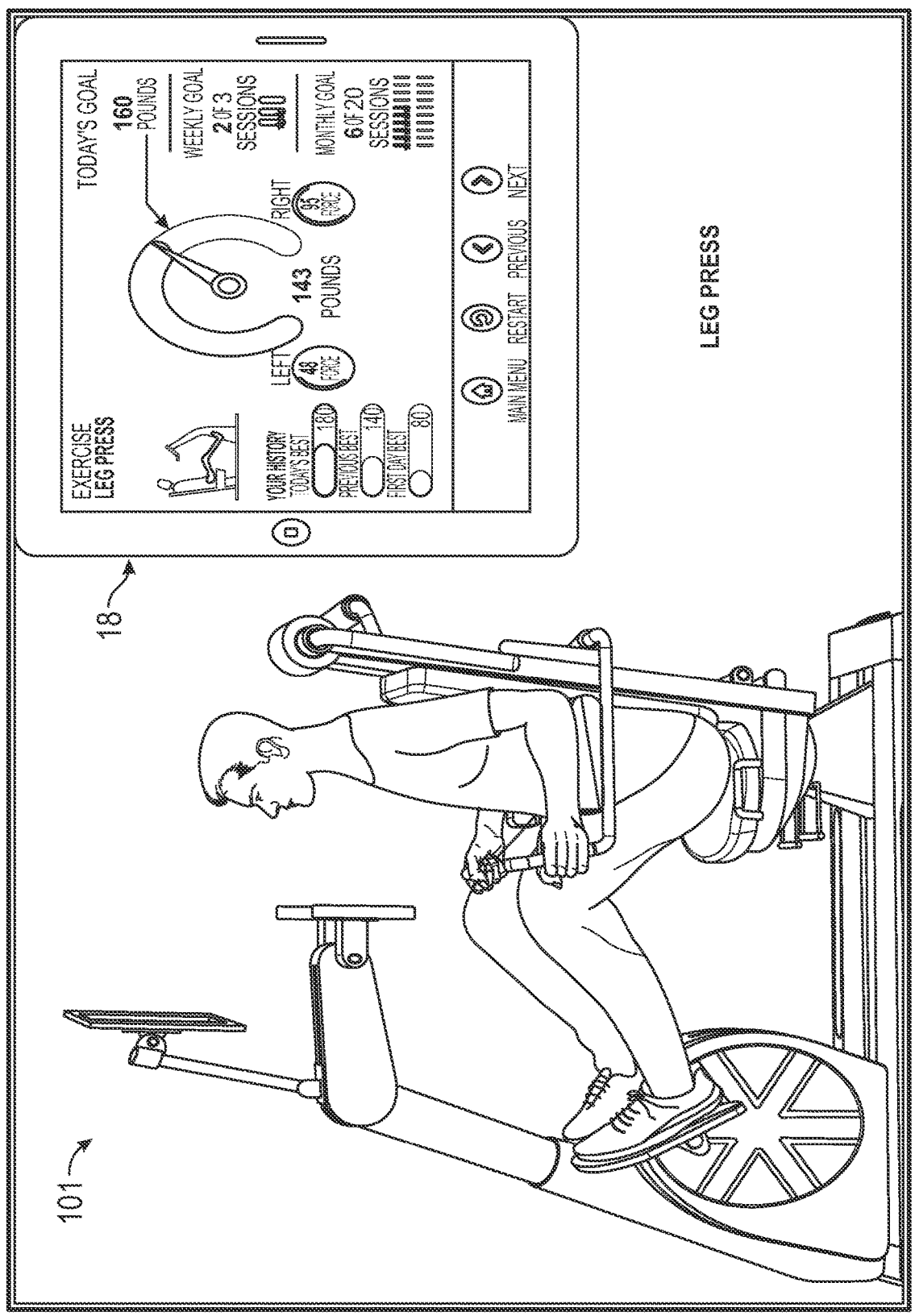
FIG. 17 illustrates a side view of the third embodiment of the isometric exercise and rehabilitation assembly with a user performing a leg-press-style exercise and a user interface presenting information to the user.

FIG. 17 illustrates a side view of the third embodiment of the isometric exercise and rehabilitation assembly 101 with a user performing a leg-press-style exercise and a user interface 18 presenting information to the user. The user interface 18 may present similar types of information as discussed above with regards to FIG. 13.

Figure 18:
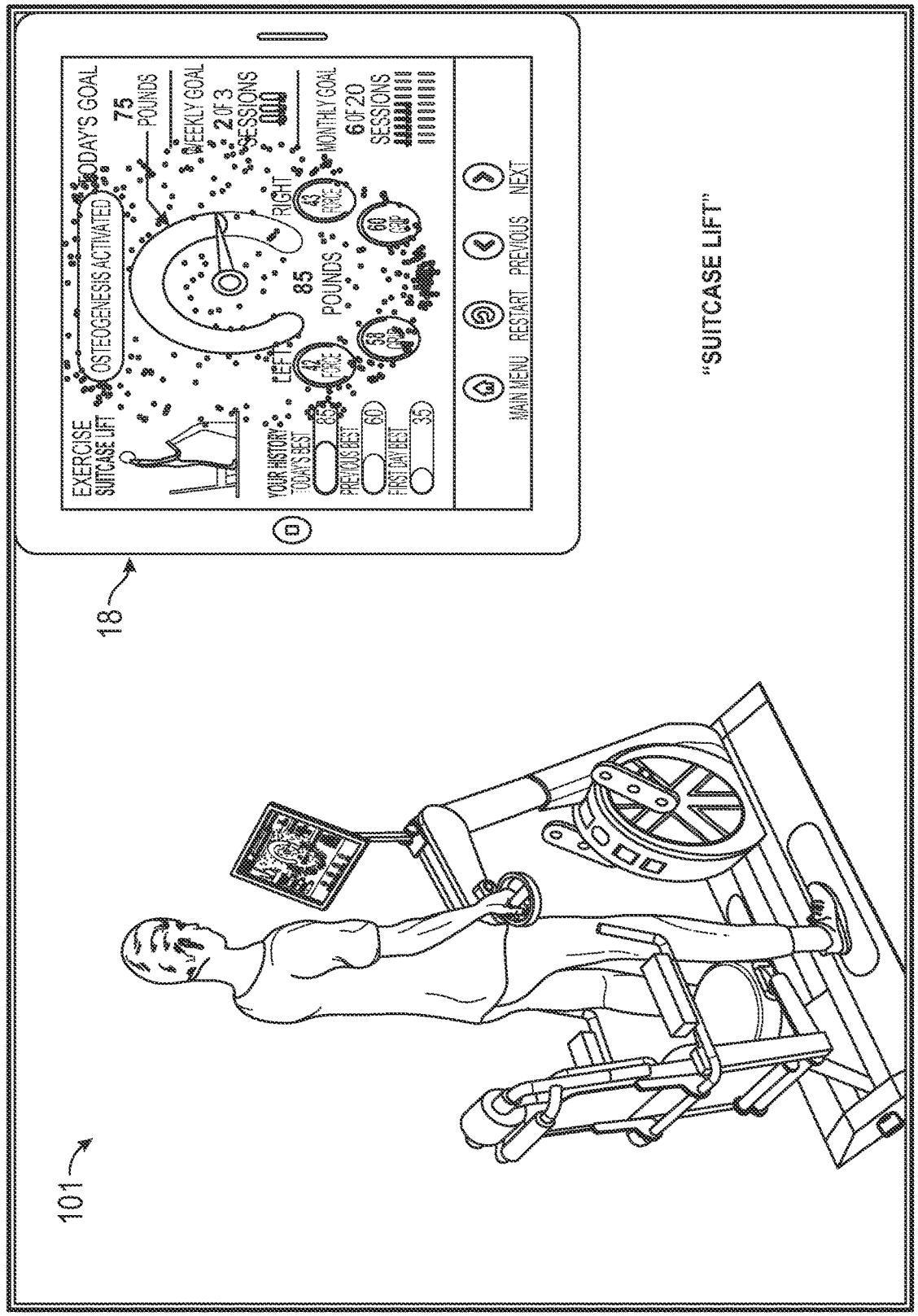
FIG. 18 illustrates a side view of the third embodiment of the isometric exercise and rehabilitation assembly with a user performing a suitcase-lift-style exercise and a user interface presenting information to the user.

FIG. 18 illustrates a side view of the third embodiment of the isometric exercise and rehabilitation assembly 101 with a user performing a suitcase-lift-style exercise and a user interface 18 presenting information to the user. The user interface 18 may present similar types of information as discussed above with regards to FIG. 11.

After a person has an injury (e.g., sprain or fractured bone), a surgery (e.g., knee replacement), or a disease (e.g., muscular dystrophy), the person's body is typically in a weakened state (e.g., physically disabled). Thus, clinicians, such as doctors and physical therapists, can prescribe exercise plans for rehabilitating their patients. The exercises in these exercise plans help restore function, improve mobility, relieve pain, improve strength, improve flexibility, and, among other benefits, prevent or limit permanent physical disability in the patients. Patients who follow their exercise plans typically show signs of physical improvement and reduced pain at a faster the rate (i.e., a faster rate of recovery or rehabilitation).

In addition, after an injury or surgery, patients typically become less active than they once were, and they may experience muscle loss. As explained above, muscles that are not used often may reduce in muscle mass and become weaker. To increase the muscle mass and/or reduce the rate of muscle loss, people may conduct exercises according to an exercise plan.

Balancing and/or resistance exercise may cause muscle tissue to increase. For example, balancing on a balance board or pushing and pulling on a stationary object (e.g., pedals of an exercise cycle) with a certain amount of force may trigger the cells in the associated muscle to change and cause the muscle mass to increase.

The subject matter disclosed herein relates to a control system for an exercise machine, not only capable of enabling an individual, preferably an individual recovering from a fracture, an injury, or a surgery, to engage easily exercises according to an exercise plan, but capable of using predetermined thresholds or dynamically calculating them, such that the person using the exercise machine can be immediately informed through real-time visual and/or other sensorial feedback, that goals of the exercise plan have been met or exceeded, thus triggering osteogenesis for the subject bone (or bones), and/or that the muscular strength threshold has been exceeded, thereby triggering muscular hypertrophy for the subject muscle (or muscles). The control system may be used to improve compliance with an exercise plan, whereby the exercise plan includes one or more exercises.

The control system may receive one or more measurements, such as load measurements, associated with forces exerted by both the left and right sides on left and right portions (e.g., pedals, base, or platform) of the exercise machine to enhance osteogenesis, bone growth, bone density improvement, stability, flexibility, range of motion, and/or muscle mass. The one or more measurements (e.g., a load measurement) may be a left measurement of a load or an increased resistance added to a left load cell on a left portion of the exercise machine (e.g., a left pedal or a left portion of the platform) and a right measurement of a load or an increased resistance added to a right load cell on a right portion of the exercise machine (e.g., a right pedal or a right portion of the platform). A user interface may be provided by the control system that presents visual representations of the separately measured left and right loads or resistances where the respective left and right load or resistances are added to the respective left and right load cells or sensors at the subject portions of the exercise machine. For example, the user interface may provide a video game that has an avatar representing the user (e.g, the patient in rehabilitation). The avatar may move in the video game and those moves may correlate with the moves of the patient. As the one or more measurements increase, the movement of the avatar may increase (e.g., if the video game is a car racing video game, as the patient increases the force exerted on the pedals, the speed of the avatar, in its car, will increase). Similarly, the control system may receive one or more measurements associated with speed, repetitions, balance, any other suitable measurement, or combination thereof. Such measurements can be used to move the avatar. The measurements can be received from sensors coupled to the exercise machine. For example, sensors can be coupled to the pedals of the exercise machine or to a base of the exercise machine.

In some embodiments, initially, the control system may determine measurements in accordance with an exercise plan associated with each exercise of the video game. For example, there may be a first level of the video game that applies a first resistance to the pedals of the exercise machine (e.g., the cycle machine) and a second level of the video game that applies a second resistance to the pedals. Further, the control system may receive measurements associated with each exercise as a patient is using the exercise machine. The control system may generate a target threshold in accordance with an exercise plan associated with each exercise of the video game. For example, there may be a first threshold associated with the first level and a second threshold associated with the second level. The exercise may be complete when the one or more measurements are received and the one or more measurements exceed one or more target thresholds. For example, if the patient is playing the first level of the video game and one or more measurements exceed a first target threshold, the first level may end and the control system will select the level two for the patient to play. In some embodiments, the control system may determine an average measurement by accumulating raw measurements over a certain period of time (e.g., 5 seconds) and averaging the raw measurements to smooth the data (e.g., eliminates jumps or spikes in data) in an average measurement.

The control system may compare the one or more measurements (e.g., raw measurements, or averaged measurements) to one or more target thresholds. In some embodiments, a single measurement may be compared to a single specific target threshold (e.g., a one-to-one relationship). In some embodiments, a single measurement may be compared to more than one specific target threshold (e.g., a one-to-many relationship). In some embodiments, more than one measurement may be compared to a single specific target threshold (e.g., a many-to-one relationship). In some embodiments, more than one measurement may be compared to more than one specific target threshold (e.g., a many-to-many relationship).

The target thresholds may be an osteogenesis target threshold, a muscular strength target threshold, a balance threshold, a speed threshold, a range of motion threshold, a repetition threshold, any other suitable threshold, or combination thereof. In addition to the threshold explanations described above, the balance target threshold, the speed threshold, and/or the range of motion threshold may be determined based on a rehabilitation protocol pertaining to the user, an age of the user, a gender of the user, a sex of the user, a height of the user, a weight of the user, a bone density of the user, an injury of the user, a type of surgery of the user, a type of bone fracture of the user, etc. A rehabilitation protocol may refer to any illness, disease, fracture, surgery, or ailment experienced by the user and any treatment instructions provided by a caretaker for recovery and/or healing. The rehabilitation protocol may also include a condition of health where the goal is avoid a problem. Any of the target thresholds may be determined based on a historical performance of the user using the exercise machine (e.g., amount of pounds lifted for a particular exercise, amount of force applied associated with each body part, the range of motion for pedaling, the level of exertion, the level of pain, etc.) and/or other exercise machines, a fitness level (e.g., how active the user is) of the user, a diet of the user, a protocol for determining a muscular strength target, a range of motion target, etc.

The control system may determine whether the one or more measurements exceed the one or more target thresholds. Responsive to determining that the one or more measurements exceed the one or more target thresholds, the control system may cause a user interface to present an indication that the one or more target thresholds have been met or exceeded and an exercise is complete. For example, the user has completed a level of the video game. Additionally, when the one or more target thresholds are met or exceeded, the control system may cause the user interface to present an indication that instructs the user to apply additional force (less than a safety limit) to attempt to set a personal maximum record or achievement (e.g., of a rate of speed, of a level of stability, a number of repetitions, of an amount of weight lifted, pressed, pulled, or otherwise exerted force) for that exercise. The control system may also determine that one or more target thresholds (e.g., a level of pain or an exersion level) are met or exceeded and end the exercise game being played. The control system may present the same game at an easier exercise game level or present a different game for the user to engage in different exercises to reduce the level of pain. In this way, the user can continue exercising rather than stopping the rehabilitation session due to pain. The video game may have one or more games, each of which have one or more exercises that target one or more muscles groups at one or more different levels of intensity.

Further, the user interface may present an indication when a measurement is approaching a target threshold for the user. In another example, when the measurement meets or exceeds the target threshold, the user interface may present an indication that the target threshold has been met or exceeded, respectively, and that the exercise is complete. The control system may provide visual and/or audio encouragement and/or coaching to the user during a video game. For example, as the user is nearing the target threshold, the control system may provide an audio of a human voice encouraging the user to maintain or increase speed on the cycling machine to earn an achievement or reach the end of the exercise game level. The control system may indicate if there are any remaining incomplete exercise game levels the video game as part of the exercise plan, that there is another game or another level (e.g., with a difference exercise and/or goal) to be completed by the user. If there are no remaining games or levels (i.e., exercises in the exercise plan) to complete, then the user interface may present an indication that all exercises in the exercise plan are complete and the user can rest. In addition, when the exercise plan is complete, the control system may generate a performance report that presents various information (e.g., charts and graphs of the right and left measurements received during each of the exercises, left and right maximum loads for the user received during each of the exercises, historical right and left measurements received in the past, comparison of the current right and left measurements with the historical right and left measurement, an amount of pounds lifted or pressed that is determined based on the measurements for each of the exercises, percent gained in measurements over time, achievements earned, goals reached, exercise game levels completed, rankings as compared to a video game history of playing, etc.).

Further, the one or more measurements may each be compared to a safety limit. For example, a left measurement and a right measurement may each be compared to the safety limit for the user. The safety limit may be determined for the user based on the user's disease protocol. There may be different safety limits for different portions of the user's body on the left and the right side, one extremity versus another extremity, a top portion of the user's body and a body portion of the user's body, etc., and for different exercises. For example, if someone underwent left knee surgery, the safety limit for a user for a left measurement for a cycling using a left leg may be different from the safety limit for a right measurement for that exercise and user. If the safety limit is exceeded, an indication may be presented on the user interface to instruct to reduce the amount of force or speed that the user is applying and/or to instruct the user to stop applying force because the safety limit has been exceeded.

Another benefit of the present disclosure is its ability to speed the healing of fractures in athletically robust individuals. Further, another benefit is the increase in muscle mass by using the exercise machine to trigger muscular hypertrophy. The control system may provide an automated interface that improves compliance with an exercise plan by using a real-time feedback loop to measure loads added during each of the exercises, (e.g. resistance applied to the pedals) compare the measurements to target thresholds and/or safety limits that are uniquely determined for the user using the exercise machine, and provide various indications based on the comparison. For example, the indications pertain to when the user should add more load, when the target thresholds are met or exceeded, when the safety limit is met or exceeded, when the exercise is complete, when the user should begin another game, when the user should begin another level of the exercise game, and so forth.

Rehabilitation Exercises and their Benefits

The following exercises achieve rehabilitation results by exposing relevant parts of a user to exercises that build strength, increase flexibility, increase range of motion, increase balance, increase coordination, decrease pain, decrease the amount of time required for recovery, or any combination thereof. In addition to the exercises machines or devices described above in this disclosure, exercise machines or devices used to facilitate the rehabilitation exercises referred to are as follows.

Cycling Machine

A cycling machine refers to a stationary bicycle used as exercise equipment and/or rehabilitation equipment. The cycling machine includes pedals configured to rotate. The cycling machine may include attached handlebars or may be used in combination with detached handlebars. The cycling machine may include an attached seat or may be used in combination with a detached seat. The cycling machine can be used to for exercise targeted to improve the following key muscle groups: gluteals, hamstrings, quadriceps, thighs, adductors, abs, and grip muscles as well as to increase flexibility, range of motion, and strength.

Balance Equipment

Balance equipment refers to an exercise machine or device, such as a balance board or a rocker device, for a user to stand on and maintain balance and control as the balance board moves in various directions. The balance board can be used to for exercise targeted to can improve mobility, flexibility, proprioception, and strength in the following key muscle groups: peroneals, gluteals, hamstrings, quadriceps, thighs, adductors, abs, and grip muscles as well as to increase flexibility, range of motion, and core strength.

The following discussion is directed to various embodiments of the present disclosure. Although these embodiments are given as examples, the embodiments disclosed should not be interpreted, or otherwise used, as limiting the scope of the disclosure, including the claims. In addition, one of ordinary skill in the art will understand that the following description has broad application, and the discussion of any embodiment is meant only to be exemplary of that embodiment, and not intended to intimate that the scope of the disclosure, including the claims, is limited to that embodiment.

Figure 19:
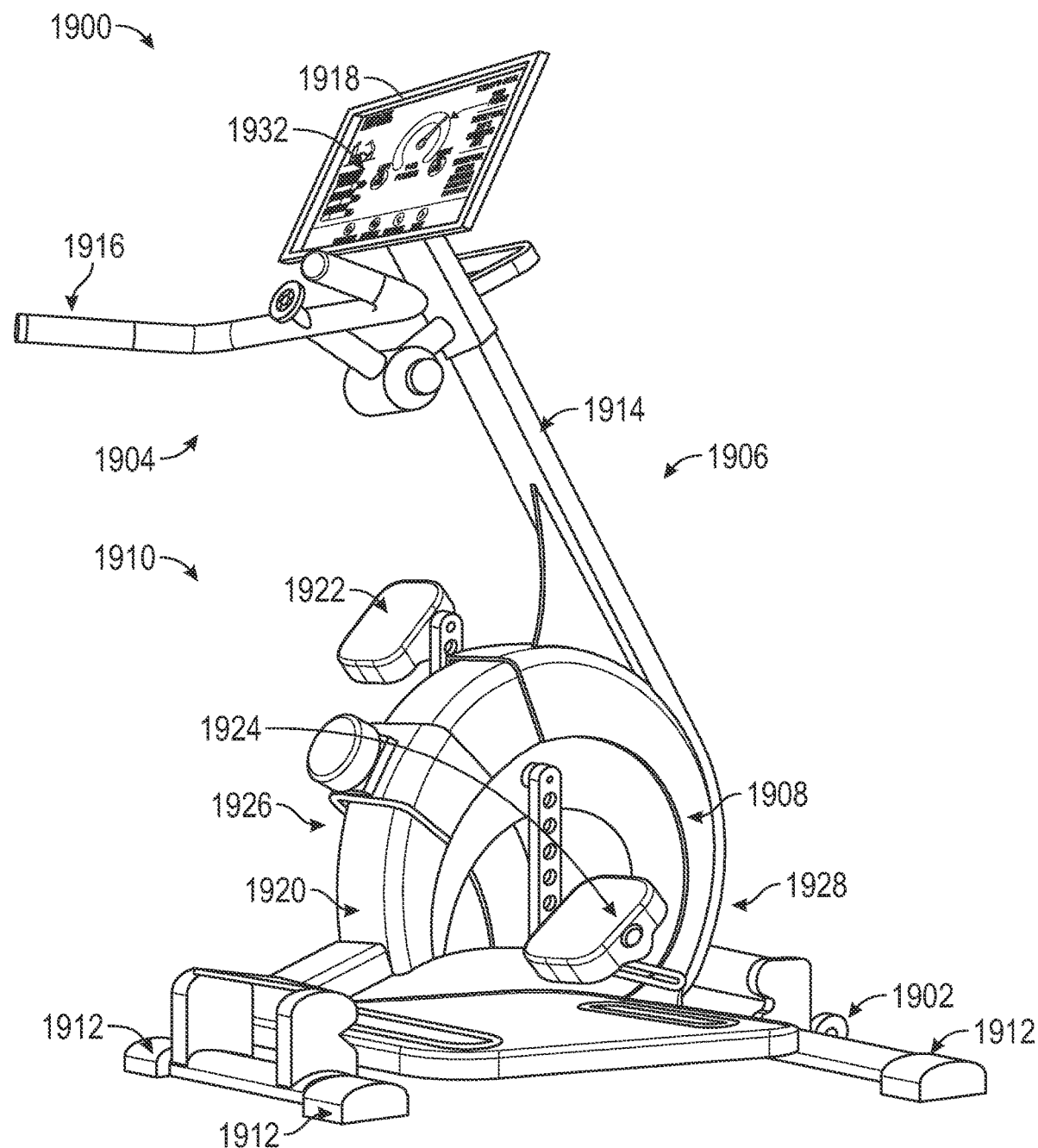
FIG. 19 illustrates a perspective view of an exercise machine.
Figure 20B:
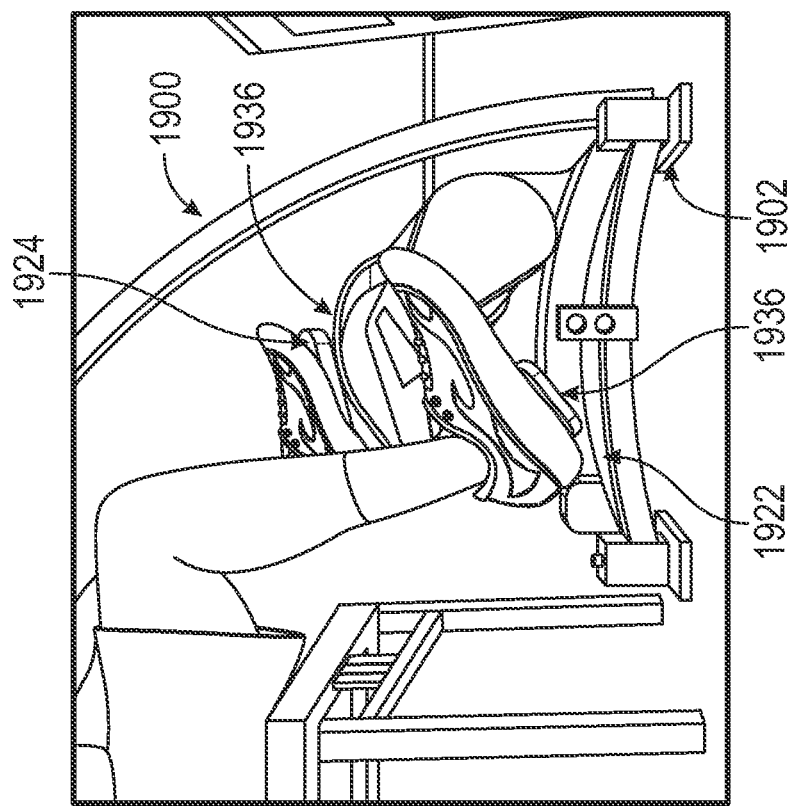
FIGS. 20A-B illustrate side views of the exercise machine.
Figure 20A:
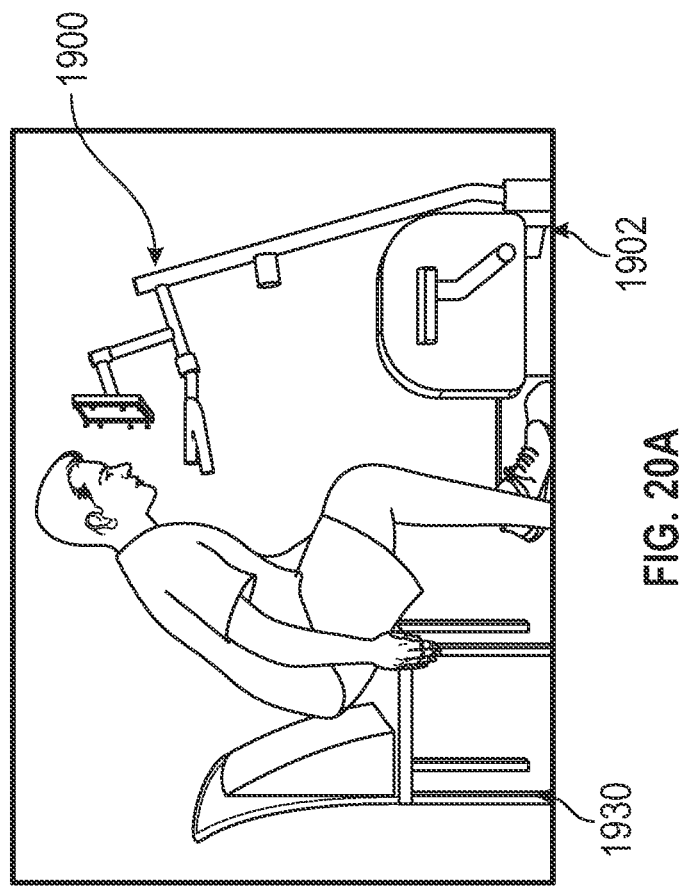

Exercise machines can include moving parts to provide dynamic exercises to facilitate rehabilitation. A dynamic exercise can be, but is not limited to an exercise where a user participates in an activity where the user moves and some resistance or load may be provided against the movement of the user. The FIGS. 19 and 20A-B illustrate embodiments of an exercise machine 1900, generally shown, for use by a user for exercise. The exercise machine 1900 can be a stationary exercise machine (e.g., cycling machine) that can be used for exercise and/or rehabilitation. The exercise machine 1900 comprises a base 1902, generally indicated, that has front and rear sides 1904, 1906 and right and left sides 1908, 1910. In the present embodiment of the base 1902, and as illustrated in the drawings, the rear side 1906 of the base 1902 wider than the front side 1904. However, the base 1902 could be of any shape. For example, the base 1902 could be rectangular, circular, rounded, trapezoidal, or square. In addition, in the present embodiment of the base 1902, the front side 1904 and the rear side 1906 can taper. For an individual who has limited mobility, the taper of the front side 1904 and the rear side 1906 allows for ease of ingress and egress onto and off of, respectively, the base 1902. However, the base 1902 could have raised rectangular edges, and the base 1902 may include a step for ingress and egress onto and off of the base 1902. Slip pads 1912 can be coupled to the base 1902 adjacent each side to prevent slipping during use of the exercise machine 1900.

Embodiments of a first housing 1914, generally indicated, can be coupled to the base 1902. The first housing 1914 can be disposed adjacent to the rear side 1906. A handlebar including one or more handles 1916 can be coupled to the first housing 1914. The handles 1916 can include grip pads to prevent slipping during use of the exercise machine 1900.

The exercise machine 1900 comprises a multidimensional exercise control system. The control system comprises a user interface 1918. The user interface can be coupled to the first housing 1914. The user interface 1918 may be or function as the user interface 18 in FIG. 1. The computing device 12 may comprise the user interface 1918 and be communicatively coupled to an exercise machine 100. The user interface 1918 may also be communicatively coupled with the computing device 15 and the cloud-based computing system 16. As used herein, a cloud-based computing system refers, without limitation, to any remote or distal computing system accessed over a network link. Each of the user interface 1918, computing device 15, and/or the exercise machine 1900 may include one or more processing devices, memory devices, and network interface devices. In some embodiments, the user interface 1918 may be included as part of the structure of the exercise machine 1900. In some embodiments, the user interface 1918 may be separate from the exercise machine 1900. For example, the user interface 1918 may be a smartphone, tablet, laptop, or the like. The computing device 12, the computing device 15, and/or the cloud-based computing system 16 can include memory to store the application 17, such as one or more video games and/or exercise plans. The video game comprises one or more exercise games. Each exercise game may include one or more exercises that target one or more parts or regions of a user's body. The parts or regions of each exercise game may be the same, different, or overlap with other exercise games. Each exercise game may include one or more levels. The levels may include different levels of intensity of exercise for one or more body parts or regions of a user. The video game can be used for engaging users to comply with an exercise plan, such as for rehabilitation purposes.

Embodiments of a second housing 1920, generally indicated, can be coupled to the base 1902. The second housing 1920 can be disposed between the front and rear sides 1904, 1906. The second housing 1920 can be disposed adjacent to and/or coupled to the first housing 1914. In the present embodiment of the second housing 1920, and as illustrated in the drawings, the second housing 1920 is cylindrical shaped. However, the base 1902 could be of any shape.

A wheel 1926 can be operatively coupled to the exercise machine 1900. In certain embodiments, the exercise machine 1900 can have the wheel 1926 coupled to the base 1902. The wheel 1926 can be a single wheel 1926, and the wheel 1926 may be a flywheel. In certain embodiments, the exercise machine 1900 can have a pair of wheels, and the wheels may be flywheels. The wheel 1926 can be disposed in the second housing 1920, and the wheel 1926 can be independently rotatable about an axis. The wheel 1926 can be disposed in in a cavity of the second housing 1920. The wheel 1926 can be partially disposed in an openings of the second housing 1920. One of skill in the art will appreciate that the wheel 1926 may be coupled to the base 1902 by various means known in the art. As one example, a support beam can extend from the base 1902 to a first axial, where an axial extends along the axis. In this embodiment, the wheel 1926 can be coupled to and independently rotatable about the axial.

In some embodiments, a motor may be disposed in the second housing 1920 and may be configured to be controlled by the computing device 12, the computing device 15, and/or the cloud-based computing system 16. The motor may be configured to operate at a desired speed, which may dynamically modified by a control instruction. The motor may be electrically coupled, physically coupled, and/or communicatively coupled to the wheel 1920, and may drive the wheel 1920 to rotate at a desired revolutions per minute, which may cause pedals 1922, 1924 to rotate at or near the desired revolutions per minute. The revolutions per minute may be dynamically modified based on an attribute of an operating parameter specified in a control instruction received from the computing device 12, the computing device 15, and/or the cloud-based computing system 16. Further, a resistance provided by pedals 1922, 1924 may be dynamically configured.

In some embodiments, the pedals 1922, 1924 may each be attached to a pedal arm for rotation about an axle. In some embodiments, the pedals 1922, 1924 may be movable on the pedal arms in order to adjust a range of motion used by a user in pedaling. For example, the pedals being located inwardly toward the axle corresponds to a smaller range of motion than when the pedals are located outwardly away from the axle. A pressure sensor may be attached or embedded within each of the pedals 1922, 1924 for measuring an amount of force applied by the user on the pedals 1922, 1924. The measurement from the sensor may be sent to the cloud-based computing system 16. The sensor may communicate wirelessly to the computing device 12, the computing device 15, the cloud-based computing system 16, the exercise machine 1900, or the like. The pedals 1922, 1924 may be moved along the pedal arms based on operating parameters provided in a control instruction generated by a machine learning model 60. For example, a motor and/or actuator communicatively coupled to the pedals 1922, 1924 may cause the pedals to move along the pedal arms to desired positions associated with desired range of motions.

A machine learning model 60 may be trained to receive input (e.g., measurements) and to output a control instruction that causes an operating parameter of the exercise device to change. In some embodiments, the operating parameter may represent or correspond to one or more resistances provided by one or more pedals 1922, 1924; a range of motion of the one or more pedals 1922, 1924; a speed of the motor; a revolutions per minute of the wheel 1920; or some combination thereof. It should be noted that the operating parameters may be controlled independently (e.g., a first pedal may be set to a first range of motion and a second pedal may be set to a second range of motion) or the operating parameters may be similarly controlled (e.g., each of the first and second pedals is set to the same range of motion).

In some embodiments, pair of pedals (e.g., a right pedal 1922 and a left pedal 1924) can be coupled to and extend from the wheel 1926. The pedals 1922, 1924 can be configured to be engaged by the user, and the pedals 1922, 1924 can facilitate rotation of the respective wheel 1926. The pedals 1922, 1924 can be movably coupled to the wheel 1926. More specifically, the pedals 1922, 1924 can be adjusted radially by the user to various positions to accommodate the needs of the user. During use of the exercise machine 1900, the user can sit in a seat 1930 and engage the pedals 1922, 1924. The seat 1930 may be detached from the exercise machine 1900. In some embodiments, the seat 1930 may be attached to the exercise machine 1900. It should be readily appreciated that the user may adjust the seat 1930 and/or the pedals 1922, 1924 to a desired position to accommodate the needs of the user for exercise or rehabilitation. When the user engages the pedals 1922, 1924, the user may apply a force to respective pedals 1922, 1924 to engage and cause rotation of a respective wheel 1926. By engaging respective pedals 1922, 1924 and applying a force to the same, the user, to support osteogenesis and/or increase a range of motion of a user's legs, engages various muscles to push the respective pedals 1922, 1924. The pedals 1922, 1924 may have straps or engagements for a user to engage with and pull the pedals 1922, 1924. Pulling the pedals 1922, 1924 may aid in the strength and rehabilitation of additional muscles. A sensor 1934 can be coupled to the right pedal 1922. An additional sensor 1936 can be coupled to the left pedal 1924. As described above, the sensors 1934, 1936 can be configured to collect sensor data correlating to the respective pedals 1922, 1924. The sensors 1934, 1936 can be a Bluetooth sensor, a load sensor, accelerometers, gyroscopes, magnetometers, any other suitable sensor, or combination thereof.

To further support osteogenesis during use of the exercise machine 1900 by a user, the exercise machine 1900 can include a first resistance mechanism (not shown). The resistance mechanism can be coupled to the base 1902, and the resistance mechanism can be disposed in the second housing 1920 adjacent to the wheel 1926. When the pedal 1922, 1924 are engaged by the user, the resistance mechanism can be configured to resist rotation of the wheel 1926. The resistance mechanisms may resist rotation of the wheel 1926 by any means known in the art.

It is to be appreciated that the exercise machine 1900 could comprise a motor coupled to each of the wheel 1926 and each motor is configured to affect or regulate the independent rotation of a respective wheel 1926. Moreover, the motor 1928 affects or regulates the independent rotation of the wheel 1926 by engaging the wheel 1926 and selectively causing or resisting rotation of the wheel 1926. The motor 1928 can engage the wheel 1926 by any means known in the art. In one example, the motor 1928 could engage gears to cause rotation of the wheel 1926. It is to be appreciated that the motor 1928 can operate congruently with or independently of the resistance mechanisms to affect or regulate the rotation of the wheel 1926. In certain embodiments, the motor 1928 can cause rotation of the wheel 1926, and the motor 1928 can resist rotation of the wheel 1926. In other embodiments with the motor 1928 and the resistance mechanism, the motor 1928 can rotate the wheel 1926 and the resistance mechanism can resist or stop rotation of the wheel 1926 when the motor 1928 stops rotating the wheel 1926. For regulating or affecting the rotation of the wheel 1926, the present disclosure allows for many variations and combinations of the motor 1928 and the resistance mechanism.

During use of the exercise machine 1900 by a user, when the user applies a force to the pedals 1922, 1924, the control system can maintain a constant rotational velocity between each of the wheel 1926. Alternatively, the wheel 1926 can be mechanically interconnected. For example, the wheel 1926 could be mechanically interconnected by a chain, belt, gear system, or any other means to maintain a constant rotational velocity between the wheel 1926.

In a further embodiment of the exercise machine 1900, a control system can be coupled to an actuator, and the control system can be configured to control the actuator. Moreover, the control system can be configured to independently vary the resistance to each of the wheel 1926 to maintain a select rotational velocity thereof, and to independently stop rotation of the wheel 1926. More specifically, the control system can control the actuator to activate the resistance mechanism to independently vary the resistance of the wheel 1926. In certain embodiments, the control system can be coupled to the motor 1928, and the control system can be configured to control the motor 1928. Additionally, the control system can be configured to independently maintain select rotational velocities of the wheel 1926, and to independently stop rotation of the wheel 1926. More specifically, the control system can control the motor 1928 to independently maintain select rotational velocities of the wheel 1926 by rotating, resisting, or stopping rotation of the wheel 1926. It is to be appreciated that the control system may control the actuator and/or the motor 1928 simultaneously or independently to maintain the select rotational velocities of the wheel 1926. For communicating the rotational velocities or accelerations of the wheel 1926 to the control system, the control system may also include sensors located on the user or coupled to the wheel 1926. With the rotational velocities or accelerations received from the sensors, the control system can determine, with a processor of the control system, a select rotational velocity of the wheel 1926. The control system can then control the motor 1928 and/or the actuator to maintain the select rotational velocities of the wheel 1926.

In some embodiment of the exercise machine 1900, a switch, not illustrated, can be disposed on the first housing 1914 for activating the control system. In another embodiment, a button, not illustrated, may be disposed on the first housing 1914 for activating the control system. In yet another embodiment, a display 1932 of a user interface 1918, such as a computer screen, iPad, or like device, can be coupled to the exercise machine 1900 to activate the control system. The switch, display 1932, and/or button may be coupled to the exercise machine 1900 by alternative or other means. For example, the switch, display 1932, and/or button could be coupled to the handle 1916. It is further to be appreciated that alternative means could be used to activate the control system and the use of the switch, display 1932, or the button, is not meant to be limiting.

In another embodiment, one or more biometric sensors, not shown, may be coupled to the exercise machine 1900 for activating the control system. The biometric sensor could be for, inter alia, detection, recognition, validation and/or analysis of data relating to: facial characteristics; a fingerprint, hand, eye (iris), or voice signature; DNA; and/or handwriting. In yet another embodiment, the biometric sensor can comprise position sensors located on the user. In addition, it is contemplated that advancements of such biometric sensors may result in alternative sensors that could be incorporated in the exercise machine 1900, i.e., biometric type sensors not currently on the market may be utilized. Further, the one or more biometric sensors may comprise a biometric system, which may be standalone or integrated.

In one embodiment, adjustment of exercise based on artificial intelligence, exercise plan, and user feedback is disclosed. An exercise plan may include one or more exercise sessions. For example, an exercise plan may include a schedule of a certain number of exercises sessions for a certain time period (e.g., 3 exercise sessions each week for 4 weeks) that, if performed by the user, should result in a desired outcome (e.g., rehabilitation of a body part, strengthen a muscle, etc.). The exercise session may include one or more exercises for various sections (e.g., warm up, strength, flexibility, cycling, cool down, etc.) The exercise plan may be generated using artificial intelligence via one or more trained machine learning models as described herein. The exercise plan may include a plan of one or more exercise sessions including exercises for a patient for rehabilitating a body part. The exercise plan may include exercises for one or more muscle groups. The exercise plan may be generated by artificial intelligence and/or prescribed by a doctor, a physical therapist, or any other qualified clinician.

For example, a machine learning model may be trained to select one or more exercises for an exercise session based on various inputs. The inputs may include the pain level of the user, the range of motion of the user, and/or characteristics of the user. These inputs may be used to determine an exercise level of the user. The machine learning model may receive the exercise level as input and select corresponding exercises from a data structure by matching the exercise level of the user to exercises having a tagged corresponding user exercise level. Various other techniques may be used to select the exercises for the exercise session.

The machine learning models may be trained to control a virtual coach executing on a computing device associated with the exercise machine 100. The virtual coach may speak via a speaker of the computing device, may be a virtual avatar displayed on the user interface 18 of the computing device 12, may cause one or more messages, emails, text, notifications, prompts, etc. to be presented on the user interface 18. The virtual coach may perform actions based on various information, such as progress of the user performing an exercise, the exercise plan details, user feedback, and the like. For example, the virtual coach may provide encouragement to the user based on the progress of the user during an exercise. The virtual coach may provide incentives, rewards, and/or certificates to the user as the user completes exercises. The virtual coach may have a particular persona that is selected for a particular user. For example, some users may respond better and perform exercises completely in response to a nice and encouraging persona for the virtual coach, while other users may respond better to a more demanding and strict (e.g., drill sergeant) persona.

By tailoring the exercise plan for the specific user and dynamically adjusting it using artificial intelligence, compliance with the exercise plan may be enhanced. Further, the user may achieve their desired goal faster by using the generated exercise plan because it is based on their progress and feedback (e.g., pain level, exercise difficulty level). By achieving the desired outcome faster, computing resources (e.g., processing, memory, network, etc.) may be reduced because the exercise machine 100, the computing device 12, and/or the cloud-based computing system 16 may not have to continuously update the exercise plan.

Further, the virtual coach may provide a companion type of feel for the user, which may further cause the user to comply with the exercise plan more efficiently and completely, thereby achieving their desired outcome faster. The virtual coach may improve the user experience of using the computing device 12 and/or the exercise machine 100 because the persona may be selected specifically for the particular user. In some instances, the user may form a bond with the persona of the virtual coach if the persona matches a friend in real life, family member, a significant other, or the like, and the bond may cause the user to feel a desire to want to listen to the virtual coach and/or complete the exercise plan such that they don't let the virtual coach down. Such a situation may also save computing resources because the exercise plan may not have to be adjusted and lengthened by adding additional exercise sessions.

As a result, various technical benefits may be achieved by the disclosed embodiments, as described above. Further, the user experience of using the exercise machine 100, the computing device 12, or both may be improved based on the disclosed techniques due to exercising with the virtual coach, the incentives, the rewards, the certificates, and the like.

Figure 21:
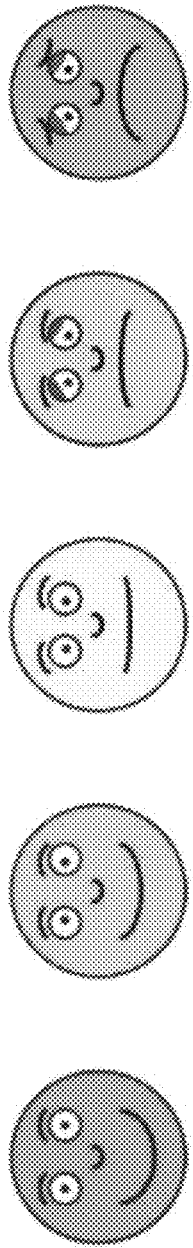
FIG. 21 illustrates an example user interface for entering a level of pain of a user.

The processing device may be configured to execute the instructions to receive user input data. As illustrated in FIG. 21, the user interface 2100 may display a screen 2102 requesting a user to provide a pain level. The user can select the level of pain (e.g., no pain, mild, moderate, severe, very severe) before an exercise begins. The level of pain may be used to determine an exercise level of the user. Once the level of pain is selected, a testing phase may be initiated where a user performs an exercise to determine their range of motion, for example. The level of pain and the range of motion may be used to determine the exercise level of the user. The user interface 2100 may provide visual and/or audio prompts for the user. The user may provide the user interface 2100 with the user input by touching the user interface 2100, speaking to the user interface 2100, or any other suitable input. The user interface 2100 may request that a user enter other user input, such as an exertion level, a difficulty of an exercise, or the like. Further, a virtual coach may read the question to the user by saying (via a speaker) "What is your knee pain level today? Please say it out loud." The processing device may be configured to execute the virtual coach to provide coaching and instructions to a user on how to use the exercise machines 100, an exercise, or any other suitable information. The instructions and/or coaching may be a prerecorded or dynamic virtual coach (e.g., a trainer or a physical therapist) and provide commands, instructions, and/or tips via audio and/or video. For example, the virtual coach may provide tips on posture and form while performing an exercise or using the exercise machine. The virtual coach may provide motivational content, such as words of encouragement to the user. The virtual coach may be provided randomly during the video game and/or it may be based on input and/or data from the user and/or sensors. The virtual coach may be data-driven. The processing device can receive user input data, sensor data, tracker data, historical data, and/or any other suitable information to obtain information, such as the difficulty level of the exercise, whether the user likes the persona of the virtual coach, and provide audio and/or visual coaching to the user.

Figure 22:
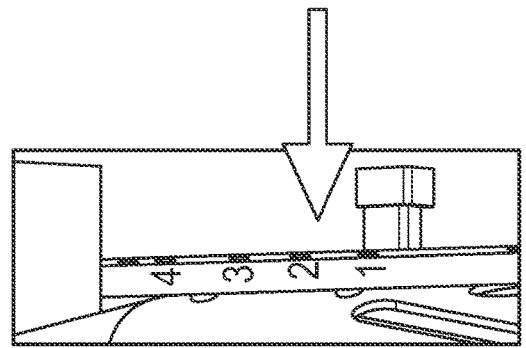
FIG. 22 illustrates an example user interface presenting a pedal setting for a session as determined by a machine learning model.

FIG. 22 illustrates an example user interface 2200 presenting a pedal setting for a session as determined by a machine learning model. The pedal setting may be dynamically determined by the machine learning model 60 for a particular exercise based on the exercise level of the user, the range of motion of the user, the characteristics of the user, or some combination thereof. The user interface 2200 may also include a prompt for the user to watch a tutorial for an exercise prior to the user actually beginning the exercise. It should be noted the virtual coach may provide audio/video instructions pertaining to the pedal setting for the session.

Figure 23:
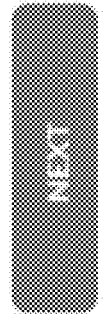
FIG. 23 illustrates an example user interface presenting an exercise session determined for a user by a machine learning model.

FIG. 23 illustrates an example user interface 2300 presenting an exercise session determined for a user by a machine learning model. The exercise session includes 5 sections: warm up cycle, seated march, sit-to-stand, calf raise, and hamstring curl. The total time for the exercise session is 18 minutes. The exercise session may be generated by the machine learning model 60 as described herein and may be presented on the user interface 2300 of the computing device 12 associated with the exercise machine 100. The virtual coach may be executed by the computing device 12 to provide audio/video instructions and description pertaining to the exercise session.

Figure 24:
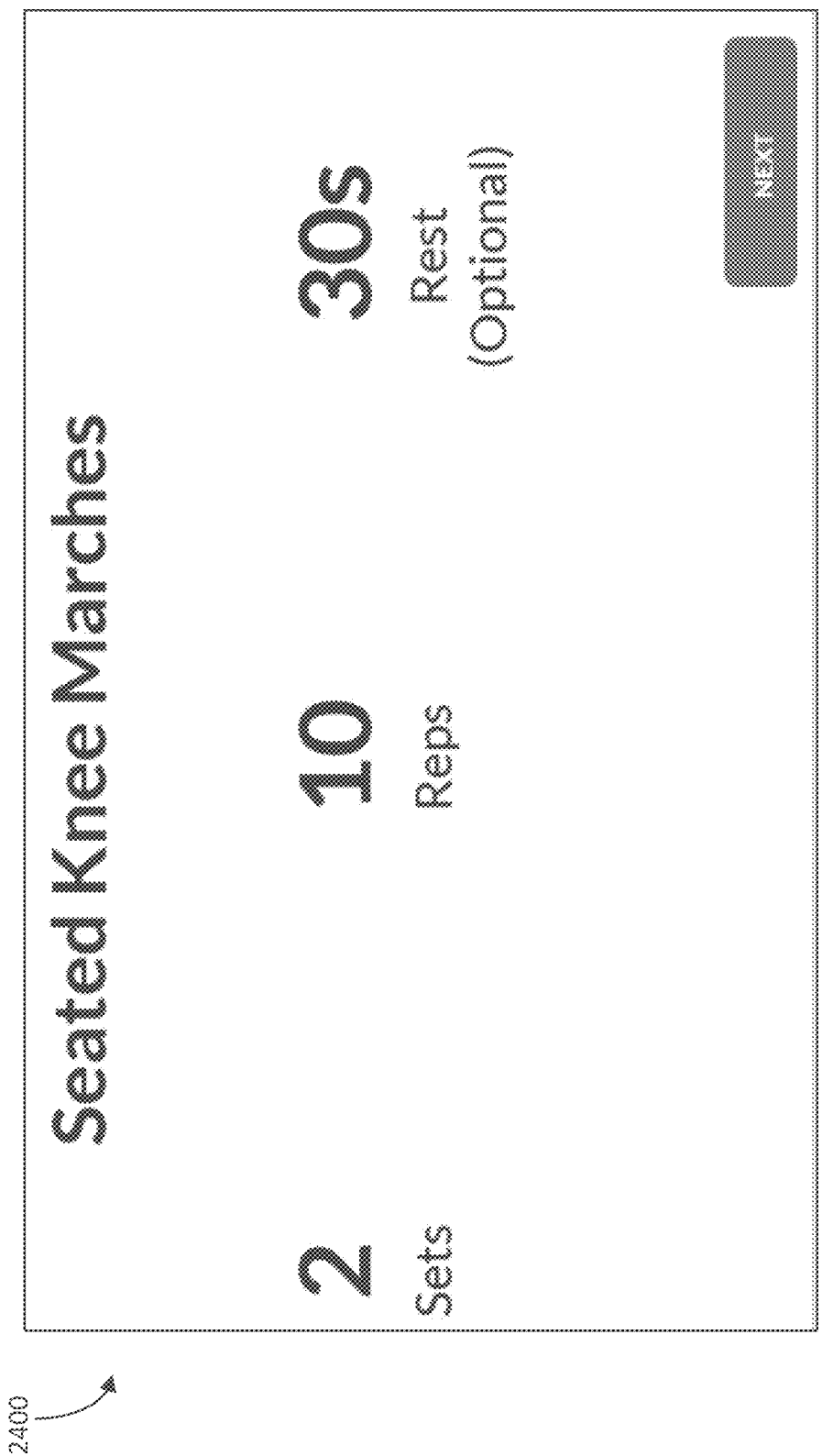
FIG. 24 illustrates an example user interface presenting details of a particular exercise for a user to perform.

FIG. 24 illustrates an example user interface 2400 presenting details of a particular exercise for a user to perform. The user interface 2400 may include details of a particular exercise: the seated knee march. For example, the user interface 2400 presents that 2 sets of 10 reps are to be performed by the user and an optional 30 second of rest between sets. The virtual coach may provide audio/video instructions and description pertaining to the details of the exercise.

Figure 25:
FIG. 25 illustrates an example user interface presenting an incentive to the user for completing a set.

FIG. 25 illustrates an example user interface 2500 presenting an incentive, reward, congratulatory message, etc. to the user for completing a set. For example, the user interface 2500 presents a notification that says "Nice work! You've finished 1 set of 2." Then the user interface 2500 presents a notification to begin the next set after the 30 second rest period expires. It should be noted that the virtual coach may provide audio/video pertaining to the incentive, reward, congratulatory message. Such interaction with the virtual coach may inspire the user to continue the exercise session and complete the next set, thereby advancing their exercise plan and recovery rate.

Figure 26:
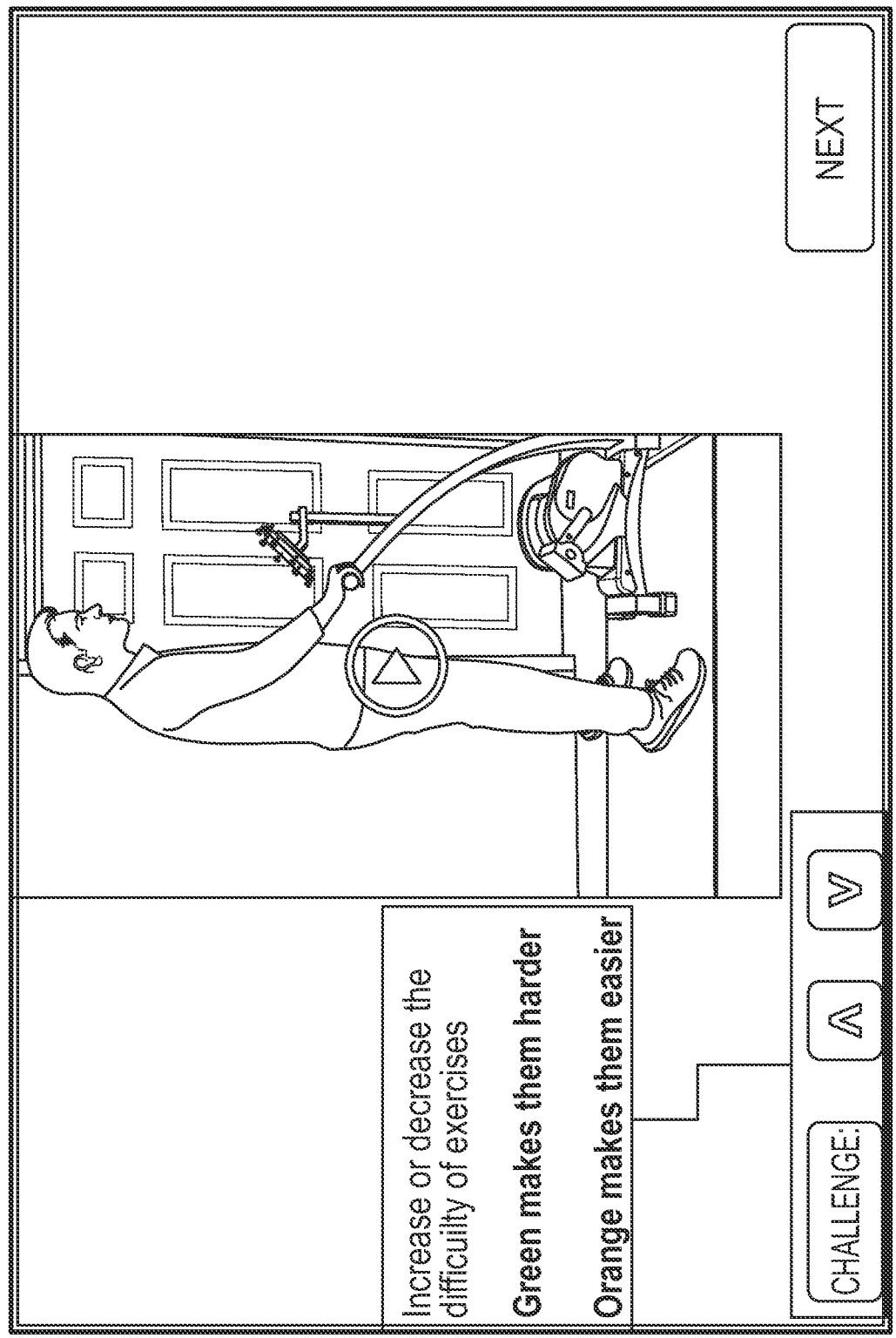
FIG. 26 illustrates an example user interface that includes options for the user to indicate whether an exercise is too easy or too hard.

FIG. 26 illustrates an example user interface 2600 that includes options for the user to indicate whether an exercise is too easy or too hard. During performance of an exercise, the user may select the options for too easy or too hard on the user interface 2600 or say the words "too easy" or "too hard". Such selection may cause the machine learning model 60 to alter the exercise, the exercise session, or both. For example, the cloud-based computing system 16 may increase or decrease the intensity of the exercise by modifying a parameter (e.g., resistance, speed, etc.) of the exercise machine 100. Further, if the options for too easy or too hard are chosen more than a threshold number of times, the machine learning model 60 may remove the exercise from the exercise session, add another exercise to the exercise session, switch to a different exercise, or the like.

Figure 27A:
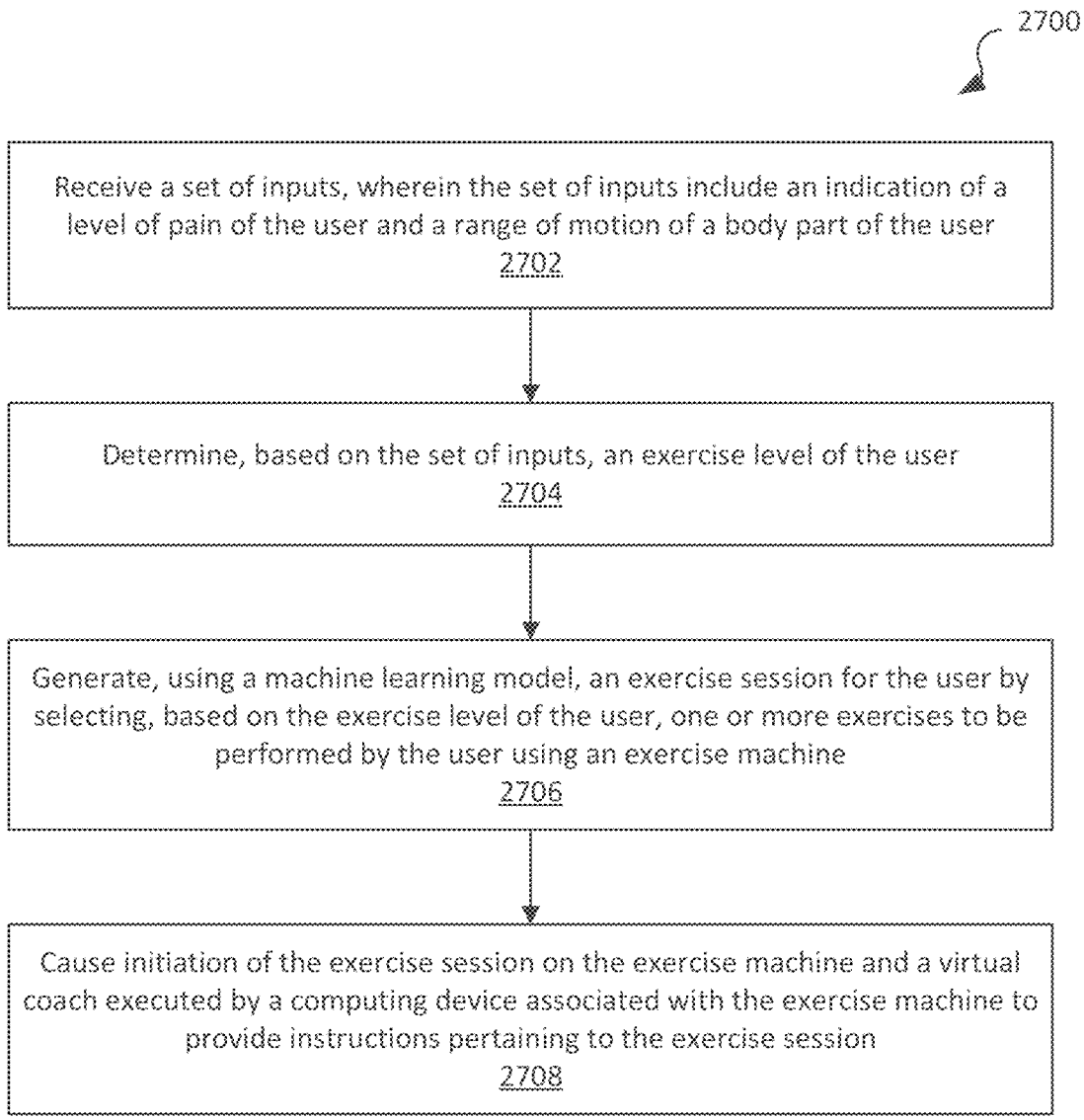
FIG. 27A illustrates an example method for generating, using a machine learning model, an exercise session for a user and causing a virtual coach to provide instructions pertaining to the exercise session.

FIG. 27A illustrates an example method 2700 for generating, using a machine learning model, an exercise session for a user and causing a virtual coach to provide instructions pertaining to the exercise session. The operations can be used to improve compliance with an exercise plan. The method 2700 may be performed by processing logic that may include hardware (circuitry, dedicated logic, etc.), firmware, software, or a combination of them. The method 2700 and/or each of their individual functions, subroutines, or operations may be performed by one or more processing devices of a control system (e.g., cloud-based computing system 16, computing device 12 of FIG. 1) implementing the method 2700. The method 2700 may be implemented as computer instructions that are executable by a processing device of the control system (e.g., a computer-readable medium may be used to store instructions that, when executed, cause a processor perform the following steps or processes of the method 2700). In certain implementations, the method 2700 may be performed by a single processing thread. Alternatively, the method 2700 may be performed by two or more processing threads, each thread implementing one or more individual functions, routines, subroutines, or operations of the methods. Various operations of the method 2700 may be performed by one or more of the cloud-based computing system 16, the computing device 12, and/or the computing device 15 of FIG. 1.

At 2702, the processing device may receive a set of inputs. The set of inputs may include an indication of a level of pain of the user, a range of motion of a body part of the user, a set of characteristics of the user, or some combination thereof. The indication of the level of pain of the user may be entered by the user using any suitable peripheral device (e.g., microphone, keyboard, touchscreen, mouse, etc.) at a particular user interface 18 displayed on a computing device 12. The range of motion of the body part of the user may be determined by the processing device by the user performing a baseline exercise for a certain amount of time. The baseline exercise may include setting a pedal at an initial position and having the user cycle at that position for a period of time. If the user does not experience any pain after the period of time, the pedal may be moved to a second position and the user may cycle for the period of time again. If the user experiences pain, then the range of motion of the user may be determined based on the previous position of the pedal when the user was able to cycle without pain. As may be appreciated, if the user does not experience pain, the position of the pedal may continue to change until the user experiences pain and the ROM of the user may be determined based on the prior position where the user did not experience pain. The characteristics of the user may include an age of the user, a height of the user, a weight of the user, a gender of the user, a condition that caused the pain in the body part, one or more procedures perform on the user, a goal of the user, whether the user is in a pre-procedure stage or a post-procedure stage, or some combination thereof. The characteristics may be included in a user profile for the user that is stored at the cloud-based computing system 16, the computing device 12, the computing device 15, or both.

At 2704, the processing device may determine, based on the set of inputs, an exercise level of the user. The exercise levels may range from 1-5, where 1 is the lowest exercise level and 5 is the most advanced exercise level. Any suitable range of exercise levels may be used. The following chart illustrates an example of how the exercise level may be determined:

| If Pain Is | & ROM Is | Then Level Is |
|---|---|---|
| 8-10 | 1-2 | 1 |
| 8-10 | 3-4 | 2 |
| 8-10 | 5 | 3 |
| 5-7 | 1-2 | 1 |
| 5-7 | 3-4 | 2 |
| 5-7 | 5 | 3 |
| 1-4 | 1-2 | 1 |
| 1-4 | 3-4 | 2 |
| 1-4 | 5 | 4 |
| 0 | 5 | 5 |

At 2706, the processing device may generate, using the machine learning model 60, an exercise session for the user by selecting, based on the exercise level of the user, one or more exercises to be performed by the user using the exercise machine 100. In some embodiments, a data structure may include entries for a set of exercises (e.g., tens, hundreds, thousands, etc.) that are each tagged with an exercise level. For example, the processing device may tag each exercise of the set of exercises with a respective user exercise level. The machine learning model 60 may access the data structure to select the exercises for the exercise session by filtering the set of exercises, as further discussed with reference to FIG. 28.

At 2708, the processing device may cause initiation of the exercise session on the exercise machine 100 and a virtual coach executed by the computing device 12 associated with the exercise machine 100 to provide instructions pertaining to the exercise session. The virtual coach may be driven by artificial intelligence via one or more trained machine learning models 60. For example, the trained machine learning models may receive various inputs, such as the exercise session for the user, the exercise being performed, instructions pertaining to the exercise being performed, completion of the exercise being performed, progress of the exercise being performed, and may be trained to provide certain outputs based on the inputs. The virtual coach may output audible noise (e.g., speech) that pertain to the various inputs. For example, the virtual coach may say, via a speaker of the computing device 12, encouraging words while a user is performing an exercise, congratulatory words when the user completes an exercise, instructions when the user is about to start another exercise, and the like. The virtual coach may have a persona (e.g., a cheerleader type of persona, a drill sergeant type of persona) that is selected based on progress of the user, feedback of the user, or both, as described further below with reference to FIG. 30.

In some embodiments, the processing device may receive, from the user while the user is performing an exercise of the one or more exercises in the exercise session, feedback pertaining to the exercise. The feedback may include an indication that the exercise is too easy or too hard. For example, the user may use a display screen or microphone of the computing device 12 to enter or say the exercise is "too easy" or "too hard". Responsive to receiving the feedback, the processing device may cause an intensity of the exercise to increase or decrease. For example, if the user says "too easy" the intensity of the exercise may be increased. If the user says "too hard", the intensity of the exercise may be decreased. Other dimensions, parameters, characteristics, etc. of the exercise or exercise session may be changed based on whether the feedback is too easy or too hard. For example, the other dimensions, parameters, characteristics, etc. may include a number of sets, a number of repetitions, a hold time, a rest time, and the like. When one of the dimensions, parameters, characteristics, etc. changes, the virtual coach may provide an indication of the change. For example, the virtual coach may say, via a speaker of the computing device 12, "The intensity for this exercise has increased".

In some embodiments, the processing device may track how many times the user has provided the feedback for a particular exercise in an exercise session or across every exercise session in an exercise plan for the user. Responsive to determining the feedback has been received more than a threshold number of times (e.g., 3, 4, 5, etc.), the processing device may control, in real-time or near real-time, the exercise machine 100 to initiate a more advanced exercise than the exercise currently being performed, a less advanced exercise than the exercise currently being performed, or the like. Further, the processing device may remove the exercise for which the feedback was received more than the threshold number of times from subsequent exercise sessions and replace it with another exercise. The processing device may cause the virtual coach to provide an indication via the computing device 12 (e.g., voice emitted through the speaker, graphic on the user interface 18, text on the user interface 18, or the like) of the change to the exercise.

In some embodiments, the processing device may monitor the progress of the user while the user uses the exercise machine to perform the one or more exercises. The progress may include an amount of time the user performs the one or more exercises, the range of motion of the user while the user performs the one or more exercises, the level of pain of the user while the user performs the one or more exercises, whether the user completes the one or more exercises, an indication of the user of a level of difficulty of the one or more exercises, or some combination. The progress may be determined based on measurement data received from any sensor associated with the exercise machine 100, any user feedback received by the computing device 12, and the like. The user may use any suitable peripheral to input the level of difficulty (e.g., too hard or too easy) while the user performs the exercises. The processing device may adjust, by executing the machine learning model 60, a subsequent exercise session based on the progress of the user. The adjusting may be based on advancing the exercise level of the user to a next exercise level, achieving a desired goal as defined by the user, a medical professional, or both, or some combination thereof.

In some embodiments, the processing device may monitor progress of the user while the user uses the exercise machine 100 to perform the one or more exercises. The processing device may cause, based on the progress of the user, an incentive, reward, or both to be elicited by the computing device 12 associated with the exercise machine 100. The incentive, reward, or both may include an animation, video, audio, haptic feedback, image, push notification, email, text, or some combination thereof. The processing device may cause the virtual coach to perform an encouraging action (e.g., shoot virtual fireworks on the user interface 18, cause an avatar displayed on the user interface 18 to dance or give a virtual high five, emit an audible noise from the speaker congratulating the user). Providing incentives, rewards, or both may encourage the user to continue to perform exercises and comply with the exercise session, which in turn, may decrease the amount of time it takes for the user to achieve their goal. Reducing the amount of time it takes for the user to achieve their goal may include technical benefits because if the user achieves their goal faster, the computing device 12, exercise machine 100, and/or the cloud-based computing system 16 may save computing resources (e.g., processing, memory, network) by not having to execute as long to guide the use through the exercise plan. That is, if the user does not comply with the exercise plan efficiently or as directed, then the exercise plan may be adjusted to add additional exercise sessions, thereby causing the computing device 12, exercise machine 100, and/or the cloud-based computing system 16 execute longer and waste computing resources until the user achieves their goal.

In some embodiments, the processing device may determine when a number of incentives, rewards, or both elicited by the computing device 12 satisfy a threshold value (e.g., 3, 4, 5). Responsive to determining that threshold value is satisfied, the processing device may cause a certificate to be transmitted to the computing device 12 and associated with an account of the user using the exercise machine 100. For example, the certificate may be stored in a digital wallet of the user's account in the application 17 executing on the computing device 12. In some embodiments, the certificate may have a particular value that may be exchanged for certain items (e.g., gift certificate, clothing, coupons, discounts, etc.).

In some embodiments, the processing device may determine, by executing the machine learning model 60, a set of audio segments for the virtual coach to say while the user performs the one or more exercises. The audio segments may be based on a state of the exercise (e.g., beginning, middle, end), progress of the user performing the exercise, or any suitable information. For example, at the initiation of the exercise, the audio segment may provide instructions to the user on the details of the exercise (e.g., 2 reps, 30 seconds, etc.). Based on the progress of the user, the audio segment may say "pedal faster" if the user is not pedaling fast enough, "good job" if the user is satisfying the criteria for the exercise, "almost finished" if the user is almost finished with the exercise, or the like. The audio segments may be dynamically determined, in real-time or near real-time, by the machine learning model 60 based on the inputs described above. It should be noted that real-time or near real-time may refer to a relatively short amount of time (e.g., less than 5 seconds) after an action occurring.

In some embodiments, the processing device may determine, by executing the machine learning model 60, a schedule of a set of exercise sessions to be performed by the user to achieve a desired goal specified by the user, a medical professional (e.g., physical therapist), or both. The machine learning model may be trained to determine the schedule based on various inputs, such as the desired goal (e.g., full recovery, near full recovery at a fastest pace possible, strength improvement, flexibility improvement, etc.), a procedure performed on the user, characteristics of the user (e.g., age, weight, height, etc.), a daily schedule of the user (e.g., job schedule, parenting schedule, school schedule, etc.), and the like. The schedule may be optimized for the user and may comply with the various inputs described above.

In some embodiments, the virtual coach may be controlled, in real-time or near real-time, by the machine learning model 60. For example, the virtual coach may provide indications (e.g., emit audible noises, present various screens or notifications or indications or avatars or graphics, etc.) via the computing device 12 as parameters of the exercise, exercise session, exercise machine 100, etc. change, or as characteristics or progress of the user changes.

FIG. 27B illustrates an example data structure 2750 including a set of exercises tagged by exercise level of a user. As depicted, the data structure 2750 (e.g., table, database, linked list, blockchain, etc.) includes columns for Exercise, Description, Image, Levels (tagged portion), Sections, Component (Exercise Goal), Swap it out with, Too Easy, Too Hard, Reps (starting level), # of sets (starting level), Time Per Rep, Rest Time Per Set, Body Part Exercised, and Intensity. In some embodiments, different columns may be used and not all of the ones depicted may be used.

The exercise Sitting Knee Extension has been tagged as a suitable exercise for levels 1, 2, and 3, and is an option for the section comprising Warm Up. It should be note that each exercise session may include various sections: warm up, cardio, strength, cycle, cool down, flexibility, etc. Each section of an exercise session may be assigned one or more exercises that are appropriate for that section, based on the entry in the data structure 2750, and the exercise level of the user that matches the level in the data structure 2750.

Figure 28:
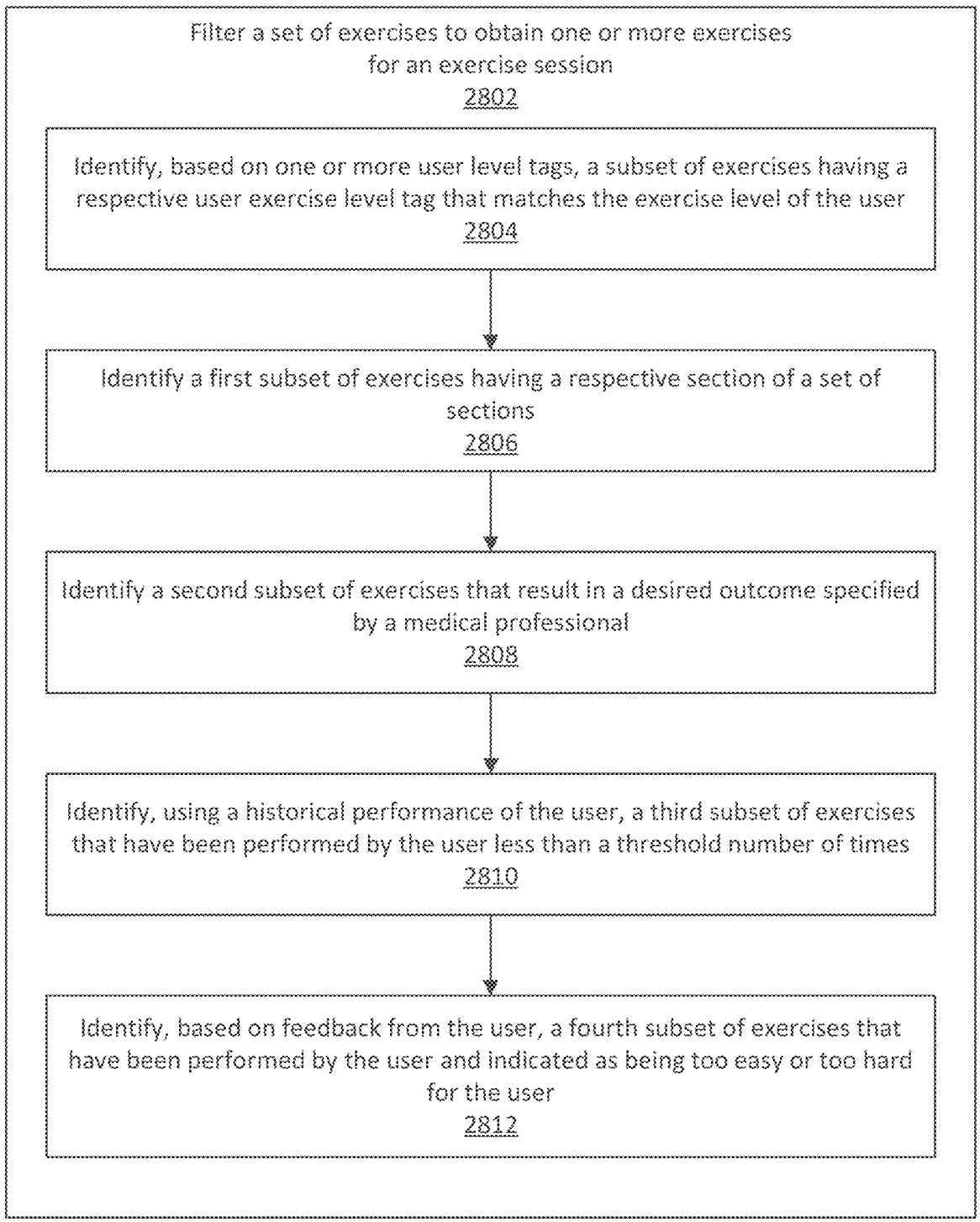
FIG. 28 illustrates an example method for filtering a set of exercises to obtain one or more exercises to include in an exercise session for a user.

FIG. 28 illustrates an example method 2800 for filtering a set of exercises to obtain one or more exercises to include in an exercise session for a user. The operations can be used to improve compliance with an exercise plan. The method 2800 may be performed by processing logic that may include hardware (circuitry, dedicated logic, etc.), firmware, software, or a combination of them. The method 2800 and/or each of their individual functions, subroutines, or operations may be performed by one or more processing devices of a control system (e.g., cloud-based computing system 16, computing device 12 of FIG. 1) implementing the method 2800. The method 2800 may be implemented as computer instructions that are executable by a processing device of the control system (e.g., a computer-readable medium may be used to store instructions that, when executed, cause a processor perform the following steps or processes of the method 2800). In certain implementations, the method 2800 may be performed by a single processing thread. Alternatively, the method 2800 may be performed by two or more processing threads, each thread implementing one or more individual functions, routines, subroutines, or operations of the methods. Various operations of the method 2800 may be performed by one or more of the cloud-based computing system 16, the computing device 12, and/or the computing device 15 of FIG. 1.

At 2802, the processing device may filter a set of exercises to obtain the one or more exercises for a particular exercise session in an exercise plan. Operation 2802 may include operations 2804, 2806, 2808, 2810, and/or 2812.

At 2804, the processing device may identify, based on the tagging of the exercises in the data structure, a subset of exercises having the respective user exercise level that matches the exercise level of the user. At 2806, the processing device may identify a first subset of exercises having a respective section of a set of sections, wherein the set of sections include warm-up, cycling, strength, flexibility, or some combination thereof. At 2808, the processing device may identify a second subset of exercises that result in a desired outcome specified by a medical professional, wherein the desired outcome pertains to increasing a range of motion, mobility, strength, flexibility, or some combination thereof. At 2810, the processing device may identify, using a historical performance of the user, a third subset of exercises that have been performed by the user less than a threshold number of times. At 2812, the processing device may identify, based on feedback from the user, a fourth subset of exercises that have been performed by the user and indicated as being too easy or too hard for the user.

In some embodiments, the processing device may select at least one of the subset of exercises, the first subset of exercises, the second subset of exercises, the third subset of exercises, or the fourth subset of exercises as the one or more exercises for the exercise session. That is, any combination of the subset, the first subset, the second subset, the third subset, and the further subset of exercises may be selected as the one or more exercises for the exercise session.

Figure 29:
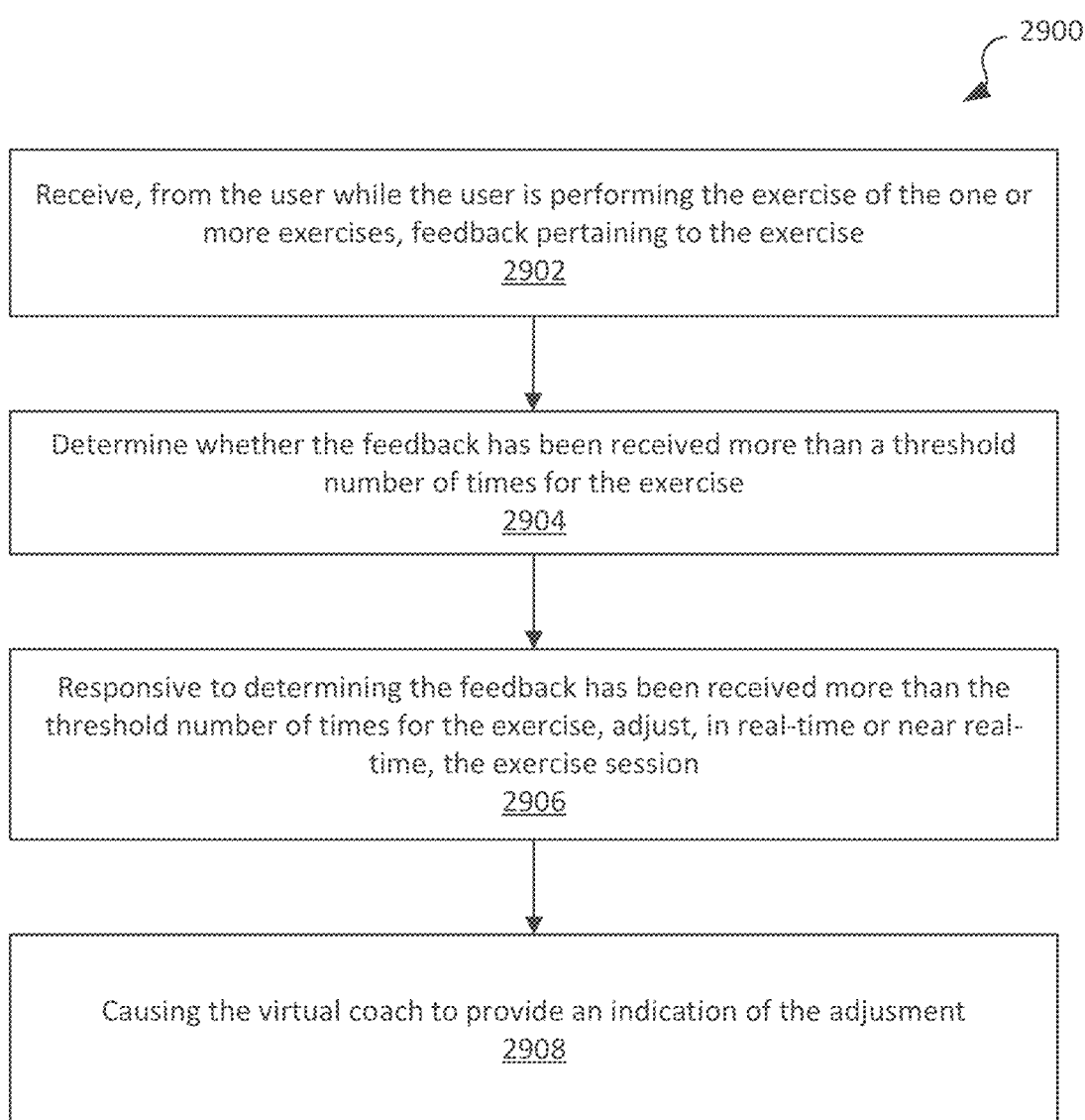
FIG. 29 illustrates an example method for adjusting an exercise session based on user feedback.

FIG. 29 illustrates an example method 2900 for adjusting an exercise session based on user feedback. The operations can be used to improve compliance with an exercise plan and may improve the user's experience using the computing device 12 and/or the exercise machine 100. The method 2900 may be performed by processing logic that may include hardware (circuitry, dedicated logic, etc.), firmware, software, or a combination of them. The method 2900 and/or each of their individual functions, subroutines, or operations may be performed by one or more processing devices of a control system (e.g., cloud-based computing system 16, computing device 12 of FIG. 1) implementing the method 2900. The method 2900 may be implemented as computer instructions that are executable by a processing device of the control system (e.g., a computer-readable medium may be used to store instructions that, when executed, cause a processor perform the following steps or processes of the method 2900). In certain implementations, the method 2900 may be performed by a single processing thread. Alternatively, the method 2900 may be performed by two or more processing threads, each thread implementing one or more individual functions, routines, subroutines, or operations of the methods. Various operations of the method 2900 may be performed by one or more of the cloud-based computing system 16, the computing device 12, and/or the computing device 15 of FIG. 1.

At 2902, the processing device may receive, from the user while the user is performing an exercise of the one or more exercises, feedback pertaining to the exercise, wherein the feedback includes an indication of a level of difficulty of the exercise. For example, the feedback may be entered by the user using any suitable peripheral (e.g., microphone, touchscreen, mouse, keyboard, etc.) of the computing device 12. The feedback may include the user saying the exercise is too easy or too hard.

At 2904, the processing device may determine whether the feedback has been received more than a threshold number of times for the exercise. At 2906, responsive to determining the feedback has been received more than the threshold number of times for the exercise, the processing device may adjust, in real-time or near real-time, the exercise session. In some embodiments, adjusting the exercise session may include changing to another exercise, controlling the exercise machine to stop the exercise, removing the exercise from the exercise session, changing an intensity of the exercise, or some combination thereof. At 2908, the processing device may cause the virtual coach to provide an indication of the adjustment. The indication may be provided via the user interface 18, a speaker of the computing device 12, or the like.

Figure 30:
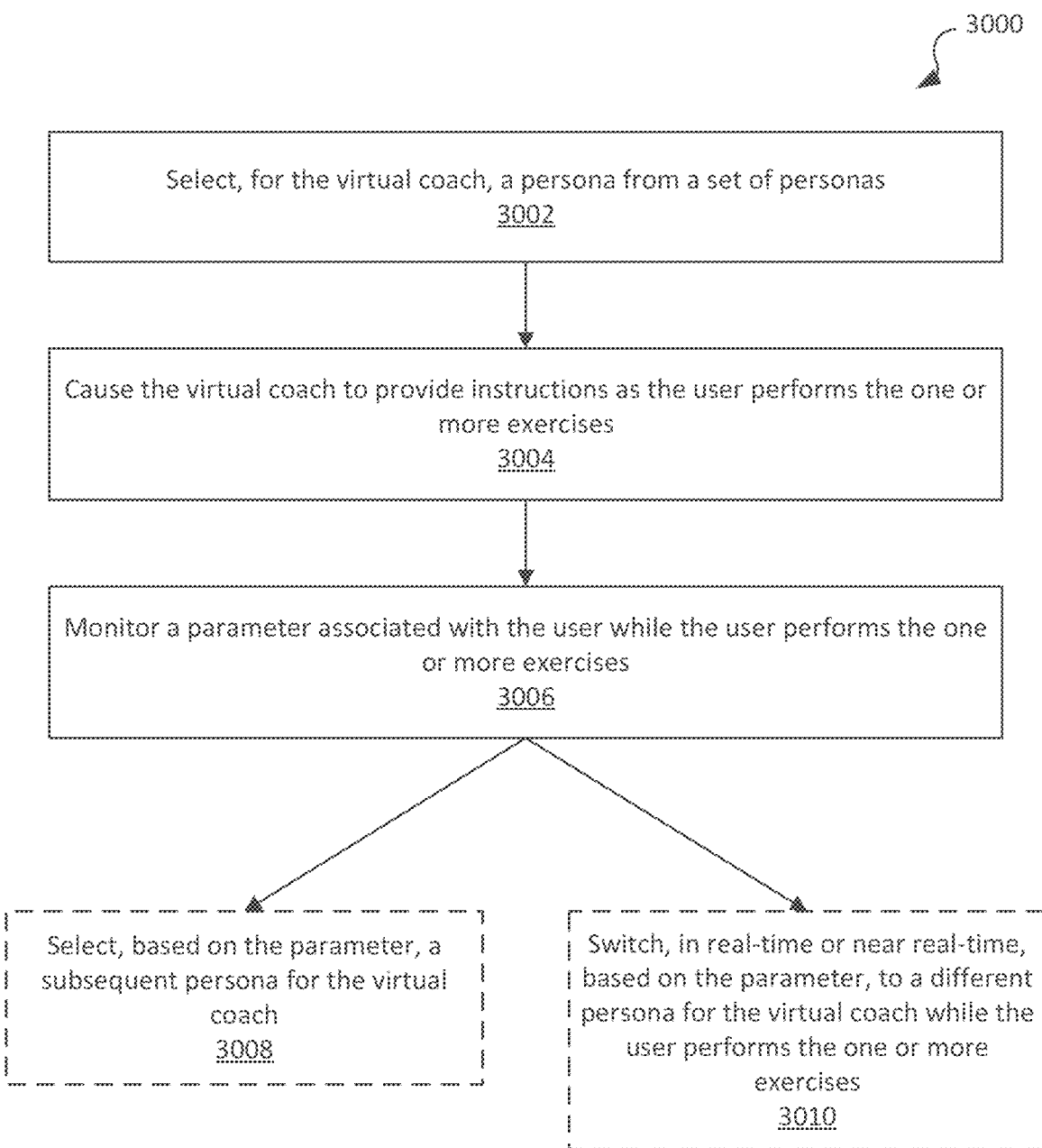
FIG. 30 illustrates an example method for selecting a persona for the virtual coach.

FIG. 30 illustrates an example method 3000 for selecting a persona for the virtual coach. The operations can be used to improve compliance with an exercise plan and may improve the user's experience using the computing device 12 and/or the exercise machine 100. The method 3000 may be performed by processing logic that may include hardware (circuitry, dedicated logic, etc.), firmware, software, or a combination of them. The method 3000 and/or each of their individual functions, subroutines, or operations may be performed by one or more processing devices of a control system (e.g., cloud-based computing system 16, computing device 12 of FIG. 1) implementing the method 3000. The method 3000 may be implemented as computer instructions that are executable by a processing device of the control system (e.g., a computer-readable medium may be used to store instructions that, when executed, cause a processor perform the following steps or processes of the method 3000). In certain implementations, the method 3000 may be performed by a single processing thread. Alternatively, the method 3000 may be performed by two or more processing threads, each thread implementing one or more individual functions, routines, subroutines, or operations of the methods. Various operations of the method 3000 may be performed by one or more of the cloud-based computing system 16, the computing device 12, and/or the computing device 15 of FIG.

At 3002, the processing device may select, for the virtual coach, a persona from a plurality of personas. The virtual coach may be implemented in computer instructions stored in a memory device and executable by a processing device. The virtual coach may include a particular voice (e.g., male, female) and have a particular persona. The persona may be randomly selected at first and the user's response to the persona may be tracked over time. The response may include whether the user performs the exercises completely or incompletely as the virtual coach guides the user through the exercises. The personas may range from a cheerleader type that provides a lot of encouragement to a drill sergeant type that is more aggressive, harsher, stricter, and/or demands compliance with the exercise or demands the user tries harder.

At 3004, the processing device may cause the virtual coach to provide instructions as the user performs the one or more exercises. The instructions may be provided visually on the user interface 18, audibly via a speaker of the computing device 12, or both.

At 3006, the processing device may monitor a parameter associated with the user while the user performs the one or more exercises. The parameter may include a vital sign (e.g., heartrate, blood pressure), sensor measurement data (e.g., ROM, pressure exerted on pedals, etc.), characteristics of the user (e.g., respiratory rate, temperature, perspiration, etc.). The monitoring may be based on any suitable sensor measurement data associated with the user, the exercise machine 100, or both. In some embodiments, the parameter pertains to a progress of the user, an indication of whether the user likes the persona of the virtual coach, or both. For example, the user may provide feedback that they like the persona of the virtual coach via the user interface 18 or by speaking to the computing device 12 via a microphone.

At 3008, the processing device may select, based on the parameter, a subsequent persona for the virtual coach. For example, if the user indicated the user does not like the persona, the processing device may select a different persona for a subsequent exercise and/or exercise session.

At 3010, the processing device may switch, in real-time or near real-time, based on the parameter, to a different persona for the virtual coach while the user performs the one or more exercises. Dynamically switching may be based on whether the user is performing the exercise well or not. For example, if the user is pedaling at substantially slower rate than desired for the exercise, the processing device may determine the user is not responding well to the persona and may switch to a different persona immediately during the exercise. The progress of the user may be tracked to see if the switch of personas impacts the progress of the user. Further, if the user indicates the user does not like the persona, the processing may switch to a different persona immediately while the user performs the exercise.

Figure 31:
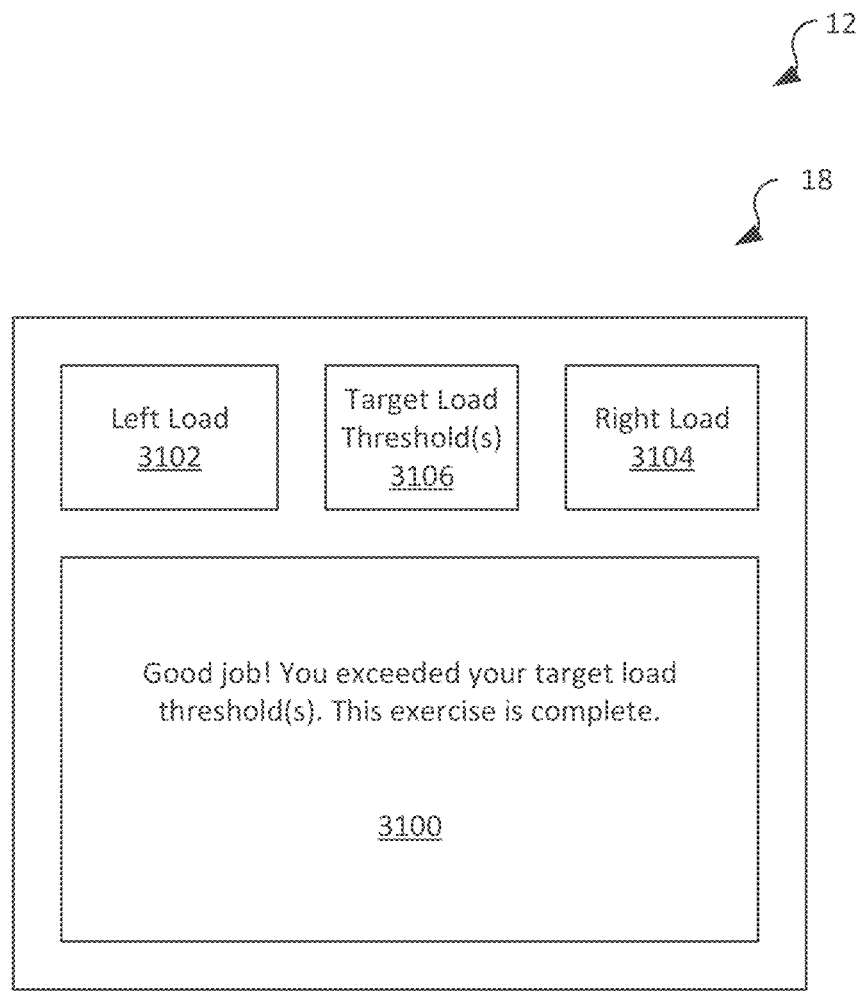
FIG. 31 illustrates an example user interface presenting an indication that an exercise is complete and congratulates the user.

FIG. 31 illustrates an example user interface 1918 presenting an indication 3100 that an exercise is complete, resulting in the user's being congratulated. For example, the indication 3100 states: "Good job! You exceeded your target load threshold(s). This exercise is complete." The user interface 1918 may present visual representations 3102 and/or 3104 for the left and right load measurements, respectively. In some embodiments, the visual representations 3102 and/or 3104 may be numerical values representing other the respective measurements. In some embodiments, the visual representation 3102 and/or 3104 may be bars on a bar chart, lines on a line chart, or any suitable visual representation.

Further, the user interface 1918 may present one or more visual representations 3106 of target load thresholds tailored for the user. For example, the one or more target thresholds may include a left target threshold, a right target threshold, or some combination thereof. Presenting the visual representations 3106 of the target thresholds concurrently with the real-time display of the measurements in the visual representations 3102 and/or 3104 may enable the user to determine how close they are to exceeding the target thresholds and/or when they exceed the target thresholds.

Figure 32:
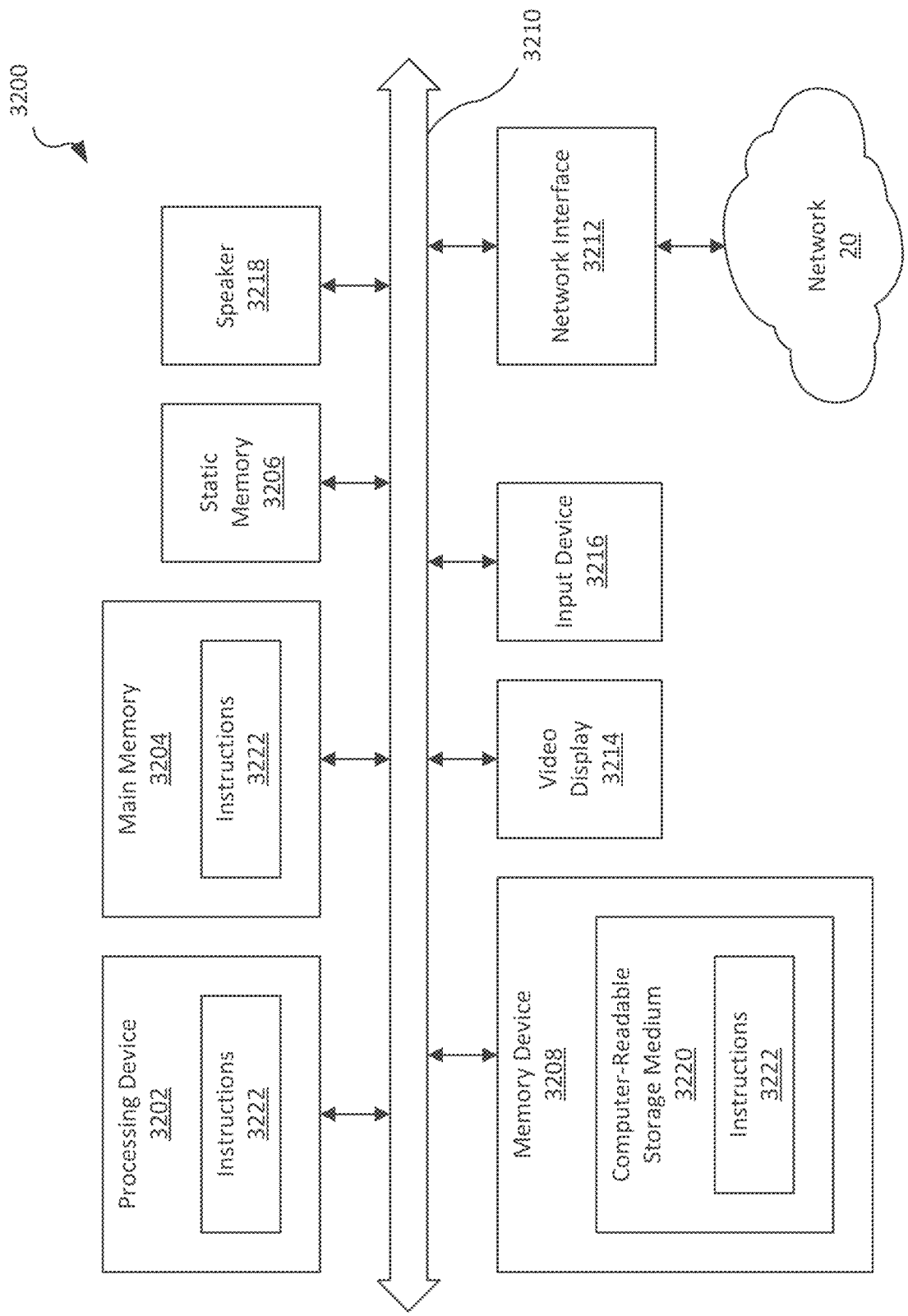
FIG. 32 illustrates an example computer system.

FIG. 32 illustrates an example computer system 3200, which can perform any one or more of the methods described herein. In one example, computer system 3200 may correspond to the computing device 12 (e.g., control system), the computing device 15, one or more servers 28 of the cloud-based computing system 16 of FIG. 1. The computer system 3200 may be capable of executing the application 17 and presenting the user interface 18 and/or the user interface 22 of FIG. 1. The computer system 3200 may be connected (e.g., networked) to other computer systems in a LAN, an intranet, an extranet, or the Internet. The computer system 3200 may operate in the capacity of a server in a client-server network environment. The computer system 3200 may be a personal computer (PC), a tablet computer, a motor controller, a goniometer, a wearable (e.g., wristband), a set-top box (STB), a personal Digital Assistant (PDA), a mobile phone, a camera, a video camera, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 3200 includes a processing device 3202, a main memory 3204 (e.g., read-only memory (ROM), flash memory, dynamic random access memory (DRAM) such as synchronous DRAM (SDRAM)), a static memory 3206 (e.g., flash memory, static random access memory (SRAM)), and a data storage device 3208, which communicate with each other via a bus 3210.

Processing device 3202 represents one or more general-purpose processing devices such as a microprocessor, central processing unit, or the like. More particularly, the processing device 3202 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 3202 may also be one or more special-purpose processing devices such as an application specific integrated circuit (ASIC), a field programmable gate array (FPGA), a digital signal processor (DSP), network processor, or the like. The processing device 3202 is configured to execute instructions for performing any of the operations and steps discussed herein.

The computer system 3200 may further include a network interface device 3212. The computer system 3200 also may include a video display 3214 (e.g., a liquid crystal display (LCD) or a cathode ray tube (CRT)), one or more input devices 3216 (e.g., a keyboard and/or a mouse), and one or more speakers 3218 (e.g., a speaker). In one illustrative example, the video display 3214 and the input device(s) 3216 may be combined into a single component or device (e.g., an LCD touch screen).

The data storage device 3208 may include a computer-readable storage medium 3220 on which the instructions 3222 (e.g., implementing the application 17 or 21 executed by any device and/or component depicted in the FIGURES and described herein) embodying any one or more of the methodologies or functions described herein are stored. The instructions 3222 may also reside, completely or at least partially, within the main memory 3204 and/or within the processing device 3202 during execution thereof by the computer system 3200. As such, the main memory 3204 and the processing device 3202 also constitute computer-readable media. The instructions 3222 may further be transmitted or received over a network via the network interface device 3212.

While the computer-readable storage medium 3220 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Figure 33:
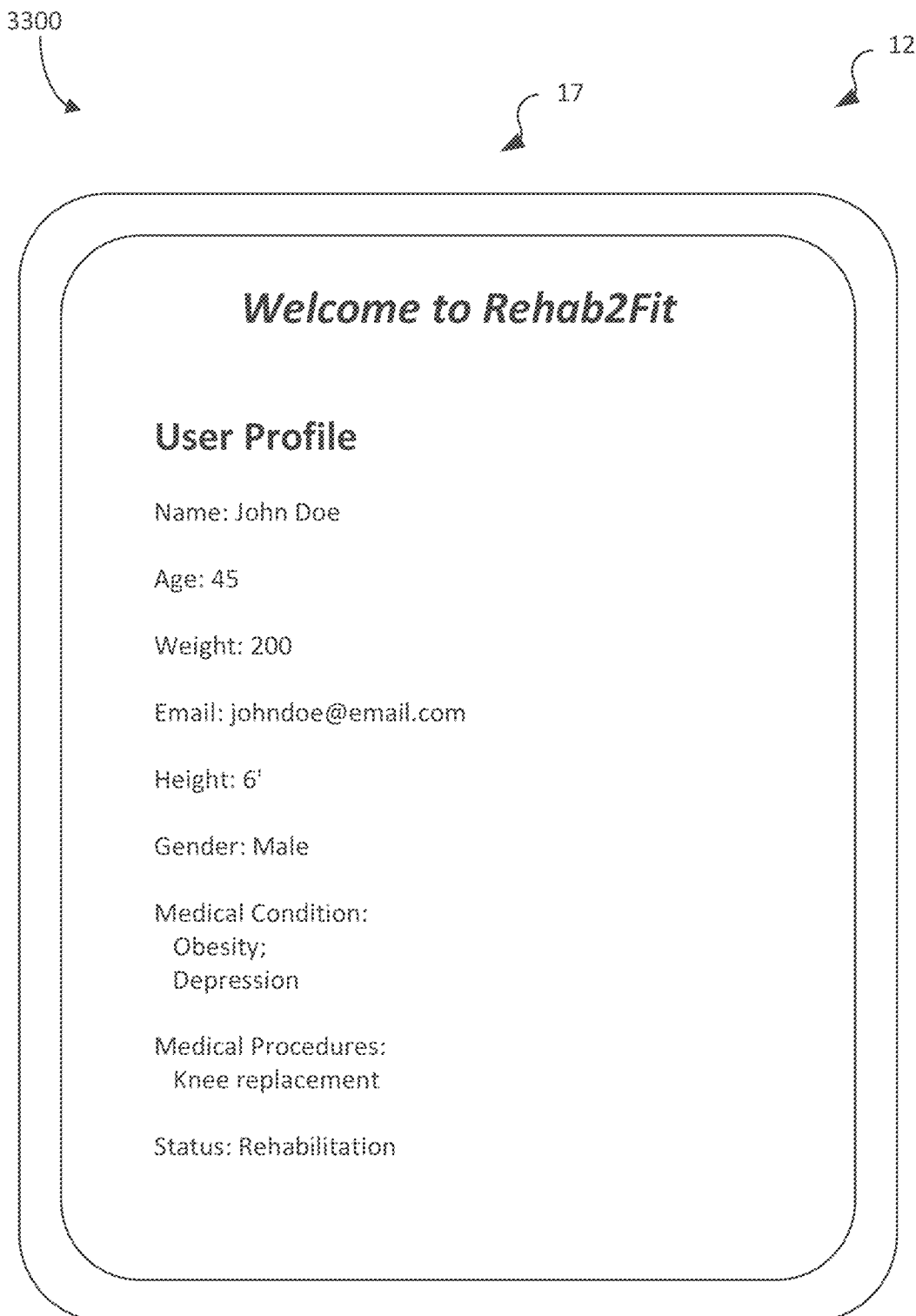
FIG. 33 illustrates an example user interface presenting a user profile.

FIG. 33 illustrates an example user interface 3300 presenting a user profile of the application 17 on the computing device 12. The user interface 3300 may include various information for a user to complete in the user profile. For example, the information may include a name ("John Doe"), an age ("45"), a weight ("200"), an email (johndoe@email.com), a height ("6"), a gender ("Male"), one or more medical conditions ("Obesity", "Depression"), one or more medical procedures ("Knee Replacement"), and one or more statuses ("Rehabilitation"). Using an input peripheral, such as a keyboard, mouse, touchscreen, microphone, etc., the user may enter the information on the user interface 3300. In some embodiments, the cloud-based computing system 16 may provide computer instructions that cause presentation of the user interface 3300. The user interface 3300 may be a website executed by a web browser, or a standalone application installed on the computing device 12 and in communication with the cloud-based computing system 16. The computing device 12 may be communicatively coupled to the exercise machine 100, and in some embodiments, the user may, using the computing device 12, control operating parameters of the exercise machine 100.

In some embodiments, the cloud-based computing system 16 and/or the computing device 12 may connect to and/or use an application programming interface (API) exposed by a third-party entity, such as an electronic medical records (EMR) system, and/or a social network system. The API may be used by the application 17 to extract information pertaining to EMR of the user, if proper authorization is given and authorization of a user account is completed. The EMR information may automatically populate the appropriate fields in the user profile. For example, the medical procedures identified in the EMR information may be populated. In some embodiments, the format of the data obtained by the API may be in a different format than the format the application 17 uses. In such an instance, the application 17 may transform the data's format into an acceptable format (e.g., extensible markup language (XML)) for the application 17. In some embodiments, the application 17 may use the API to access the user's information on a social media or social network system (e.g., Facebook®, Twitter®, Instagram®, etc.) to obtain information publicly available on the social network system.

Figure 34:
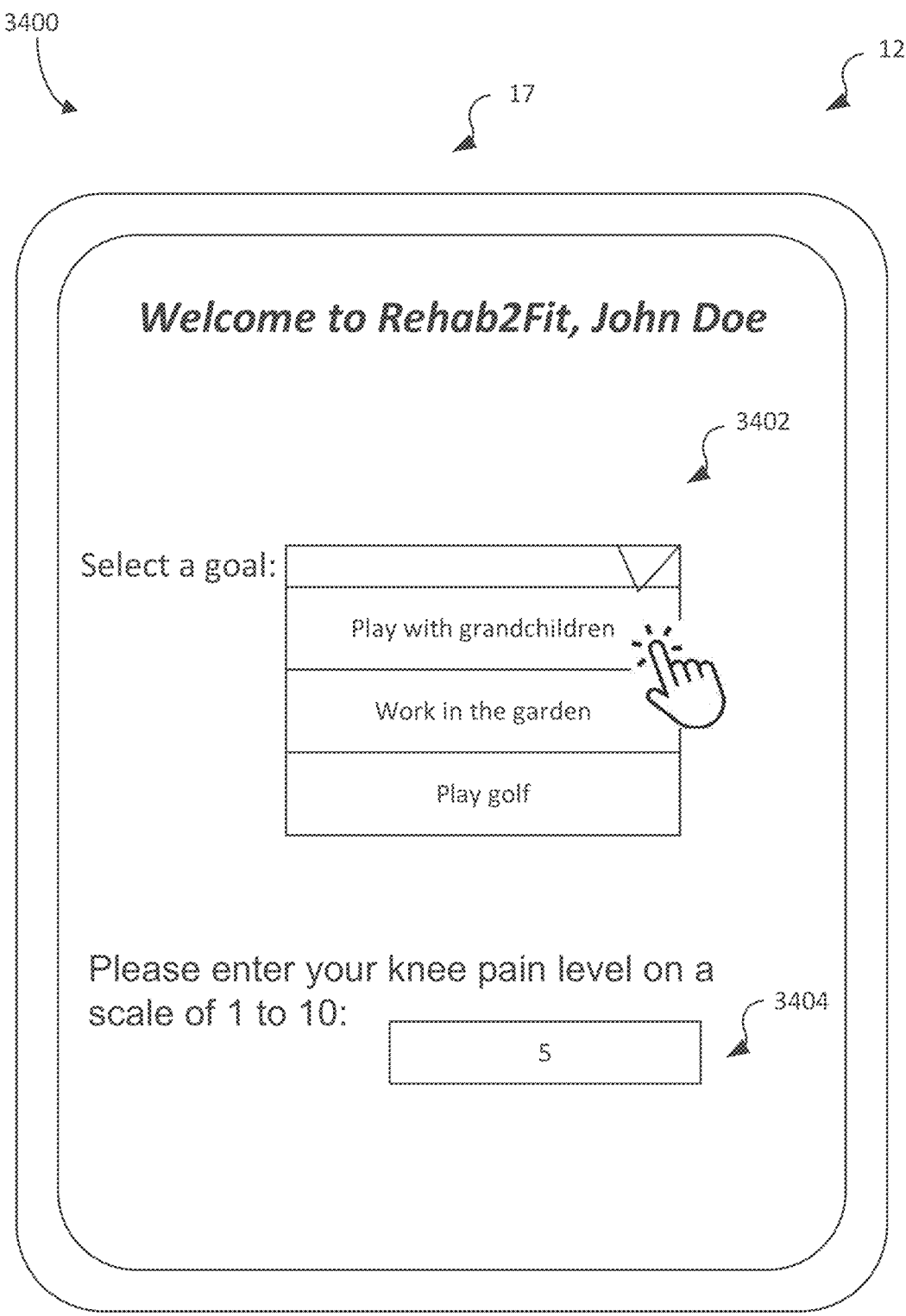
FIG. 34 illustrates an example user interface for selecting a physical activity goal and a pain level.

FIG. 34 illustrates an example user interface 3400 for selecting a physical activity goal and a pain level. As depicted, graphical element 3402 may be used to select the physical activity goal. The graphical element 3402 is itself depicted as a dropdown menu but any suitable graphical element may be used (e.g., input box, checklist, etc.). In the example, the user has used a touchscreen to select a physical activity goal "Play with grandchildren". Further, graphical element 3404 may be used to enter a pain level the user is currently experiencing. Graphical element 3404 may be any suitable graphical element capable of receiving input.

The received input of the physical activity level and the pain level may be used by the one or more machine learning models 60 to generate an improved exercise plan. For example, the machine learning model may determine, using a data source including various associations, including, for example, the levels of attainment associated with achieving the physical activity level, where the levels of attainment may include range of motion, strength, endurance, balance, intelligence, neurological responsiveness, emotional well-being, and mobility. Further, the machine learning model 60 may determine which body portions to target for the various levels of attainment, and which exercises to select to include in the exercise plan that target the appropriate body portions. In some embodiments, the pain level reported by the user may be used to select exercises, difficulty levels of the exercises, and the like.

Figure 35:
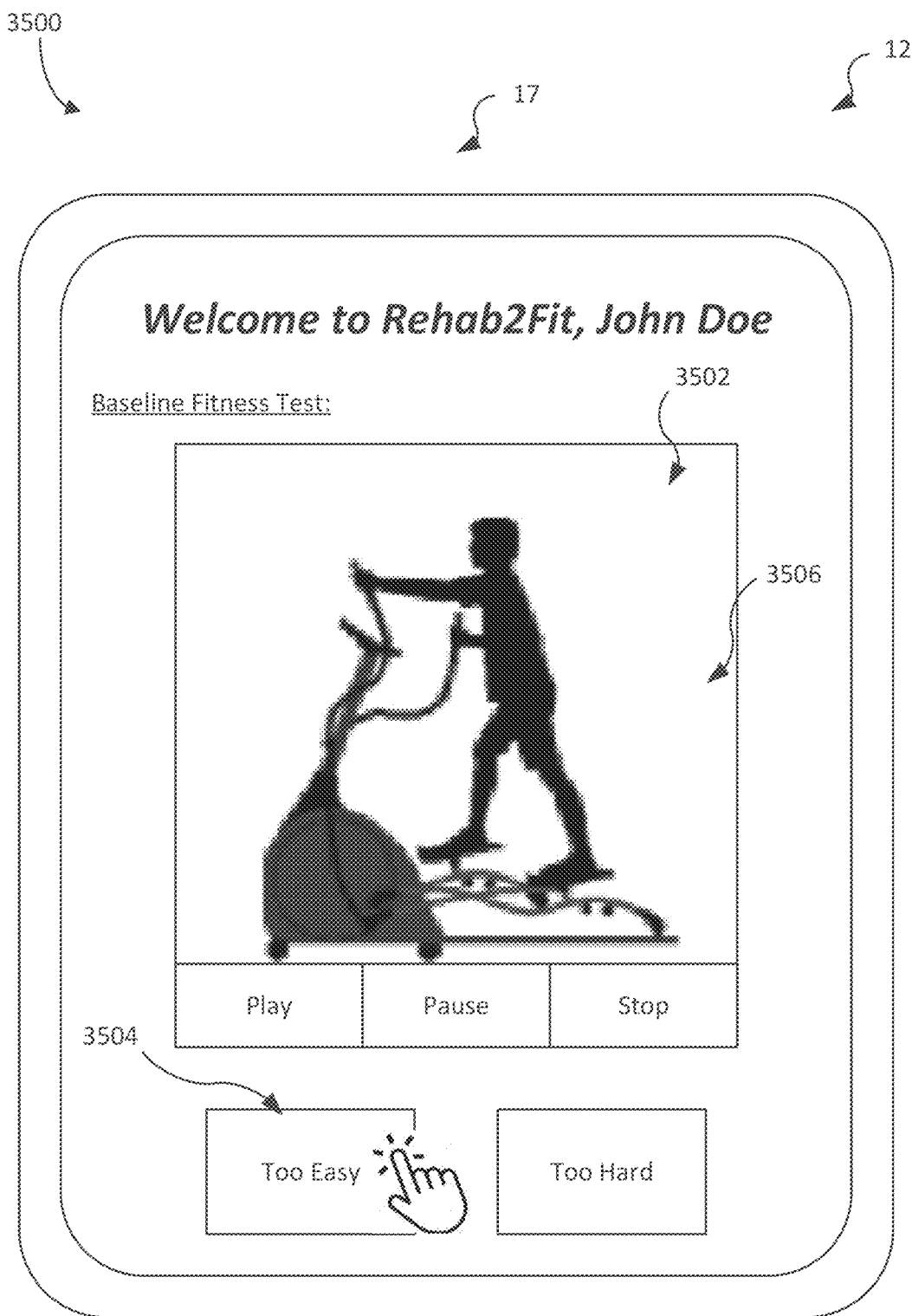
FIG. 35 illustrates an example user interface presenting information pertaining to a first exercise of a baseline fitness test.

In some embodiments, upon the user's selecting the physical activity goal and the pain level, an onboarding protocol that uses a baseline fitness test may be initiated. For example, FIG. 35 illustrates an example user interface 3500 presenting information pertaining to a first exercise 3502 of a baseline fitness test. The baseline fitness test may select an exercise for the user to perform, and the exercise difficulty level for the first exercise 3502 may be set to an easiest difficulty level. As the user performs the first exercise, the following may be obtained: characteristics of the user, performance measurements of the user, user-reported difficulty level of the exercise, user-reported pain level of the user, and the like. For example, the user may select a graphical element 3504 (button) to indicate that the first exercise is too easy.

Selection of the graphical element 3504 may cause the machine learning model 60 to select a next exercise that is more difficult. The onboarding protocol may include exercises having tiered difficulty levels and may select for subsequent exercises for the user to perform, wherein the subsequent exercises advance in difficulty until the user has either completed all of the exercises or reached a point where the user can no longer perform the exercise because it is too difficult or painful. The machine learning model 60 may determine a fitness level for the user based on a completion state (e.g., a degree of completion, a percentage of completion, a value of completion, etc.) of a last exercise performed by the user. The machine learning model 60 may select a difficulty level for each exercise in the improved exercise plan by associating the difficulty level for each exercise with the fitness level of the user.

In some embodiments, a multimedia segment (e.g., recording or feed) may be presented in a digital media player 3506. The multimedia segment may include video and/or audio of a coaching character providing instructions and guidance on how to perform the first exercise. Various options may be provided by the digital media player that enable the user to play, pause, or stop the multimedia segment. There may be options to enable the user to fast forward or rewind the multimedia segment, as well.

Figure 36:
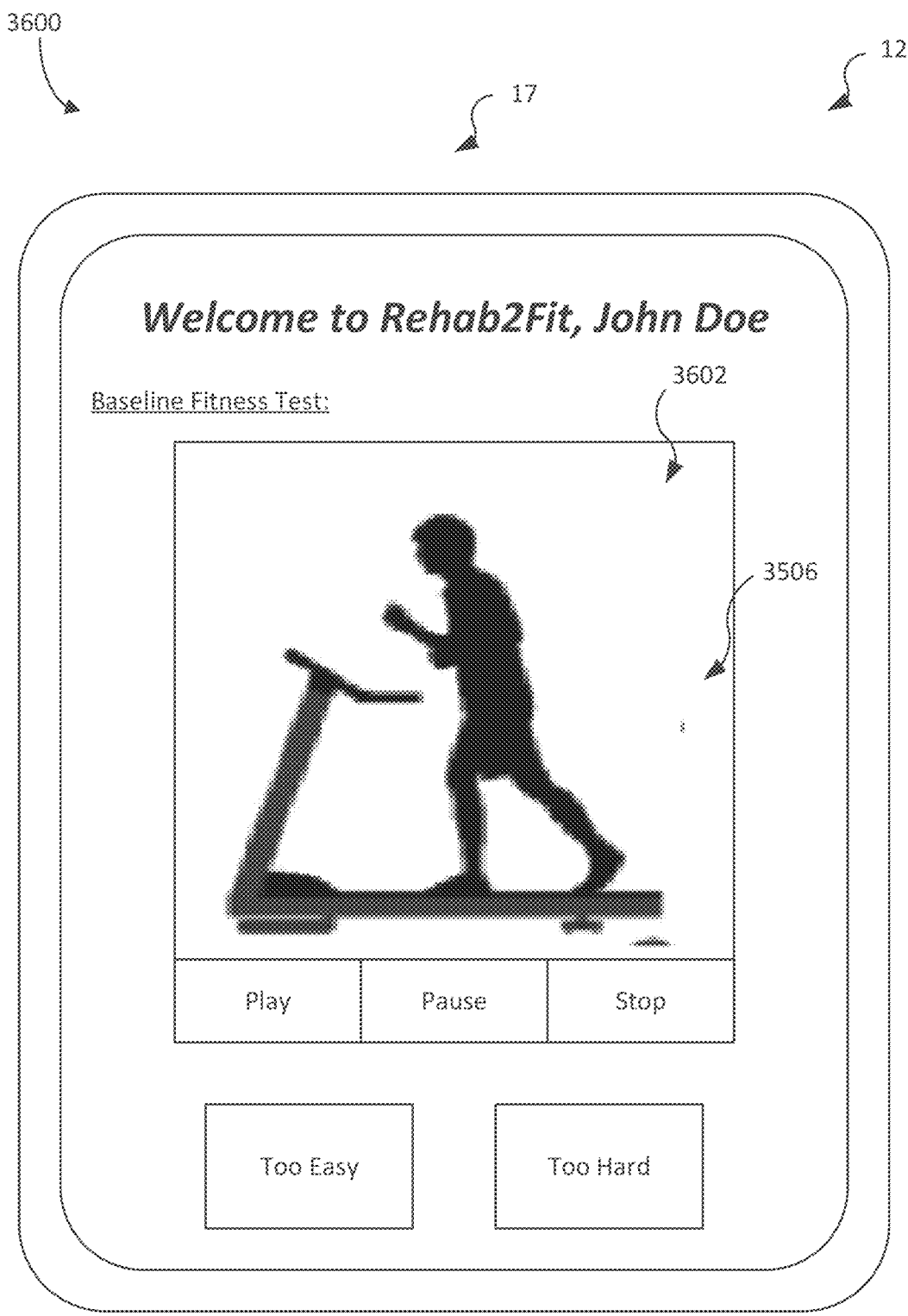
FIG. 36 illustrates an example user interface presenting information pertaining to a second exercise of a baseline fitness test.

FIG. 36 illustrates an example user interface 3600 presenting information pertaining to a second exercise 3602 of the baseline fitness test. As depicted, a different multimedia segment is being played in the digital media player 3506. The new multimedia segment may include video and/or audio of a coaching character providing information and guidance to the user pertaining how to perform the second exercise 3602. The second exercise 3602 may be selected as a result of the user indicating the previous exercise was too hard or too easy. In some embodiments, the second exercise 3602 may be selected by default by the machine learning model 60. After the baseline fitness test is performed by the user, the machine learning model 60 may determine the fitness level of the user, and use the fitness level of the user to select the exercises and/or their difficulty levels in the improved exercise plan.

Figure 37:
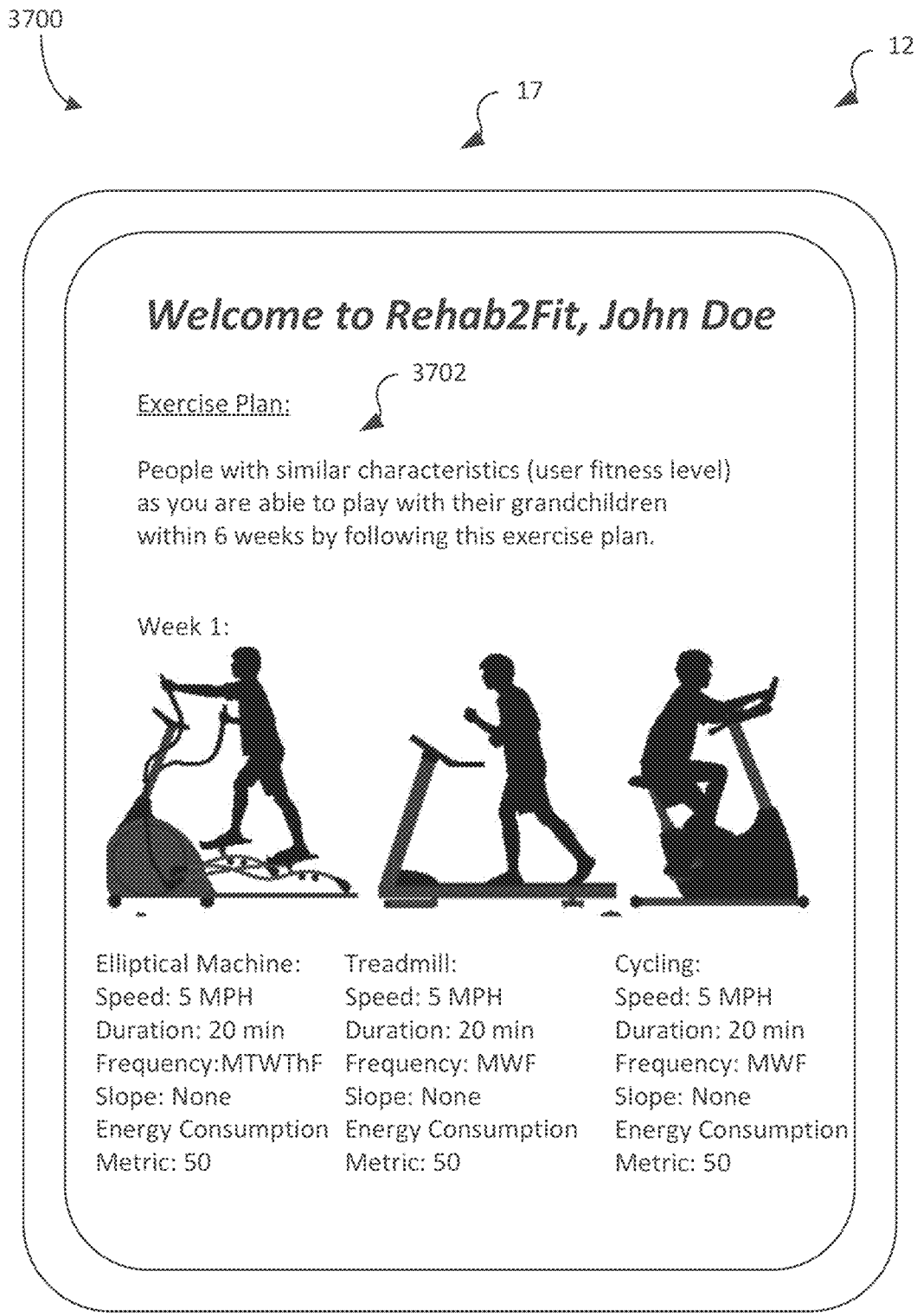
FIG. 37 illustrates an example user interface presenting a generated exercise plan for a user.

FIG. 37 illustrates an example user interface 3700 presenting a generated exercise plan 3702 for a user. The user interface 3700 presents a first week of exercises for the user to perform. The exercise plan 3702 indicates "People with similar characteristics (user fitness level) as you are able to play with their grandchildren within 6 weeks by following this exercise plan." As described further herein, the exercises included in the exercise week 1 schedule may include exercises prioritized for the levels of attainment associated with the selected physical activity goal. For example, the exercises depicted all relate to cardiovascular health and moving, which correspond with a mobility and endurance level of attainment, both of which may be ranked higher for a physical activity goal of playing with grandchildren. This technique may enable ensuring the appropriate body portions of the user are targeted via proper exercises to achieve the levels of attainment, and thereby achieve the physical activity goal.

As further depicted, each exercise includes an energy consumption metric ("50"). The energy consumption metric may vary for each exercise and it may provide a target metric for the user to achieve during each exercise. The energy consumption metric may be based on a combination of various types of information and metrics associated therewith, such as a metabolic indicator associated with performing the exercise, fitness results of the user, and/or a user-reported pain level of the user, among other information. The energy consumption metric may be determined for the user while they perform the exercise, and when the target energy consumption metric has been exceeded, the user may be done with the exercise. The application 17 may track the user's progress over time if and when the user exceeds or meets the target energy consumption metric. Each determined energy consumption metric for each exercise may be summed to determine an energy score associated with an amount of energy it will take to achieve the physical activity goal. If the summed energy consumption metrics equal or exceed the energy score, then the user may have enough energy to achieve the physical activity goal. As may be appreciated, the user may exceed or match the energy score faster or slower than predicted based on a number of factors, such as their performance, their drive, their health (e.g., physical and mental), their compliance with the exercise plan, and the like.

Figure 38:
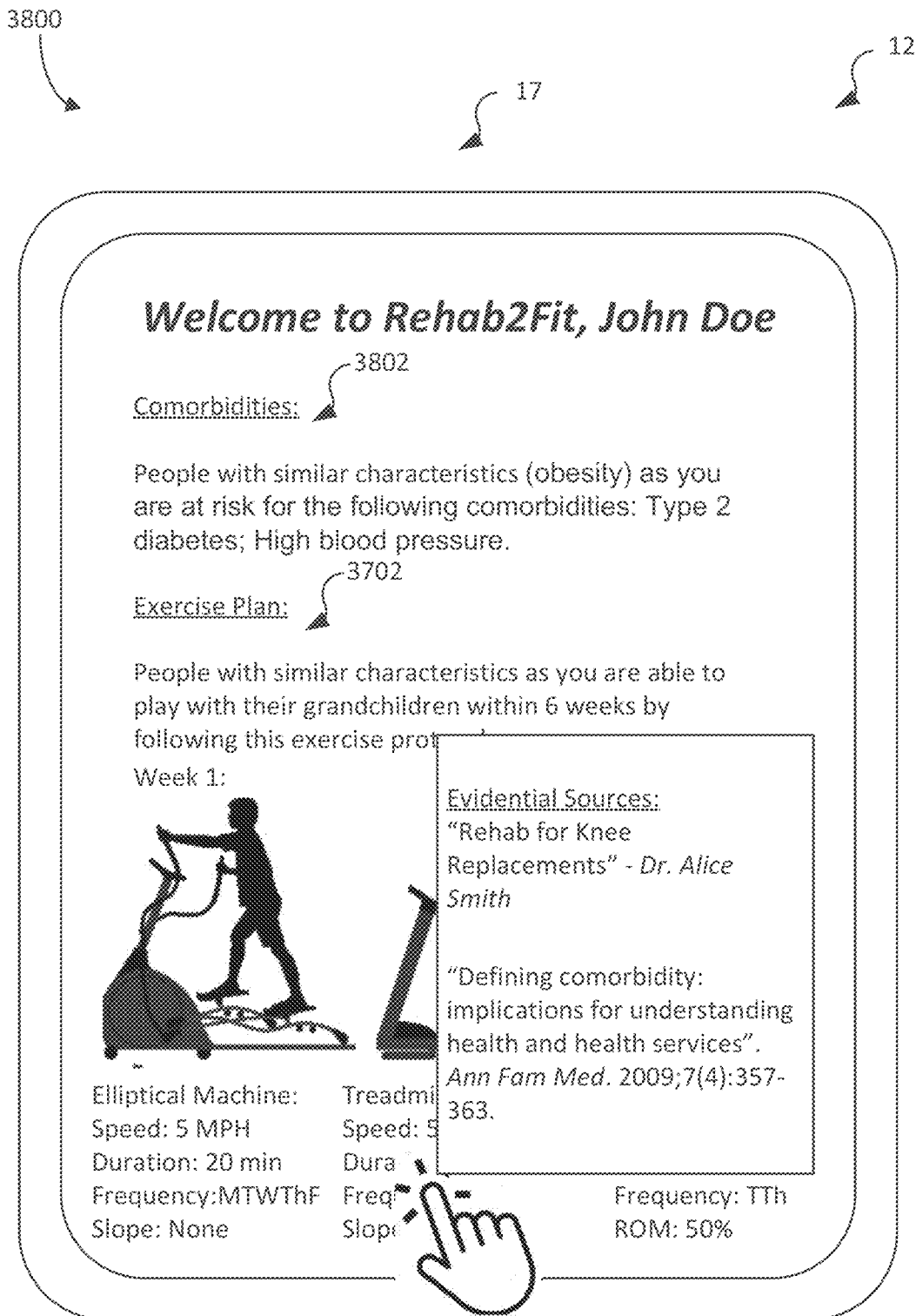
FIG. 38 illustrates an example user interface presenting information pertaining to a user's comorbidities, week one of an exercise plan, and evidential source pertaining to the comorbidities and the exercise plan.

FIG. 38 illustrates an example user interface 3800 presenting information pertaining to a user's comorbidities 3802, week one of an exercise plan 3702, and evidential source 3804, wherein the evidential source 3804 pertains to the comorbidities and the exercise plan. The information may be stored and accessed in the data source 67. The machine learning model 60 may be trained to receive input data (e.g., characteristics of the user, performance measurements of the user, user-reported pain levels, user-reported difficulty levels of exercises, etc.) and to output comorbidity information. For example, the machine learning model 60 may match the input data of the user with one or more other users or cohorts to determine that the one or more similarly situated users or cohorts are associated with certain comorbidities, and to output the certain comorbidities 3802 on the user interface 3800. The resources used by the data source 67 and the machine learning model 60 may be curated by health professionals and may be associated with certifications of authenticity, board review, board approval, evidence-based guidelines or the like. As depicted, evidential sources 3804 are presented in a pop-up window overlaid on the exercise plan 3702 when the user hovers over or "taps" on a particular part of the user interface 3800 with an input peripheral (e.g., touchscreen). The evidential sources 3804 provide information about the resources used by the machine learning models 60 to determine the comorbidity information 3802 and the exercise plan 3702. For example, the evidential source 3804 indicates one resource used was "Rehab for Knee Replacements'—Dr. Alice Smith", and another resource used was "'Defining comorbidity implications understanding health and health service'. Ann Fam Med. 2009; 7(4):357-363". The comorbidity information 3802 indicates "People with similar characteristics (obesity) as you are at risk for the following comorbidities: Type 2 diabetes; High blood pressure."

Figure 39:
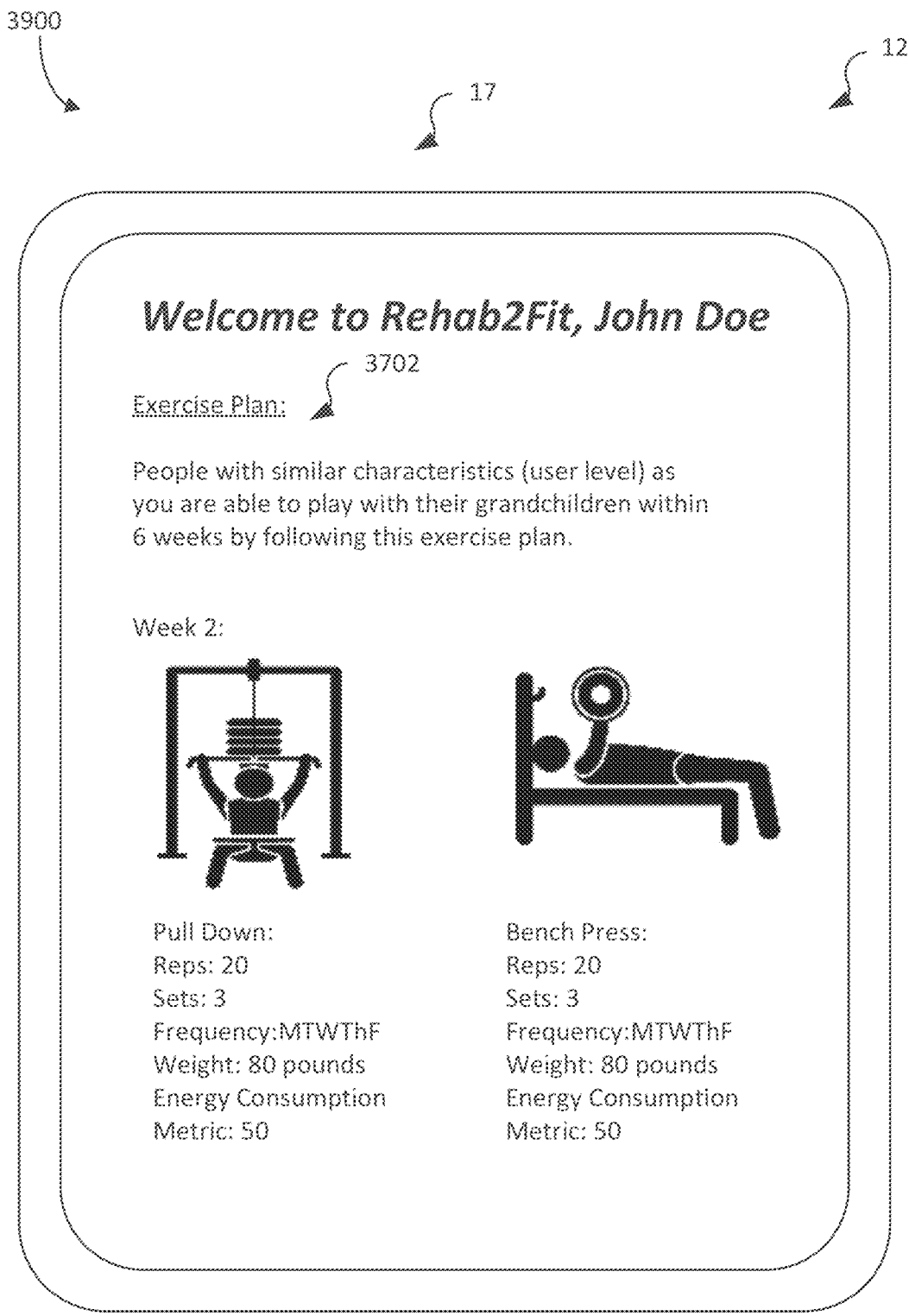
FIG. 39 illustrates an example user interface presenting information pertaining to week two of an exercise plan for a user.

FIG. 39 illustrates an example user interface 3900 presenting information pertaining to week two of an exercise plan 3702 for a user. As depicted, the exercises included in week two of the exercise plan 3702 target the upper body of the user, whereas the exercises in week one of the exercise plan 3702 targeted the lower body of the user and cardiovascular health of the user. To ameliorate boredom, improve engagement, improve compliance, and the like, the exercises may be selected and arranged differently between the various weeks of the exercise plan 3702. Further, to focus on different levels of attainment and their associated body portions that are used to achieve the levels of attainment, the exercises may be differentiated between weeks. The exercises selected in week two in the exercise plan 3702 may be related to the upper body to improve strength to enable a user to pick up their grandchild, for example, while playing with the grandchild. The exercise plan 3702 also includes other information pertaining to each exercise, such as a type of exercise, a number of repetitions, a number of sets, a frequency, an amount of weight, and/or the energy consumption metric.

Figure 40:
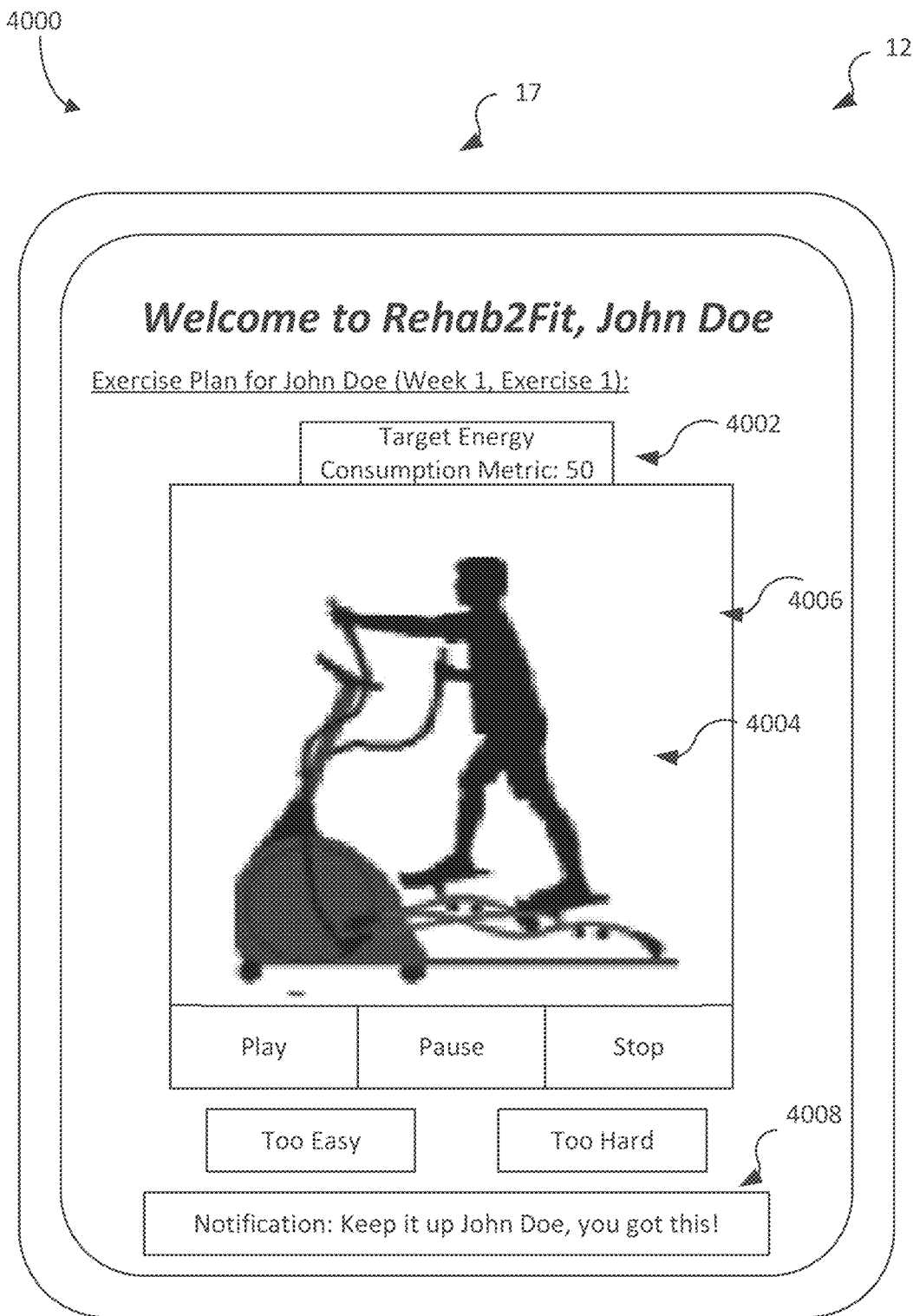
FIG. 40 illustrates an example user interface presenting information pertaining to a target energy consumption metric for an exercise.

FIG. 40 illustrates an example user interface 4000 presenting information pertaining to a target energy consumption metric 4002 for an exercise. In some embodiments, the user may initiate the exercise plan 3702 by selecting from any of the user interfaces depicted herein the first exercise to begin. As depicted, the multimedia segment 4004 begins playback via the digital media player 4006. The target energy consumption metric 4002 for the first exercise in week one of the exercise plan 3702 is depicted as being 50. In some embodiments, the user's energy consumption metric may be dynamically determined as the user performs the exercise and also presented in the user interface 4000 such that the user is apprised of their progress toward meeting or exceeding the target energy consumption metric. Also, as depicted, a notification 4008 is presented in the user interface 4000. The notification 4008 may be selected and presented by one or more machine learning models 60 trained to identify when a user may benefit from a certain notification. For example, the machine learning model 60 may determine that the user has reported the exercise is too hard, and may determine to provide a motivational quote, such as "Keep it up John Doe, you got this!"

FIG. 41A-41E illustrates an example data source 67 including information pertaining to exercises and physical activity goals. As depicted in FIG. 41A, a table 4100 includes information pertaining to exercises and physical ability goals (also referred to as a "life goal" in the table 4100). The table 4100 has columns labeled "ID", "Name", "MET Score", "Description", "Difficulty (E, M, H)", "Exercise Levels", "Sections", "Life Goals", and "Difficulty Decrease ID". For example, a first row having ID "1" indicates the exercise is named "Sitting Knee Extension", has a MET score of "3.5", has a description of "Start with feet on ground while sitting in chair. Then lift one foot and straighten the knee and hold", has a difficulty of "M" (medium), has exercise levels of "1, 2, 3", is associated with sections "3, 4", and decreases difficulty ID of "2". A MET score may also be referred to as a MET indicator and may refer to a ratio of working metabolic rate of a person relative to the person's resting metabolic rate. Metabolic rate is the rate of energy expended per unit of time. It may refer to one way to describe the intensity of an exercise or activity. The Sections may include identifiers for exercise sections, such as "1—warmup", "2—cardio", "3—strength", "4—flexibility", "5—cooldown", and/or "6—cycling".

FIG. 41B illustrates an example data source 67 including information pertaining to levels of attainment associated with physical ability goals, as depicted in FIG. 41D. The levels of attainment may be also referred to "components" in FIG. 1D. The levels of attainment table 4110 may include identifiers (ID) and names ("1—Range of Motion (ROM)", "2—Strength", "3—Endurance", "4—Balance", "5—Mobility", etc.). Each of the levels of attainment may be associated with one or more body portions. FIG. 41C depicts a table 4120 including identifiers (ID) and names for body portions ("1—Hip Flexor", "2—Posterior Hip", "3—Hamstring", "4—Lateral Hip", etc.

FIG. 41D illustrates an example data source 67 including information pertaining to the various physical ability goals, the body portions to target to achieve the physical ability goal, and rankings of the levels of attainment to prioritize when selecting exercises and scheduling an exercise plan. For example, row 2 having ID 2 is a physical ability goal named "Getting up/down stairs". The body parts that need to be improved are listed in a comma delimited list. That is, an ID or tag or key is included in the list and each of the IDs corresponds to a particular body part, as shown in FIG. 41C. Further, the table 4130 includes a prioritization of which levels of attainment should be more heavily weighted when selecting exercises. The component 1 ("ROM") is shown as receiving a priority of "1", which in this example represents a highest priority, whereas component 3 ("Endurance") is shown as receiving a priority of "4", which in this example represents a second to lowest priority. Based on the rankings, the machine learning model 60 may be trained to select various types of exercises for the exercise plan.

FIG. 41C illustrates an example data source 67 including information related to the relative weights each level of attainment and their associated percentages of exercises should be given when determining the exercise plan for a 6-week period of time. The relative weights for the levels of attainment and percentages of exercises related to those levels of attainment that should be included in the exercise plan add up to a value of 1 for each week. For example, for the first week in the table 4140, the first component receives a priority percentage of 0.4 for its associated exercises, the second component receives a priority percentage of 0.4 for its associated exercises, the third component receives a priority percentage of 0.2 for its associated exercises, the fourth component receives a priority percentage of 0 for its associated exercises, and the fifth component receives a priority percentage of 0 for its associated exercises. The priority percentages add up to 1, as shown in the "Total %". As depicted, in some embodiments, the priority percentages shift over the course of the 6-week time period, such that more exercises are selected for the fourth and fifth components as the time progresses. Such a technique may enable ensuring that each component is properly worked on in order to achieve the physical ability goal. Also, a useful technique to ameliorate boredom is to vary the types of exercises performed each week, which may thereby lead to improved compliance with the exercise plan.

Figure 42:
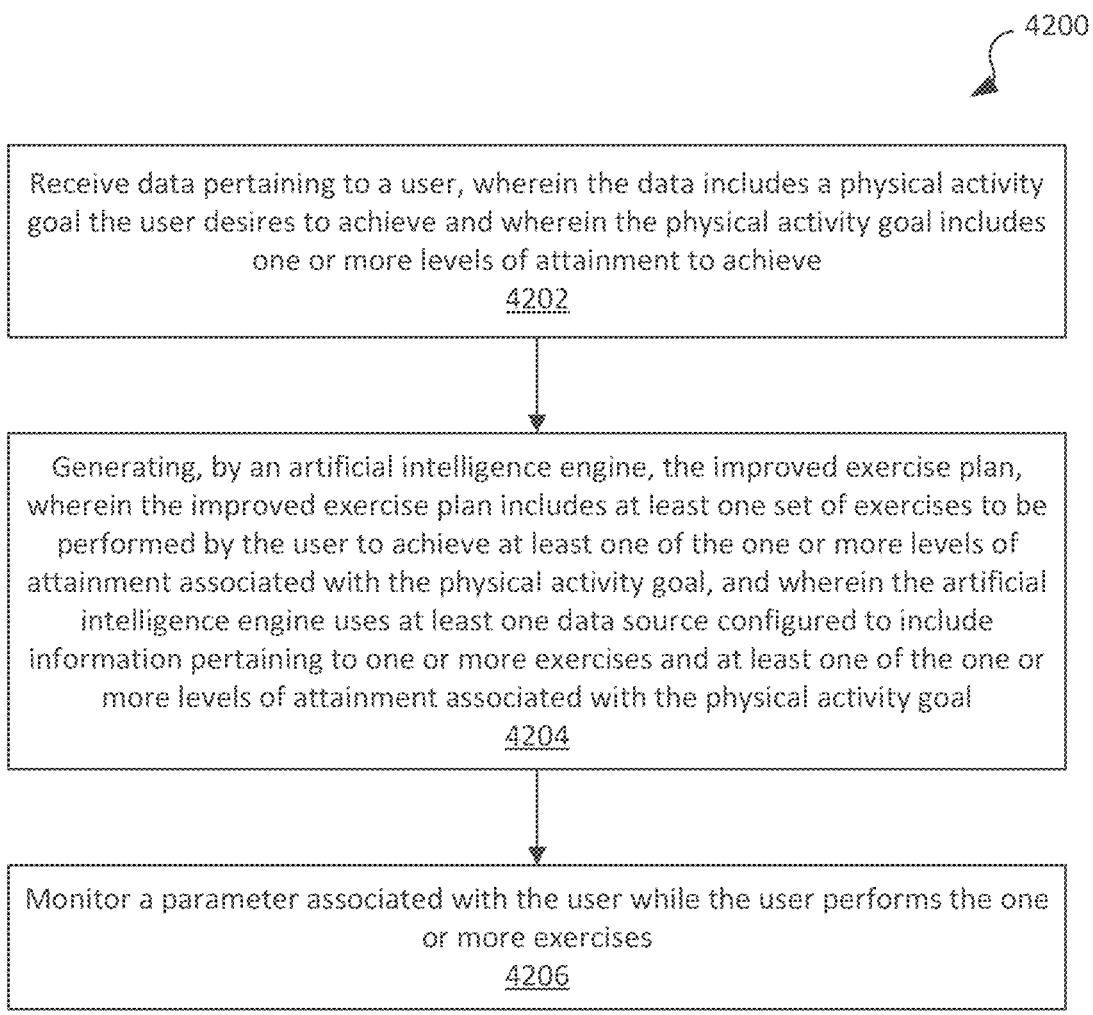
FIG. 42 illustrates an example method for generating an exercise plan based on a selected physical activity goal.

FIG. 42 illustrates an example method 4200 for generating, based on a selected physical activity goal, an exercise plan. The method 4200 may be performed by processing logic that may include hardware (circuitry, dedicated logic, etc.), firmware, software, or a combination of them. The method 4200 and/or each of their individual functions, subroutines, or operations may be performed by one or more processing devices of a control system (e.g., cloud-based computing system 16, computing device 12 of FIG. 1) implementing the method 4200. The method 4200 may be implemented as computer instructions executable by a processing device (e.g., a computer-readable medium may be used to store instructions that, when executed, cause a processor to perform the following steps or processes of the method 4200). In certain implementations, the method 4200 may be performed by a single processing thread. Alternatively, the method 4200 may be performed by two or more processing threads, each thread implementing one or more individual functions, routines, subroutines, or operations of the methods. Various operations of the method 4200 may be performed by one or more of the cloud-based computing system 16, the computing device 12, and/or the computing device 15 of FIG. 1.

The method 4200 may enable generating an improved exercise plan for a user to perform using at least an exercise machine 100. At 4202, the processing device may receive data pertaining to the user. The data pertaining to the user may include at least one selection of a physical activity goal the user desires to achieve. In some embodiments, the user may select more than one physical activity goal to achieve. The physical activity goals may include any activity that includes physical motion of a portion of the user's body. For example, the physical activity goals may include ameliorating knee pain, traversing stairs, gardening, performing yardwork, playing, walking, running, meditating, learning faster, improving concentration, improving focus, increasing response time to stimuli, improving relationships, improving sex drive, changing a state of mind, improving cardiovascular performance, improving heart rate, improving blood pressure, sitting without pain, standing without pain, feeling energized, performing more advanced exercises, performing more exercises, carrying groceries, performing house chores, losing weight, or some combination thereof. In some embodiments, the user may use a user interface including one or more graphical elements to select the physical activity goal via the computing device 12.

In some embodiments, the processing device may execute a machine learning model 60 trained to generate the exercise plan using an energy score. An energy score may refer to an amount of energy it takes to achieve the physical activity goal. The energy score may be based on a metabolic indicator associated with performing each exercise. The energy score may be an accumulation of at least all the metabolic indicators for the exercises included in the exercise plan. An energy consumption metric may be associated with each exercise, and the energy consumption metric may be determined using the metabolic indicator for an exercise, user fitness test results, user-reported pain levels, an indication of a pain level the user is in, heartrate, step count, blood pressure, perspiration, blood oxygen levels, body temperature, or some combination thereof. The energy score may indicate that by performing the exercises included in the exercise plan, the user will have enough energy to be able to achieve the physical activity goal. To determine whether the user exerted enough energy for that particular exercise, progress toward the energy score may be tracked at each exercise by calculating the energy consumption metric. One or more graphical elements (e.g., charts, tables, etc.) may be used to dynamically visualize, by depicting respective energy consumption metrics over a time series, the progress the user is making toward the energy score.

Each of the physical activity goals may include one or more levels of attainment to achieve. As described herein, the one or more levels of attainment may refer to range of motion, strength, endurance, balance, intelligence, neurological responsiveness, emotional well-being, cardiovascular well-being, and/or mobility. The levels of attainment may be associated with each physical activity goal. For example, a gardening physical activity goal may cause an exercise plan to be generated that includes exercises that improve the levels of attainment involving range of motion (e.g., kneeling down and bending over to garden) and endurance (e.g., energy consumed by gardening), more than the level of attainment of mobility (e.g., since the user is typically not moving around very much while planting flowers or the like). The levels of attainment may be quantified by, measured by, or associated with measurements (e.g., range of motion extension and/or flexion angles, exerted force measurements, amount of weight lifted, pressed, or curled, etc.), achievements (e.g., number of sets completed, number of repetitions completed, number of exercise sessions completed, weight lost, calories consumed, steps walked, etc.), and the like. The measurements may be obtained via one or more sensors associate with the exercise machine 100, the user, or the environment in which the user uses the exercise machine 100. In some embodiments, the sensor may be a wearable device that the user wears while using and while not using the exercise machine 100. For example, a step counting wearable may be worn by the user while not engaged in an active exercise session (e.g., while walking around a grocery store, etc.).

The data obtained from the sensors may enable monitoring the user's comprehensive lifestyle to enable predicting when the user will achieve the physical activity goal accurately and to provide recommendations pertaining to the user's health. In some embodiments, data from each user of the application 17, the exercise machine 100, or both, may be monitored and stored to enable training the machine learning models 60 to perform one or more functions. For example, the machine learning models 60 may be generated using training data that enables the machine learning models 60 to receive input data (e.g., characteristic of the user, performance measurement, pain level of the user, etc.) pertaining to the users and/or the selected physical activity goal and to predict a length of time it will take the user to achieve the physical activity goal if they comply with a particular exercise plan. The machine learning models 60 may identify patterns between the data pertaining to the user and other data pertaining to other users, and may determine that the other users, by following the recommended exercise plan, achieved the same physical activity goals in the length of time. In some embodiments, the processing device may transmit the amount of time it will take the user to achieve the physical activity goal to the computing device 12 for presentation. In some embodiments, the machine learning models 60 may be generated and trained to receive the data pertaining to the user and determine one or more comorbidities of the user (e.g., the user is at risk for diabetes because they are overweight and depressed, etc.). The machine learning models 60 may be trained to identify patterns between the user and other users that have similar data and may determine the similarly situated users have the comorbidities.

At 4204, the processing device may generate, by executing the artificial intelligence engine 65, the improved exercise plan. The artificial intelligence engine 65 may generate the machine learning models 60 trained to perform the generating of the improved exercise plan using the data source. The improved exercise plan may include at least one set of exercises to be performed by the user to achieve at least one of the one or more levels of attainment associated with the physical activity goal. The artificial intelligence engine 65 may use at least one data source 67 configured to include information pertaining to one or more information pertaining to one or more exercises and at least one of the one or more levels of attainment associated with the physical activity goal.

In some embodiments, the data source may include a set of rankings and each ranking of the set of rankings may pertain to a priority level for each of the one or more levels of attainment pertaining to achieving the physical activity goal. The set of exercises selected may be arranged in the improved exercise plan based on the set of rankings. For example, for a physical activity goal of gardening, the levels of attainment of range of motion and endurance may be ranked higher than the level of attainment of mobility, and as a result, exercises that target the portion(s) of the body associated with achieving range of motion and endurance may be prioritized in the exercise plan. Prioritizing those exercises may refer to including more exercises that are associated with the higher ranking levels of attainment, including more repetitions and/or sets for those exercises, including longer durations for performing the exercises, and the like. In some embodiments, (i) a first portion of the set of exercises associated with a level of attainment having a certain ranking may be included in a set of initial exercises to perform in the improved exercise plan, and (ii) a second portion of the set of exercises associated with the level of attainment having another ranking may be included as a set of last exercises to perform in the improved exercise plan.

The data source 67 may include a first association between the physical activity goal and the one or more levels of attainment pertaining to achieving the physical activity goal, a second association between the one or more levels of attainment and one or more body portions of a human being, and a third association between the one or more body portions and one or more exercises that target the one or more body portions. The processing device may select the at least one set of exercises based on the first association, the second association, and the third association in order to provide an exercise plan that targets the body portions associated with the levels of attainment for the physical activity goal. In some embodiments, the data source 67 may include exercises that are curated by one or more health professionals, such as a trainer, a medical doctor, a physical therapist, a surgeon, or the like. Further, the associations between the levels of attainment, exercises, body portions, and the like may be curated, filtered, reviewed, revised, and the like by the health professionals.

In some embodiments, to generate the improved exercise plan, the processing device may execute the one or more machine learning models 60 trained to use an onboarding protocol, a fitness level of the user. The onboarding protocol may include exercises with tiered difficulty levels. The onboarding protocol may advance a difficulty level for a subsequent exercise in the exercises when the user completes an exercise in the exercises. The fitness level of the user may be determined based on a completion state (e.g., percentage, amount completed, performance measurement, user-report difficulty level, user-reported pain level, etc.) of a last exercise performed by the user. The machine learning models 60 may select a difficulty level for each exercise in the improved exercise plan by associating the difficulty level for each exercise with the fitness level of the user. This onboarding protocol may be referred to as a baseline fitness test. One purpose of the onboarding protocol may be to match user's having particular fitness levels with exercises that have difficulty levels the user should be able to perform, and to optimize compliance and enhance an amount of time it takes to achieve the physical activity goal.

At 4206, the processing device may transmit the improved exercise plan to a computing device. For example, the improved exercise plan may be transmitted to computing device 12 and may be presented by the user interface 18 of the application 17. In some embodiments, the processing device may execute the artificial intelligence engine 65 and/or machine learning models 60 to transmit a signal to the exercise machine 100. In response to the exercise machine 10 receiving the signal, a portion of the exercise machine 100 may be adjusted. The adjustment may be based on an attribute of an operating parameter specified in the improved exercise plan. For example, an attribute of a speed operating parameter may indicate a particular pedaling exercise should be performed at 5 miles per hour. When the exercise machine 100 receives the signal including a control instruction specifying the speed at which a motor of the exercise machine 100 should operate, a processing device of the exercise machine 100 may use the attribute of the operating parameter to control the motor to operate at 5 miles per hour. There may be numerous attributes and numerous operating parameters specified in the improved exercise plan. For example, each exercise selected may be associated with various attributes for various operating parameters. The exercises and their attributes of operating parameters may be selected in order to improve a rate at which the user achieves the physical activity goal, improve compliance, ameliorate boredom, enhance enjoyment, and the like. Based on characteristics of the user, performance measurements of the user, user-reported difficulty levels of exercises, and/or user-reported pain levels, the exercises and attributes of operating parameters may change dynamically as a user performs the exercise plan.

In some embodiments, the processing device prompts, via the computing device 12, the user for feedback pertaining to one or more levels of enjoyment while performing the improved exercise plan. The set of exercises in the improved exercise plan are arranged in a performance order to ameliorate boredom based on the one or more levels of enjoyment. For example, a machine learning model 60 may be trained to match patterns between the user and other users that performed exercise plans, and to determine the other similar matched users indicated they enjoyed a particular order of exercises in an exercise plan or did not enjoy the particular order. The machine learning model 60 may be trained to select the exercises and/or an order of the exercises for a user based on whether the user has experienced they enjoy the exercise and/or order or other users indicated they enjoyed the exercise and/or order. In some embodiments, a healthcare professional (e.g., physical therapist, etc.) may use empirical evidence and/or data to select the exercises and/or performance order to maximize enjoyment, minimize boredom, and/or maximize compliance. In some embodiments, the machine learning models 60 may be trained to solve optimization (e.g., maximization, minimization, etc.) problems to generate an improved exercise plan.

In some embodiments, the processing device may determine a fitness level of a user. The fitness level of the user may be determined by one or more machine learning models 60 using data pertaining to the user. The data may include characteristics of the user, such as height, weight, age, medical history, etc., performance measurements (e.g., range of motion, speed, force, exercise duration, etc.), and indications of pain levels provided by the user. The fitness level of the user may include a value or quantification using any suitable scale. For example, a scale of 1 to 5 may be used to rate the fitness level of the user. A 1 may indicate the user is a beginner or has a lowest fitness level and a 5 may indicate the user is an elite athlete and has a highest fitness level.

In some embodiments, the processing device may cause presentation of a user interface on the computing device 12, and the user interface may present multimedia of a coaching character configured to provide instructions on how to perform an exercise of the improved exercise plan. Based on the determined fitness level of the user, the processing device may modify the multimedia (e.g., video, and/or audio) of a coaching character (e.g., a human, a virtual representation of a human, an animated character, an augmented reality character, a virtual reality character, etc.) performing an exercise in the improved exercise plan. The modifying of the multimedia may include slowing down playback of the video if the user has a low fitness level (e.g., 1, 2, etc.) or speeding up playback of the video if the user has a high fitness level (e.g., 3, 4, 5, etc.). The multimedia may be selected from the data source 67. The data source 67 may store numerous multimedia files and each multimedia file may correspond with a particular exercise (e.g., a video of a coaching character performing a seated bar curl). The processing device may modify the multimedia playback according to the user's fitness level such that the user has an engaging, productive, enjoyable, and/or appropriate exercise session.

In some embodiments, based on one or more factors, the processing device may pair an audio clip and a video clip to generate a paired audio and video clip. The one or more factors may include a fitness level of the user, types of exercises included in the improved exercise plan, one or more characteristics of the user (e.g., height, weight, age, gender, medical history, medical procedures, etc.), one or more performance measurements (e.g., range of motion, force, speed, distance, etc.), a sensor measurement, feedback from the user pertaining to a difficulty of an exercise, or some combination thereof. While the user performs the improved exercise plan, the processing device may cause playback of the paired audio and video clip. For example, if the user indicates that an exercise is too hard using the user interface, then the processing device may generate a paired audio and video clip that provides an encouraging statement (e.g., "Almost done!", "You got this", etc.) and/or slows down playback speed of the coaching character performing the exercise in the video. Such a technical solution may also provide engaging, productive, enjoyable, and/or appropriate exercise sessions for the user. The user's experience using the computing device and/or exercise machine 100 may be enhanced, thereby improving technology.

In some embodiments, the processing device may transmit a notification for presentation on the computing device 12. The notification may include an indication that an exercise performed by the user also helps to achieve a second physical activity goal. For example, the user may be performing a leg press exercise using the exercise machine 100, and the leg press exercise may have been selected because it improves a strength level of attainment; however, the leg press exercise may also improve mobility, and thus, the notification may be presented on the computing device 12 to indicate the same. Further, the notification can indicate that improving mobility may help the user achieve a physical activity goal of jogging a mile, playing with their grandchildren, or any suitable physical goal associated with the mobility level of attainment.

In some embodiments, while the user performs the exercise plan using the exercise machine 100, the processing device may monitor one or more characteristics of the user, performance measurements of the user, user-reported pain feedback, and the like. The processing device may determine whether an exercise in the set of exercises results in a desired outcome. The processing device may determine an exercise is successful if the user exceeds a performance measurement threshold, completes the exercise to a certain threshold percentage, reports they are not experiencing pain, or the like. The artificial intelligence engine 65 may generate one or more machine learning models 60 that are trained to generate improved exercise plans based on whether the exercise in the set of exercises results in the desired outcome. Accordingly, the processing device may implement a feedback look to iteratively improve the generated exercise plans according to whether they are providing desired results.

Figure 43:
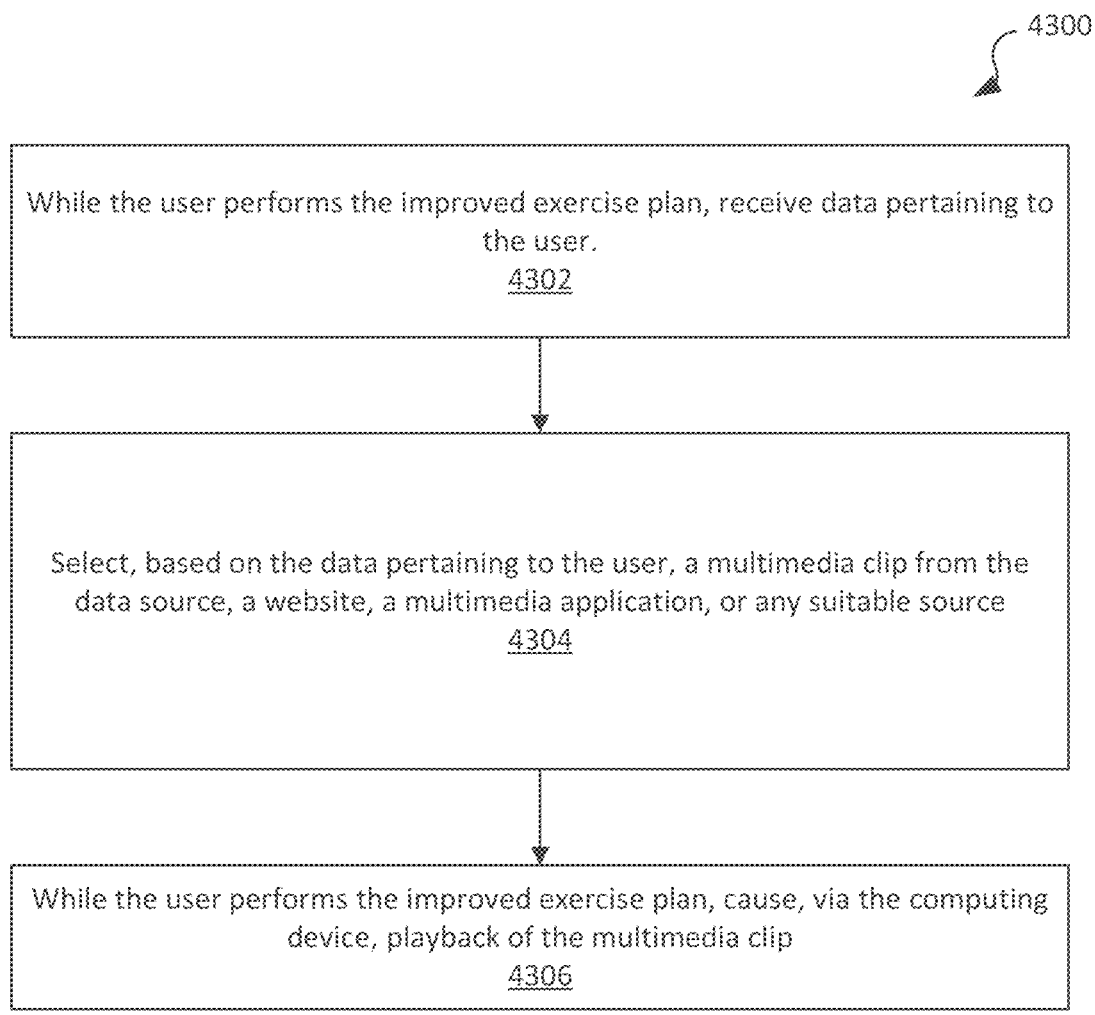
FIG. 43 illustrates an example method for selecting a multimedia clip for a user based on data pertaining to the user.

FIG. 43 illustrates an example method 4300 for selecting a multimedia clip for a user based on data pertaining to the user. The method 4300 may be performed by processing logic that may include hardware (circuitry, dedicated logic, etc.), firmware, software, or a combination of them. The method 4300 and/or each of their individual functions, subroutines, or operations may be performed by one or more processing devices of a control system (e.g., cloud-based computing system 16, computing device 12 of FIG. 1) implementing the method 4300. The method 4300 may be implemented as computer instructions that are executable by a processing device (e.g., a computer-readable medium may be used to store instructions that, when executed, cause a processor perform the following steps or processes of the method 4300). In certain implementations, the method 4300 may be performed by a single processing thread. Alternatively, the method 4300 may be performed by two or more processing threads, each thread implementing one or more individual functions, routines, subroutines, or operations of the methods. Various operations of the method 4300 may be performed by one or more of the cloud-based computing system 16, the computing device 12, and/or the computing device 15 of FIG. 1.

At 4302, while the user performs the improved exercise plan, the processing device may receive data pertaining to the user. The data pertaining to the user may include one or more characteristics of the user, performance measurements, sensor measurements, user-reported difficulty of an exercise, user-reported pain level, or some combination thereof.

At 4304, the processing device may select, based on the data pertaining to the user, a multimedia clip from the data source 67, a website (e.g., music video streaming website), a multimedia application (e.g., music video streaming website), or any suitable source. In some embodiments, the artificial intelligence engine 65 may generate one or more machine learning models 60 trained to select the multimedia clip based on the data pertaining to the user. For example, the data pertaining to the user may indicate the user is having a difficult time completing an exercise, and the machine learning model 60 may be trained to select a motivational audio clip to playback using the computing device 12 in real-time or near real-time as the user performs the exercise. At 4306, while the user performs the improved exercise plan, the processing device cause, via the computing device 12, playback of the multimedia clip.

Figure 44:
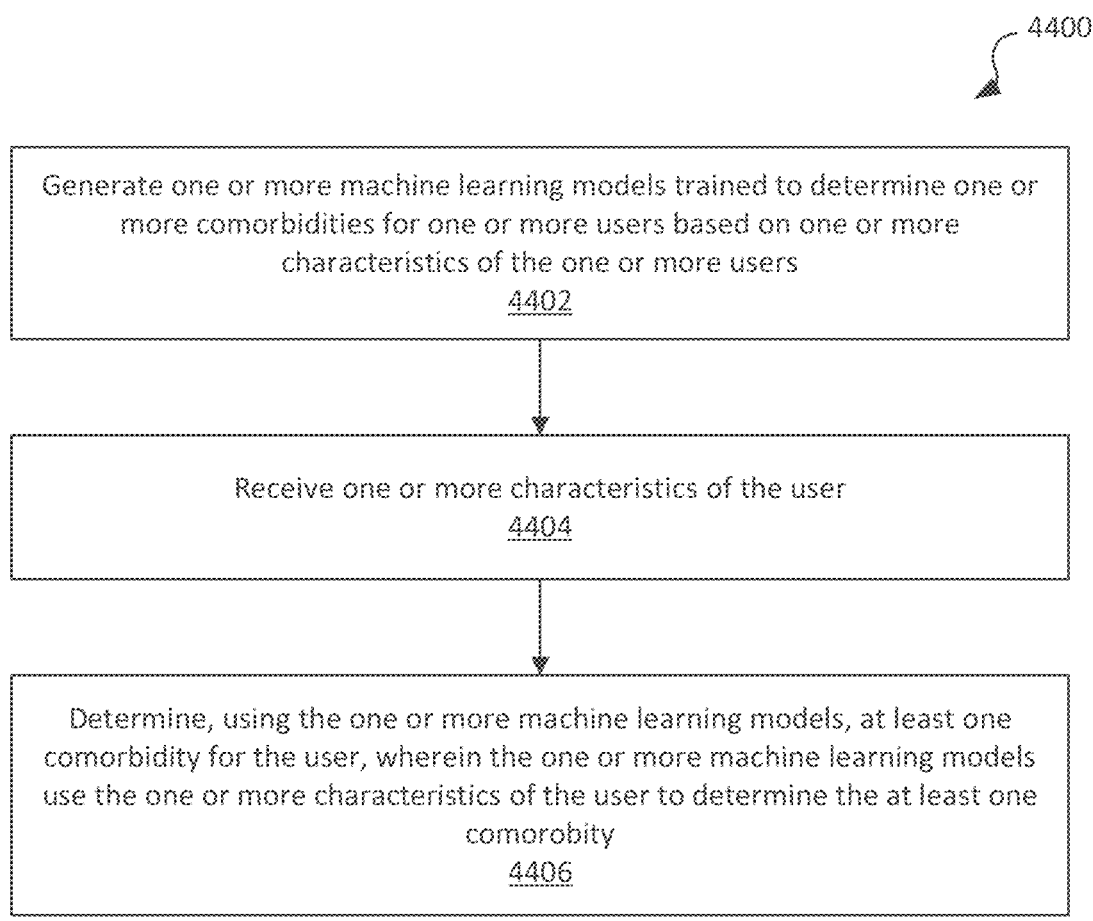
FIG. 44 illustrates an example method for determining, using one or more machine learning models, at least one comorbidity for a user.

FIG. 44 illustrates an example method 4400 for determining, using one or more machine learning models, at least one comorbidity for a user. The method 4400 may be performed by processing logic that may include hardware (circuitry, dedicated logic, etc.), firmware, software, or a combination of them. The method 4400 and/or each of their individual functions, subroutines, or operations may be performed by one or more processing devices of a control system (e.g., cloud-based computing system 16, computing device 12 of FIG. 1) implementing the method 4400. The method 4400 may be implemented as computer instructions that are executable by a processing device (e.g., a computer-readable medium may be used to store instructions that, when executed, cause a processor perform the following steps or processes of the method 4400). In certain implementations, the method 4400 may be performed by a single processing thread. Alternatively, the method 4400 may be performed by two or more processing threads, each thread implementing one or more individual functions, routines, subroutines, or operations of the methods. Various operations of the method 4400 may be performed by one or more of the cloud-based computing system 16, the computing device 12, and/or the computing device 15 of FIG. 1.

At 4402, the processing device may execute the artificial intelligence engine 65 to generate one or more machine learning models 60 trained to determine one or more comorbidities for one or more users based on one or more characteristics of the user one or more users. The machine learning models 60 may be trained with training data that maps inputs to corresponding target outputs. For example, the training data may map certain characteristics of users as inputs to comorbidities as outputs. The characteristics may include information pertaining to medical histories, familial medical histories, medical procedures, demographics, psychographics, physical, mental, emotional, cardiovascular, neurological, performance measurements, user-reported difficulties of exercises, user-reported pain levels, and the like.

At 4404, the processing device may receive one or more characteristics of a particular user. The processing device may input the one or more characteristics of the particular user into the trained machine learning model 60. The trained machined machine learning model 60 may use the one or more characteristics of the user to determine at least one comorbidity for the user. The processing device may cause a notification to be presented on the user interface of the computing device 12. In some embodiments, there are various resources (e.g., medical papers, medical journal, evidence-based guidelines) that are referenced by the machine learning models 60 when determining what the comorbidities of the user are. The resources may be curated by health professionals and approved to be included in the data source 67. The data source 67 may be referred to as a multi-disciplinary repository that includes resources and exercises curated from health professionals having different backgrounds, such as physical therapy, medicine, neurology, cardiology, psychology, etc. Thus, the data source 67 may be used as a single source to provide improved exercise plans and notifications to enable a person to improve their entire lifestyle (e.g., physical and mental).

Figure 45:
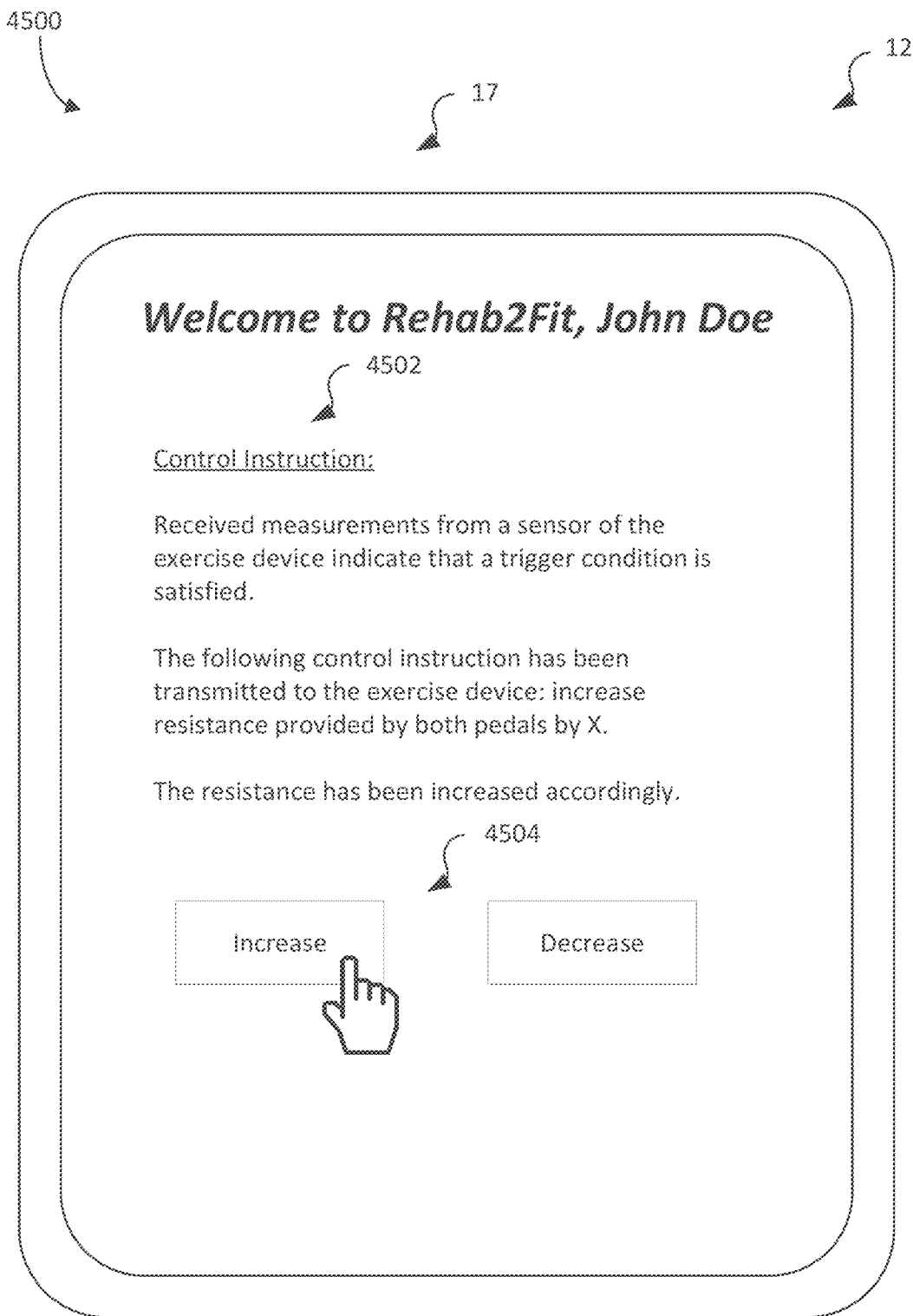
FIG. 45 illustrates an example user interface presenting information pertaining to a control instruction.

FIG. 45 illustrates an example user interface 4500 presenting information pertaining to a control instruction 4502. The user interface 4500 may be provided by the application 17 on the computing device 12. The control instruction 4502 may enable the presentation of an explanation of what has occurred. The explanation may be in words, in symbols, in graphical elements, or in any other form or combination thereof. For example, the explanation in FIG. 45 is depicted as stating "Received measurements from a sensor of the exercise device indicate that a trigger condition is satisfied." The measurements may be associated with a force exerted on the one or more pedals, a revolution per minute of the one or more pedals, a speed of rotation of the one or more pedals, an angular moment of the one or more pedals, a range of motion of the one or more pedals, a radius of an arc traversed by the one or more pedals, or some combination thereof. One or more sensors may obtain the one or more measurements, and the one or more sensors may be included in any suitable portion of the exercise device 100. For example, the one or more sensors may be include pressure sensors (e.g., load cells), proximity sensors, temperature sensors, haptic sensors, piezoelectric sensors, electrical sensors, mechanical sensors, chemical sensors, electromechanical sensors, electrochemical sensors or mechanicochemical sensors, etc. The measurements may be communicated wirelessly to the cloud-based computing system 16 and/or the computing device 12. The measurements may be input into a machine learning model 60 trained to generate the control instruction 4502 as output.

The control instruction 4502 also provides additional explanation, "The following control instruction has been transmitted to the exercise device: increase resistance provided by both pedals by X." This additional explanation indicates that the measurements received from the one or more sensors resulted in the resistance provided by both pedals being increased by X (e.g., X may be a value, an amount, a percentage, etc.). The control instruction 4502 may also indicate that "The resistance has been increased accordingly." Presenting the control instruction 4502 on the user interface 4500 may provide clarity and enhance an understanding of the user as to why the resistance provided by the pedals has been changed.

Although resistance is shown as the operating parameter modified by the control instruction 4502, any suitable operating parameter of the pedals and/or motor may be modified, such as range of motion, revolutions per minute, speed, etc. Further, the operating parameters may be modified identically, similarly or completely independently on different sides of the exercise device 100. Further, the pedals may include foot pedals, hand pedals, or some combination thereof.

The user interface 4500 may include various graphical elements 4504 (e.g., buttons): a button associated with increasing the resistance, and a button associated with decreasing the resistance. The user may use an input peripheral, such as a mouse, a keyboard, a microphone, a touchscreen, etc. to select one of the graphical elements 4504. For example, as depicted by a hand cursor, the user may select the button to cause the resistance to increase. The selection may be transmitted to the cloud-based computing system 16 and/or the computing device 12. The selection may cause a control instruction to be generated and transmitted to the exercise device 100. The control instruction may cause an operating parameter associated with the resistance to increase. In some embodiments, when generating subsequent exercise sessions, the selection may cause one or more machine learning models 60 to be retrained to learn the user's preferences for resistance levels.

Figure 46:
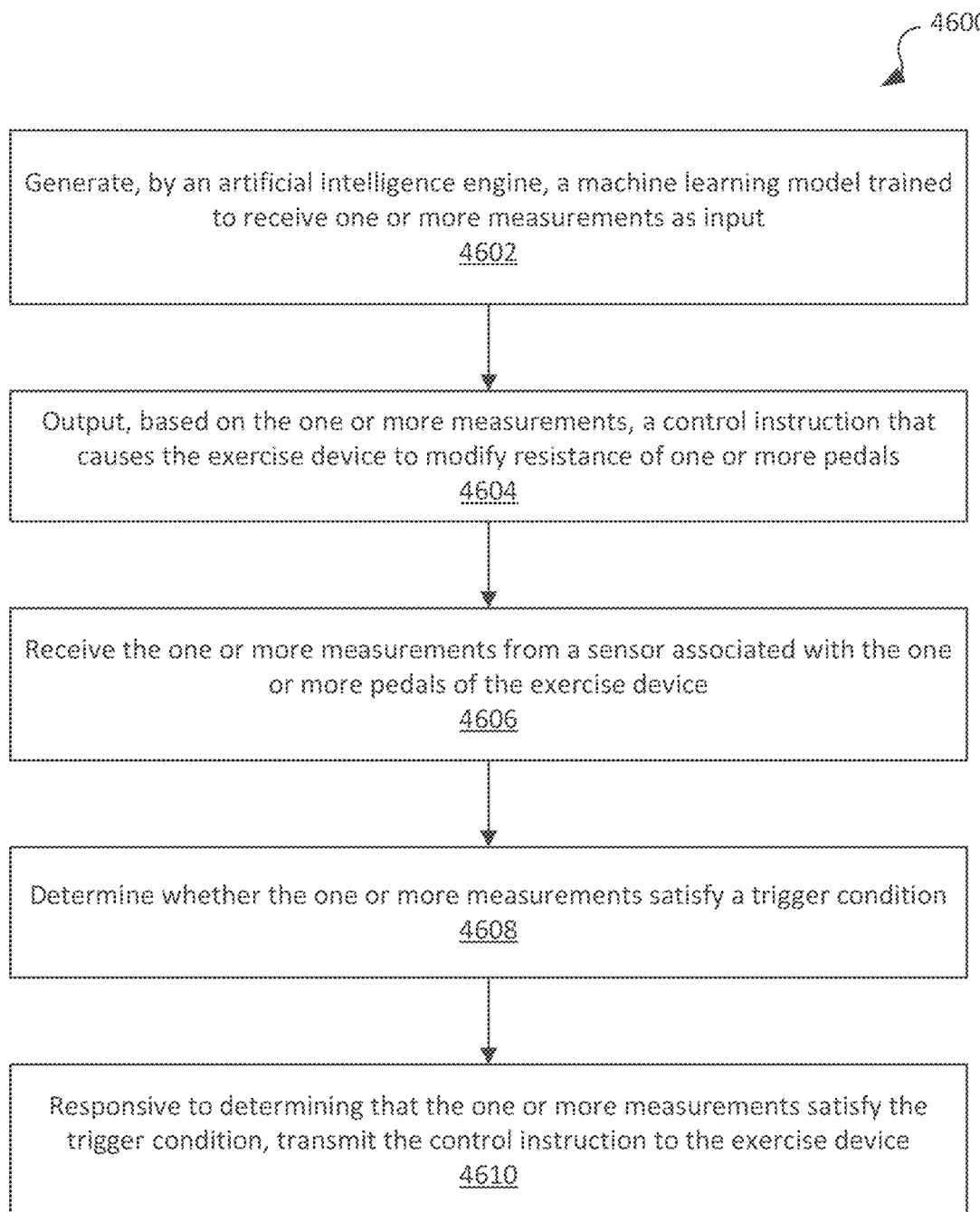
FIG. 46 illustrates an example method for transmitting a control instruction that causes resistance of one or more pedals to be modified.

FIG. 46 illustrates an example method 4600 for transmitting a control instruction that causes the resistance of one or more pedals to be modified. The method 4600 may be performed by processing logic that may include hardware (circuitry, dedicated logic, etc.), firmware, software, or a combination of them. The method 4600 and/or each of its individual functions, subroutines, methods (e.g., object oriented programming), or operations may be performed by one or more processing devices of a control system (e.g., cloud-based computing system 16, computing device 12 of FIG. 1) implementing the method 4600. The method 4600 may be implemented as computer instructions executable by a processing device of the control system (e.g., a computer-readable medium may be used to store instructions that, when executed, cause a processor to perform the following steps or processes of the method 4600). The method 4600 may be performed in a similar manner to that of the method 2700. Various operations of the method 4600 may be performed by one or more of the cloud-based computing system 16, the computing device 12, the exercise machine 100, and/or the computing device 15 of FIG. 1.

In some embodiments, one or more machine learning models 60 may be generated and trained by the artificial intelligence engine 65 and/or the training engine 50 to perform one or more of the operations of the method 4600. For example, to perform the one or more operations, the processing device may execute the one or more machine learning models 60. In some embodiments, the one or more machine learning models 60 may be iteratively retrained to select different features capable of enabling optimization of output. The features that may be modified may include a number of nodes included in each layer of the machine learning models 60, an objective function executed at each node, a number of layers, various weights associated with outputs of each node, and the like.

The method 4600 may use the artificial intelligence engine 65 to modify resistance of one or more pedals of an exercise device 100. The pedals may be foot pedals, hand pedals, or some combination thereof. At 4602, the processing device may generate, by the artificial intelligence engine 65, a machine learning model 60 trained to receive one or more measurements as input. In some embodiments, the one or more measurements may be associated with a force exerted on the one or more pedals, a revolution per minute of the one or more pedals, a speed of rotation of the one or more pedals, an angular moment of the one or more pedals, a range of motion of the one or more pedals, a radius of an arc traversed by the one or more pedals, a degree of flexion, a degree of extension, a skill level, or some combination thereof.

At 4604, the processing device may output, based on the one or more measurements, a control instruction that causes the exercise device 100 to modify the resistance of the one or more pedals. In some embodiments, the control instruction may cause other operating parameters associated with the exercise device to be modified. For example, any combination of the resistance, range of motion, speed, revolutions per minute, etc. may be modified by the control instruction.

At 4606, the processing device may receive the one or more measurements from a sensor associated with the one or more pedals of the exercise device 100. As described herein, the sensor may include a pressure sensor including one or more load cells, proximity sensors, haptic sensors, piezoelectric sensors, optical sensors, temperature sensors, electrical sensors, mechanical sensors, chemical sensors, electromechanical sensors, electrochemical sensors or mechanicochemical sensors or the like. There may be multiple sensors disposed in, on, around, or near the exercise device 100. The multiple sensors may be configured to obtain the one or more measurements. The sensors may include a processing device, a memory device, a network interface device, a sensing device, etc. The sensors may be configured to wirelessly communicate the one or more measurements to the computing device 12 and/or the cloud-based computing system 16.

At 4608, the processing device may determine whether the one or more measurements satisfy a trigger condition. In some embodiments, the trigger condition may include the one or more measurements being less than a threshold value, less than or equal to a threshold value, equal to a threshold value, more than or equal to a threshold value, or more than a threshold value. For example, if a user is able to cycle at a range of motion of 50 degrees, and the trigger condition includes a range of motion being above 45 degrees, then the trigger condition may be satisfied.

In some embodiments, the processing device may include receiving one or more characteristics of a user operating the exercise device 100. For example, the one or more characteristics may include personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, a comorbidity, or some combination thereof. The performance information may include, e.g., an elapsed time of using an exercise device, an amount of force exerted on a portion of the exercise device, a range of motion achieved on the exercise device, a duration of use of the exercise device, a speed of a portion of the exercise device, an indication of a plurality of pain levels using the exercise device, or some combination thereof. The measurement information may include, e.g., one or more vital signs of the user, a respiration rate of the user, a heartrate of the user, a temperature of the user, an SpO2-measurement of the blood oxygen level of the user (e.g., oxygen saturation level), a blood pressure of the user, a glucose level of the user, other suitable measurement information of the user, microbiome related data pertaining to the user, or a combination thereof.

In some embodiments, based on the one or more characteristics of the user and the one or more measurements, the processing device may determine whether the trigger condition has been satisfied. For example, if the user is over a certain age and the measurement indicates the user has a certain heartrate, then the trigger condition may become satisfied.

At 4610, responsive to determining that the one or more measurements and/or the one or more characteristics of the user satisfy the trigger condition, the processing device may transmit the control instruction to the exercise device 100. In some embodiments, transmitting the control instruction to the exercise device 100 may cause the exercise device 100 to modify the resistance of the one or more pedals in real-time or near real-time. In some embodiments, while a user uses the exercise device 100 to perform an exercise (e.g., cycling), the resistance of the one or more pedals may be modified. In some embodiments, the modification may include modifying the resistance by the same degree, percentage or amount provided by a pedal on each side of the exercise device 100, or modifying the resistance a different degree, percentage or amount on different sides of the exercise device 100. In some embodiments, the control instruction may be associated with changing an operating parameter (e.g., speed, revolutions per minute) of a motor connected to the one or more pedals of the exercise device 100.

In some embodiments, transmitting the control instruction to the exercise device 100 may cause the exercise device 100 to modify a parameter associated with a pedal on each side of the exercise device 100 a same degree, percentage or amount or a different degree, percentage or amount. The parameter may include a range of motion, resistance, speed of a motor, revolutions per minute, or some combination thereof.

In some embodiments, responsive to determining that the trigger condition has been satisfied, the processing device may modify another operating parameter (e.g., different than resistance) of the exercise device 100. The another operating parameter may include a number of revolutions per minute, a speed value, a torque value, a temperature degree, a vibration level, or some combination thereof.

In some embodiments, the processing device may receive a second input from the user. The second input may include an instruction to modify an operating parameter of the exercise device 100. The second input may be received via a microphone, a touchscreen, a keyboard, a mouse, a proprioceptive sensor, or some combination thereof. For example, the second input may include a spoken voice from the user, wherein the spoken voice instructs the exercise device 100 to increase resistance. Accordingly, the processing device may use natural language processing to digitize an audio signal representing the spoken voice and to process the digitized audio signal. Based on the digitized audio signal, the processing device may transmit a control instruction that causes the resistance provided by one or more of the pedals to be increased in real-time or near real-time.

In some embodiments, the processing device may present the control instruction on a user interface of a computing device associated with the exercise device 100. In some embodiments, the processing device may receive a selection from the computing device, and based on the selection, may modify the resistance of the one or more pedals, range of motion of the one or more pedals, speed of a motor, or some combination thereof.

In some embodiments, the machine learning model 60 may be retrained based on the selection from the user because the selection may indicate a preference of the user, that the user is in pain, that the exercise is too easy for the user, that the exercise is too hard for the user, or some combination thereof. In some embodiments, the selection may cause the machine learning model 60 to select a different exercise to be immediately performed in place of an exercise currently being performed, to select a different exercise to be subsequently performed in an exercise session, or both. In some embodiments, the selection may cause the artificial intelligence engine 65 to modify a feature of the machine learning model 60, such that the machine learning model 60 accounts for the selection when generating additional exercise sessions and/or exercise plans. For example, the feature may include a weight of a node, a number of nodes in a layer, a number of layers, or some combination thereof. Such a technique may improve the exercises that are selected, such that they are based on input from the user.

Figure 47:
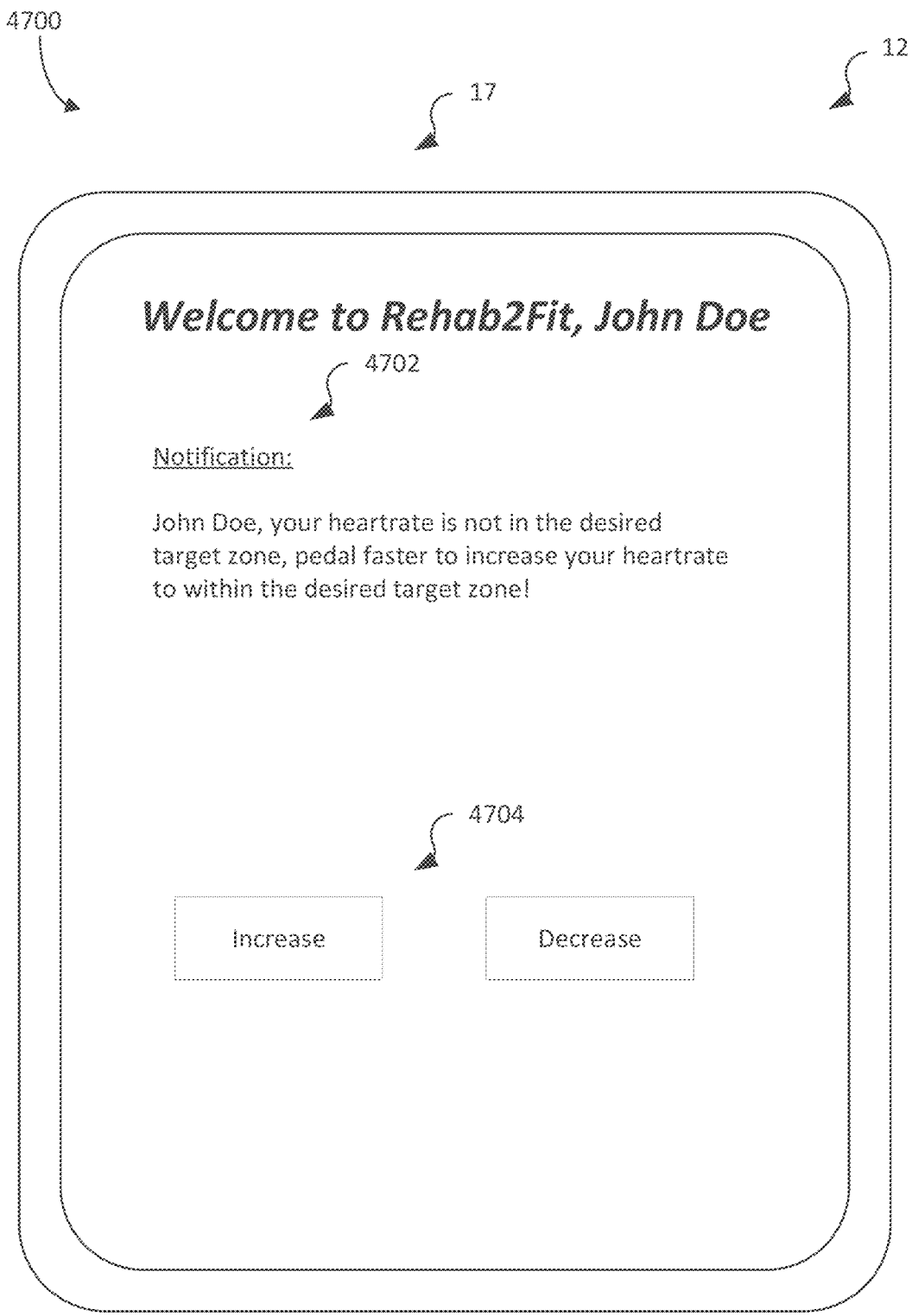
FIG. 47 illustrates an example user interface presenting information pertaining to a notification.

FIG. 47 illustrates an example user interface 4700 presenting information pertaining to a notification 4702. The user interface 4700 is presented by the application 17 on the computing device 12. A control action may be performed as a result of the computing device 12 and/or the cloud-based computing 16 (e.g., machine learning models 60) determining that one or more measurements indicate, during an interval training session, that one or more characteristics of a user iares not within or is within a desired target zone. The one or more measurements may be received from a wearable device worn by a user while the user performs an interval training session. The one or more measurements may include one or more vital signs of the user, a respiration rate of the user, a heartrate of the user, a temperature of the user, an SpO2-measurement of the blood oxygen level of the user (e.g., oxygen saturation level), a blood pressure of the user, a perspiration rate of the user, a glucose level of the user, a revolutions per minute, a number of steps, a speed, an amount of force, other suitable measurement information of the user, microbiome related data pertaining to the user, or a combination thereof. In some embodiments, the notification 4702 may include feedback to encourage the user to perform, during the interval training session, an exercise within the target training zone. For example, the depicted notification 4702 indicates "John Doe, your heartrate is not in the desired target zone, pedal faster to increase your heartrate to within the desired target zone!"

The desired target zone for each user may be tailored based on the one or more characteristics of the user. The one or more characteristics may pertain to personal information, performance information, and/or measurement information. The personal information may include, e.g., demographic, psychographic or other information, such as an age, a weight, a gender, a height, a body mass index, a medical condition, a familial medication history, an injury, a medical procedure, a medication prescribed, a comorbidity, or some combination thereof. The performance information may include, e.g., an elapsed time of using an exercise device, an amount of force exerted on a portion of the exercise device, a range of motion achieved on the exercise device, a duration of use of the exercise device, an indication of a plurality of pain levels using the exercise device, or some combination thereof. The measurement information may include, e.g., one or more vital signs of the user, a respiration rate of the user, a heartrate of the user, a temperature of the user, an SpO2-measurement of the blood oxygen level of the user (e.g., oxygen saturation level), a blood pressure of the user, a glucose level of the user, other suitable measurement information of the user, microbiome related data pertaining to the user, a perspiration rate, or some combination thereof.

Further, the desired target zone may be based on a physical activity goal specified by the user. For example, the user may have selected to be able to play with their grandchildren, and the desired target zone may be tailored according to one or more aspects (e.g., domains including flexibility, strength, endurance, etc.) associated with the selected physical activity goal and/or the characteristics of the user.

The user interface 4700 may include various graphical elements 4704 (e.g., buttons): a button associated with increasing the resistance, and a button associated with decreasing the resistance. The user may use an input peripheral, such as a mouse, a keyboard, a microphone, a touchscreen, a virtual or augmented reality input device, etc. to select one of the graphical elements 4704. For example, as depicted by a hand cursor, the user may select the button to cause the resistance to increase. The selection may be transmitted to the cloud-based computing system 16 and/or the computing device 12. The selection may cause a control instruction to be generated and transmitted to the exercise device 100. The control instruction may cause an operating parameter associated with the resistance to increase. In some embodiments, the selection may cause one or more machine learning models 60 to be retrained to learn the user's preferences for resistance levels when generating subsequent exercise sessions.

Figure 48:
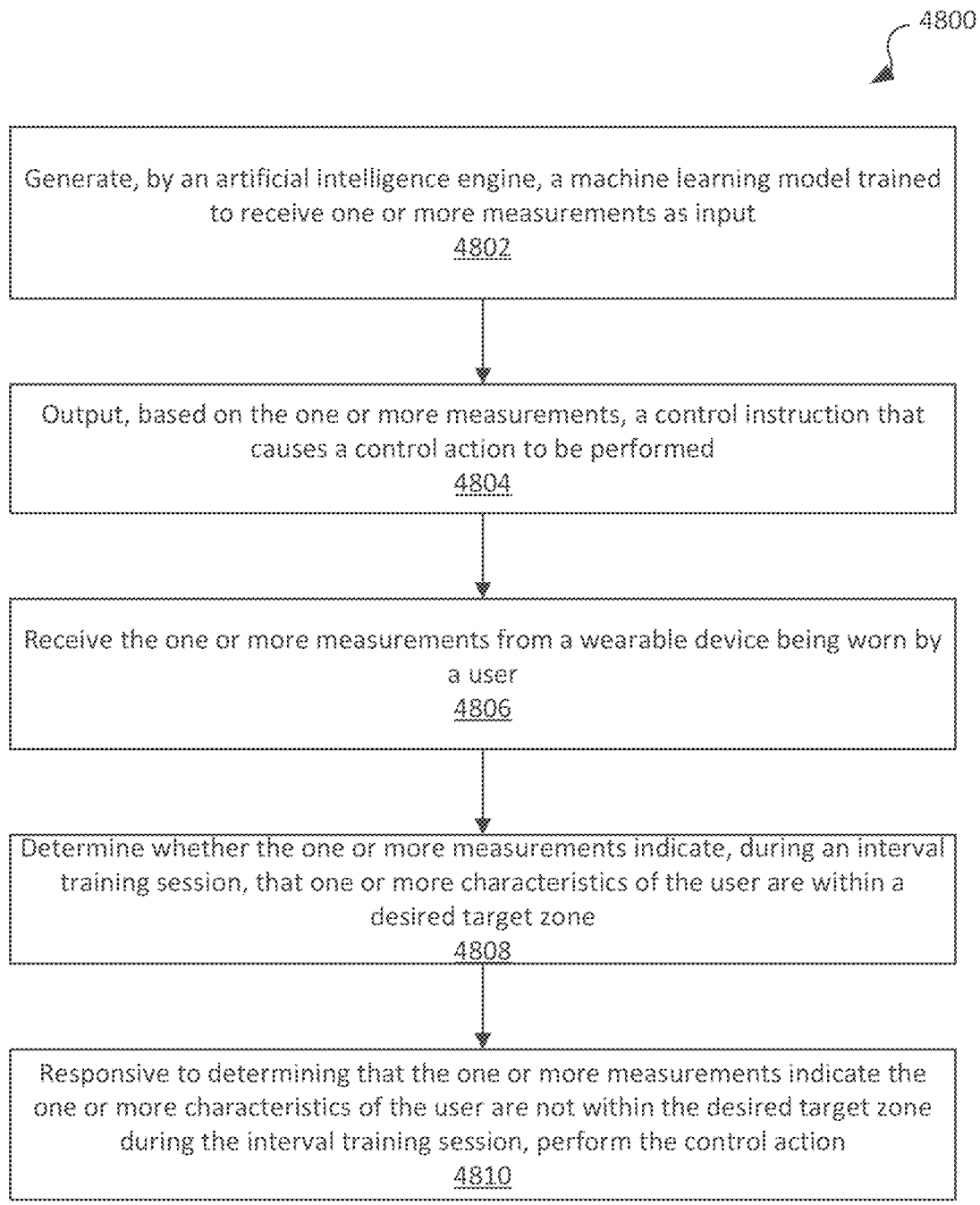
FIG. 48 illustrates an example method for transmitting a control instruction that causes a control action to be performed based on one or more measurements from a wearable device.

FIG. 48 illustrates an example method 4800 for transmitting a control instruction that causes a control action to be performed based on one or more measurements from a wearable device. The method 4800 may be performed by processing logic that may include hardware (circuitry, dedicated logic, etc.), firmware, software, or a combination of them. The method 4800 and/or each of its individual functions, subroutines, methods (e.g., object oriented programming), or operations may be performed by one or more processing devices of a control system (e.g., cloud-based computing system 16, computing device 12 of FIG. 1) implementing the method 4800. The method 4800 may be implemented as computer instructions executable by a processing device of the control system (e.g., a computer-readable medium may be used to store instructions that, when executed, cause a processor to perform the following steps or processes of the method 4800). The method 4800 may be performed in similar manner to that of the method 2700. Various operations of the method 4800 may be performed by one or more of the cloud-based computing system 16, the computing device 12, the exercise machine 100, and/or the computing device 15 of FIG. 1.

In some embodiments, one or more machine learning models 60 may be generated and trained by the artificial intelligence engine 65 and/or the training engine 50 to perform one or more of the operations of the method 4800. For example, to perform the one or more operations, the processing device may execute the one or more machine learning models 60. In some embodiments, the one or more machine learning models 60 may be iteratively retrained to select different features capable of enabling the optimization of output. The features that may be modified may include a number of nodes included in each layer of the machine learning models 60, an objective function executed at each node, a number of layers, various weights associated with outputs of each node, and the like.

The method 4800 may use the artificial intelligence engine 65 to perform a control action. The control action may be based on one or more measurements from a wearable device or smart device (e.g., a watch, a necklace, an anklet, a bracelet, a belt, a ring, a hat, a shoe, a piece of clothing, an earplug, etc.). The wearable device or smart device may be worn by a user performing an exercise or while the user is not performing the exercise and is stationary, relaxing, sleeping, or the like.

At 4802, the processing device may generate, by the artificial intelligence engine 65, a machine learning model 60 trained to receive the one or more measurements as input. In some embodiments, the one or more measurements may include one or more vital signs of the user, a respiration rate of the user, a heartrate of the user, a temperature of the user, an SpO2-measurement of the blood oxygen level of the user (e.g., oxygen saturation level), a blood pressure of the user, a glucose level of the user, other suitable measurement information of the user, microbiome related data pertaining to the user, a perspiration rate, a revolutions per minute, a number of steps, a speed, an amount of force, or some combination thereof.

At 4804, the processing device may output, based on the one or more measurements, a control instruction that causes the control action to be performed. In some embodiments, the control action may include transmitting a notification for presentation on a user interface of a computing device associated with the exercise device 100. The notification may include feedback to encourage the user to perform, during the interval training session, an exercise within the target training zone. In some embodiments, the control action may include controlling an operating parameter of the exercise device 100. For example, the control instruction may be received by a processing device of the exercise device 100, and based on the control instruction, the processing device may transmit a signal to control the operating parameter (e.g., resistance, range of motion, speed, revolutions per minute, etc.).

At 4806, the processing device may receive the one or more measurements from the wearable device being worn by a user. The one or more measurements may be received at a certain periodicity, on demand, or when certain trigger events occur, for example. The one or more measurements may be received during an interval training session. In some embodiments, the interval training session may be included in an exercise plan associated with a rehabilitation program which the user is performing. In some embodiments, the interval training session may include short, high intensity bursts of activity with periods of rest and recovery between. In other words, rest and exercise intervals of controlled duration may be alternated during an interval training session.

At 4808, the processing device may determine whether the one or more measurements indicate, during an interval training session, that one or more characteristics of the user are within a desired target zone. The one or more characteristics of the user may be associated with an activity level determined based on physiological factors associated with the one or more measurements. The physiological factors may include heart rate, respiratory rate, perspiration rate, muscular state, readiness state, or the like. In some embodiments, the characteristic of the user may be associated with a physiological state (e.g., resting, active, hyperactive, etc.) based on the one or more measurements. The characteristic of the user may be determined to be within the desired target zone when a value, attribute, score, measure, property, etc. associated with the characteristic is within a certain range (e.g., desired target zone). The certain range may be any numerical range, quantifiable range, quantitative range, etc.

In some embodiments, responsive to determining that the one or more measurements indicate, during the interval training session, that the characteristic of the user is within the desired target zone, performing the control action, wherein the performing includes transmitting a notification to a computing device associated with an exercise device. The notification may provide a motivational message to the user.

At 4810, responsive to determining that the one or more measurements indicate the characteristic of the user is not within the desired target zone during the interval training session, the processing device may perform the control action.

In some embodiments, the processing device may receive data associated with the user. In some embodiments, based on the data and the one or more measurements, the processing device may predict, via the machine learning model 60, a medical condition (e.g., hypertension, asthma, diabetes, etc.) associated with the user. For example, the machine learning model 60 may be trained on a corpus of training data that matches patterns between certain user data and measurements associated with the presence (or absence) of certain medical conditions.

In some embodiments, the processing device may receive second input from the user. The second input may include an instruction to modify an operating parameter of the exercise device 100. The second input may be received via a microphone, a touchscreen, a virtual or augmented reality input device, a keyboard, a mouse, a proprioceptive sensor, or some combination thereof. For example, the second input may include a spoken voice from the user that instructs the exercise device 100 to increase resistance. Accordingly, the processing device may use natural language processing to digitize an audio signal representing the spoken voice and to process the digitized audio signal. Based on the digitized audio signal, the processing device may transmit a control instruction that causes the resistance provided by one or more of the pedals to be increased in real-time or near real-time.

Figure 49:
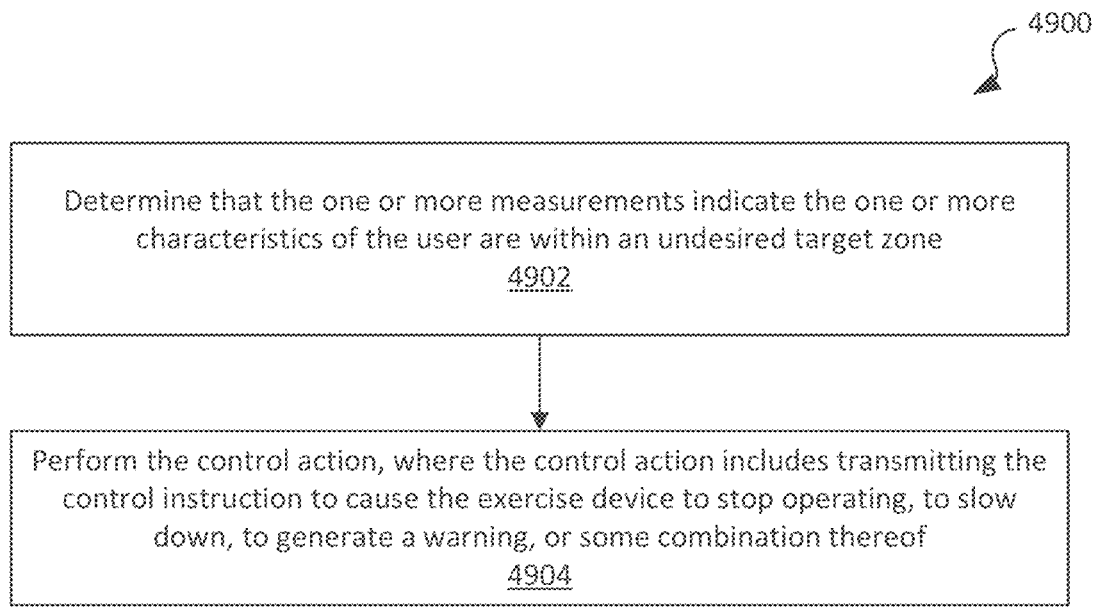
FIG. 49 illustrates another example method for transmitting a control instruction that causes a control action to be performed based on one or more measurements from a wearable device.

FIG. 49 illustrates another example method 4900 for transmitting a control instruction that causes a control action to be performed based on one or more measurements from a wearable device. The method 4900 may be performed by processing logic that may include hardware (circuitry, dedicated logic, etc.), firmware, software, or a combination of them. The method 4900 and/or each of its individual functions, subroutines, methods (e.g., object oriented programming), or operations may be performed by one or more processing devices of a control system (e.g., cloud-based computing system 16, computing device 12 of FIG. 1) implementing the method 4900. The method 4900 may be implemented as computer instructions executable by a processing device of the control system (e.g., a computer-readable medium may be used to store instructions that, when executed, cause a processor to perform the following steps or processes of the method 4900). The method 4900 may be performed in a manner similar to that of the method 2700. Various operations of the method 4900 may be performed by one or more of the cloud-based computing system 16, the computing device 12, the exercise machine 100, and/or the computing device 15 of FIG. 1.

In some embodiments, one or more machine learning models 60 may be generated and trained by the artificial intelligence engine 65 and/or the training engine 50 to perform one or more of the operations of the method 4900. For example, to perform the one or more operations, the processing device may execute the one or more machine learning models 60. In some embodiments, the one or more machine learning models 60 may be iteratively retrained to select different features capable of enabling the optimization of output. The features that may be modified may include a number of nodes included in each layer of the machine learning models 60, an objective function executed at each node, a number of layers, various weights associated with outputs of each node, and the like.

At 4902, the processing device may determine that the one or more measurements indicate the characteristic of the user is within an undesired target zone. In some embodiments, the undesired target zone may include ranges for excessive heartrates, blood pressures, temperatures, and/or perspiration rates, for example.

At 4904, responsive to determining the one or more measurements indicate the characteristic of the user is within the undesired target zone, the processing device may perform the control action that includes transmitting the control instruction to cause the exercise device 100 to stop operating, to slow down, to speed up, to generate a warning, or some combination thereof. Further, the control action may include transmitting a notification to be presented by the computing device 12, and the notification may include a warning, an alert, or the like instructing the user to stop exercising or slow down.

Figure 50:
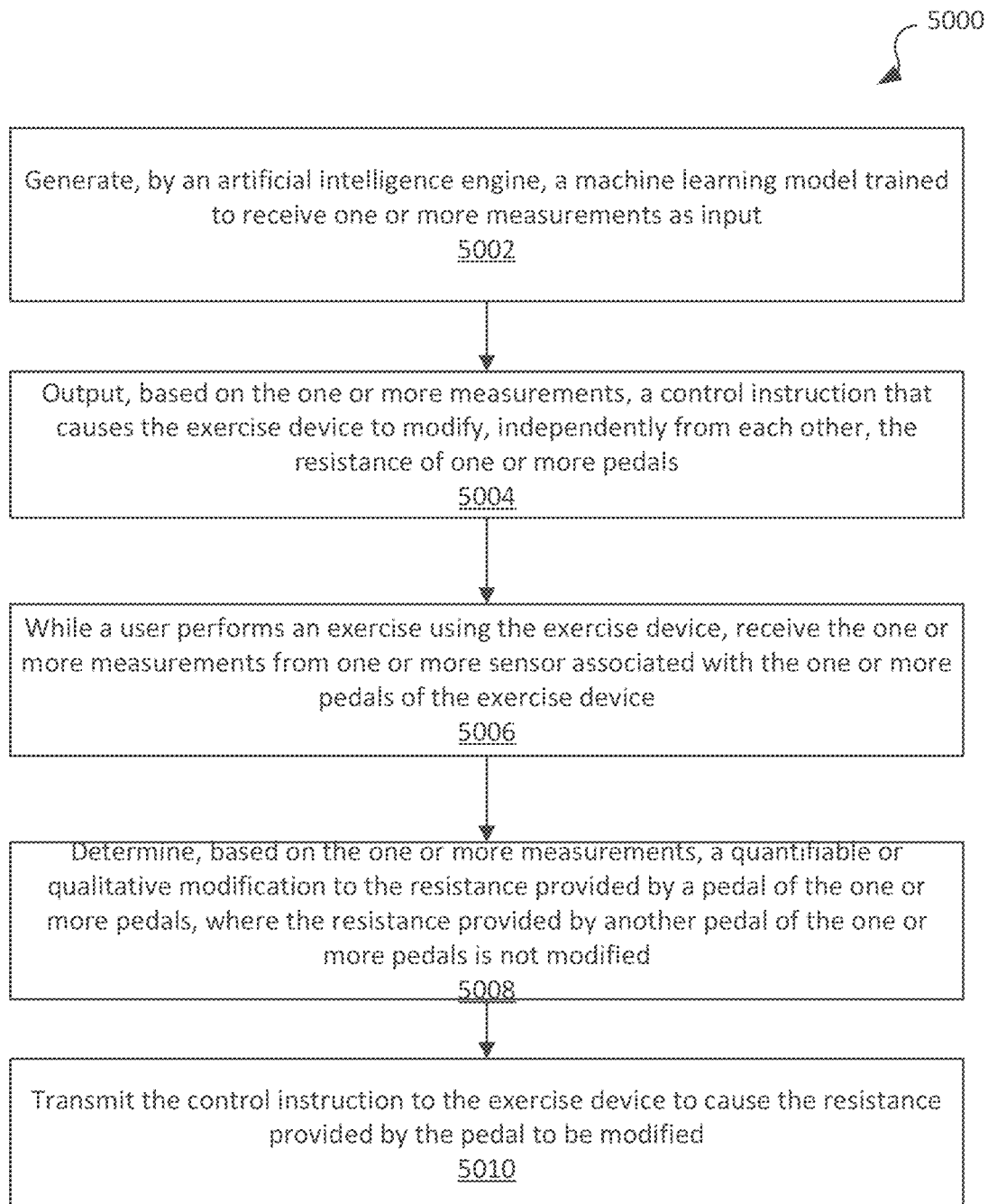
FIG. 50 illustrates an example method for independently controlling resistance provided by different pedals.

FIG. 50 illustrates an example method 5000 for independently controlling the resistance provided by different pedals. The method 5000 may be performed by processing logic that may include hardware (circuitry, dedicated logic, etc.), firmware, software, or a combination of them. The method 5000 and/or each of its individual functions, subroutines, methods (e.g., object oriented programming), or operations may be performed by one or more processing devices of a control system (e.g., cloud-based computing system 16, computing device 12 of FIG. 1) implementing the method 5000. The method 5000 may be implemented as computer instructions executable by a processing device of the control system (e.g., a computer-readable medium may be used to store instructions that, when executed, cause a processor to perform the following steps or processes of the method 5000). The method 5000 may be performed in a manner similar to that of the method 2700. Various operations of the method 5000 may be performed by one or more of the cloud-based computing system 16, the computing device 12, the exercise machine 100, and/or the computing device 15 of FIG. 1.

In some embodiments, one or more machine learning models 60 may be generated and trained by the artificial intelligence engine 65 and/or the training engine 50 to perform one or more of the operations of the method 5000. For example, to perform the one or more operations, the processing device may execute the one or more machine learning models 60. In some embodiments, the one or more machine learning models 60 may be iteratively retrained to select different features capable of enabling the optimization of output. The features that may be modified may include a number of nodes included in each layer of the machine learning models 60, an objective function executed at each node, a number of layers, various weights associated with outputs of each node, and the like.

At 5002, the processing device may generate, by the artificial intelligence engine 65, a machine learning model 60 trained to receive one or more measurements as input. In some embodiments, the one or more measurements are associated with a force exerted on the one or more pedals, a revolution per minute of the one or more pedals, a speed of rotation of the one or more pedals, an angular moment of the one or more pedals, a range of motion of the one or more pedals, a radius of an arc traversed by the one or more pedals, a degree of flexion, a degree of extension, a skill level, or some combination thereof.

At 5004, the processing device may output, based on the one or more measurements, a control instruction that causes the exercise device to modify, independently from each other, the resistance of the one or more pedals. The control instruction may cause modification of any combination of operating parameters, such as the resistance, range of motion, speed, revolutions per minute, etc. The control instruction may include a value for configuring the operating parameter of the exercise device 100. The control instruction may be received by a processing device of the exercise device 100, and the processing device may transmit a control signal to appropriate circuitry (e.g., motor, pedal, actuator, etc.) to control the operating parameter of the exercise device 100.

At 5006, while a user performs an exercise using the exercise device, the processing device may receive the one or more measurements from one or more sensors associated with the one or more pedals of the exercise device 100. As described herein, the sensor may include a pressure sensor including one or more load cells, proximity sensors, haptic sensors, piezoelectric sensors, optical sensors, temperature sensors, electrical sensors, mechanical sensors, chemical sensors, electromechanical sensors, electrochemical sensors or mechanicochemical sensors, or the like. There may be multiple sensors disposed in, on, around, or near the exercise device 100. The multiple sensors may be configured to obtain the one or more measurements. The sensors may include a processing device, a memory device, a network interface device, a sensing device, etc. The sensors may be configured to wireless communicate the one or more measurements to the computing device 12 and/or the cloud-based computing system 16.

At 5008, the processing device may determine, based on the one or more measurements, a quantifiable or qualitative modification to the resistance provided by a pedal of the one or more pedals. In some embodiments, the quantifiable or qualitative modification may include a specific force (e.g., newtons) or pounds of resistance to be provided by the pedal of the one or more pedals. In some embodiments, the resistance provided by another pedal of the one or more pedals is not modified. In some embodiments, range of motion for one pedal may be modified independently from the range of motion for another pedal. In some embodiments, revolutions per minute for one pedal may be modified independently than the revolutions per minute for another pedal. In some embodiments, any combination of operating parameters (e.g. resistance, range of motion, revolutions per minute, etc.) may be modified independently for different pedals. In some embodiments, the pedals may include hand pedals, foot pedals, or some combination thereof.

At 5010, the processing device may transmit the control instruction to the exercise device 100 to cause the resistance provided by the pedal to be modified. In some embodiments, the control instruction may automatically cause the resistance provided by the pedal to be modified in real-time or near real-time. In some embodiments, the pedal may be actuated by an affected limb, and the affected limb is associated with rehabilitation, prehabilitation, post-habilitation, or some combination thereof. In some embodiments, the another pedal of the one or more pedals may be actuated by a second limb.

In some embodiments, the processing device may include presenting a notification on a user interface of a computing device associated with the user and/or the exercise device 100. The notification may include a prompt to modify the resistance provided by the pedal. In some embodiments, the processing device may cause an audio device (e.g., speaker) to generate a notification. The notification may include a prompt (e.g., auditory, visual, haptic, etc.) to modify the resistance provided by the pedal, a range of motion provided by the pedal, a speed of the pedal, a revolutions per minute of the pedal, etc.

In some embodiments, the processing device may receive one or more subsequent measurements from the one or more sensors. The processing device may determine whether the one or more subsequent measurements indicate at least one of the at least two strength characteristic levels for the at least two limbs of the user. Responsive to determining that the one or more subsequent measurements indicate at least one of the at least two strength characteristic levels for the at least two limbs, the processing device may modify a value of resistance to be provided by the one or more pedals.

In some embodiments, the processing device may receive a second input from the user. The second input may include an instruction to modify an operating parameter of the exercise device 100. The second input may be received via a microphone, a touchscreen, a keyboard, a mouse, a proprioceptive sensor, or some combination thereof. For example, the second input may include a spoken voice, wherein the spoken voice instructs the exercise device 100 to increase resistance. Accordingly, the processing device may use natural language processing to digitize an audio signal representing the spoken voice and to process the digitized audio signal. Based on the digitized audio signal, the processing device may transmit a control instruction that causes the resistance provided by one or more of the pedals to be increased in real-time or near real-time.

Figure 51:
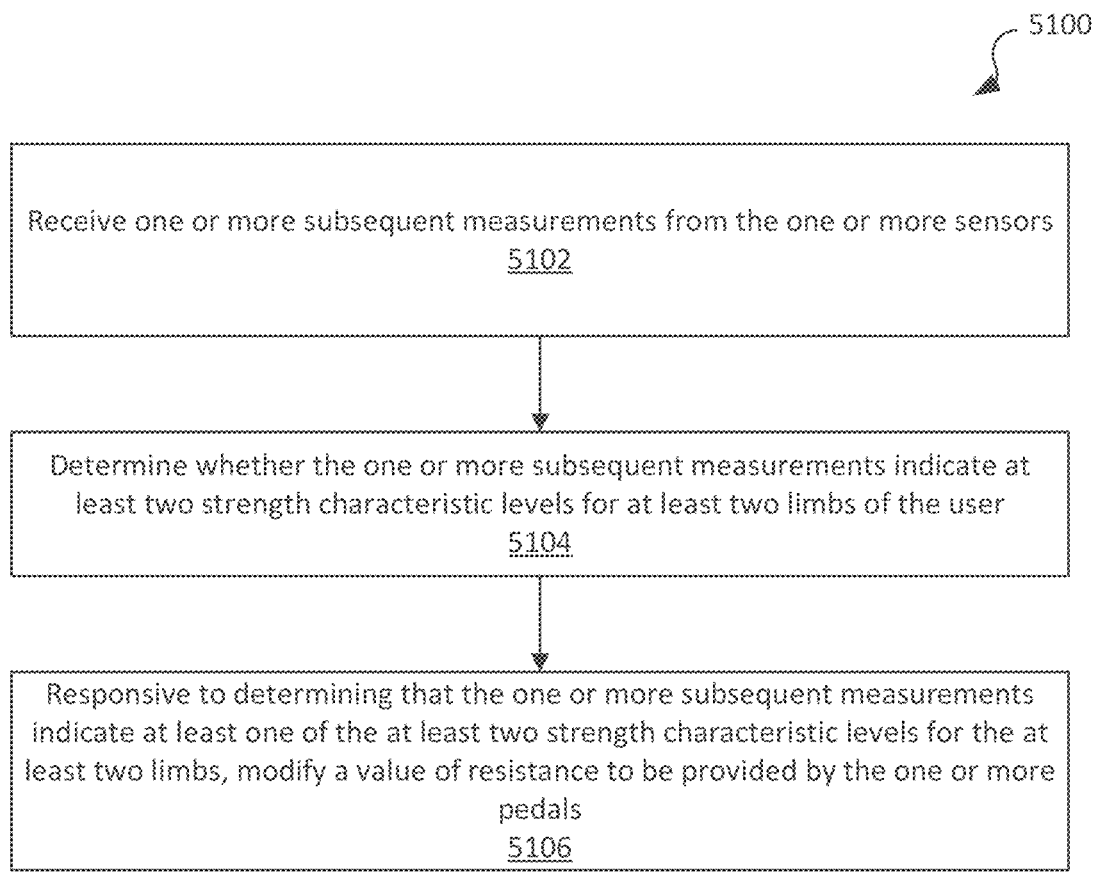
FIG. 51 illustrates an example method for modifying the resistance provided by one or more pedals based on a measured strength characteristic level of a limb of user.

FIG. 51 illustrates an example method 5100 for modifying, based on a measured strength characteristic level of a limb of user, the resistance provided by one or more pedals. The method 5100 may be performed by processing logic that may include hardware (circuitry, dedicated logic, etc.), firmware, software, or a combination of them. The method 5100 and/or each of its individual functions, subroutines, methods (e.g., object oriented programming), or operations may be performed by one or more processing devices of a control system (e.g., cloud-based computing system 16, computing device 12 of FIG. 1) implementing the method 5100. The method 5100 may be implemented as computer instructions executable by a processing device of the control system (e.g., a computer-readable medium may be used to store instructions that, when executed, cause a processor perform the following steps or processes of the method 5100). The method 5100 may be performed in a manner similar to that of the method 2700. Various operations of the method 5100 may be performed by one or more of the cloud-based computing system 16, the computing device 12, the exercise machine 100, and/or the computing device 15 of FIG. 1.

In some embodiments, one or more machine learning models 60 may be generated and trained by the artificial intelligence engine 65 and/or the training engine 50 to perform one or more of the operations of the method 5100. For example, to perform the one or more operations, the processing device may execute the one or more machine learning models 60. In some embodiments, the one or more machine learning models 60 may be iteratively retrained to select different features capable of enabling the optimization of output. The features that may be modified may include a number of nodes included in each layer of the machine learning models 60, an objective function executed at each node, a number of layers, various weights associated with outputs of each node, and the like.

At 5102, the processing device may receive one or more subsequent measurements from the one or more sensors. At 5104, the processing device may determine whether the one or more subsequent measurements indicate at least two strength characteristic levels for at least two limbs of the user. The at least two strength characteristic levels may be associated with an amount of force able to be exerted by a first limb on a first pedal and an amount of force able to be exerted by a second limb on a second pedal. For example, the strength characteristic level may be configured to be 100 pounds of force. If the force exerted by each of the first and second limb on the first and second pedal is equal to or greater than 100 pounds of force, then the first and second limb achieve the strength characteristic level. In such an instance, an affected limb may have recovered to be as strong as the other unaffected limb.

At 5106, responsive to determining that the one or more subsequent measurements indicate at least one of the at least two strength characteristic levels for the at least two limbs, the processing device may modify the resistance to be provided by the one or more pedals. For example, if the affected limb actuates a pedal that generates measurements indicating the affected limb has achieved the strength characteristic level, then the affected limb may have recovered to a sufficient degree. Accordingly, the resistance provided by the pedal associated with the affected limb may be adjusted or modified similarly to the resistance provided by a pedal associated with the unaffected or other limb.

Figure 52:
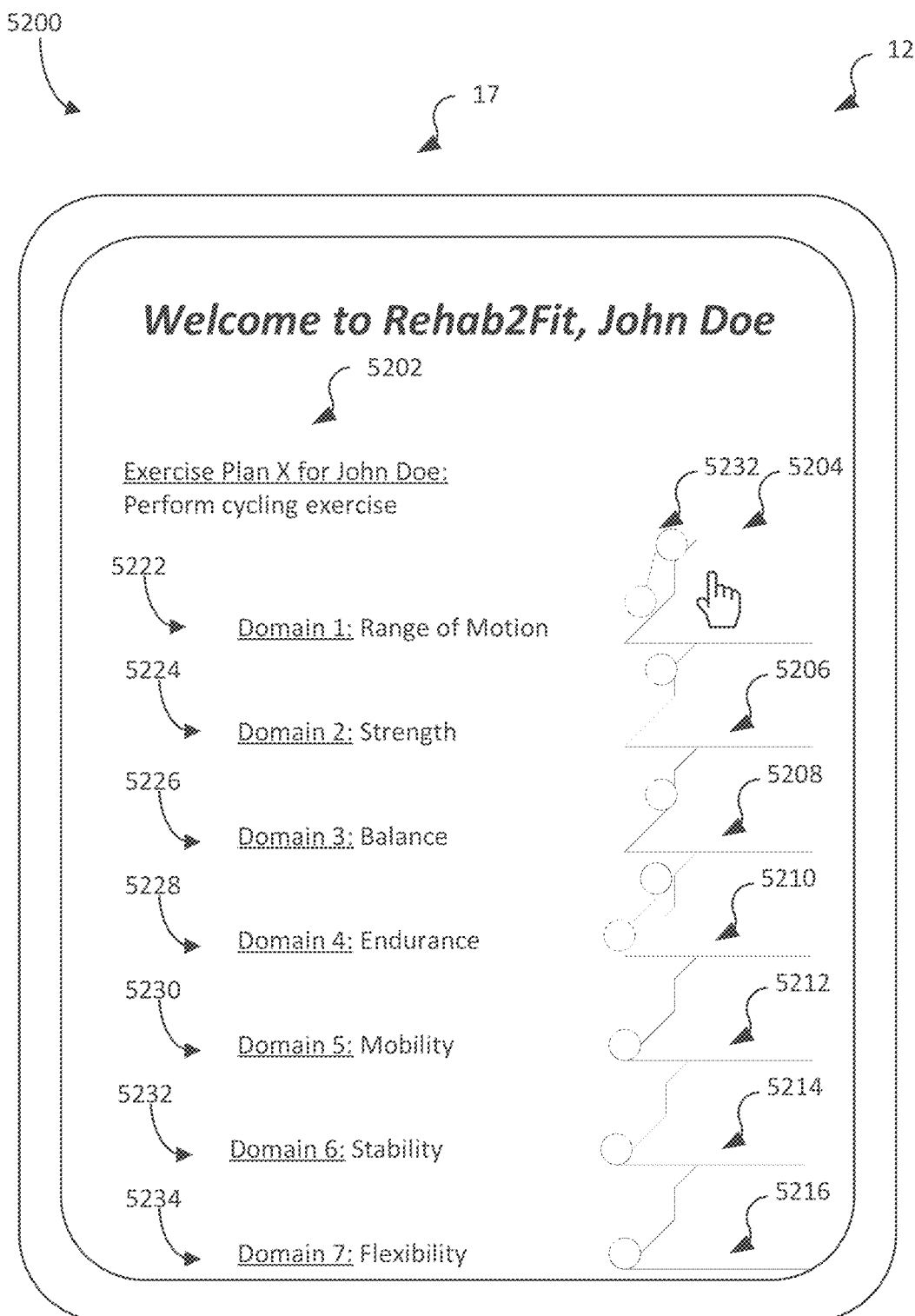
FIG. 52 illustrates an example user interface presenting respective graphical elements for different domains associated with a user.

FIG. 52 illustrates an example user interface 5200 presenting respective graphical elements 5204, 5206, 5208, 5210, 5212, 5214, and 5216 for different domains associated with a user. The user interface 5200 is presented by the application 17 on the computing device 12. As depicted, John Doe is performing "Exercise Plan X" (5202) and the exercise plan currently instructs John Doe to "Perform cycling exercise". There are five domains presented in the user interface 5200. The domains are associated with health and/or fitness characteristics desired by the user for a certain physical activity goal. The domains may be associated with range of motion, strength, balance, endurance, mobility, stability, pliability, flexibility, or some combination thereof. Each of the domains may be presented in a respective section 5222, 5224, 5226, 5228, 5230, 5232, and 5234 of the user interface 5200. The domains may include Domain 1: Range of Motion; Domain 2; Strength; Domain 3: Balance; Domain 4: Endurance; Domain 5: Mobility; Domain 6: Stability; and Domain 7: Flexibility. In some embodiments, there may be any suitable number and/or combination of domains that are included in an exercise plan based on a desired physical activity goal.

Each domain is associated with a respective graphical element, and as depicted, the graphical element represents a side of a mountain. Any suitable graphical element may be used (e.g., a rope climb, a road, a building, a river, etc.). An icon 5232 (e.g., represented as a circle) may be presented relative to the graphical element 5204. The position of the icon 5232 relative to the graphical element 5204 may represent a progress of the user with regard to the specific domain. For example, when the icon 5232 is located at a bottom of the graphical element 5204, then the user has not made any progress toward that particular domain associated with the graphical element 5204. However, if the icon is located at a top of the graphical element, then the user has completed progress toward that particular domain associated with the graphical element 5204. As depicted, with regard to the graphical element 5204 associated with the Range of Motion domain, the icon 5232 may move in real-time (as depicted by the dashed circle moving, via the dashed line, to the enclosed circle) as the user performs an exercise, such as cycling, and the user increases progress towards a target goal or desired completion state. As further, depicted by graphical element 5210 associated with the Endurance domain, the icon has advanced in real-time as the user performs the cycling exercise. Accordingly, as the user performs various exercises, any suitable number of domains may be modified to reflect the user's progress accurately.

Figure 53:
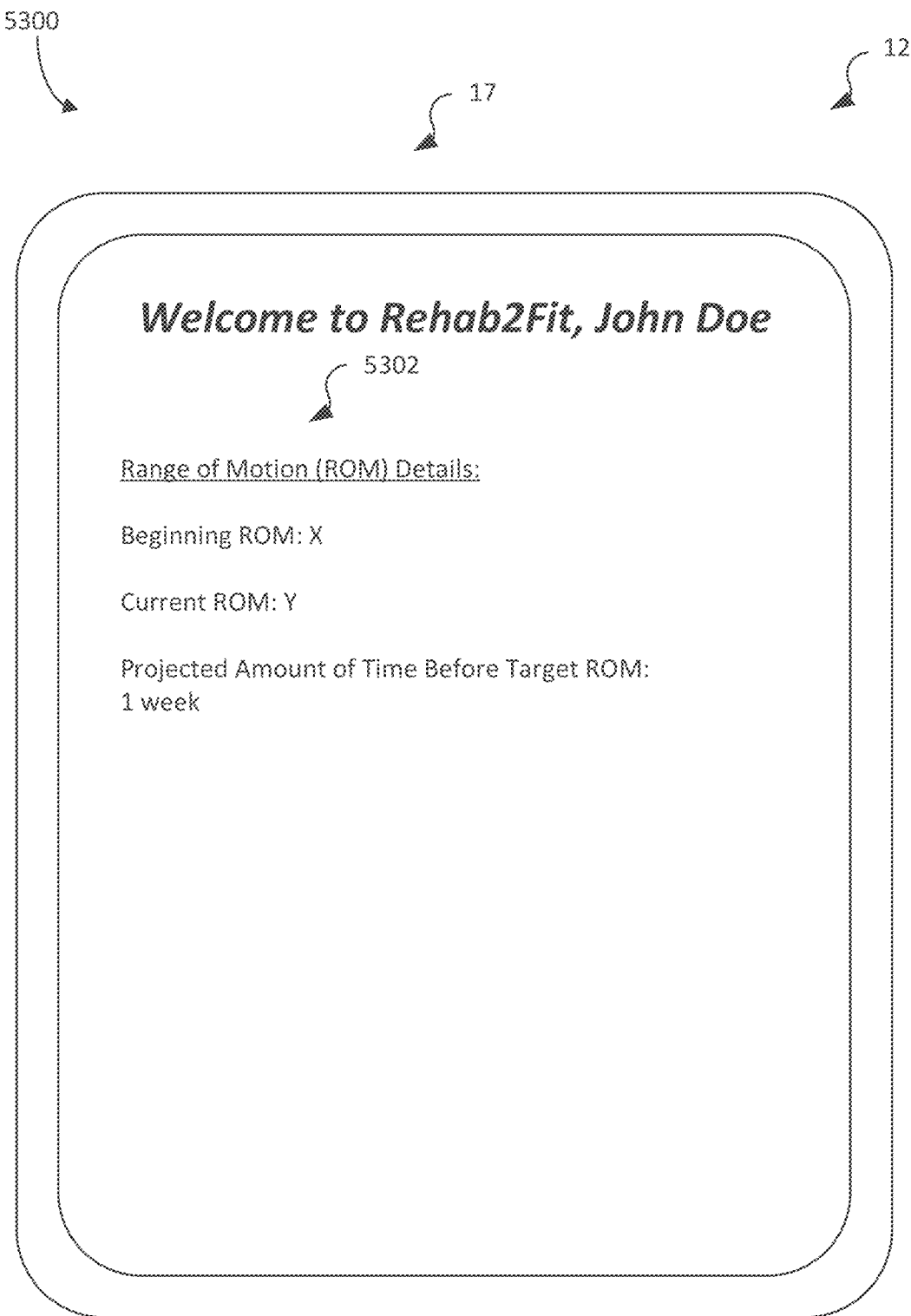
FIG. 53 illustrates an example user interface presenting detailed information of a domain selected from FIG. 52.

As depicted, the user may select (e.g., via hand cursor), a particular graphical element 5204 associated with a domain to drill down to view more detailed information pertaining to that domain (e.g., Range of Motion). Accordingly, FIG. 53 illustrates an example user interface 5300 presenting detailed information of a domain selected from FIG. 52. The user interface 5300 is presented by the application 17 on the computing device 12. As depicted, additional information 5302 may include "Range of Motion (ROM) Details". The details may include "Beginning ROM: X," "Current ROM: Y," and "Projected Amount of Time Before Target ROM: 1 week." Accordingly, the user may be presented with information indicating an amount of progress the user has made with regard to the selected domain. A machine learning model 60 may be trained to analyze the progress the user has made, and based on the analysis, project an amount of time before a target ROM is achieved.

Figure 54:
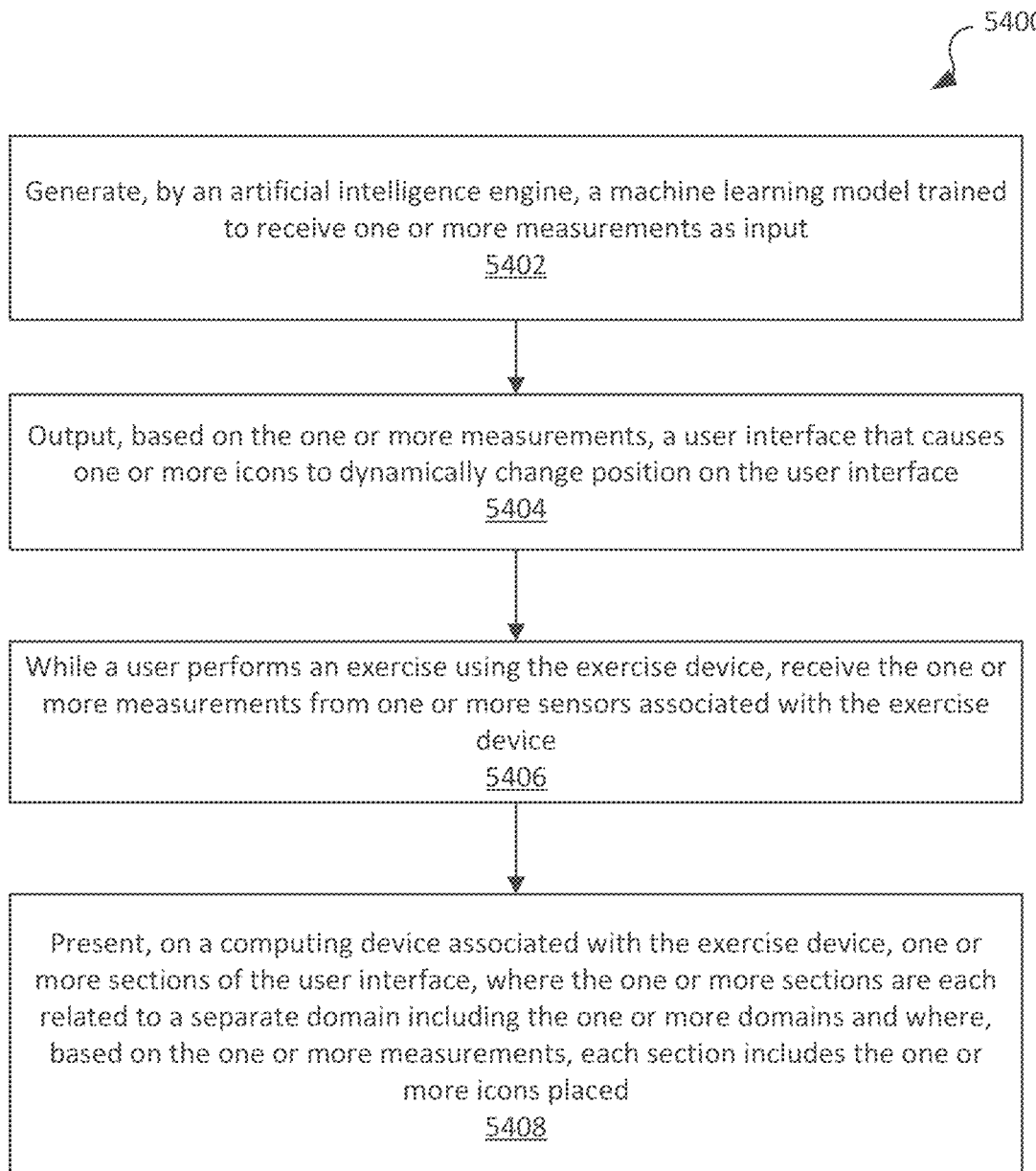
FIG. 54 illustrates an example method for dynamically moving, based on one or more measurements associated with a user, graphical elements in sections associated with domains.

FIG. 54 illustrates an example method 5400 for dynamically moving, based on one or more measurements associated with a user, graphical elements in sections associated with domains. The method 5400 may be performed by processing logic that may include hardware (circuitry, dedicated logic, etc.), firmware, software, or a combination of them. The method 5400 and/or each of its individual functions, subroutines, methods (e.g., object oriented programming), or operations may be performed by one or more processing devices of a control system (e.g., cloud-based computing system 16, computing device 12 of FIG. 1) implementing the method 5400. The method 5400 may be implemented as computer instructions executable by a processing device of the control system (e.g., a computer-readable medium may be used to store instructions that, when executed, cause a processor perform to the following steps or processes of the method 5400). The method 5400 may be performed in a manner similar to that of the method 2700. Various operations of the method 5400 may be performed by one or more of the cloud-based computing system 16, the computing device 12, the exercise machine 100, and/or the computing device 15 of FIG. 1.

In some embodiments, one or more machine learning models 60 may be generated and trained by the artificial intelligence engine 65 and/or the training engine 50 to perform one or more of the operations of the method 5400. For example, to perform the one or more operations, the processing device may execute the one or more machine learning models 60. In some embodiments, the one or more machine learning models 60 may be iteratively retrained to select different features capable of enabling the optimization of output. The features that may be modified may include a number of nodes included in each layer of the machine learning models 60, an objective function executed at each node, a number of layers, various weights associated with outputs of each node, and the like.

The method 5400 may use the artificial intelligence engine 65 to present a user interface capable of presenting the progress of a user in one or more domains. At 5402, the processing device may generate, by the artificial intelligence engine 65, a machine learning model 60 trained to receive one or more measurements as input. In some embodiments, the one or more measurements may be associated with a force exerted on the one or more pedals, a revolution per minute of the one or more pedals, a speed of rotation of the one or more pedals, an angular moment of the one or more pedals, a range of motion of the one or more pedals, a radius of an arc traversed by the one or more pedals, a degree of flexion, a degree of extension, a skill level, or some combination thereof.

At 5404, the processing device may output, based on the one or more measurements, a user interface that causes one or more icons to dynamically change position on the user interface. The icons may represent an amount of progress the user has made in a respective domain associated with an exercise plan. Each domain may have a target progress goal toward which the user is striving. The target progress goal may be represented by a number, a value, a percentage, a state, etc.

At 5406, while a user performs an exercise using the exercise device, the processing device may receive the one or more measurements from one or more sensors associated with the exercise device 100. As described herein, the one or more sensors may include a pressure sensor including one or more load cells, proximity sensors, haptic sensors, piezoelectric sensors, optical sensors, temperature sensors, electrical sensors, mechanical sensors, chemical sensors, electromechanical sensors, electrochemical sensors or mechanicochemical sensors or the like. There may be multiple sensors disposed in, on, around, or near the exercise device 100. The multiple sensors may be configured to obtain the one or more measurements. The sensors may include a processing device, a memory device, a network interface device, a sensing device, etc. The sensors may be configured to wireless communicate the one or more measurements to the computing device 12 and/or the cloud-based computing system 16.

At 5408, the processing device may present, on a computing device associated with the exercise device 100, one or more sections of the user interface. The one or more sections may include independent graphical elements, objects, representations, or the like. The one or more sections may include overlapping graphical elements, objects, representations, or the like. In some embodiments, one section may share an aspect (e.g., border, graphical element, region, object, shape, representation, text, etc.) with another section. The one or more sections may each include respective text, graphical elements, colors, and the like. The one or more sections may be each related to a separate domain including the one or more domains and wherein, based on the one or more measurements, each section may include the one or more icons placed. In some embodiments, the processing device may present each of the one or more sections as portions of a mount on the user interface. The portions may include parts, subsections, sections, portions, segments, or the like.

In some embodiments, the processing device may predict, based on the progress the user has made in each of the one or more domains, a completion date for an exercise plan. The predicting may be performed by the processing device executing a machine learning model 60 trained to receive the progress and output the predicted completion date. For example, the machine learning model 60 may be trained using a corpus of training data that includes inputs of various progression as measured with respect to the domains matched to completion statistics of the exercise plan.

In some embodiments, the processing device may receive, via an input peripheral, a selection of a domain, wherein the selection includes the one or more domains. In some embodiments, the processing device may present additional information related to the progress of the user associated with the selected domain. In some embodiments, the additional information may include characteristics, details, attributes, properties, parameters, values, descriptions, identifiers, and the like. In some embodiments, the one or more domains may include range of motion, strength, balance, endurance, mobility, stability, pliability, flexibility, pain, or some combination thereof.

In some embodiments, the processing device may receive a second input from the user. The second input may include an instruction to modify an operating parameter of the exercise device 100. The second input may be received via a microphone, a touchscreen, a keyboard, a mouse, a proprioceptive sensor, or some combination thereof. For example, the second input may include a spoken voice from the user that instructs the exercise device 100 to increase resistance. Accordingly, the processing device may use natural language processing to digitize an audio signal representing the spoken voice and process the digitized audio signal. Based on the digitized audio signal, the processing device may transmit a control instruction that causes the resistance provided by one or more of the pedals to be increased in real-time or near real-time.

Figure 55:
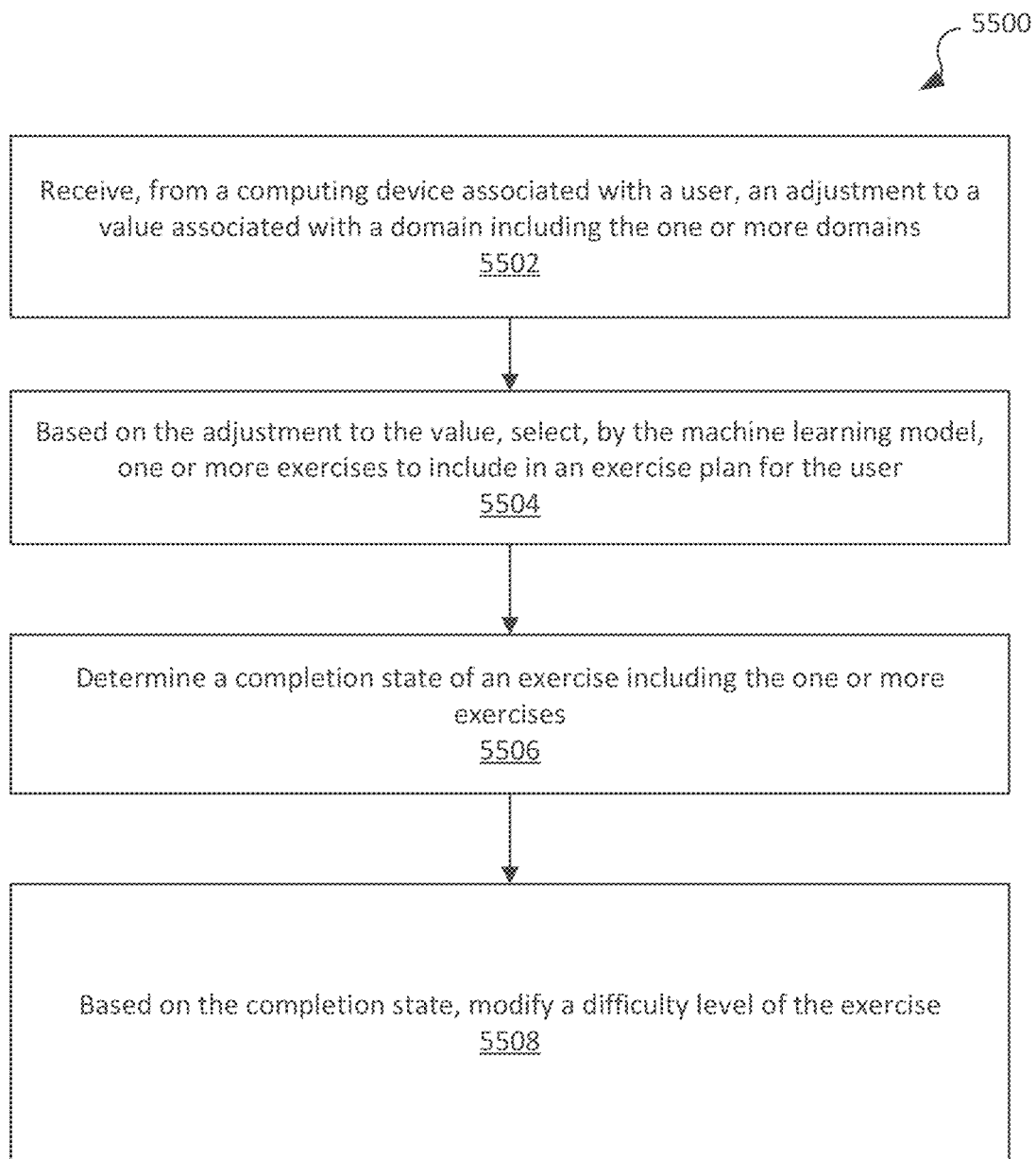
FIG. 55 illustrates an example method for modifying an exercise plan based on adjustment made by a user.

FIG. 55 illustrates an example method 5500 for modifying an exercise plan based on adjustment made by a user. The method 5500 may be performed by processing logic that may include hardware (circuitry, dedicated logic, etc.), firmware, software, or a combination of them. The method 5500 and/or each of its individual functions, subroutines, methods (e.g., object oriented programming), or operations may be performed by one or more processing devices of a control system (e.g., cloud-based computing system 16, computing device 12 of FIG. 1) implementing the method 5500. The method 5500 may be implemented as computer instructions executable by a processing device of the control system (e.g., a computer-readable medium may be used to store instructions that, when executed, cause a processor to perform the following steps or processes of the method 5500). The method 5500 may be performed in a manner similar to that of the method 2700. Various operations of the method 5500 may be performed by one or more of the cloud-based computing system 16, the computing device 12, the exercise machine 100, and/or the computing device 15 of FIG. 1.

In some embodiments, one or more machine learning models 60 may be generated and trained by the artificial intelligence engine 65 and/or the training engine 50 to perform one or more of the operations of the method 5500. For example, to perform the one or more operations, the processing device may execute the one or more machine learning models 60. In some embodiments, the one or more machine learning models 60 may be iteratively retrained to select different features capable of enabling the optimization of output. The features that may be modified may include a number of nodes included in each layer of the machine learning models 60, an objective function executed at each node, a number of layers, various weights associated with outputs of each node, and the like.

At 5502, the processing device may receive, from the computing device associated with the user, an adjustment to a value associated with a domain comprising the one or more domains. That is, the user is enabled to configure their progress in any of the domains as they desire. For example, the user may increase their completion progress toward a range of motion goal in the domain associated with range of motion.

At 5504, based on the adjustment to the value, the processing device may select, by the machine learning model 60, one or more exercises to include in an exercise plan for the user. Continuing the above example, since the user increased their completion progress toward the range of motion goal, the machine learning model 60 may select exercises with ranges of motion increased in relation to the completion progress indicated by the user.

At 5506, the processing device may determine a completion state of an exercise including the one or more exercises. The completion state may be determined based on a metric associated with the exercise (e.g., elapsed time, distance traveled, number of repetitions completed, number of sets completed, range of motion achieved, force achieved, speed achieved, etc.). The completion state may be represented by a percentage, an amount, a binary value (e.g., 1 or 0), or any suitable indicator.

At 5508, based on the completion state, the processing device may modify a difficulty level of the exercise. For example, if the completion state indicates the completion state for the exercise is below a threshold completion level, then the difficulty for the exercise may be reduced. Continuing the above example, if the completion state indicates the user is not able to sufficiently complete the exercise having the range of motion increased by the user, then the difficulty may be decreased for that exercise (e.g., the range of motion may be decreased back to a prior value describing a past progress of the user in the domain associated with range of motion). If the completion state indicates the completion state for the exercise is above the threshold completion level, then the difficulty for the exercise may be maintained or increased. The machine learning model may be retrained to select exercises having the increased range of motion and/or an increased difficulty level.

Figure 56:
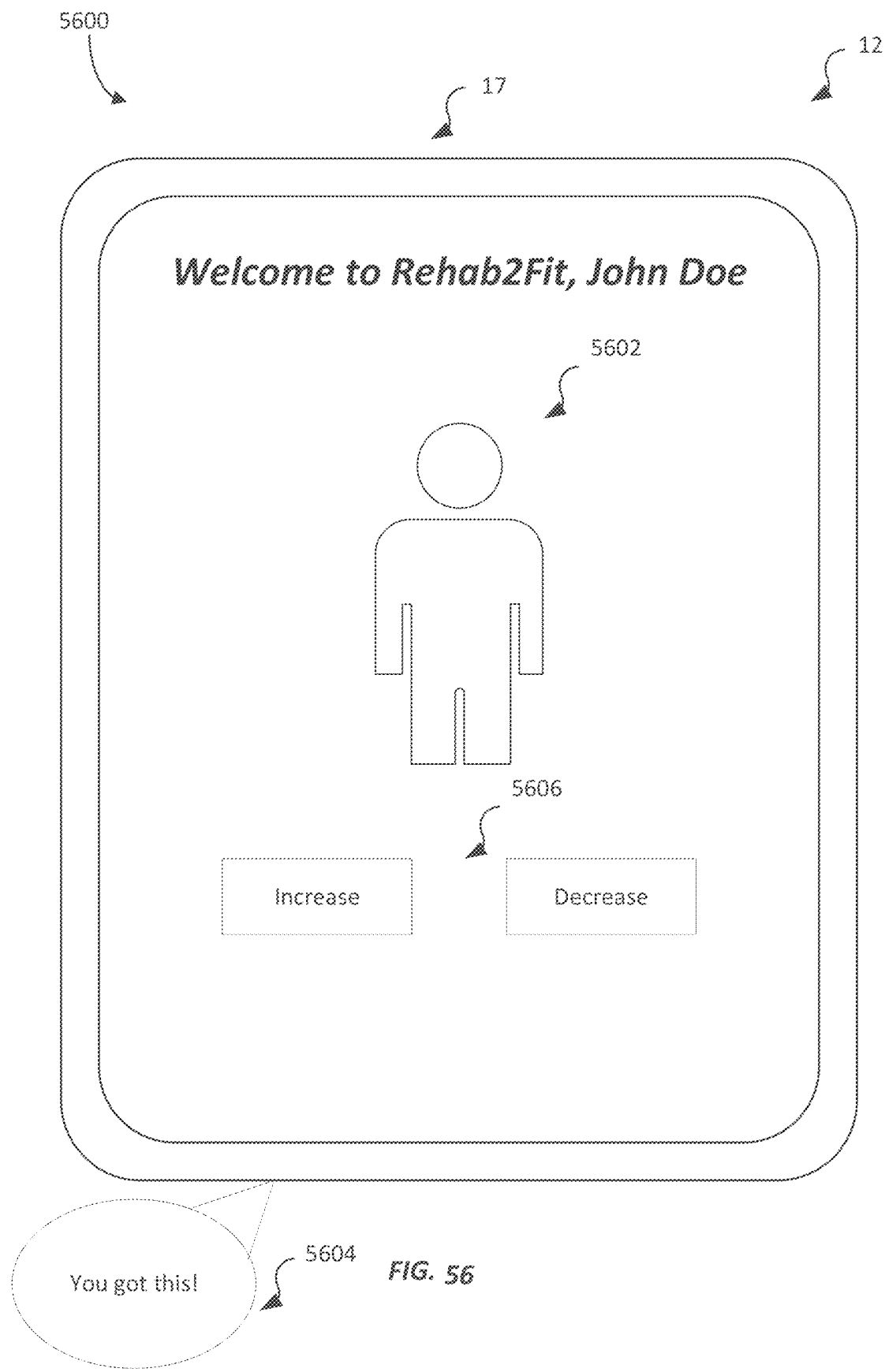
FIG. 56 illustrates an example user interface presenting an animated virtual character, wherein, responsive to user input, the animated virtual character performs a movement.

FIG. 56 illustrates an example user interface 5600 presenting an animated virtual character 5602 performing a movement as a result of user input. The input may be received via any suitable input peripheral, such as a microphone, a keyboard, a mouse, a touchscreen, etc. For example, the user may say "increase resistance" and the microphone may receive the audio signal, wherein the audio signal may include the spoken words. A processing device may be configured to transform the audio signal into a digitized audio signal that can be processed by using natural language processing. The processing device (e.g., of the computing device 12 and/or the cloud-based computing system 16) may process text included in the audio and generate a control instruction that causes the resistance provided by the pedals of the exercise device 100 to be increased.

The virtual character 5602 may be animated to graphically move and to audibly generate a motivational quote 5604 to the user. In some embodiments, the virtual character 5602 may include a virtual coach as described further herein. In some embodiments, the virtual character 5602 may include a live-person performing an exercise in real-time. In some embodiments, the virtual character 5602 may include a prerecording of a live-person performing an exercise.

The user interface 5600 may include various graphical elements 5606 (e.g., buttons): a button associated with increasing the resistance, and a button associated with decreasing the resistance. The user may use an input peripheral, such as a mouse, a keyboard, a microphone, a touchscreen, etc. to select one of the graphical elements 5606. For example, as depicted by a hand cursor, the user may select the button to cause the resistance to increase. The selection may be transmitted to the cloud-based computing system 16 and/or the computing device 12. The selection may cause a control instruction to be generated and transmitted to the exercise device 100. The control instruction may cause an operating parameter associated with the resistance to increase. In some embodiments, when generating subsequent exercise sessions, the selection may cause one or more machine learning models 60 to be retrained to learn the user's preferences for resistance levels.

Figure 57:
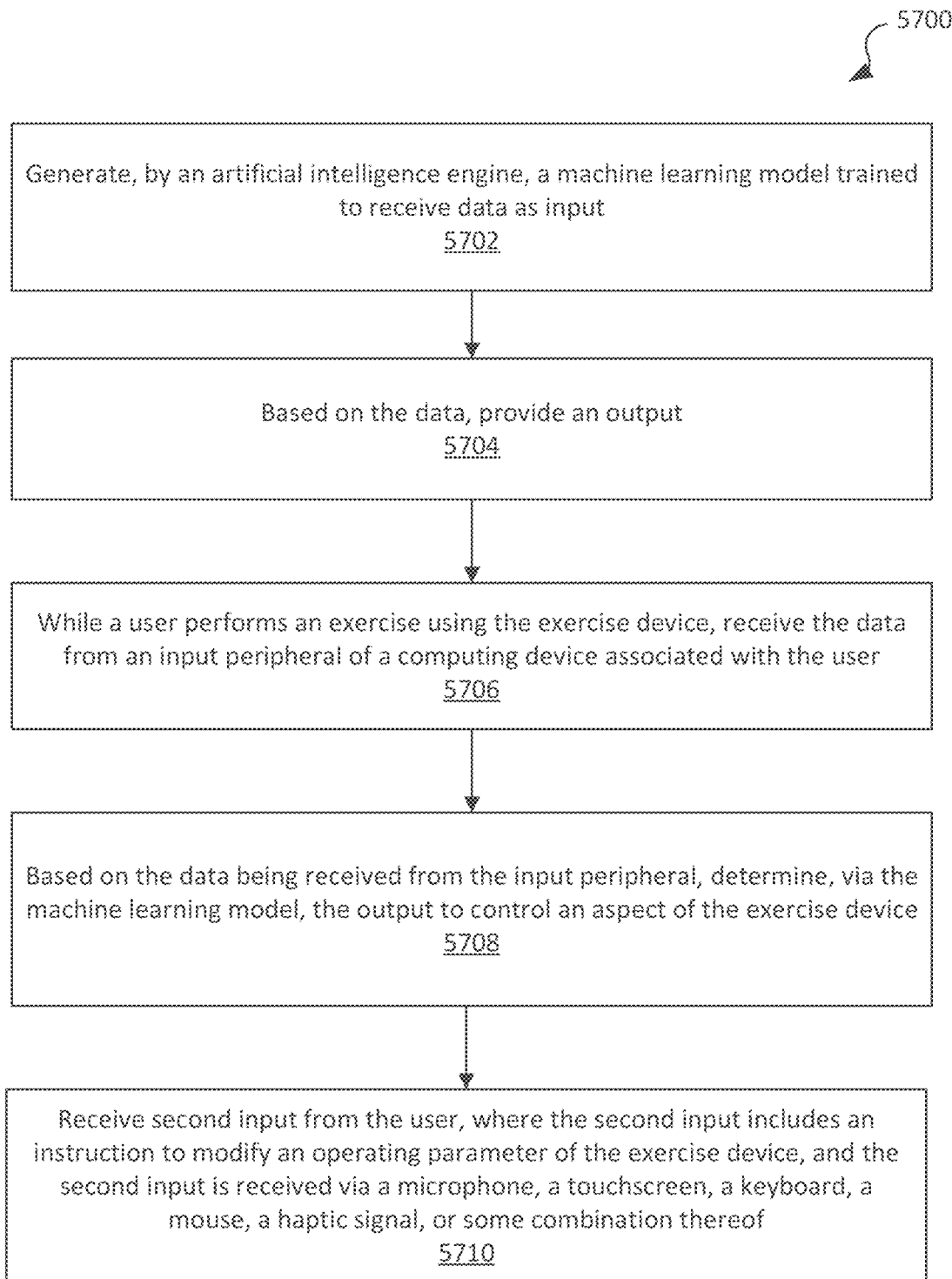
FIG. 57 illustrates an example method for determining an output to control an aspect of an exercise bike based on input received from the user.

FIG. 57 illustrates an example method 5700 for determining an output to control an aspect of an exercise bike based on input received from the user. The method 5700 may be performed by processing logic that may include hardware (circuitry, dedicated logic, etc.), firmware, software, or a combination of them. The method 5700 and/or each of its individual functions, subroutines, methods (e.g., object oriented programming), or operations may be performed by one or more processing devices of a control system (e.g., cloud-based computing system 16, computing device 12 of FIG. 1) implementing the method 5700. The method 5700 may be implemented as computer instructions executable by a processing device of the control system (e.g., a computer-readable medium may be used to store instructions that, when executed, cause a processor to perform the following steps or processes of the method 5700). The method 5700 may be performed in a manner similar to that of the method 2700. Various operations of the method 5700 may be performed by one or more of the cloud-based computing system 16, the computing device 12, the exercise machine 100, and/or the computing device 15 of FIG. 1.

In some embodiments, one or more machine learning models 60 may be generated and trained by the artificial intelligence engine 65 and/or the training engine 50 to perform one or more of the operations of the method 5700. For example, to perform the one or more operations, the processing device may execute the one or more machine learning models 60. In some embodiments, the one or more machine learning models 60 may be iteratively retrained to select different features capable of enabling the optimization of output. The features that may be modified may include a number of nodes included in each layer of the machine learning models 60, an objective function executed at each node, a number of layers, various weights associated with outputs of each node, and the like.

During an exercise session, the method 5700 may use the artificial intelligence engine 65 to interact with a user of an exercise device 100. At 5702, the processing device may generate, by the artificial intelligence engine 65, a machine learning model 60 trained to receive data as input. In some embodiments, the data may include an electronic recording of a voice of the user received via a microphone associated with the computing device. In some embodiments, the data may be associated with a difficulty of an exercise the user is currently performing, and the processing device may modify an exercise plan based on the data. In some embodiments, the data may include an indication from the user that an exercise is too difficult, and the machine learning model may be trained to select a less difficult exercise for the user in a subsequent exercise session.

At 5704, based on the data, the processing device may generate an output. In some embodiments, the output may include a virtual character animated to graphically move and to audibly generate a motivational quote to the user. In some embodiments, the output may include a control instruction that causes the exercise device 100 to change an operating parameter. In some embodiments, the operating parameter may include changing a range of motion of one or more pedals, changing a speed of a motor, changing a revolutions per minute of a motor, changing a parameter of a fan associated with the exercise bike, changing a temperature of a portion of the exercise bike, changing a haptic setting of a portion of the exercise bike, or some combination thereof.

At 5706, while a user performs an exercise using the exercise device 100, the processing device may receive the data from an input peripheral of a computing device 12 associated with a user. The input peripheral may include a microphone, a keyboard, a mouse, a touchscreen, etc.

At 5708, based on the data being received from the input peripheral, the processing device may determine, via the machine learning model 60, the output to control an aspect of the exercise device 100. An "aspect" may refer to a characteristic, an attribute, a property, a part, information, detail, a controlling mechanism, or some combination thereof. For example, the aspect may refer to controlling an amount of resistance provided by one or more pedals, a range of motion provided by one or more pedals, a speed provided by one or more pedals and/or a motor, a revolutions per minute of one or more pedals and/or a wheel, etc.

In some embodiments, the processing device may select a virtual character, a prerecorded message, or both, to present via the computing device. The virtual character, the prerecorded message, or both may include a motivational quote. The virtual character may be a virtual coach, as described herein. Further, the virtual character may be a live-person performing an exercise in real-time. The virtual character may be a prerecorded live-person performing a an exercise.

In some embodiments, the processing device may receive second input from the user. The second input may include an instruction to modify an operating parameter of the exercise device 100. The second input may be received via a microphone, a touchscreen, a keyboard, a mouse, a proprioceptive sensor, or some combination thereof. For example, the second input may include spoken voice from the user that instructs the exercise device 100 to increase resistance. Accordingly, the processing device may use natural language processing to digitize an audio signal representing the spoken voice and process the digitized audio signal. Based on the digitized audio signal, the processing device may transmit a control instruction that causes the resistance provided by one or more of the pedals to be increased in real-time or near real-time.

Figure 58:
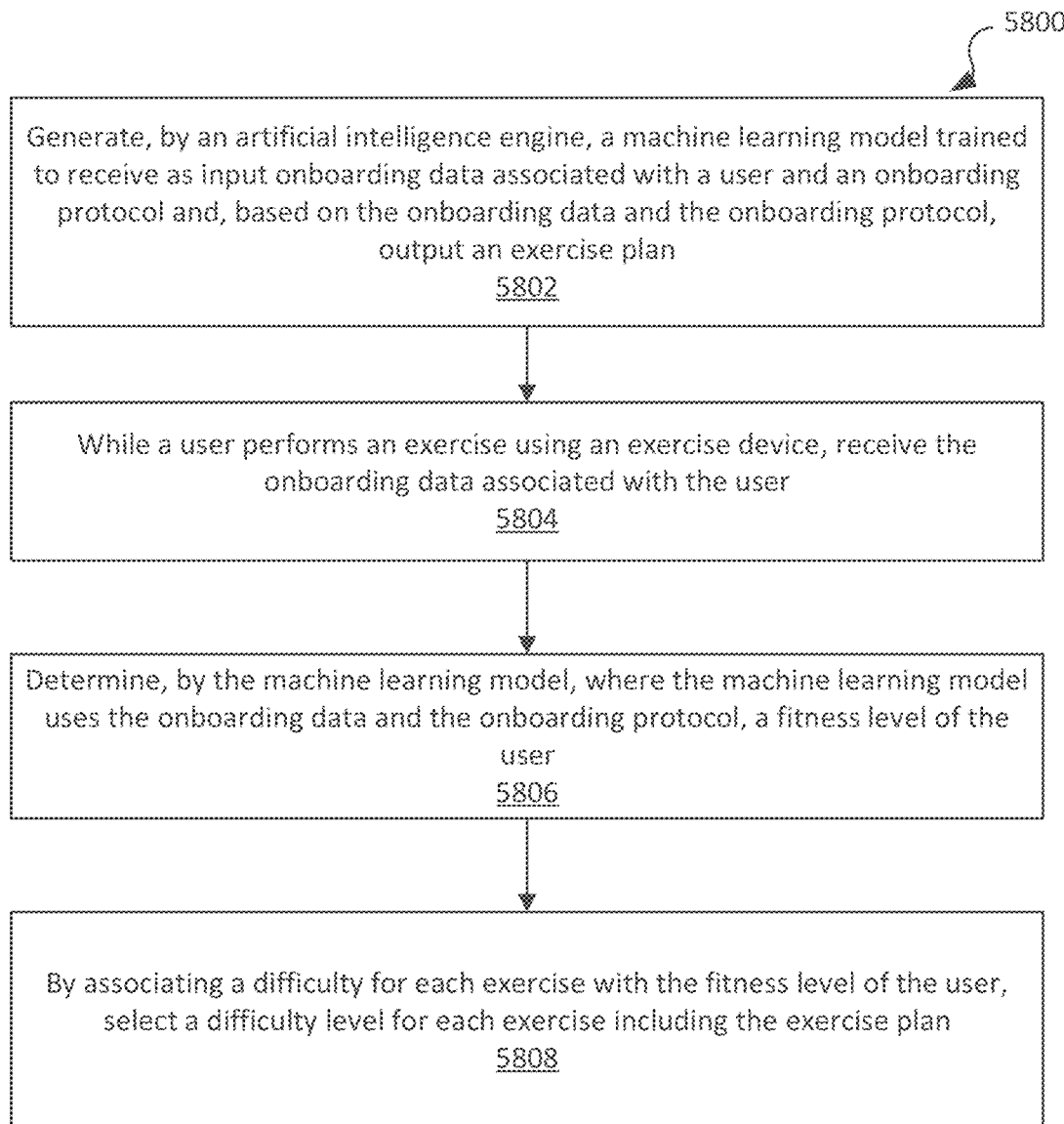
FIG. 58 illustrates an example method for using an onboarding protocol to generate an exercise plan for a user.

FIG. 58 illustrates an example method 5800 for using an onboarding protocol to generate an exercise plan for a user. The method 5800 may be performed by processing logic that may include hardware (circuitry, dedicated logic, etc.), firmware, software, or a combination of them. The method 5800 and/or each of its individual functions, subroutines, methods (e.g., object oriented programming), or operations may be performed by one or more processing devices of a control system (e.g., cloud-based computing system 16, computing device 12 of FIG. 1) implementing the method 5800. The method 5800 may be implemented as computer instructions executable by a processing device of the control system (e.g., a computer-readable medium may be used to store instructions that, when executed, cause a processor to perform the following steps or processes of the method 5800). The method 5800 may be performed in a manner similar to that of the method 2700. Various operations of the method 5800 may be performed by one or more of the cloud-based computing system 16, the computing device 12, the exercise machine 100, and/or the computing device 15 of FIG. 1.

In some embodiments, one or more machine learning models 60 may be generated and trained by the artificial intelligence engine 65 and/or the training engine 50 to perform one or more of the operations of the method 5800. For example, to perform the one or more operations, the processing device may execute the one or more machine learning models 60. In some embodiments, the one or more machine learning models 60 may be iteratively retrained to select different features capable of enabling optimization of output. The features that may be modified may include a number of nodes included in each layer of the machine learning models 60, an objective function executed at each node, a number of layers, various weights associated with outputs of each node, and the like.

The method 5800 may use the artificial intelligence engine 65 to onboard a user for an exercise plan. In some embodiments, onboarding may refer to the fulfillment of a set of conditions that form a predicate needed to enable the user to start using the system. At 5802, the processing device may generate, by the artificial intelligence engine 65, a machine learning model 60 trained to receive as input onboarding data associated with a user and an onboarding protocol and, based on the onboarding data and the onboarding protocol, to output an exercise plan.

At 5804, while the user performs an exercise using the exercise device 100, the processing device may receive the onboarding data associated with the user. The onboarding data may include one or more measurements may be associated with a force exerted on the one or more pedals, a revolution per minute of the one or more pedals, a speed of rotation of the one or more pedals, an angular moment of the one or more pedals, a range of motion of the one or more pedals, a radius of an arc traversed by the one or more pedals, a degree of flexion, a degree of extension, a skill level, or some combination thereof. The onboarding data may also include an indication of a pain level the user experiences while performing an exercise. The onboarding data may include personal information associated with the user and/or performance information associated with the user.

At 5806, the processing device may determine, by the machine learning model 60 using the onboarding data and the onboarding protocol, a fitness level of the user. The onboarding protocol may include exercises with tiered difficulty levels. The exercises may be associated with a plurality of domains comprising range of motion, strength, balance, endurance, mobility, stability, pliability, flexibility, pain, or some combination thereof. When the user completes an exercise included in the exercises, the onboarding protocol may increase a difficulty level for a subsequent exercise included in the exercises. Based on a completion state of a last exercise performed by the user, the fitness level of the user may be determined.

At 5808, by associating the difficulty level for each exercise with the fitness level of the user, the processing device may select a difficulty level for each exercise included in the exercise plan. In some embodiments, the machine learning model 60 may be trained to generate the exercise plan to reduce a pain level of the user, a dependency of the user on a certain medication (preferably opioids or other addictive drugs), or some combination thereof.

In some embodiments, as the user performs the exercise plan, the processing device may receive one or more measurements from one or more sensors, the computing device associated with the user and/or exercise device 100, or some combination thereof. Based on the one or more measurements, the processing device may modify a portion of the exercise plan to include different exercises. For example, the portion of the exercise plan that is modified may include one exercise, two exercises, three exercises, or any suitable number of exercises. That is, any combination of exercises may be modified in the exercise plan. Modification may refer to addition, change, deletion, etc. In some embodiments, the processing device may present the exercise plan on a computing device associated with the exercise device 100.

In some embodiments, the processing device may receive feedback from the user. The feedback may pertain to a pain level of the user, an enjoyment level of the user performing the exercise plan, or some combination thereof. Based on the feedback, the processing device may modify the exercise plan to include different exercises.

In some embodiments, a virtual character may be presented on a computing device associated with the exercise device 100 or the user. The virtual character may include a coach that provides instructions regarding how to properly perform an exercise. The virtual coach may be animated on the user interface and may perform the proper movements associated with the exercise. Further, the coach may speak and audio representing the virtual coach's speech may be generated. The speech may include instructions regarding how to properly perform the exercise. The virtual character may be a virtual avatar, a live person presented in real-time, a pre-recorded live person, etc.

In some embodiments, the processing device may receive input from the user. The input may include an instruction to modify an operating parameter of the exercise device 100. The input may be received via a microphone, a touchscreen, a keyboard, a mouse, a proprioceptive sensor, or some combination thereof. For example, the input may include a spoken voice from the user that instructs the exercise device 100 to increase a resistance. Accordingly, the processing device may use natural language processing to digitize an audio signal representing the spoken voice and to process the digitized audio signal. Based on the digitized audio signal, the processing device may transmit a control instruction that causes the resistance provided by one or more of the pedals to be increased in real-time or near real-time.

The various aspects, embodiments, implementations or features of the described embodiments can be used separately or in any combination. The embodiments disclosed herein are modular in nature and can be used in conjunction with or coupled to other embodiments, including both statically-based and dynamically-based equipment. In addition, the embodiments disclosed herein can employ selected equipment such that they can identify individual users and auto-calibrate threshold multiple-of-body-weight targets, as well as other individualized parameters, for individual users.

Consistent with the above disclosure, the examples of systems and method enumerated in the following clauses are specifically contemplated and are intended as a non-limiting set of examples.

CLAUSES

1. A computer-implemented method for using an artificial intelligence engine to modify resistance of one or more pedals of an exercise device, wherein the computer-implemented method comprises:
    generating, by the artificial intelligence engine, a machine learning model trained to receive one or more measurements as input;
    outputting, based on the one or more measurements, a control instruction that causes the exercise device to modify the resistance of the one or more pedals;
    receiving the one or more measurements from a sensor associated with the one or more pedals of the exercise device;
    determining whether the one or more measurements satisfy a trigger condition; and
    responsive to determining that the one or more measurements satisfy the trigger condition, transmitting the control instruction to the exercise device.

2. The computer-implemented method of any preceding clause, wherein transmitting the control instruction to the exercise device causes the exercise device to modify the resistance of the one or more pedals in real-time or near real-time, wherein the modification comprises modifying the resistance a same amount provided by a pedal on each side of the exercise device, or modifying the resistance a different amount on different sides of the exercise device.

3. The computer-implemented method of any preceding clause, wherein, while a user uses the exercise device to perform an exercise, the resistance of the one or more pedals is modified.

4. The computer-implemented method of any preceding clause, wherein the one or more pedals comprise one or more foot pedals, one or more hand pedals, or some combination thereof.

5. The computer-implemented method of any preceding clause, wherein the one or more measurements are associated with a force exerted on the one or more pedals, a revolution per minute of the one or more pedals, a speed of rotation of the one or more pedals, an angular moment of the one or more pedals, a range of motion of the one or more pedals, a radius of an arc traversed by the one or more pedals, or some combination thereof.

6. The computer-implemented method of any preceding clause, further comprising:
    presenting the control instruction on a user interface of a computing device associated with the exercise device.

7. The computer-implemented method of any preceding clause, further comprising receiving a selection from the computing device, and based on the selection, modifying the resistance of the one or more pedals, range of motion of the one or more pedals, speed of a motor, or some combination thereof.

8. The computer-implemented method of any preceding clause, wherein the control instruction is associated with changing an operating parameter of a motor connected to the one or more pedals of the exercise device.

9. The computer-implemented method of any preceding clause, further comprising:
    receiving one or more characteristics of a user operating the exercise device; and
    based on the one or more characteristics of the user and the one or more measurements, determining whether the trigger condition is satisfied.

10. The computer-implemented method of any preceding clause, further comprising:
    responsive to determining that the trigger condition has been satisfied, modifying another operating parameter of the exercise device, wherein the another operating parameter comprises a number of revolutions per minute, a speed, a torque, a temperature, a vibration, or some combination thereof.

11. The computer-implemented method of any preceding clause, further comprising:
    receiving second input from the user, wherein the second input comprises an instruction to modify an operating parameter of the exercise device, and the second input is received via a microphone, a touchscreen, a keyboard, a mouse, a proprioceptive sensor, or some combination thereof.

12. The computer-implemented method of any preceding clause, wherein transmitting the control instruction to the exercise device causes the exercise device to modify a parameter associated with a pedal on each side of the exercise device a same amount or a different amount, wherein the parameter comprises range of motion, resistance, speed of a motor, revolutions per minutes, or some combination thereof.

13. A tangible, non-transitory computer-readable medium storing instructions that, when executed, cause a processing device to:
    generate, by an artificial intelligence engine, a machine learning model trained to receive one or more measurements as input;
    output, based on the one or more measurements, a control instruction that causes an exercise device to modify resistance of one or more pedals of the exercise device;
    receive the one or more measurements from a sensor associated with the one or more pedals of the exercise device;
    determining whether the one or more measurements satisfy a trigger condition; and
    responsive to determining that the one or more measurements satisfy the trigger condition, transmitting the control instruction to the exercise device.

14. The computer-readable medium of any preceding clause, wherein transmitting the control instruction to the exercise device causes the exercise device to modify the resistance of the one or more pedals in real-time or near real-time, wherein the modification comprises modifying the resistance a same amount provided by a pedal on each side of the exercise device, or modifying the resistance a different amount on different sides of the exercise device.

15. The computer-readable medium of any preceding clause, wherein, while a user uses the exercise device to perform an exercise, the resistance of the one or more pedals is modified.

16. The computer-readable medium of any preceding clause, wherein the one or more pedals comprise one or more foot pedals, one or more hand pedals, or some combination thereof.

17. The computer-readable medium of any preceding clause, wherein the one or more measurements are associated with a force exerted on the one or more pedals, a revolution per minute of the one or more pedals, a speed of rotation of the one or more pedals, an angular moment of the one or more pedals, a range of motion of the one or more pedals, a radius of an arc traversed by the one or more pedals, or some combination thereof.

18. The computer-readable medium of any preceding clause, wherein the processing device is configured to:
    present the control instruction on a user interface of a computing device associated with the exercise device.

19. The computer-readable medium of any preceding clause, further comprising receiving a selection from the computing device, and based on the selection, modifying the resistance of the one or more pedals, range of motion of the one or more pedals, speed of a motor, or some combination thereof.

20. A system comprising:
a memory device storing instructions; and
a processing device communicatively coupled to the memory device, wherein
the processing device executes the instructions to:
generate, by an artificial intelligence engine, a machine learning model trained to receive one or more measurements as input;
output, based on the one or more measurements, a control instruction that causes an exercise device to modify resistance of one or more pedals of the exercise device;
receive the one or more measurements from a sensor associated with the one or more pedals of the exercise device;
determining whether the one or more measurements satisfy a trigger condition; and
responsive to determining that the one or more measurements satisfy the trigger condition, transmitting the control instruction to the exercise device.

No part of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle.

The foregoing description, for purposes of explanation, used specific nomenclature to provide a thorough understanding of the described embodiments. However, it should be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The information below may provide a guideline of the rules employed in delivering an effective, well-structured exercise program for rehab, conditioning, and/or long-term fitness adapted to the capabilities of each user. The information below is for explanatory purposes and the subject matter of the present disclosure is not limited to the examples provided below.

a) Initially a processing device (e.g., cloud-based computing system 16, computing device 15, or both) may filter users into their correct exercise levels.
b) Then the processing device may determine what combination of exercises is appropriate for the users in beginning their training.
c) As the users complete exercise sessions a machine learning model may learn the user's ability and tracks their progress, adjusts their exercises in exercise sessions accordingly, and determines when the users can advance to the next exercise level.

One objective may be to deliver the most effective exercise plan devised for each user, the exercise plan may be defined as one people actually engage in fully, frequently, and consistently.

2. Determining a User's Exercise Level
Exercise levels may range from 1 to 5. Placing a user in an exercise level may be a function of measuring the individual's Range-of-Motion (ROM) and establishing the Degree-of-Knee-Pain they are experiencing.

How The Combination of Pain and ROM Test Results Define Levels:
Pain—the level of pain as indicated by the user (they will enter this into the system manually by typing or voice)
ROM—the result of their Range-of-Motion test

| If Pain Is | & ROM Is | Then Level Is |
| --- | --- | --- |
| 8-10 | 1-2 | 1 |
| 8-10 | 3-4 | 2 |
| 8-10 | 5 | 3 |
| 5-7 | 1-2 | 1 |
| 5-7 | 3-4 | 2 |
| 5-7 | 5 | 3 |
| 1-4 | 1-2 | 1 |
| 1-4 | 3-4 | 2 |
| 1-4 | 5 | 4 |
| 0 | 5 | 5 |

How the Combination of Level and ROM Test Results Define Resistance:

| If Level Is | & ROM Is | Resistance Is |
| --- | --- | --- |
| 1 | 1-2 | Notch 1-2 |
| 2 | 3-4 | Notch 3-4 |
| 3-5 | 5 | Notch 5 | a) Measuring ROM
The User is instructed as follows:
1. Set both pedals of the exercise cycle to the lowest level of movement required to turn the wheel a full revolution, i.e., the smallest radius, ROM-Notch Setting 1 of 5.
2. Test both legs simultaneously as follows:
   (a) Beginning at the lowest ROM setting on each pedal, pedal for a maximum of one minute or until the onset of pain in either knee.
   (b) If there is no pain in either knee during the first minute of pedalling, increase the radius setting of the pedal by one-notch and pedal for an additional minute.
   (c) Continue this process of simultaneously increasing the ROM-Notch settings for the radius of each pedal by one notch and pedaling for an additional minute until experiencing knee pain.
3. If pedaling at a radius of 5 ROM Notches is pain free, record the opening ROM Settings as 5 for each pedal.
   (a) Otherwise, when pain is experienced in either knee, stop pedaling, and
      (i) record the opening ROM Notch Setting for the affected leg as one notch less than the notch that produced the pain, and
      (ii) and set the pedal for the affected leg to the notch recorded.
4. If pain is experienced at a ROM Notch Setting of 1 notch, or if the degree of pain experienced is greater than a 3-intensity on a scale of 10 at any notch, stop the ROM testing immediately, refer to our "User Ramp-Up To Cycling" video, and follow its instructions.

5. If the degree of pain is a 3-intensity or less continue the ROM test by resuming pedaling, with the pedal for the affected leg at the notch set in 3(i) and continue the ROM test for the other leg as follows:
   (i) Increase the setting by one notch for the radius of the pedal being used by the other leg and pedal for an additional minute or until experiencing knee pain in the other leg.
   (ii) when pain is experienced, stop pedaling, and:
      1. record the opening ROM Notch setting for the other leg as one notch less than the notch that produced the pain, and
      2. and set the pedal for the other leg to the notch recorded.
   (iii) if pain is not experienced in the other leg, set the pedal for the other leg to ROM Notch 5.
a) Establishing Degree of Pain
The processing device may ask (e.g., via the virtual coach (artificial intelligence driver) and displays to the user an array of emoticons/terms reflecting various degrees of pain.
   i. The user responds (e.g., by voice) or selects the one most closely representing the user's degree of knee pain at the time of making the selection.
   ii. Users report (e.g., by voice) or enters onto the dashboard their degree of pain each time they log in.
b) Tracking ROM and Degree of Knee Pain to Advance Through the Exercise Levels
   i. The status of ROM is tested and Degree of Knee Pain is reported on a 5-Exercise Session interval, i.e., both are updated every 6th session.
      1. Every 5th login the system displays a notice and alerts the User (e.g., by voice) that the next login will begin with a ROM test.
   ii. During the ROM test the system guides the user by the display and (e.g., by voice) as follows: if a user pedals at a ROM radius greater than indicated for their current exercise level, they will advance to the higher exercise level upon meeting the following additional requirements:
      1. improvement in Degree of Pain, and
      2. during the two subsequent Exercise Sessions demonstrating the prior Exercise Level is too easy by:
         (a) using the new pedal radius, and
         (b) pedalling without pain.
c) Heart Rate Test: Level 1-3
   i. The user attaches the wrist tracker to their arm to begin their initial heart rate test (cycling). The intensity of the workout will stay steady for 3-minutes to measure their baseline heart rate. At the end of the 3 minutes, the processing device records the user's heart rate.
d) Heart Rate Test: Level 4-5
   i. The user attaches the wrist tracker to their arm for the test (cycling). When the test begins, the intensity of the workout slowly increases the user's heart rate reaches the "Test Zone". This zone is individually computed to be near 75 percent of the maximum heart rate for the user's profile. When the user reaches the Test Zone, the system holds the intensity steady for 3 minutes. At the end of the 3 minutes, the processing device records the user's heart rate and power output. This data along with the user's age and weight, are computed to produce a "Fitness Score" baseline.
e) Fitness Test: Portable Product
   i. Strength Test: Pushup test for motivation by tracking progress over time, but no impact on protocol design. Frequency of fitness testing: every 8 weeks
f) Fitness Test: Subsequent Products
   i. Strength Test: Pushup test and use inputs to drive phases—if the user performs poorly in strength, make the next 8-week phase focused on strength building, if the user performs poorly or average on endurance make next 8-week phase focused on building endurance, etc. Frequency of fitness testing: every 8 weeks
3. Exercise Sessions
a) Composition of Each Exercise Level
   i. Levels 1-3 Exercise Sessions
      1. Cycle: 5-minutes
      2. Warm-up: 5-minutes+(−) 30 seconds
      3. Strength Building: 5-minutes+(−) 30 seconds
      4. Cool Down: 5-minutes+(−) 30 seconds
   ii. Levels 4-5 Exercise Sessions
      1. Warm-up: 2-minutes+(−) 30 seconds
      2. Cardio: 8-minutes+(−) 30 seconds
      3. Strength Building: 8-minutes+(−) 30 seconds
      4. Flexibility: 5-minutes+(−) 30 seconds
      5. Cool Down: 2-minutes+(−) 30 seconds
   iii. Level 4-5+ Options for exercise selection
      1. Once users reach full ROM and no pain, an option is provided to the users of picking their own 8 week programs or having the system pick the program
      2. Programs can be based on the result of the user's fitness test or can be randomized (ideally they will be based on the user's Fitness Test)
      3. The system can devise a phased program to address a deficiency in their fitness test (i.e., user is average or poor in endurance so the 8 week phase is aimed at improving endurance)
      4. The user can choose an 8 week program based on the deficiency in their fitness test (i.e., the user is alerted he/she is average or poor in endurance so the user picks 8 week phase is aimed at improving endurance)
      5. The system can randomly assign an 8 week program
      6. The user can select any 8 week program
      7. Programs can also be based on achieving a fitness or activity of daily living goal.
         (a) A user selects a goal from a pre-loaded picklist (this will be selected from market research about common fitness/activities of daily living goals)
         (b) Based on the goal selected the system designs an 8 week program that addresses the performance requirement to achieving that goal.
b) Exercise Filtering:
   i. Exercise Selection:
      1. First filter exercises by exercise level
      2. Then filter exercises within each exercise level by section (warm up, cycling, strength, flexibility, cool down)
      3. Then filter exercises within each section by "Time to Complete"
         (a) Exercise combination should equal+/−30 seconds from 5 minutes per section.
   ii. Incorporate the user's historical data
      1. Block out exercises completed often (e.g., within a certain time period, each exercise session, etc.)
      2. Start new sessions with reps/sets based on previous session output (e.g., ended with 6 reps so start next session with 6 reps)
   iii. Session Counter
      1. The system will keep a cumulative log of every time a user logs in and completes a session. After every 5th login and completion, the next session will begin with a ROM test.

c) Evaluative Sessions
i. The first two sessions for every user will be evaluative.
ii. All exercises during Evaluative Sessions may be Level-1 exercises irrespective of the user's actual Exercise Level as determined in #2 above.
iii. After completing the Evaluative Sessions successfully, users may receive exercises based upon their exercise level as rated in #2 above.
iv. Every exercise may be announced by the display, virtual coach, etc. and (e.g., by voice).
 1. The user may be required to watch the exercise tutorial the first two times an exercise is presented. Thereafter, the User will be given the option by the display, virtual coach, etc. and (e.g., by voice) to watch the tutorial or to "Skip" it (e.g., by voice) or by making an entry to the dashboard.
4. Exercise Adaptations
a) When a User Presses or Commands (e.g., by Voice) the Too Easy Button
 i. The exercise they are then performing may automatically increase 15% in intensity (rounded up to the nearest whole number) in one of the following dimensions, according to the exercise:
  1. Number of Sets (Increase)
  2. Number of Repetitions (Increase)
  3. Hold Time (Increase)
  4. Rest Time (Reduce)
  The duration of exercise sessions (3a above) may be extended by the additional time required for the user to perform exercises at an increased intensity.
 ii. Users may press the display button or say (e.g., by voice) "Too Easy" up to three times per exercise per exercise session. Each time:
  1. the User will be alerted on the dashboard and by the virtual coach to the degree of difficulty increase in repetitions and sets, and
  2. will have the option of pressing or saying (e.g., by voice) "Too Hard" on the new level, and the repetitions and sets may immediately revert to their prior values.
 iii. Users may perform the Baseline Exercise for 3 Exercise Sessions before the "Too Easy" button becomes available to use.
b) When a User Presses Button or Says (e.g., by Voice) Too Hard
 i. The key exercise dimension for non-cycling exercise drops:
  1. the first time by 20% of the original amount (rounded down to the nearest whole number), then
  2. the second time by 40% of the original amount, then
  3. the third time by 80% of the original amount.
 ii. The key exercise dimension for cycling drops:
  1. first by reducing the Resistance Level setting, then
  2. by reducing the ROM setting.
 iii. If a user presses button or says (e.g., by voice) "Too Hard" 3 times on the same exercise in the same session, a push notification message may appear and ask if everything is alright and ask if they want to continue with the exercise.
 iv. If a user presses button or says (e.g., by voice) "Too Hard" a 4th time, the exercise will stop, and a push notification and notification may let the user know to stop this exercise for the session.

c) When a User Presses Button or Says (e.g., by Voice) Skip
 i. The system may record the exercise was skipped, and may begin the exercise at the user's previous exercise level the next time the exercise is shown.
5. In-Session Exercise Switching
a) When a user has completed the Baseline Version of an exercise 3 times, the system may switch out exercises by randomly delivering one of four variations of the same exercise.
 Variation 1—Sets
 Variation 2—Repetitions
 Variation 3—Hold Times
 Variation 4—Rest Time
b) If a user has performed an exercise (including the Baseline & variations) in 15 sessions, the user will be asked through a push notification if they would like to swap out the exercise for another.
6. Counting Reps & Sets
a) Exercises may be timed to our rep time per exercise on our exercise database:
 i. This informs the system of sets/reps completed
 ii. Reps will be calculated by dividing the amount of time the user completed the exercise by the rep time per exercise
  1. EX:User does an exercise for 1 minute and the rep time per exercise in the dashboard is 30 seconds—the user completed 2 reps of that exercise
 iii. Users will be able to stop an exercise at any point by pressing "Skip" on the screen or by saying "Skip".
 iv. The system determines an exercise is completed in one of two ways:
  1. The total time per exercise (as directed by the database) has elapsed
  2. A user presses "Next" on the screen or says "Next".
b) Users have the option of personally reporting reps/sets completed by entering the data on the screen or by saying the number of each after each exercise.
7. Completing an Exercise or an Exercise Session
a) System Default: Communicating the completion of both exercises and exercise sessions can be accomplished by using either a button or by voice.
 i. Completing an Exercise: user pushes "Next" button or says "Next".
 ii. Completing an Exercise Session: user pushes "End Session" button or says "End Session".
b) User Choice: Do the exercises continually until pushing the "Stop" button or saying "Stop".
8. Advancing Out of Levels
If a user conducts their ROM test, and pedals at a ROM radius consistent with a radius higher than their current level:
 On the user's next 2 subsequent sessions
  Their cycling portion will be done at the increased radius.
 If the user does not indicate an increase in pain when logging in for those 2 subsequent cycle portions, the user may be advanced to the new level in their next session.
9. Exercise Session Example for Level-1
a) Warm Up Cycling
 5 minutes at the ROM level during setup
b) Exercises
 Squats—Chair rise
  5 times 2 sets
30 second rest between each set
Calf Raises
10-20 times
2 sets
30 second rest between each set
Hamstring Curl
Hold for 5 seconds
5 times
2 sets
30 second rest between each set
Standing Hip Extension
Hold for 5 seconds
5 times
2 sets
30 second rest between each set
Standing Hip Abduction
Hold for 5 seconds
5 times
2 sets
30 second rest between each set
Seated Hip Adduction
Hold for 5 seconds
5 times
2 sets
30 second rest between each set
c) Strengthening Cycling
After pedaling for 3 minutes, increase the arc one notch.
5-8 minutes, at a comfortable pace, 4-5/10 level
d) Cool Down
Seated hamstring stretch (end)
Hold for 2 seconds
10 times per side
Moving on to Levels 4 & 5
At these levels a user may have full range of motion and their pain may be almost gone.
The next step may include helping them with their fitness goals (ex: playing with grandkids, golfing, skiing) by adding resistance, endurance, cardio and loading exercises in a protocol/program tailored to that goal
Level 4 Session Example—25 mins
Warm Up
Stretching—5 minutes
Cardio
Cycling Program: Ride In The Park—5 minutes
Strength
Band Exercises: Chest Press, Seated Row, Squats—5 minutes
Flexibility
Goddess, Seated Twist, Stand Hip Adduction—5 minutes
Cool Down
Seated Marching, Hip Extension, Hamstring Curl—5 minutes
Level 5 Session Example—25 mins
Warm Up
Stretching—5 minutes
Cardio
Cycling Program: Pike's Peak—5 minutes
Strength
Band Exercises: Bicep Curl, Shoulder Press, Pull Apart—5 minutes
Flexibility
Seated Hamstring Stretch, Hip Abduction, Calf Raise,—5 minutes
Cool Down
Seated Side Step, Seated Ankle Pumps, Sitting Knee Extensions—5 minutes
Additional Algorithm Rules
Each exercise may target at least one body part. The body part targets may be tagged in the data structures as follows:
whole leg
lateral hip
medial hip
posterior hip
hamstrings
quadriceps
hip flexion
Each session may include at least one exercise that targets each of the body parts listed.
The exercises per session must not exceed a percentage (e.g., 5, 10, 20, 30, 40, 50, etc.) of one particular body part target.
The number of exercises assigned to each body part may be be tabulated. The selection of an exercise for any body part, should not result in total exercises for that body part exceeding the total of any other body part by more than one.
Resistance (Cycling)

| Level 1 | Level 2 | Level 3 | Level 4 | Level 5 |
|---|---|---|---|---|
| NA | NA | 1/Easy | 2/Easy | 6/Medium |
|  | 1/Back/pull |  | 3/Easy | 7/Medium |
|  |  |  | 4/Medium | 8/Hard |
|  |  |  | 5/Medium | 10/Hard |

Bands

| Level 1 | Level 2 | Level 3 | Level 4 | Level 5 |
|---|---|---|---|---|
| 1/Mini | 1/Mini | 1/Mini | 1/Mini | 1/Mini |
|  | 2/Thin | 2/Thin | 2/Thin | 2/Thin |
|  |  |  | 3/Heavy | 3/Heavy |

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

What is claimed is:

1. A computer-implemented method for using an artificial intelligence engine to modify resistance of one or more pedals of an exercise device, wherein the computer-implemented method comprises:
    generating, by the artificial intelligence engine, a machine learning model, wherein the machine learning model is trained using training data comprising inputs of one or more measurements mapped to outputs of one or more control instructions;
    receiving the one or more measurements from one or more sensors respectively associated with the one or more pedals of the exercise device;
    outputting, by the machine learning model, a control instruction of the one or more control instructions, wherein the control instruction causes the exercise device to modify the resistance of the one or more pedals, and the control instruction is generated based on the one or more measurements;
    determining whether the one or more measurements satisfy a trigger condition;

responsive to determining that the one or more measurements satisfy the trigger condition, transmitting the control instruction to the exercise device;

determining whether the trigger condition is satisfied further based on one or more characteristics of a user of the exercise device, wherein the one or more characteristics of the user comprise at least one of personal information about the user, an elapsed time of using the exercise device, an indication of a plurality of pain levels, one or more vital signs of the user, a respiration rate of the user, a heartrate of the user, a temperature of the user, a blood oxygen level of the user, a blood pressure of the user, and a glucose level of the user;

responsive to determining that the trigger condition is satisfied further based on the one or more characteristics of the user, executing the control instruction at the exercise device; and responsive to executing the control instruction, presenting, on a user interface of a computing device associated with the exercise device, the control instruction and an explanation of a cause for executing the control instruction.

2. The computer-implemented method of claim 1, wherein transmitting the control instruction to the exercise device causes the exercise device to modify the resistance of the one or more pedals in real-time or near real-time, wherein a modification comprises modifying the resistance a same amount provided by the one or more pedals of the exercise device, or modifying the resistance a different amount on different sides of the exercise device.

3. The computer-implemented method of claim 1, wherein, while a user uses the exercise device to perform an exercise, the resistance of the one or more pedals is modified.

4. The computer-implemented method of claim 1, wherein the one or more pedals comprise one or more foot pedals, one or more hand pedals, or some combination thereof.

5. The computer-implemented method of claim 1, wherein the one or more measurements are associated with a force exerted on the one or more pedals, a revolution per minute of the one or more pedals, a speed of rotation of the one or more pedals, an angular moment of the one or more pedals, a range of motion of the one or more pedals, a radius of an arc traversed by the one or more pedals, or some combination thereof.

6. The computer-implemented method of claim 1, further comprising receiving a selection from the computing device, and based on the selection, modifying the resistance of the one or more pedals, range of motion of the one or more pedals, speed of a motor, or some combination thereof.

7. The computer-implemented method of claim 1, wherein the control instruction is associated with changing an operating parameter of a motor connected to the one or more pedals of the exercise device.

8. The computer-implemented method of claim 1, further comprising:
responsive to determining that the trigger condition has been satisfied, modifying another operating parameter of the exercise device, wherein the another operating parameter comprises a number of revolutions per minute, a speed, a torque, a temperature, a vibration, or some combination thereof.

9. The computer-implemented method of claim 1, further comprising:
receiving a second input from the user, wherein the second input comprises an instruction to modify an operating parameter of the exercise device, and the second input is received via a microphone, a touchscreen, a keyboard, a mouse, a proprioceptive sensor, or some combination thereof.

10. The computer-implemented method of claim 1, wherein transmitting the control instruction to the exercise device causes the exercise device to modify a parameter associated with the one or more pedals of the exercise device a same amount or a different amount, wherein the parameter comprises range of motion, resistance, speed of a motor, revolutions per minutes, or some combination thereof.

11. A tangible, non-transitory computer-readable medium storing instructions that, when executed, cause a processing device to:

generate, by an artificial intelligence engine, a machine learning model, wherein the machine learning model is trained using training data comprising inputs of one or more measurements mapped to outputs of one or more control instructions;

receive the one or more measurements from one or more sensors respectively associated with one or more pedals of the exercise device;

output, by the machine learning model, a control instruction of the one or more control instructions, wherein the control instruction causes an exercise device to modify resistance of the one or more pedals of the exercise device, and the control instruction is generated based on the one or more measurements;

determining whether the one or more measurements satisfy a trigger condition;

responsive to determining that the one or more measurements satisfy the trigger condition, transmitting the control instruction to the exercise device;

further determining, based on one or more characteristics of a user of the exercise device, whether the trigger condition is satisfied, wherein the one or more characteristics of the user comprise at least one of personal information about the user, an elapsed time of using the exercise device, an indication of a plurality of pain levels, one or more vital signs of the user, a respiration rate of the user, a heartrate of the user, a temperature of the user, a blood oxygen level of the user, a blood pressure of the user, and a glucose level of the user; and responsive to determining that the trigger condition is satisfied further based on the one or more characteristics of the user, executing the control instruction at the exercise device; and responsive to executing the control instruction, present, on a user interface of a computing device associated with the exercise device, the control instruction and an explanation of a cause for executing the control instruction.

12. The computer-readable medium of claim 11, wherein transmitting the control instruction to the exercise device causes the exercise device to modify the resistance of the one or more pedals in real-time or near real-time, wherein a modification comprises modifying the resistance a same amount provided by the one or more pedals of the exercise device, or modifying the resistance a different amount on different sides of the exercise device.

13. The computer-readable medium of claim 11, wherein, while the user uses the exercise device to perform an exercise, the resistance of the one or more pedals is modified.

14. The computer-readable medium of claim 11, wherein the one or more pedals comprise one or more foot pedals, one or more hand pedals, or some combination thereof.

15. The computer-readable medium of claim 11, wherein the one or more measurements are associated with a force exerted on the one or more pedals, a revolution per minute of the one or more pedals, a speed of rotation of the one or more pedals, an angular moment of the one or more pedals, a range of motion of the one or more pedals, a radius of an arc traversed by the one or more pedals, or some combination thereof.

16. The computer-readable medium of claim 11, further comprising receiving a selection from the computing device, and based on the selection, modifying the resistance of the one or more pedals, range of motion of the one or more pedals, speed of a motor, or some combination thereof.

17. A system comprising:
a memory device storing instructions; and
a processing device communicatively coupled to the memory device, wherein the processing device executes the instructions to:
generate, by an artificial intelligence engine, a machine learning model, wherein the machine learning model is trained using training data comprising inputs of one or more measurements mapped to outputs of one or more control instructions;
receive the one or more measurements from one or more sensors respectively associated with the one or more pedals of the exercise device;
output, by the machine learning model, a control instruction of the one or more control instructions, wherein the control instruction causes an exercise device to modify resistance of one or more pedals of the exercise device, and the control instruction is generated based on the one or more measurements;
determine whether the one or more measurements satisfy a trigger condition;
responsive to determining that the one or more measurements satisfy the trigger condition, transmit the control instruction to the exercise device;
further determine, based on one or more characteristics of a user of the exercise device, whether the trigger condition is satisfied wherein the one or more characteristics of the user include at least one of personal information about the user, an elapsed time of using the exercise device, an indication of a plurality of pain levels, one or more vital signs of the user, a respiration rate of the user, a heartrate of the user, a temperature of the user, a blood oxygen level of the user, a blood pressure of the user, and a glucose level of the user;
responsive to determining that the trigger condition is satisfied further based on the one or more characteristics of the user, cause the control instruction to be executed at the exercise device; and
responsive to executing the control instruction, present, on a user interface of a computing device associated with the exercise device, the control instruction and an explanation of a cause for executing the control instruction.

* * * * *